(12) United States Patent
Haura

(10) Patent No.: US 10,139,410 B2
(45) Date of Patent: *Nov. 27, 2018

(54) PROTEIN-PROTEIN INTERACTION AS BIOMARKERS

(71) Applicant: H. LEE MOFFITT CANCER CENTER AND RESEARCH INSTITUTE, INC., Tampa, FL (US)

(72) Inventor: Eric B. Haura, Tampa, FL (US)

(73) Assignee: H. LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/796,755

(22) Filed: Oct. 28, 2017

(65) Prior Publication Data

US 2018/0156798 A1 Jun. 7, 2018

Related U.S. Application Data

(63) Continuation of application No. 14/348,152, filed as application No. PCT/US2012/057633 on Sep. 27, 2012, now Pat. No. 9,804,160.

(60) Provisional application No. 61/540,212, filed on Sep. 28, 2011.

(51) Int. Cl.
*G01N 33/569* (2006.01)
*G01N 33/574* (2006.01)

(52) U.S. Cl.
CPC . *G01N 33/56966* (2013.01); *G01N 33/57407* (2013.01); *G01N 33/57484* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,303,310 B1 | 10/2001 | Lautar et al. | |
| 7,049,076 B2 | 5/2006 | Lee et al. | |
| 9,804,160 B2* | 10/2017 | Haura | G01N 33/57407 |
| 2005/0221280 A1 | 10/2005 | Westwick et al. | |
| 2008/0286781 A1 | 11/2008 | Monahan et al. | |
| 2009/0017050 A1 | 1/2009 | Powell et al. | |

FOREIGN PATENT DOCUMENTS

WO WO 2011/050069 4/2011

OTHER PUBLICATIONS

Xu et al., Interface, 2011, vol. 8, pp. 555-567.*
Wu et al. Genome Biology, 2010, vol. 11, pp. 1-23.*
Tascilar et al. (Annals of Oncology 10,Suppl. 4:S107-S110, 1999).*
Tockman et al. (Cancer Research 52:2711s-2718s, 1992).*
Barabasi A-L. et al. "Network biology: understanding the cell's functional organization" *Nat Rev Genet*, 2004, 5:101-113.
Barabasi A-L. "Network medicine—from obesity to the "diseasome"" *N Engl J Med*, 2007, 357:404-407.
Bordeaux J. et al. "Antibody validation" *Biotechniques*, 2010, 48:197-209.
Bürckstümmer T. et al. "An efficient tandem affinity purification procedure for interaction proteomics in mammalian cells" *Nature Methods*, 2006, 3:1013-1019.
Clark G. et al. "Clinical utility of epidermal growth factor receptor expression for selecting patients with advanced non-small cell lung cancer for treatment with erlotinib" *J Thorac Oncol*, 2006, 1:837-846.
Clark G. et al. "Smoking history and epidermal growth factor receptor expression as predictors of survival benefit from erlotinib for patients with non-small-cell lung cancer in the National Cancer Institute of Canada Clinical Trials Group Study BR.21" *Clin Lung Cancer*, 2006, 7:389-394.
Descot A. et al. "Negative regulation of the EGFR-MAPK cascade by actin-MAL-mediated Mig6/Errfi-1 induction" *Mol Cell*, 2009, 35:291-304.
Engelman J. et al. "ErbB-3 mediates phosphoinositide 3-kinase activity in gefitinib-sensitive non-small cell lung cancer cell lines" *Proc Natl Acad Sci USA*, 2005, 102:3788-3793.
Engelman J. et al. "MET amplification leads to gefitinib resistance in lung cancer by activating ERBB3 signaling" *Science*, 2007, 316:1039-1043.
Faber A. et al. "Differential induction of apoptosis in HER2 and EGFR addicted cancers following PI3K inhibition" *Proc Natl Acad Sci USA*, 2009, 106:19503-19508.
Fernbach N. et al. "Acid elution and one-dimensional shotgun analysis on an Orbitrap mass spectrometer: an application to drug affinity chromatography" *J Proteome Res*, 2009, 8:4753-4765.
Frosi Y. et al. "A two-tiered mechanism of EGFR inhibition by RALT/MIG6 via kinase suppression and receptor degradation" *J Cell Biol*, 2010, 189:557-571.
Gale N. et al. "Grb2 mediates the EGF-dependent activation of guanine nucleotide exchange on Ras" *Nature*, 1993, 363:88-92.
Gao J. et al. "Mirk/Dyrk1B, a novel therapeutic target, mediates cell survival in non-small cell lung cancer cells" *Cancer Biol Ther*, 2009, 8:1671-1679.
Gavin A-C. et al. "Proteome survey reveals modularity of the yeast cell machinery" *Nature*, 2006, 440:631-636.
Gavin A-C. et al. "Functional organization of the yeast proteome by systematic analysis of protein complexes" *Nature*, 2002, 415:141-147.
Glatter T. et al. "An integrated workflow for charting the human interaction proteome: insights into the PP2A system" *Mol Syst Biol*, 2009, 5:237.

(Continued)

*Primary Examiner* — Lisa V Cook

(74) *Attorney, Agent, or Firm* — Saliwanchik, Lloyd & Eisenschenk

(57) ABSTRACT

The subject invention pertains to materials and methods for the classification of cancers as sensitive or resistant to treatments based on protein-protein interactions, treatment of cancer, identification of biomarkers, identification of protein-protein interaction modulators, and selection of cancer treatments.

20 Claims, 31 Drawing Sheets

(56) References Cited

OTHER PUBLICATIONS

Goh K-I. et al. "The human disease network" *Proc Natl Acad Sci USA*, 2007, 104:8685-8690.

Golas J. et al. "SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice" *Cancer Res*, 2003; 63:375-381.

Golas J. et al. "SKI-606, a Src/Abl inhibitor with in vivo activity in colon tumor xenograft models" *Cancer Res*, 2005, 65:5358-5364.

Gong Y. et al. "High expression levels of total IGF-1R and sensitivity of NSCLC cells in vitro to an anti-IGF-1R antibody (R1507)" *PLoS One*, 2009, 4:e7273.

Gorgoulis V. et al. "Activation of the DNA damage checkpoint and genomic instability in human precancerous lesions" *Nature*, 2005, 434:907-913.

Gstaiger M. and Aebersold R. "Applying mass spectrometry-based proteomics to genetics, genomics and network biology" *Nat Rev Genet*, 2009, 10:617-627.

Haura E. et al. "Using iTRAQ(R) Combined with Tandem Affinity Purification to Enhance Low-abundance Proteins Associated with Somatically-mutated EGFR Core Complexes in Lung Cancer" *J Proteome Res*, 2011, 10:182-190.

Haura E. et al. "A Pilot Study of Preoperative Gefitinib for Early-Stage Lung Cancer to Assess Intratumor Drug Concentration and Pathways Mediating Primary Resistance" *J Thorac Oncol*, 2010, 5:1806-1814.

Haura E. et al. "Phase I/II study of the Src inhibitor dasatinib in combination with erlotinib in advanced non-small-cell lung cancer" *J Clin Oncol*, 2010, 28:1387-1394.

Haura E. et al. "Activated epidermal growth factor receptor-Stat-3 signaling promotes tumor survival in vivo in non-small cell lung cancer" *Clin Cancer Res*, 2005, 11:8288-8294.

Henney A. and Superti-Furga G. "A network solution" *Nature*, 2008, 455:730-731.

Hilsenbeck S. and Clark G. "Practical p-value adjustment for optimally selected cutpoints" *Stat Med*, 1996, 15:103-112.

Jarvius M. et al. "In situ detection of phosphorylated platelet-derived growth factor receptor beta using a generalized proximity ligation method" *Mol Cell Proteomics*, 2007, 6:1500-1509.

Jemal A. et al. "Cancer statistics, 2008" *CA Cancer J Clin*, 2008, 58:71-96.

Kim L. et al. "Src kinases as therapeutic targets for cancer" *Nat Rev Clin Oncol*, 2009, 6:587-595.

Koos B. et al. "Platelet-derived growth factor receptor expression and activation in choroid plexus tumors" *Am J Pathol*, 2009, 175:1631-1637.

Kowanetz K. et al. "Suppressors of T-cell receptor signaling Sts-1 and Sts-2 bind to Cbl and inhibit endocytosis of receptor tyrosine kinases" *J Biol Chem*, 2004, 279:32786-32795.

Li J. et al. "A chemical and phosphoproteomic characterization of dasatinib action in lung cancer" *Nat Chem Biol*, 2010, 6:291-299.

Lim J. et al. "A protein-protein interaction network for human inherited ataxias and disorders of Purkinje cell degeneration" *Cell*, 2006, 125:801-814.

Lynch T. et al. "Activating mutations in the epidermal growth factor receptor underlying responsiveness of non-small-cell lung cancer to gefitinib" *N Engl J Med*, 2004, 350:2129-2139.

Massinen S. et al. "Functional interaction of DYX1C1 with estrogen receptors suggests involvement of hormonal pathways in dyslexia" *Hum Mol Genet*, 2009, 18:2802-2812.

Melin J. et al. "Ligation-based molecular tools for lab-on-a-chip devices" *N Biotechnol*, 2008, 25:42-48.

Metro G. et al. "In situ protein expression of RRM1, ERCC1, and BRCA1 in metastatic breast cancer patients treated with gemcitabine-based chemotherapy" *Cancer Invest*, 2010, 28:172-180.

Miller R. and Siegmund D. "Maximally selected chi-square statistics" *Biometrics*, 1982, 38:1011-1016.

Paez J.G. et al. "EGFR mutations in lung cancer: Correlation with clinical response to gefitinib therapy" *Science*, 2004, 304:1497-1500.

Pao W. et al. "EGF receptor gene mutations are common in lung cancers from "never smokers" and are associated with sensitivity of tumors to gefitinib and erlotinib" *Proc Natl Acad Sci USA*, 2004, 101:13306-13311.

Pawson T. and Linding R. "Network medicine" *FEBS Lett*, 2008, 582:1266-1270.

Raguz J. et al. "Suppressor of T-cell receptor signalling 1 and 2 differentially regulate endocytosis and signalling of receptor tyrosine kinases" *FEBS Lett*, 2007, 581:4767-4772.

Reynolds C. et al. "Randomized phase III trial of gemcitabine-based chemotherapy with in situ RRM1 and ERCC1 protein levels for response prediction in non-small-cell lung cancer" *J Clin Oncol*, 2009, 27:5808-5815.

Rozakis-Adcock M. et al. "Association of the Shc and Grb2/Sem5 SH2-containing proteins is implicated in activation of the Ras pathway by tyrosine kinases" *Nature*, 1992, 360:689-692.

Sha N. et al. "Bayesian variable selection in multinomial probit models to identify molecular signatures of disease stage" *Biometrics*, 2004, 60:812-819.

Söderberg O. et al. "Direct observation of individual endogenous protein complexes in situ by proximity ligation" *Nature Methods*, 2006, 3:995-1000.

Söderberg O. et al. "Characterizing proteins and their interactions in cells and tissues using the in situ proximity ligation assay" *Methods*, 2008, 45:227-232.

Söderberg O. et al. "Proximity ligation: A specific and versatile tool for the proteomic era" *Genet Eng*, 2007, 28:85-93.

Song, L. et al. "Dasatinib (BMS-354825) selectively induces apoptosis in lung cancer cells dependent on epidermal growth factor receptor signaling for survival" *Cancer Res*, 2006, 66:5542-5548.

Sordella R. et al. "Gefitinib-sensitizing EGFR mutations in lung cancer activate anti-apoptotic pathways" *Science*, 2004, 305:1163-1167.

Taylor I. et al. "Dynamic modularity in protein interaction networks predicts breast cancer outcome" *Nat Biotechnol*, 2009, 27:199-204.

Wang L. et al. "Hybrid huberized support vector machines for microarray classification and gene selection" *Bioinformatics*, 2008, 24:412-419.

Yildirim M. et al. "Drug-target network" *Nat Biotechnol*, 2007, 25:1119-1126.

Yoshida T. et al. "Targeting epidermal growth factor receptor: Central signaling kinase in lung cancer" *Biochem Pharmacol*, 2010, 80:613-623.

Yue P. and Turkson J. "Targeting STAT3 in cancer: How successful are we?" *Expert Opin Investig Drugs*, 2009, 18:45-56.

Zheng Z. et al. "Small tumor size and limited smoking history predicts activated epidermal growth factor receptor in early-stage non-small cell lung cancer" *Chest*, 2005, 128:308-316.

Zheng, Z. et al. "DNA synthesis and repair genes RRM1 and ERCC1 in lung cancer" *N Engl J Med*, 2007, 356: 800-808.

Zheng Z. et al. "Thymidylate synthase in situ protein expression and survival in stage I nonsmall-cell lung cancer" *Cancer*, 2008, 112:2765-2773.

Zheng Z. et al. "In situ detection of EGFR-Grb2 Interaction in Lung Cancer Using Proximal Ligation Assays" poster presented at Duolink Users meeting in LaJolla, CA, Sep. 19-20, 2011.

Arora and Scholar "Role of Tyrosine Kinase Inhibitors in Cancer Therapy" *The Journal of Pharmacology and Experimental Therapeutics*, 2005, 315(3):971-979.

Naruo et al. "Epidermal growth factor receptor mutation in combination with expression of MIG6 alters gefitnib sensitivity" *BMC Systems Biology*, Feb. 18, 2011, 5(29):1-14.

Agelaki et al. "Caveolin-1 regulates EGFR signaling in MCF-7 breast cancer cells and enhances gefitnib-induced tumor cell inhibition" *Cancer Biology & Therapy*, Aug. 1, 2009, 8(15):1470-1477.

Tascilar et al. "Role of tumor markers and mutations in cells and pancreatic juice in the diagnosis of pancreatic cancer" *Annals of Oncology*, 1999, 10(Suppl. 4):S107-S110.

(56) References Cited

OTHER PUBLICATIONS

Tockman et al. "Considerations in bringing a cancer biomarker to clinical application" *Cancer Research (Suppl.)*, 1992, 52:2711s-2718s.

Xu et al. "Prediction of human protein-protein interaction by a mixed Bayesian model and its application to exploring underlying cancer-related pathway crosstalk" *J.R. Soc. Interface*, 2011, 8:555-567.

Wu et al. "A human functional protein interaction network and its application to cancer data analysis" *Genome Biology*, 2010, 11(R53):1-23.

\* cited by examiner

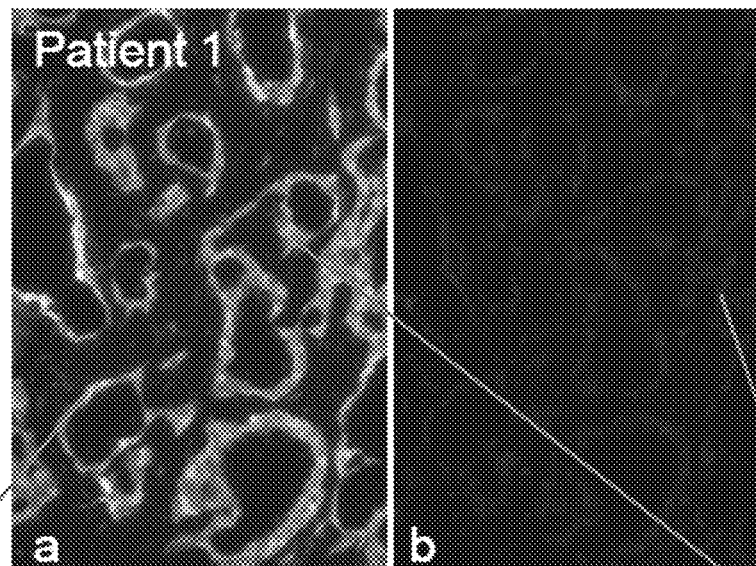
Green  FIG. 12A-1   FIG. 12A-2  Blue
Red
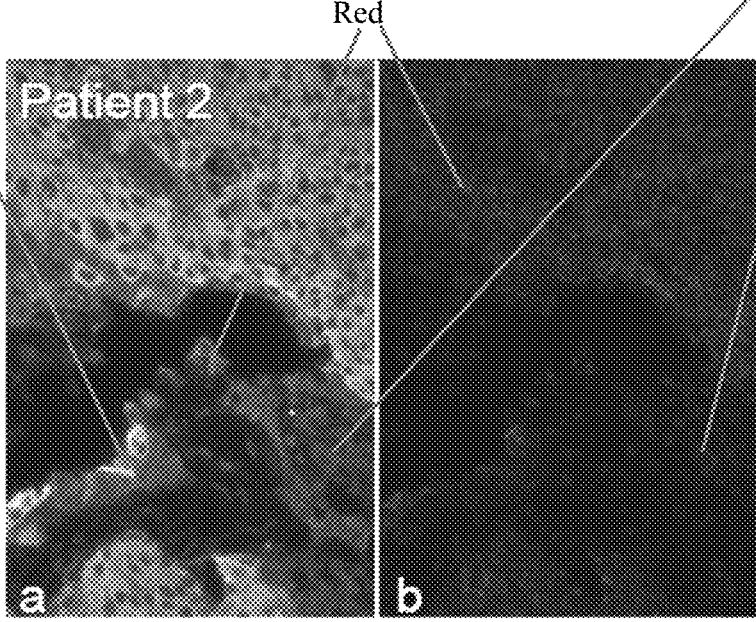
FIG. 12B-1   FIG. 12B-2

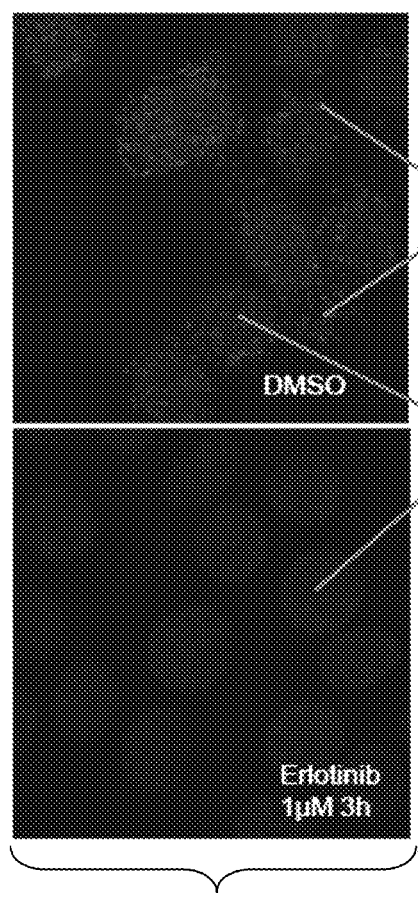 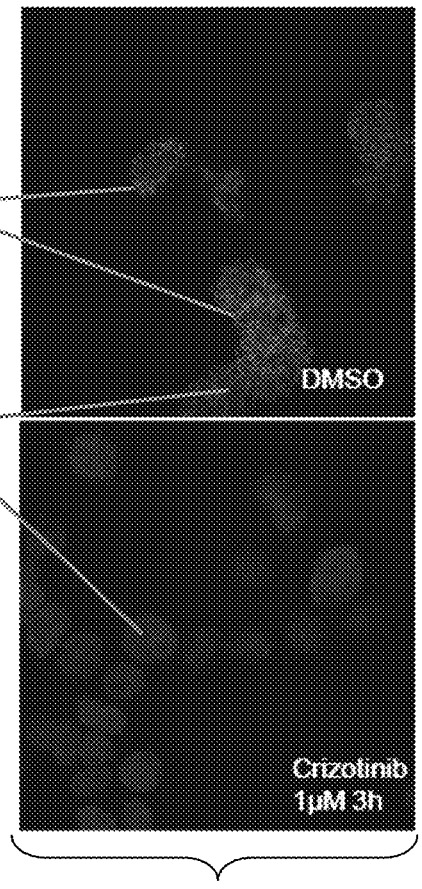
FIG. 15B                    FIG. 15C
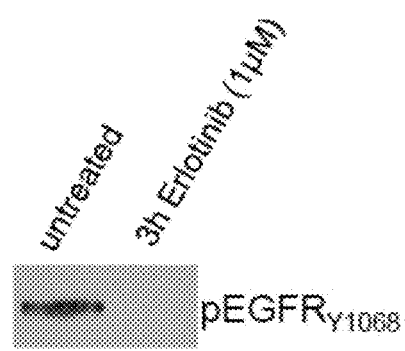
FIG. 15B-1

Blue                    Blue

PROTEIN-PROTEIN INTERACTION AS BIOMARKERS

CROSS-REFERENCE TO RELATED APPLICATIONS

The present application is a continuation of U.S. application Ser. No. 14/348,152, filed Mar. 28, 2014, now U.S. Pat. No. 9,804,160, which is the National Stage of International Application No. PCT/US2012/057633, filed Sep. 27, 2012, which claims the benefit of U.S. Provisional Application Ser. No. 61/540,212, filed Sep. 28, 2011, each of which is hereby incorporated by reference herein in its entirety, including any figures, tables, nucleic acid sequences, amino acid sequences, and drawings.

GOVERNMENT SUPPORT

This invention was made with government support under Grant No. CA119997 awarded by the National Institutes of Health. The government has certain rights in the invention.

BACKGROUND OF THE INVENTION

A better understanding of tumor subsets that benefit from treatment is of critical importance to enable personalized medicine. For this reason, a number of molecular approaches to classify cancer and identify responsive subsets are now being tested. Proteomic strategies (which examine global patterns of protein expression or phosphorylation) are also being used to identify subsets of tumors. This includes classic immunohistochemistry approaches to measure protein expression in paraffin fixed tumor sections, use of phospho-specific antibodies to measure specific phosphorylation events on particular proteins, proteomic profiling tools (such as reverse phase protein arrays), and mass spectrometry based approaches. Biomarker systems to measure protein-protein interaction biomarkers in cancer have lagged behind these other tools. This is an important missing component of most biomarker strategies, as cellular signaling requires proper formation of signaling complexes and networks of proteins that act in concert to produce a physiological signal.

It is known that oncoproteins, such as epidermal growth factor receptor (EGFR) or V-Ki-ras2 Kirsten rat sarcoma viral oncogene homolog (KRAS), produce a signaling network comprised of a defined set of molecules that lead to "oncogene addiction" and cell transformation. A better understanding of the oncoprotein signaling network could uncover novel therapeutic targets or therapeutic strategies and allow "network medicine" to become a reality.

BRIEF SUMMARY OF THE INVENTION

The subject invention pertains to materials and methods for the identification of malignancies as suitable for treatment, treatment of malignancies, and selection of treatments (prophylactic and/or therapeutic interventions). The oncoprotein signaling network can provide biomarkers categorized by protein-protein interactions (PPI) that carry information to guide clinical decision making. The present invention includes materials and methods for determining the responsiveness of a malignancy to a therapeutic intervention, such as a modulator (inhibitor or inducer) of the PPI, by measuring PPI in a sample of the cancer.

Aspects of the invention include a method for assessing the sensitivity of a malignancy to a potential treatment; a method for treating a malignancy in a subject that is predetermined to be sensitive to a PPI modulator based on a PPI profile obtained from a sample of the malignancy; a kit for quantitatively detecting the proximity of target binding partners within a cancer PPI network; a kit for quantitatively detecting the proximity of target binding partners within a tertiary interaction (an interaction of three or more target binding partners); a method for the identification of a biomarker; and a method for identifying an agent as a PPI modulator.

Assays such as proximity ligation assays (PLAs) can be used to quantitatively measure defined PPI in the cancer sample and determine PPI expression patterns to establish a relationship to clinical outcome. PLA technology is capable of detecting single protein events such as protein interactions (e.g., protein dimerization) and modifications (e.g., protein phosphorylation) in tissue and cell samples prepared for microscopy. Two interacting proteins in a complex are identified with two primary antibodies (of different species) specific for the protein—one primary antibody for each interacting protein (Söderberg O. et al., "Direct observation of individual endogenous protein complexes in situ by proximity ligation", *Nat. Methods.*, 2006 December; 3(12): 995-1000; and Jarvius M. et al., "In situ detection of phosphorylated platelet-derived growth factor receptor beta using a generalized proximity ligation method", *Mol. Cell Proteomics*, 2007 September; 6(9):1500-9, which are each incorporated herein by reference in its entirety"). Species-specific secondary antibodies (referred to herein as "PLA probes" or "proximity probes") each have a unique short nucleic acid strand attached to it. When the PLA probes are in close proximity (e.g., less than 40 nm), the nucleic acid strands (through the addition of two circle-forming oligonucleotides) become ligated together by enzymatic ligation and form a circle that functions as a template for amplification (see FIG. 2A). Because the distance of the nucleic acid strands is small, only proteins that interact will allow ligation. After the amplification reaction, the resulting rolling circular amplification (RCA) serves as a target for labeled (e.g., fluorescently labeled) complimentary oligonucleotide probes (see FIG. 2B), which allow for detection (e.g., visualization) and quantification of the product (e.g., using a florescent microscope). This technique greatly amplifies the signal for each antigen recognition event. In this way, the signal is amplified by generating an amplified nucleic acid surrogate of the binding partners (proteins) in sufficient proximity to produce a signal. The signal from each detected pair of proximity probes can be visualized, e.g., as a fluorescent dot, and quantified (counted) and assigned to a specific subcellular location (localization of signal) based on microscopy images.

The methods and kits of the invention make use of PLAs to measure PPI in cell samples, e.g., cancer samples. The PPIs may be binary (having two protein binding partners) or tertiary (having three or more protein binding partners). Proteins within a tertiary interaction may be bound to one or more proteins within the PPI. For measurement of binary interactions, oligonucleotide probes for one type of signal (for example, one color, such as red). For measurement of tertiary interactions, a second signal that is discernable from the first signal is required for detection of the second interaction. Instead of two primary antibodies, three primary antibodies can be used, each of a different species (mouse, rabbit, and goat, for example). For example, in measuring a tertiary interaction between protein binding partners represented as A, B, and C, two separate PLAs are carried out, with a first signal (e.g., red signal) representing interaction between A and B, and a second signal (distinguishable from the first signal) representing interaction between B and C (e.g., green signal). Optionally, for visualization, the images can be constructed showing each signal (e.g., red and green signals) with overlay.

PPI measurements can be taken of virtually any oncoprotein and its binding partner(s). In some embodiments, the oncoprotein comprises epidermal growth factor receptor (EGFR). As EGFR is a key kinase in lung cancer, in some embodiments, the oncoprotein comprises EGFR and the cancer sample is a lung cancer sample.

One aspect of the invention concerns a method for assessing the sensitivity of a malignancy to a treatment based on PPI. The method for assessing the sensitivity of a malignancy to a treatment comprises comparing a protein-protein interaction (PPI) profile obtained from a sample of the malignancy to a reference PPI profile. The sample PPI profile represents the abundance of target binding partners that are in proximity to each other within the sample. A negative result (lack of PPI) in a sample would indicate a lack of sensitivity to the PPI modulator and be useful clinically to avoid giving patients unnecessary PPI modulator therapy. A positive result (presence of PPI) would indicate that the malignancy is potentially sensitive to the PPI modulator and allow the clinician to give the PPI modulator therapy to those patients who would be most likely to benefit. As a specific example, the method may be used for determining whether there is no EGF signaling in a sample such as spleen tissue, and this kind of a negative result can be useful clinically to avoid giving patients unnecessary EGF receptor inhibitor therapy, or alternatively be used to give the therapy to those patients who would be most likely to benefit.

PPI profiles (e.g., sample PPI profile, and reference PPI profile) may each be expressed as a value representative of the abundance of target binding partners in proximity to each other within the sample. The sample PPI profile and reference PPI profile may be expressed by any method useful for comparison purposes, such as a numeric value, score, cutoff (threshold), or other expression. For example, a negative result in which a PPI profile in a sample does not reach the cutoff would be useful clinically to avoid giving patients unnecessary PPI modulator therapy. A positive result in which a PPI profile in a sample is at or above the cutoff would indicate potential sensitivity and allow the clinician to give the PPI modulator therapy to those patients who would be most likely to benefit.

In some embodiments of the methods and kits of the invention, the target PPI is that of a known cancer signaling network. Binding members of a target PPI may include protein products of oncogenes or tumor suppressor genes, for example. In some embodiments, the sample PPI profile represents the abundance of target binding partners that are in proximity to each other within the sample, wherein at least one of the target binding partners is selected from among EGFR, ALK, MET, IGFR, Src, ErbB3, Mig6, Grb2, Sts1, p85, and Hsp90.

In some embodiments of the methods and kits of the invention, the target binding partners are selected from among EGFR and ErbB3; EGFR and Grb2; EGFR and Mig6; EGFR and Sts1, EGFR and Src; EGFR and Hsp90; ErbB3 and p85; ALK and EML4; MET and Gab1; IGFR and IRS; Hsp90 and Cdc37; ALK and Shc1; EGFR and Shc1.

In some embodiments of the methods and kits of the invention, the PPI comprises a tyrosine kinase, such as the human tyrosine kinases listed in Tables 3 and 4. In some embodiments, the PPI comprises an interaction between the binding partners listed in Table 5 (human tyrosine kinase interactions).

PLAs can be used to generate biomarkers against receptor tyrosine kinases (RTKs). RTKs are important proteins in cancer and highly "druggable" targets. Approximately twenty different RTK classes have been identified thus far. In some embodiments of the methods and kits of the invention, at least one of the target binding partners is an RTK. In some embodiments of the methods and kits of the invention, at least one of the target binding partners is of an RTK class selected from among RTK class I (EGF receptor family; ErbB family), RTK class II (insulin receptor family), RTK class III (PDGF receptor family), RTK class IV (FGF receptor family) RTK class V (VEGF receptors family), RTK class VI (HGF receptor family), RTK class VII (Trk receptor family), RTK class VIII (Eph receptor family), RTK class IX (AXL receptor family), RTK class X (LTK receptor family), RTK class XI (TIE receptor family), RTK class XII (ROR receptor family), XIII (DDR receptor family), RTK class XIV (RET receptor family), RTK class XV (KLG receptor family), RTK class XVI (RYK receptor family), and RTK class XVII (MuSK receptor family).

In some embodiments of the methods and kits of the invention, one or more of the binding partners of the target PPI have one or more sequence mutations that are known to be associated with occurrence of the malignancy. In other embodiments, the binding partners of the target PPI do not harbor (lack) any sequence mutations known to be associated with occurrence of the malignancy, or with sensitivity to a treatment such as a PPI modulator. In some embodiments, the binding partners of the target PPI and the downstream effectors of the target PPI do not harbor any sequence mutations known to be associated with occurrence of the malignancy, or with sensitivity to a treatment such as a PPI modulator. Such sequence aberrations in a subject or in a sample can be detected using methods known in the art (e.g., mutation analysis). Typically, abnormalities in nucleic acid sequences are identified by comparison to reference sequence data (sequences of normal cells or cancer cells) on databases, such as GenBank and EMBL, and specific data resources such as Cancer Gene Census (mutated genes causally implicated in human cancer), COSMIC (Catalogue of Somatic Mutations in Cancer), and CGP Resequencing Studies (somatic mutations from large scale resequencing of genes in human cancer). Mutations causing or contributing to cancer may be large-scale mutations, involving the deletion or addition of a portion of a chromosome, or small-scale mutations, including point mutations, deletions, insertions, which may occur in the promoter region of a gene and affect its expression, may occur in the coding sequence and alter the stability or function of the gene's protein product.

The sample may be any cell sample potentially harboring the target protein(s). For example, a cytology sample may be obtained from a tissue selected from breast, ovaries, esophagus, stomach, colon, rectum, anus, bile duct, brain, endometrium, lung, liver, skin, prostate, kidney, nasopharynx, pancreas, head and neck, kidney, lymphoma, leukemia, cervix, and bladder. The sample may be a solid or non-solid tumor specimen. The tumor specimen may be a carcinoma. The sample may be a new cancer, recurrent cancer, primary cancer, or metastasized (secondary) cancer.

The sample may be obtained by methods known in the art, such as surgery, biopsy, or from blood (e.g., circulating tumor cells), ascites, or pleural effusion. The sample may be processed using methods known in the art. For example, the sample may be fresh, frozen, or formalin-fixed and paraffin-embedded (FFPE).

Preferably, the treatment against which the sample is being assessed for sensitivity/resistance is a PPI modulator (i.e., a PPI inhibitor or PPI inducer). However, the treatment may be a treatment other than a PPI modulator.

Another aspect of the invention concerns a method for treating a malignancy in a subject, comprising administering a protein-protein interaction (PPI) modulator to the subject, wherein the subject is predetermined to be sensitive to the PPI modulator based on a PPI profile obtained from a sample of the malignancy. In some embodiments, the PPI modulator is an inhibitor of the PPI of the PPI profile (i.e., a PPI inhibitor). In some embodiments, the PPI modulator is an inducer of the PPI of the PPI profile (i.e., a PPI inducer).

Another aspect of the invention concerns a method for treating a malignancy in a subject, comprising:

(a) assessing the sensitivity of a malignancy in the subject, comprising comparing a protein-protein interaction (PPI) profile obtained from a sample of the malignancy to a reference PPI profile; and (b) administering a PPI modulator to the subject if the malignancy is assessed to be sensitive to the PPI modulator; and withholding the PPI modulator from the subject if the malignancy is assessed to be resistant to the PPI modulator. In some embodiments, the PPI modulator is an inhibitor of the PPI of the PPI profile (i.e., a PPI inhibitor). In some embodiments, the PPI modulator is an inducer of the PPI of the PPI profile (i.e., a PPI inducer).

The invention includes also includes kits useful for carrying out methods of the invention, (e.g., methods for the classification of cancers as sensitive or resistant to treatments based on protein-protein interactions, treatment of cancer, identification of biomarkers, identification of protein-protein interaction modulators, and selection of cancer treatments). Thus, one aspect of the invention concerns a kit for detecting the proximity of target binding partners within a cancer protein-protein interaction network, comprising a primary antibody to at least one of the target binding partners, and a proximity probe comprising a secondary antibody (that binds to the primary antibody) with an oligonucleotide conjugated thereto. In preferred embodiments, the kit comprises:

a first primary antibody to a first target binding partner;

a second primary antibody to a second target binding partner;

a first proximity probe comprising a first secondary antibody (that binds to the first primary antibody) with an oligonucleotide conjugated thereto; and a second proximity probe comprising a second secondary antibody (that binds to the second primary antibody) with an oligonucleotide conjugated thereto, wherein when the oligonucleotides of the first and second proximity probes are in sufficient proximity to each other, the oligonucleotides of the proximity probes interact in the presence circle-forming oligonucleotides by enzymatic ligation and form a circular product that is amplified by rolling circle replication, producing an amplification product. Optionally, the kit further comprises a labeled oligonucleotide probe that hybridizes with the amplification product, allowing detection and quantification of the amplification product (representing the association (close proximity) of the target binding partners).

Another aspect of the invention concerns a kit for detecting the proximity of target binding partners within tertiary PPI (a complex having three or more protein binding partners), referred to herein as the "tertiary interaction kit". The target PPI may be within a cancer signaling network, but is not limited to such applications. The tertiary interaction kit can be used to study viruses, for example, in which a viral protein forms an interaction with protein A and protein B in a cell, giving rise to a tertiary complex. Identification of this tertiary PPI may be diagnostic of an active infection or yield important information about the prognosis or predict the correct therapy. In cancer, a tertiary complex may provide important information about the therapeutic efficacy.

The tertiary interaction kit comprises:

a first primary antibody to a first target binding partner of the tertiary interaction;

a second primary antibody to a second target binding partner of the tertiary interaction;

a third primary antibody to a third target binding partner of the tertiary interaction;

a first proximity probe comprising a first secondary antibody (that binds to the first primary antibody) with an oligonucleotide conjugated thereto; and a second proximity probe comprising a second secondary antibody (that binds to the second primary antibody) with an oligonucleotide conjugated thereto;

a third proximity probe comprising a third secondary antibody (that binds to the third primary antibody) with an oligonucleotide conjugated thereto;

wherein when the oligonucleotides of the first and second proximity probes are in sufficient proximity to each other, the oligonucleotides of the first and second proximity probes interact in the presence circle-forming oligonucleotides by enzymatic ligation and form a circular product that is amplified by rolling circle replication, producing a first amplification product; and wherein when the oligonucleotides of the second and third proximity probes are in sufficient proximity to each other, the oligonucleotides of the second and third proximity probes interact in the presence of circle-forming oligonucleotides by enzymatic ligation and form a circular product that is amplified by rolling circle replication, producing a second amplification product. Optionally, the kit detecting proximity of binding partners within a tertiary PPI further comprises a first labeled oligonucleotide probe that hybridizes with the first amplification product, allowing detection and quantification of the first amplification product (representing the association (close proximity) of the first and second target binding partners), and a second labeled oligonucleotide probe that hybridizes with the second amplification product, allowing detection and quantification of the second amplification product (representing the association of the second and third target binding partners). Each primary antibody is of a different species (e.g., mouse, rabbit, and goat, for example). Preferably, the label of the first labeled oligonucleotide yields a signal (e.g., a color) that is distinguishable from that of the second labeled oligonucleotide (red and green, for example). An additional primary antibody, proximity probe, and (optionally) oligonucleotide probe can be included in the kit for each additional target binding partner within the tertiary PPI to be measured. Optionally, images can be constructed for visualization showing each signal with overlay (e.g., red and green overlay).

In the various kits of the invention, each kit can include instructions or packaging materials that describe how to use a compound or composition (e.g., a reagent such as a primary antibody, a secondary antibody, a labeled oligonucleotide probe that hybridizes with the amplification product) of the kit. Within the kit, the secondary antibody may be uncojugated or conjugated to an oligonucleotide (making the secondary antibody a proximity probe). The kits may also comprise, e.g., polymerase (for the amplification reaction), ligase (for the ligation reaction), a buffering agent, a preservative, or a protein stabilizing agent.

The kits may also comprise components necessary for detecting the label (e.g., an enzyme or substrate). The kit may also contain a control sample or a series of control samples that can be assayed and compared to a test sample. Each kit can include one or more containers for individually enclosing each component of the kit. Containers of the kits can be of any suitable material, e.g., glass, plastic, metal, etc., and of any suitable size, shape, or configuration. The one or more containers are can be enclosed within outer packaging.

The kits of the invention may be used by contacting the cell-containing sample with the primary antibodies (allowing the primary antibodies to bind to their respective protein targets), contacting the sample with the proximity probes (allowing the proximity probes to bind to their respective antibody targets), allowing the nucleic acid strands (also referred to as arms) of the proximity probes to ligate if binding in close proximity (adding ligase if necessary), amplifying the ligation product (adding polymerase if necessary) to produce an amplification product, and measuring the amplification product corresponding to the interaction of each pair of protein targets within the PPI. Measurement of the amplification product can be made using methods known in the art for detecting and quantifying nucleic acid amplification products, e.g., by adding a labeled oligonucleotide that hybridizes to a sequence of the amplification product, and analyzing the sample by visualizing the amplification product (as represented by the label signal) with an appropriate visualization device, such as a confocal or fluorescence microscope.

Another aspect of the invention concerns a method for measuring protein-protein interactions having three or more binding partners (a tertiary interaction) in a sample, comprising:

contacting the sample with three or more primary antibodies to three or more corresponding target binding partners within a target tertiary interaction;

contacting the sample with three or more proximity probes (first, second, and third proximity probes) comprising a secondary antibody that binds to the corresponding first antibody, wherein each proximity probe has an oligonucleotide conjugated thereto;

wherein when the oligonucleotides of the first and second proximity probes are in sufficient proximity to each other, the oligonucleotides of the first and second proximity probes interact in the presence circle-forming oligonucleotides by enzymatic ligation and form a circular product that is amplified by rolling circle replication, producing a first amplification product; and wherein when the oligonucleotides of the second and third proximity probes are in sufficient proximity to each other, the oligonucleotides of the second and third proximity probes interact in the presence of circle-forming oligonucleotides by enzymatic ligation and form a circular product that is amplified by rolling circle replication, producing a second amplification product; and measuring the first and second amplification products.

In some embodiments, measurement of the first and second amplification products comprises contacting the sample with two or more labeled oligonucleotides, comprising a first labeled oligonucleotide that hybridizes to a sequence of the first amplification product, and a second labeled oligonucleotide that hybridizes to a sequence of the second amplification product, to produce labeled amplification products, wherein the labels are distinguishable from one another; and measuring the PPIs by visualizing the labeled amplification products. An additional primary antibody, proximity probe, and labeled oligonucleotide can be used for each additional target binding partner within the tertiary PPI.

Another aspect of the invention concerns a method for the identification of a biomarker, comprising selecting two or more target binding partners within a cancer sample; generating a PPI profile for the two or more target binding partners; and comparing the PPI profile to the responsiveness of the cancer to a treatment in vitro and/or in vivo (for example, in xenograft animal models or human subjects). Correlation between the PPI profile to the responsiveness of the cancer to a treatment of the cancer in vitro and/or in vivo is indicative of a biomarker for treatment responsiveness for the cancer. In some embodiments, the treatment is a kinase inhibitor (e.g., a tyrosine kinase inhibitor (TKI)). In some embodiments, at least one of the two or more target binding partners comprises a receptor tyrosine kinase (RTK). In some embodiments, RTK is within RTK class I-XVII. Preferably, responsiveness of the treatment to the cancer in vitro, or in vivo with xenograft animal models, is determined with the subject's cancer cells; however, cancer cell lines known to be predictive of responsiveness to the subject's cancer type may be utilized to compare with the PPI profile.

Another aspect of the invention concerns a method for identifying an agent as a PPI modulator, comprising: contacting cancer cells with a candidate agent in vitro or in vivo; and determining whether the candidate agent modulates a selected PPI in a sample of the cancer cells. The candidate agent may be any substance that potentially modulates (increases, decreases, or otherwise alters) the PPI. The candidate agent may be a small molecule, polypeptide, or nucleic acid, for example. Determination of changes in PPI can be made by comparing a first PPI profile of the cancer cells obtained prior to the contacting step to a second PPI profile of the cancer cells obtained after the contacting step, wherein a change in the PPI is indicative of a PPI modulator.

BRIEF DESCRIPTION OF THE DRAWINGS

FIGS. 1A-1D demonstrate how interaction data (e.g., from literature or affinity-purification mass spectrometry) can be used to generate pairs of proteins to study as biomakers for treatment efficacy using proximity ligation assays.

FIG. 3A shows strong signals in PC9 cell line that are dramatically reduced after treated with erlotinib (FIG. 3B). Negative controls are shown in FIGS. 3C to 3F: no anti-rabbit $2^{nd}$ antibody with PLUS DNA chain (FIG. 3C); no anti-mouse $2^{nd}$ antibody with MINUS DNA chain (FIG. 3D), no rabbit anti-Grb2 antibody (FIG. 3E); no mouse anti-EGFR antibody (FIG. 3F).

Figure 1A:
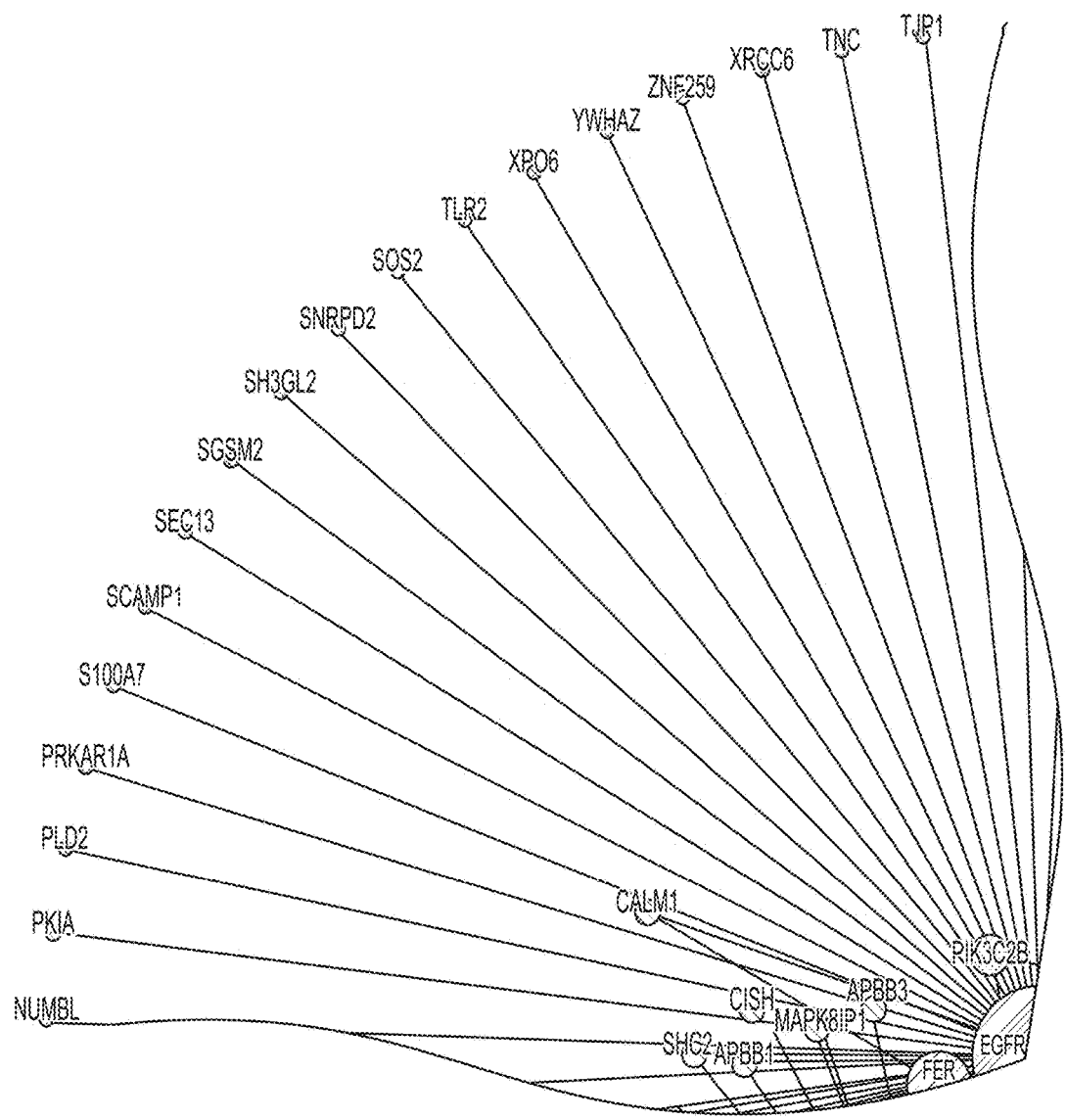
FIGS. 1A-1D show physical mapping of protein-protein interactions involving EGFR, showing 201 interactions with EGFR.
Figure 1B:
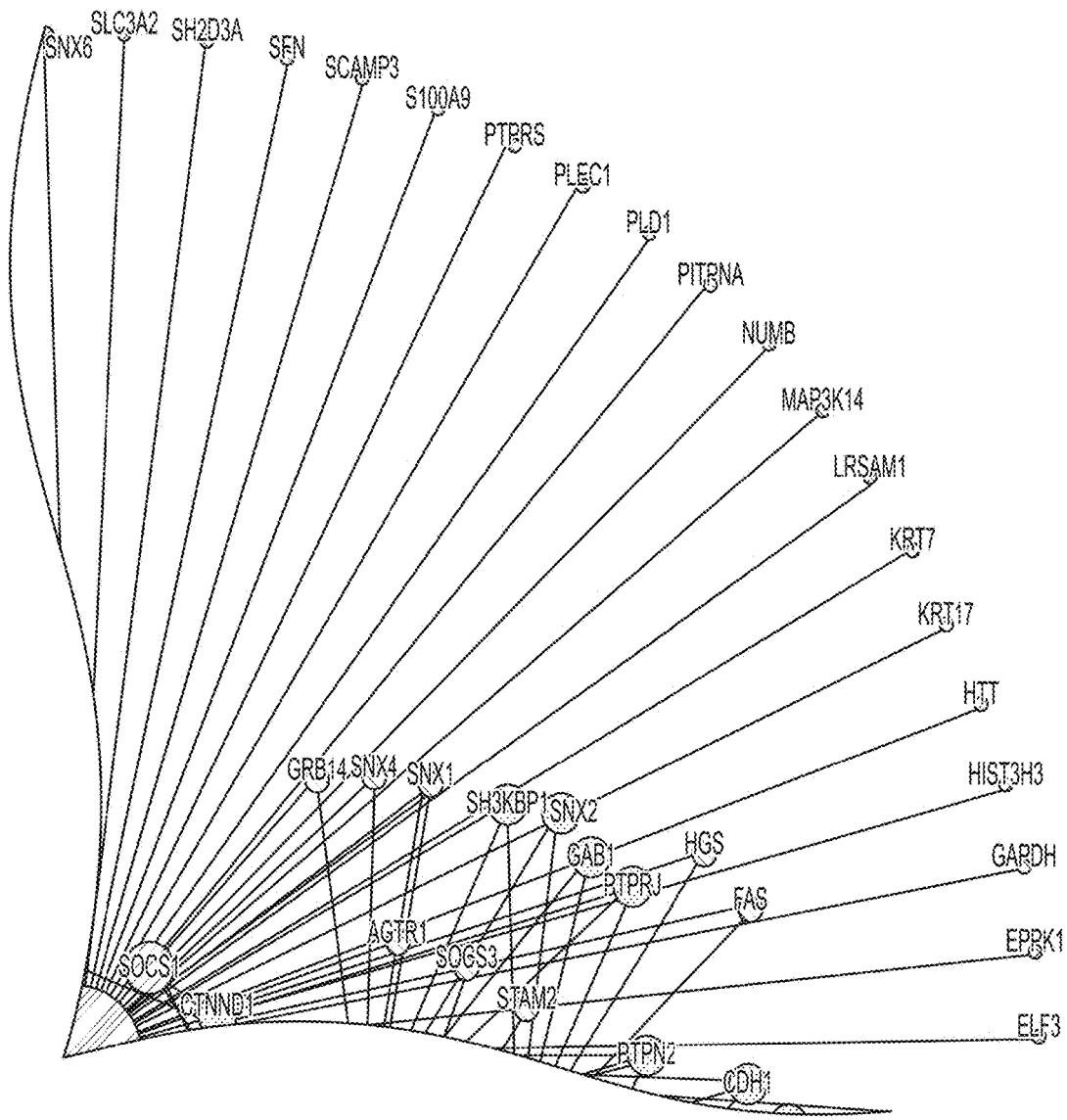
Figure 1C:
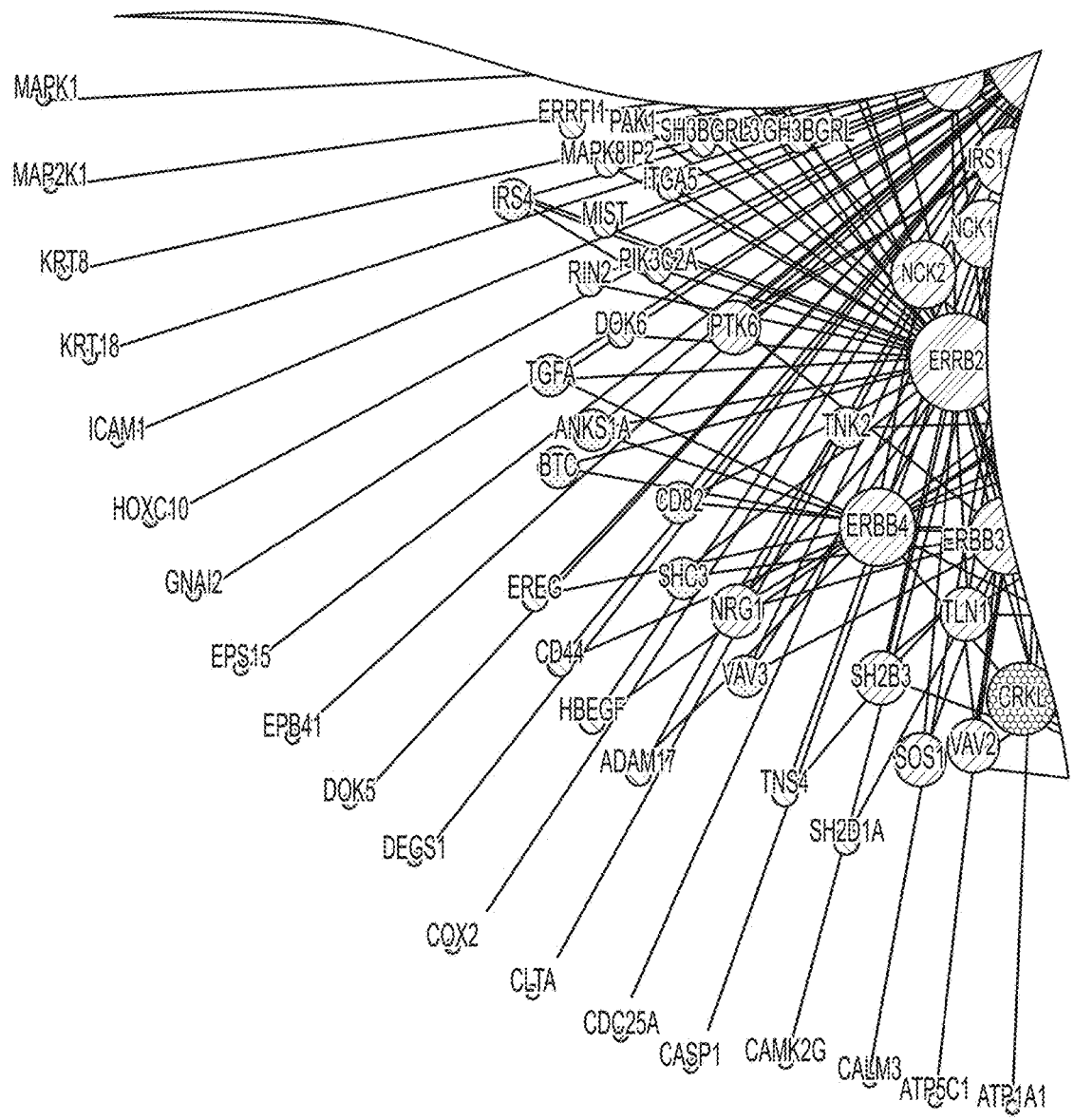
Figure 1D:
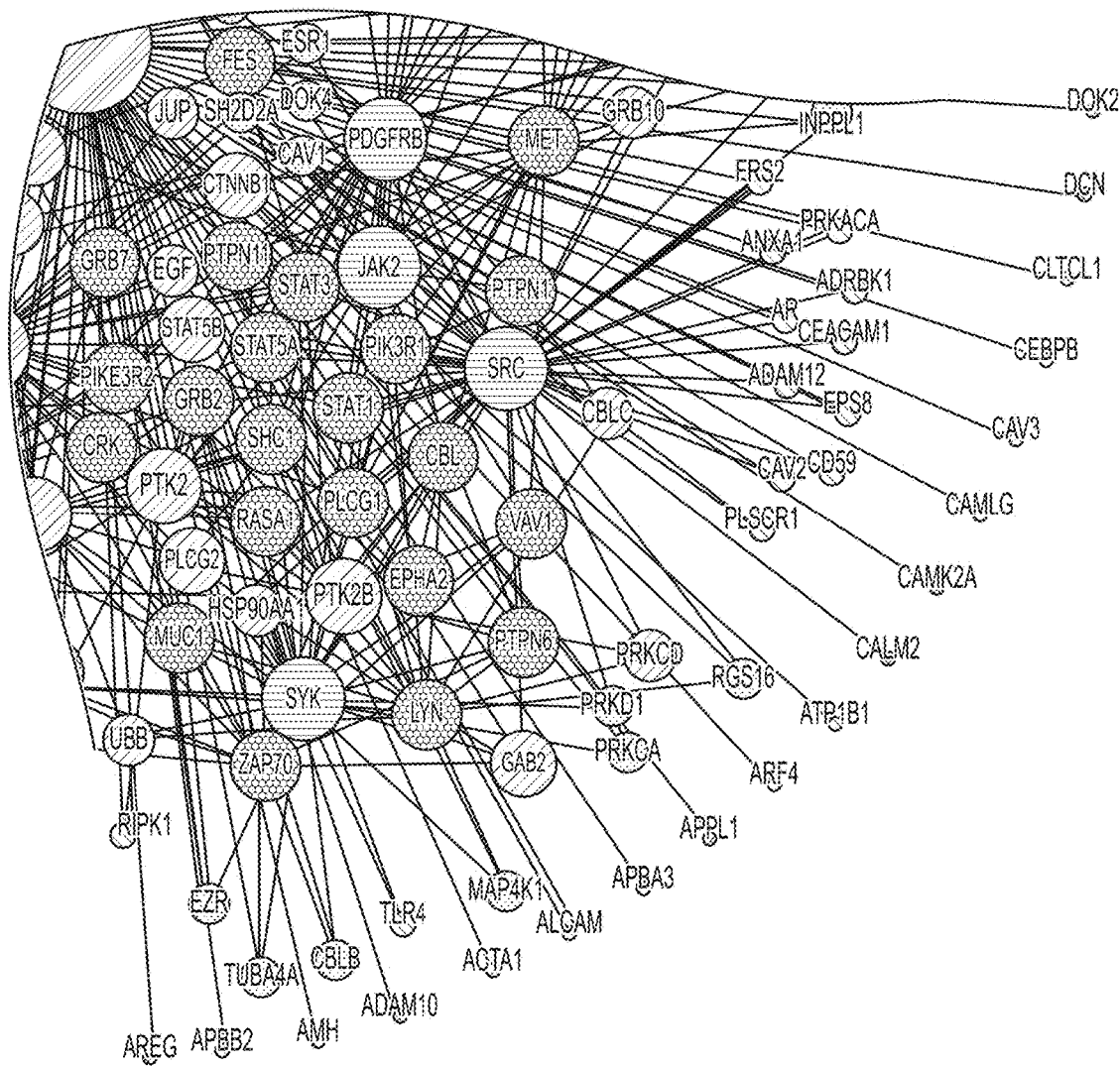
Figures 2A, 2B:
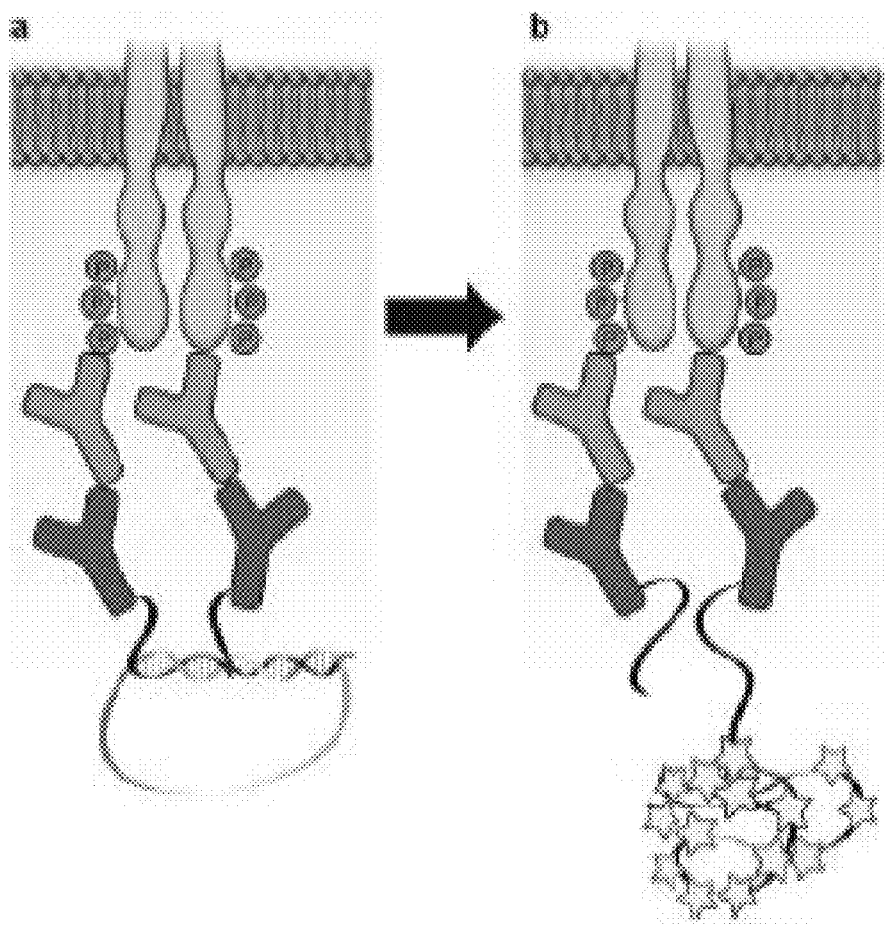
FIGS. 2A and 2B are diagrams showing the proximity ligation assay (PLA) scheme.
Figure 3A:
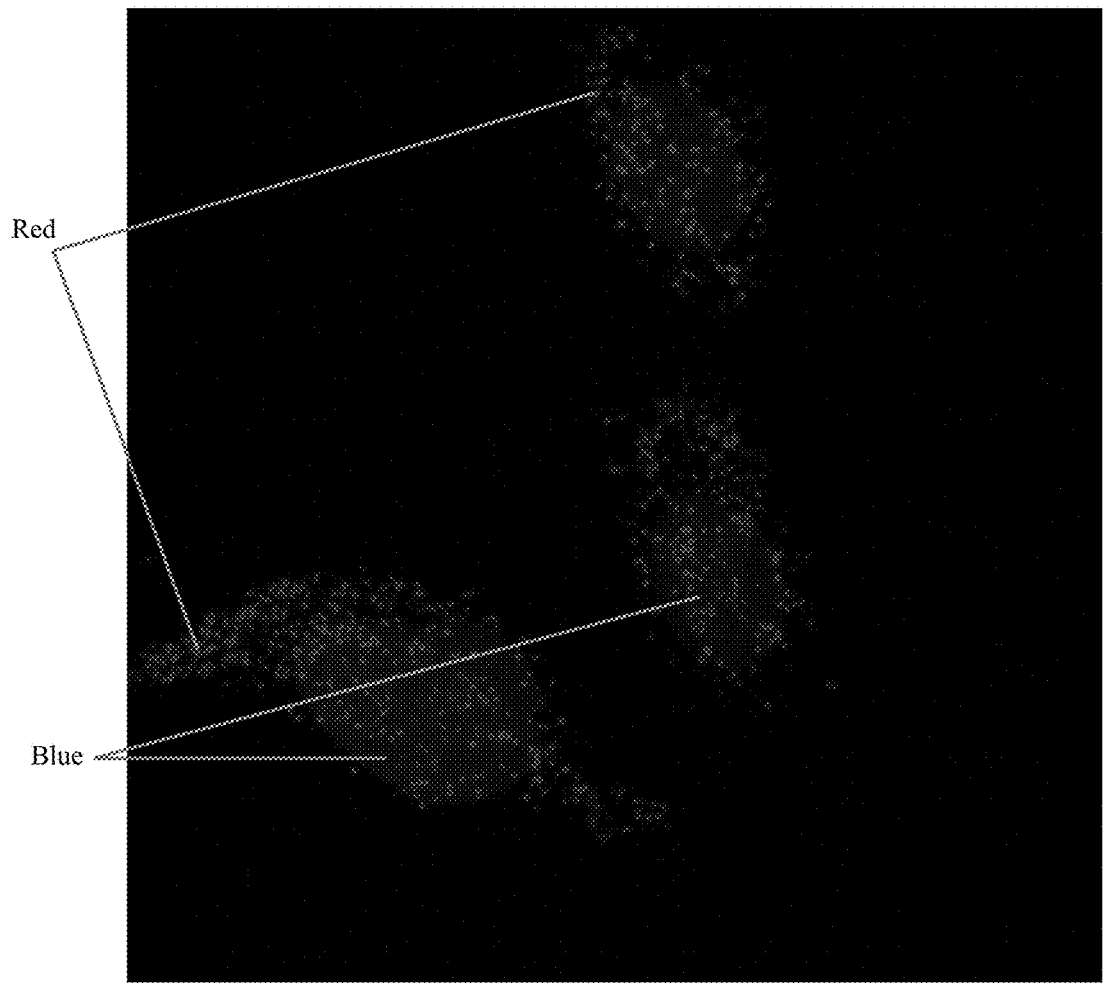
FIGS. 3A-3F show results of an EGFR-GRB2 PLA in situ. Red dots are signal of EGFR-GRb2 interaction detected by PLA using confocal images with 10 z-sections merged.
Figure 3B:
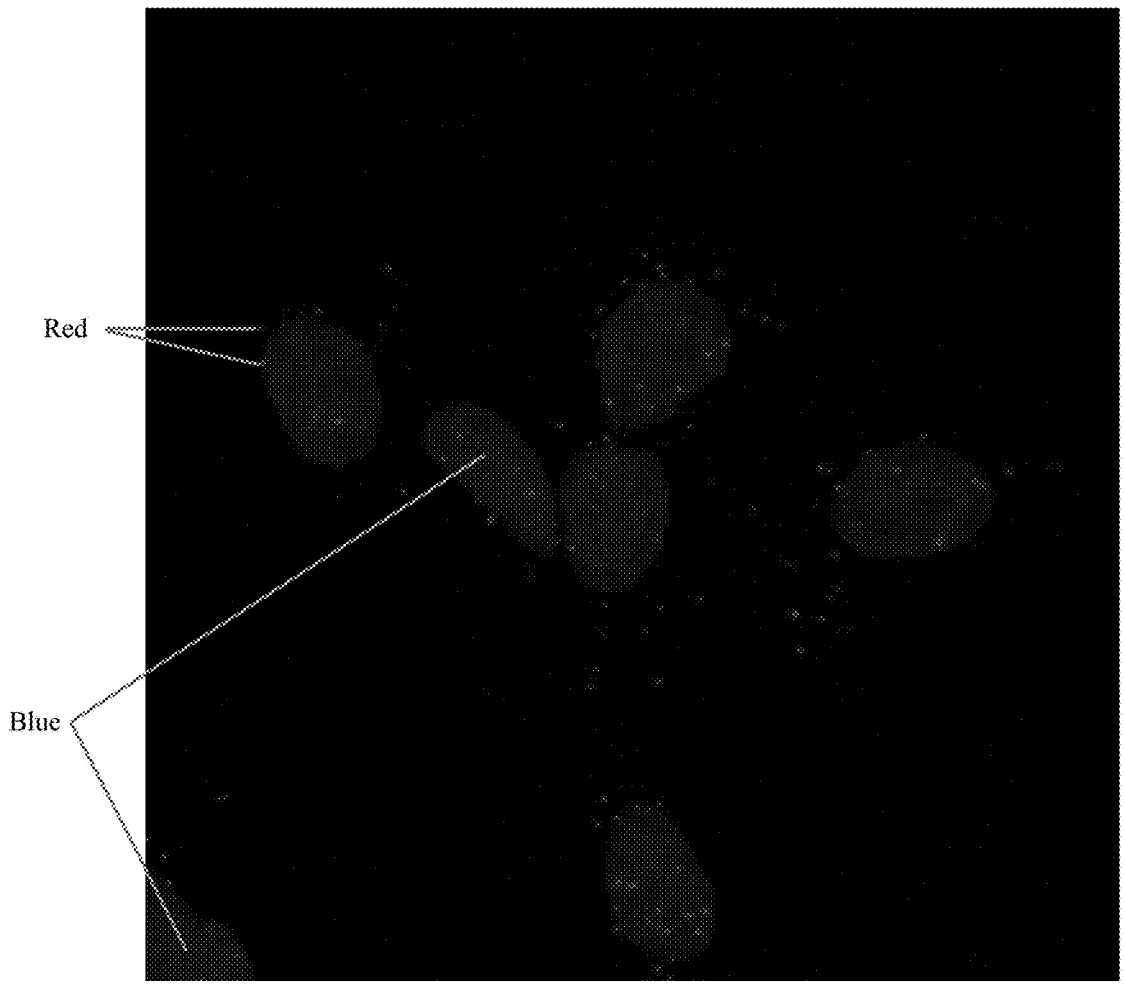
Figure 3C:
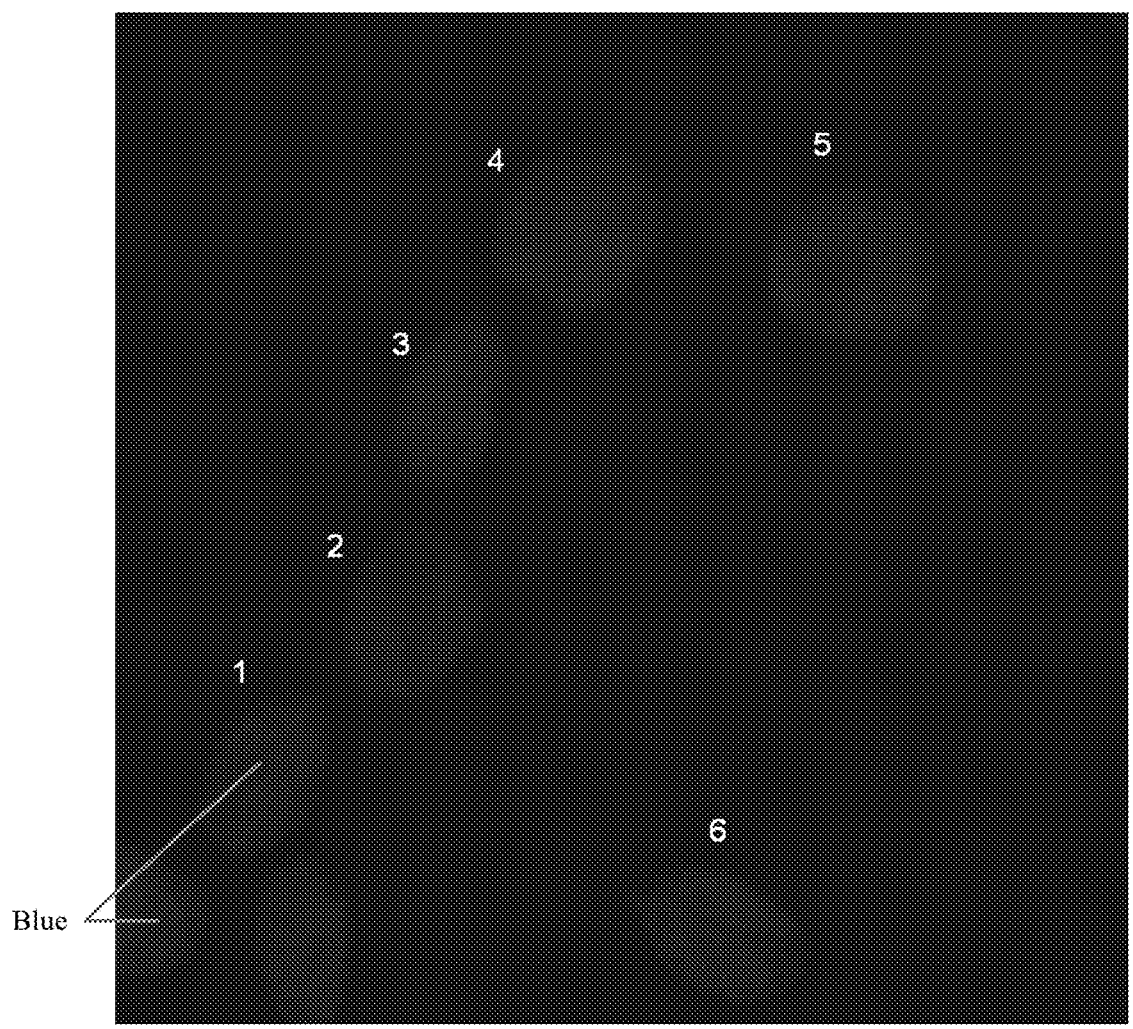
Figure 3D:
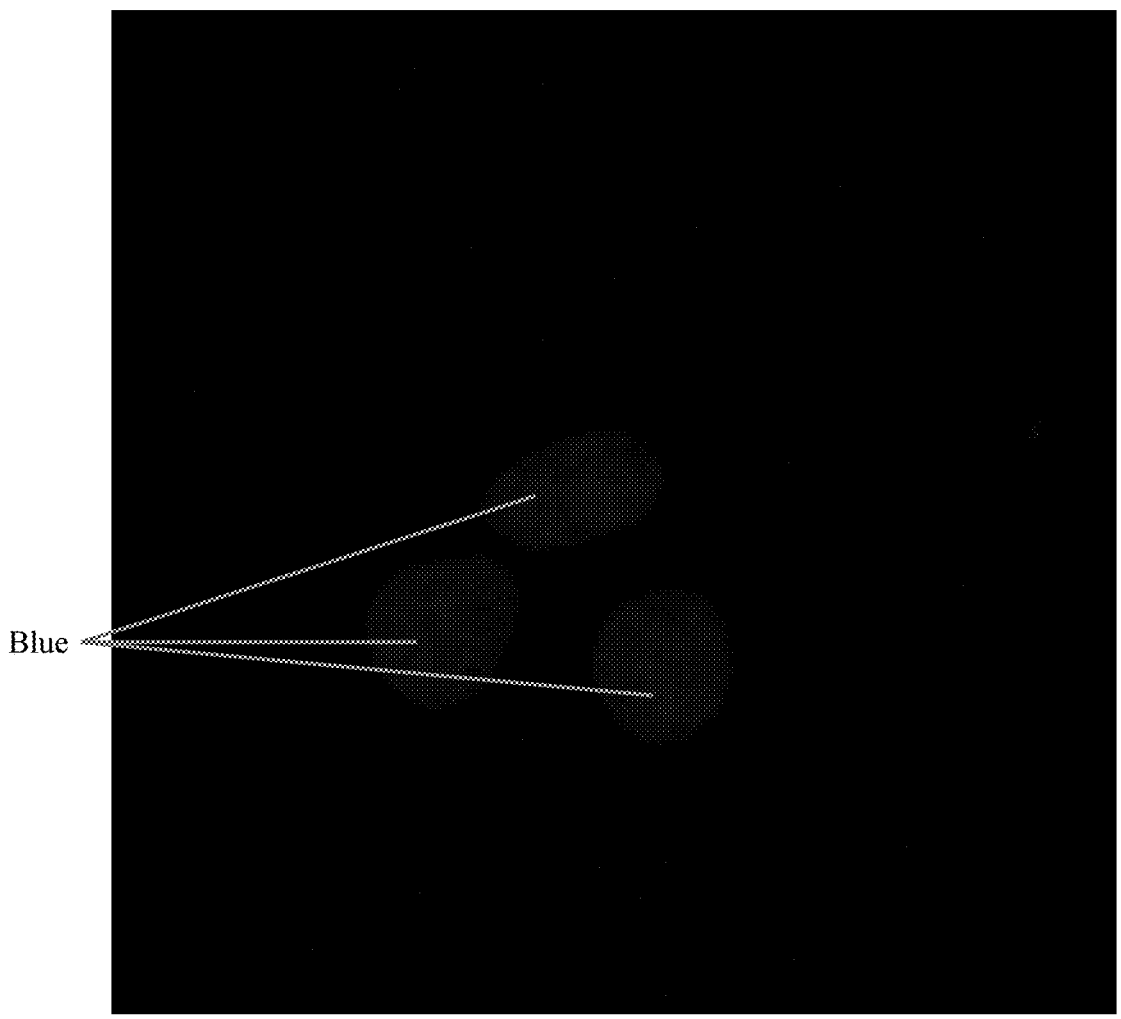
Figure 3E:
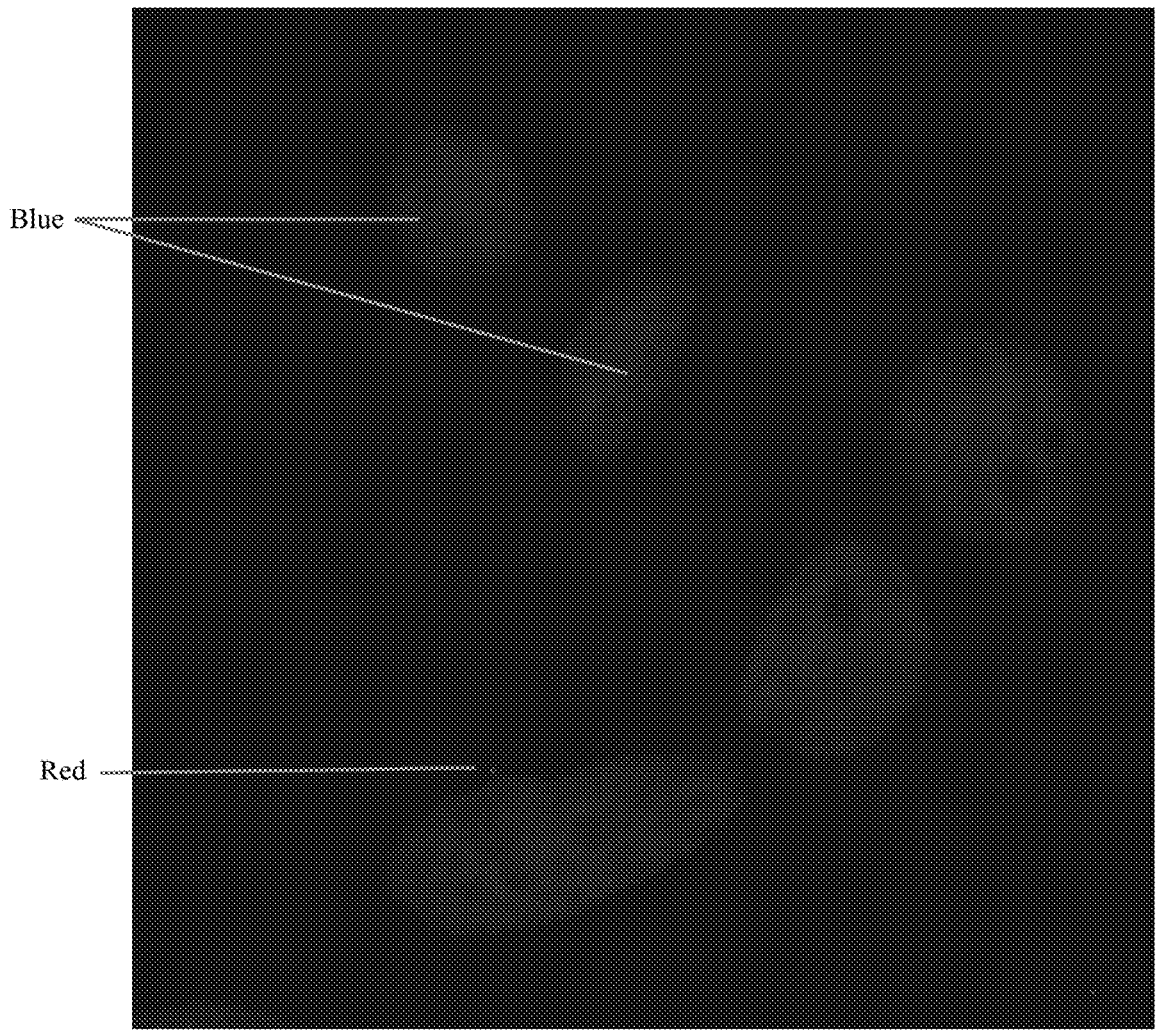
Figure 3F:
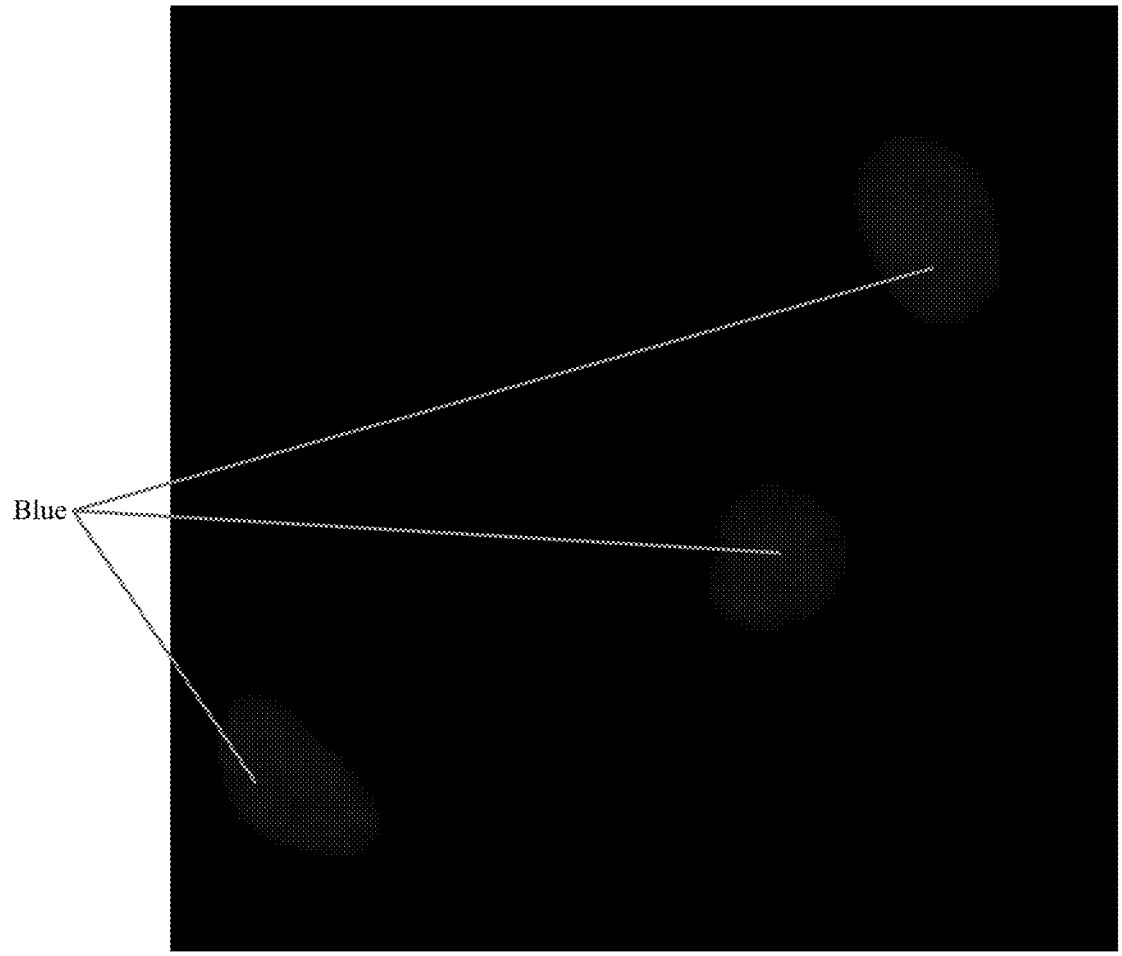
Figure 4A:
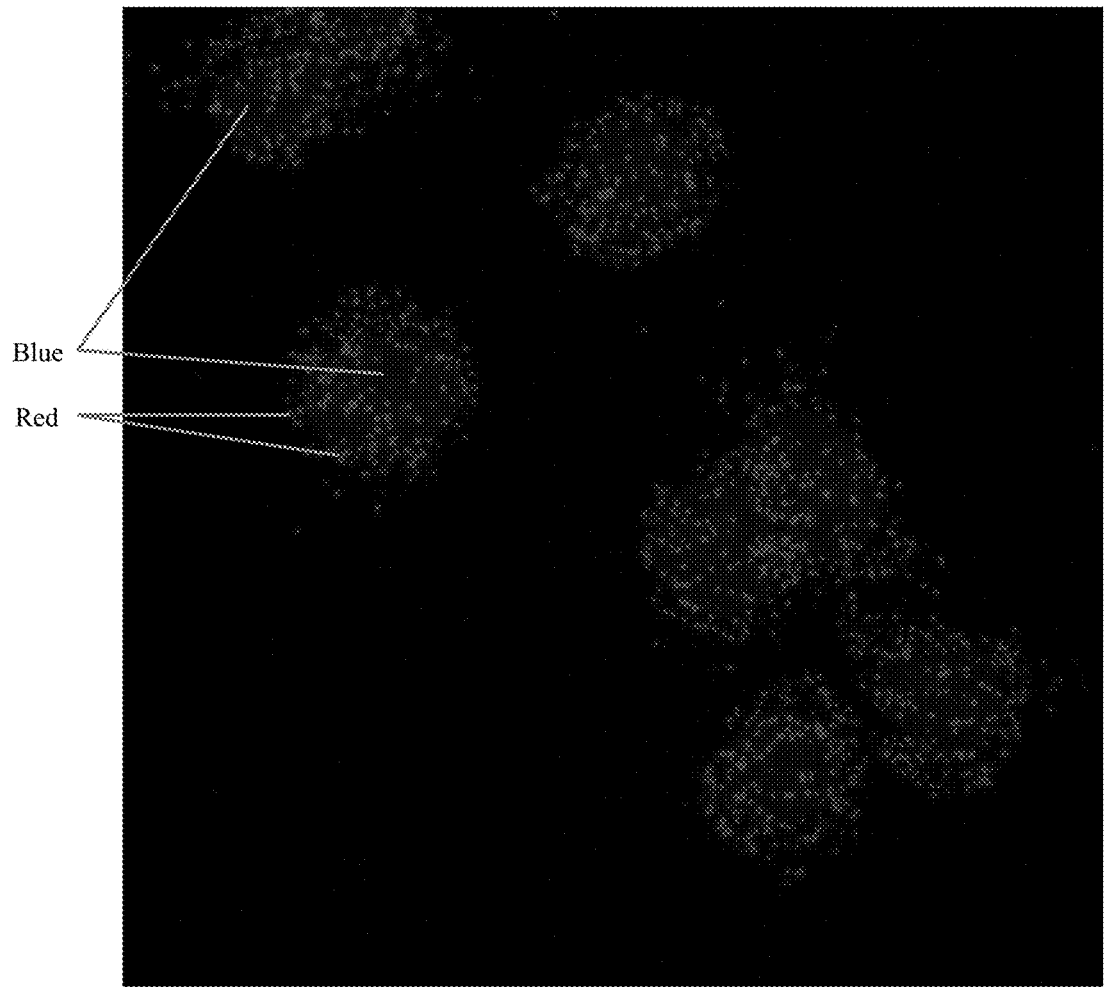
FIGS. 4A and 4B show results of EGFR-Grb2 PLA in the PC9 lung cancer cell line. PC9 lung cancer cells harboring an activating EGFR mutation were examined for PLA using EGFR and Grb2 antibodies. Control untreated cells (FIG.
Figure 4B:
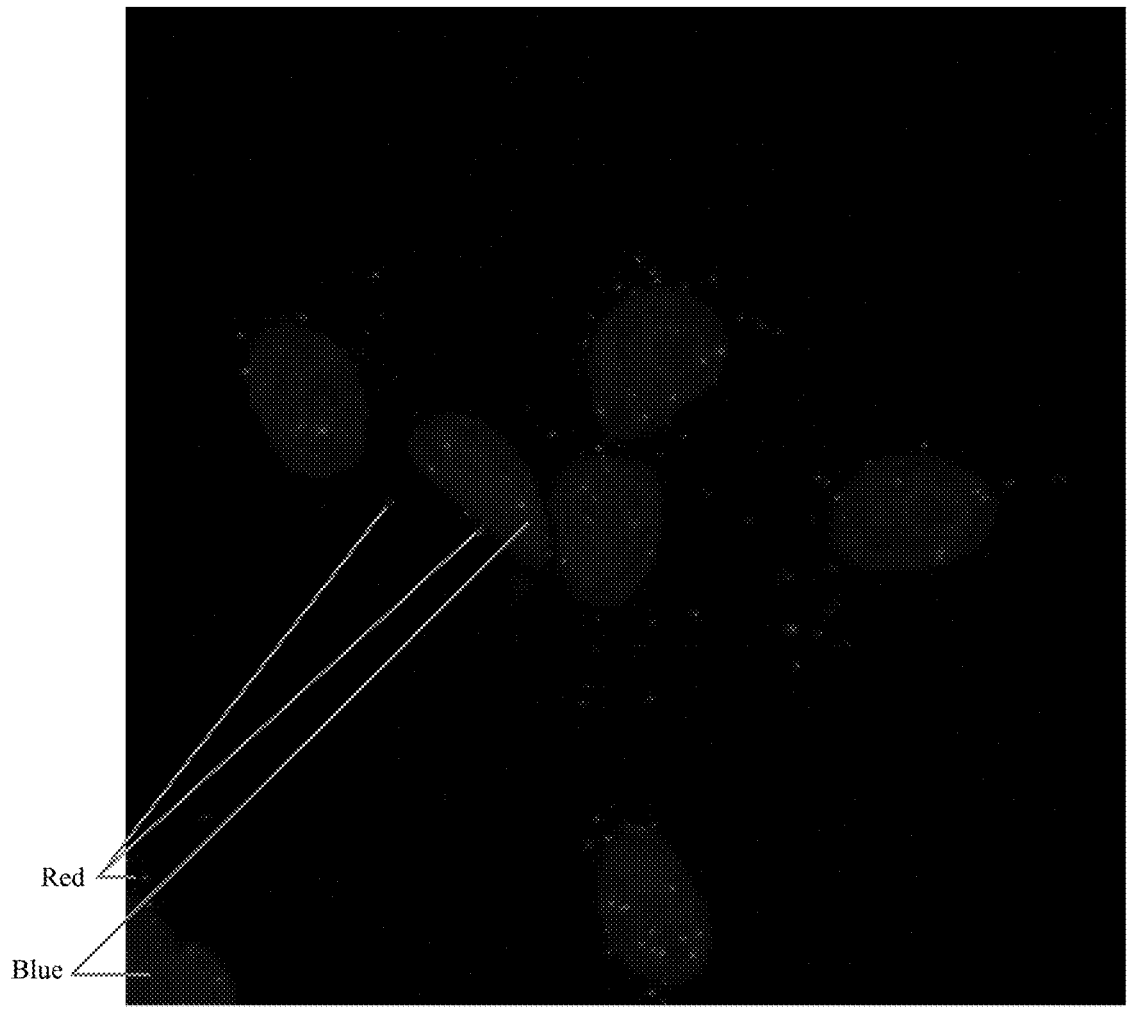

4A) were examined as well as cells exposed to erlotinib, a small molecule epidermal growth factor tyrosine kinase inhibitor (EGFR TKI) (FIG. 4B). Erlotinib inhibits EGFR tyrosine phosphorylation and prevents Grb2 binding (data now shown) thus serving as a perturbation to examine PLA. As shown here, the EGFR-Grb2 PLA signal (red dots) is strong across multiple cells and strongly repressed by erlotinib. Blue stain=DAPI that stains nuclei. This figure also demonstrates the feasibility of performing EGFR-Grb2 PLA (and potential other useful PLA biomarkers) on low numbers of cells (and may work with cytology specimens or other scant tumor biopsy specimens).

Figure 5A:
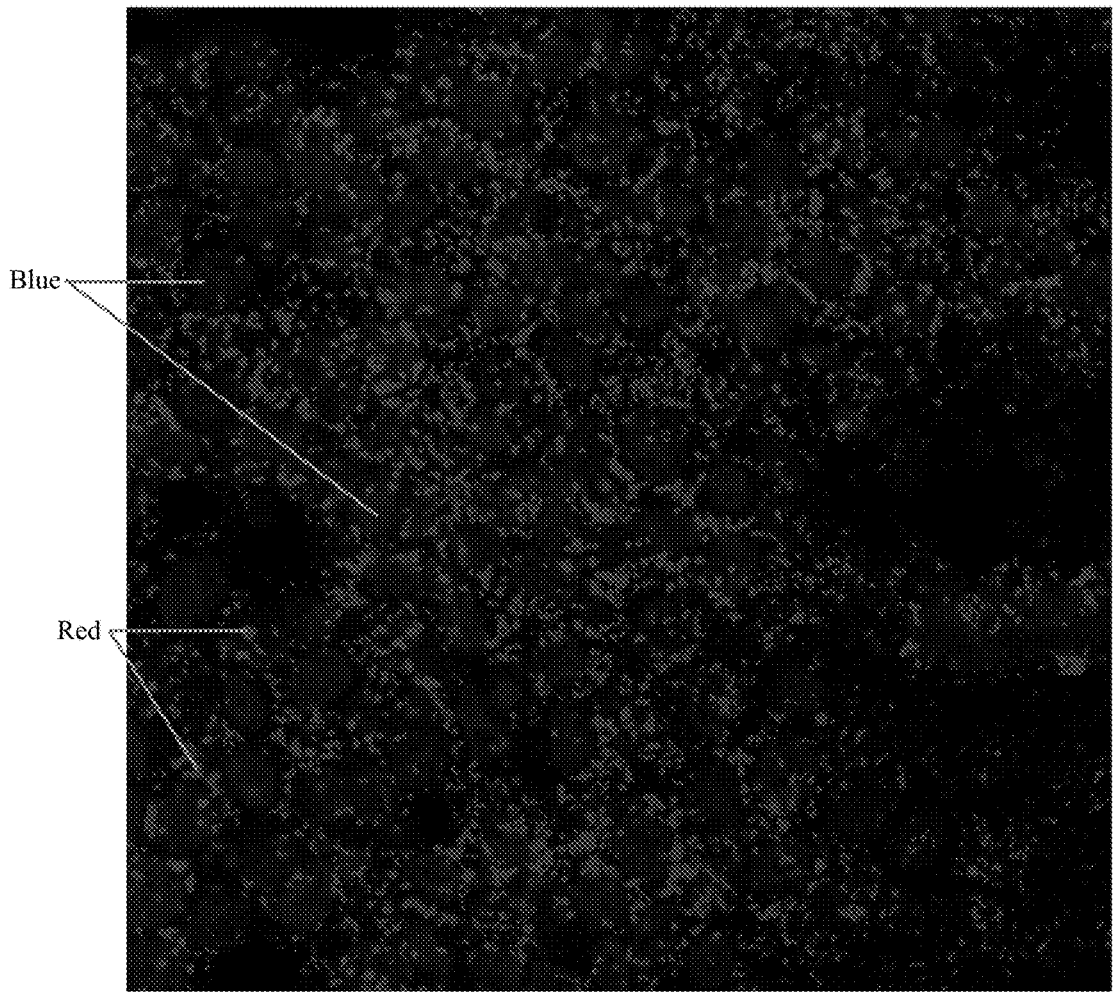
Figure 5B:
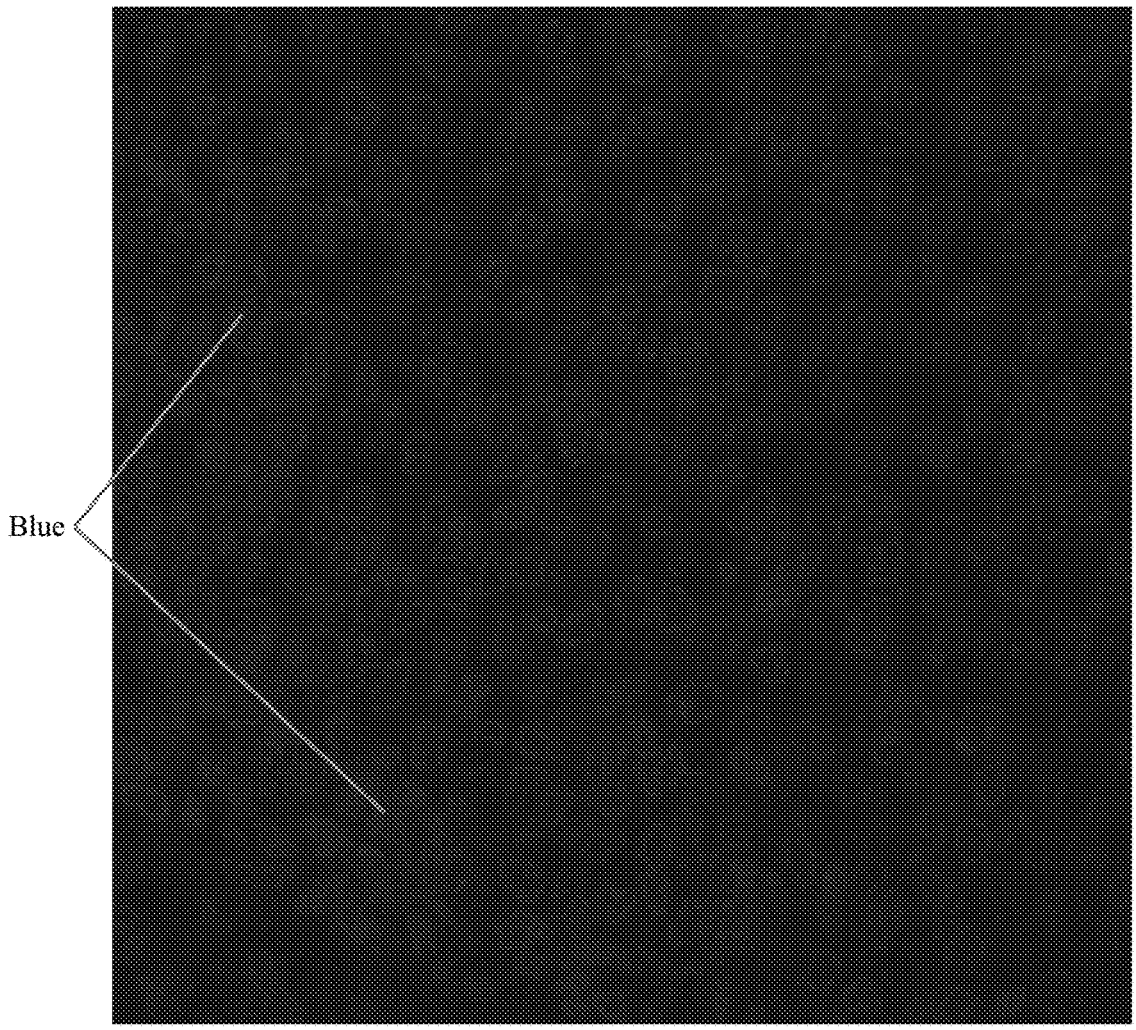

FIGS. 5A and 5B show results of EGFR-Grb2 PLA in lung cancer tumor tissues (in vivo). Formalin-fixed paraffin-embedded (FFPE) tumor tissue from a surgically resected adenocarcinoma of the lung was used for EGFR-Grb2 PLA. As a negative control, FFPE spleen tissue was chosen, as this tissue does not express EGFR protein. As shown in FIG. 5A, the lung adenocarcinoma has strong signal (red dots), compared to spleen that has no signal, shown in FIG. 5B. The blue signal is DAPI that stains for nuclei.

Figure 6A:
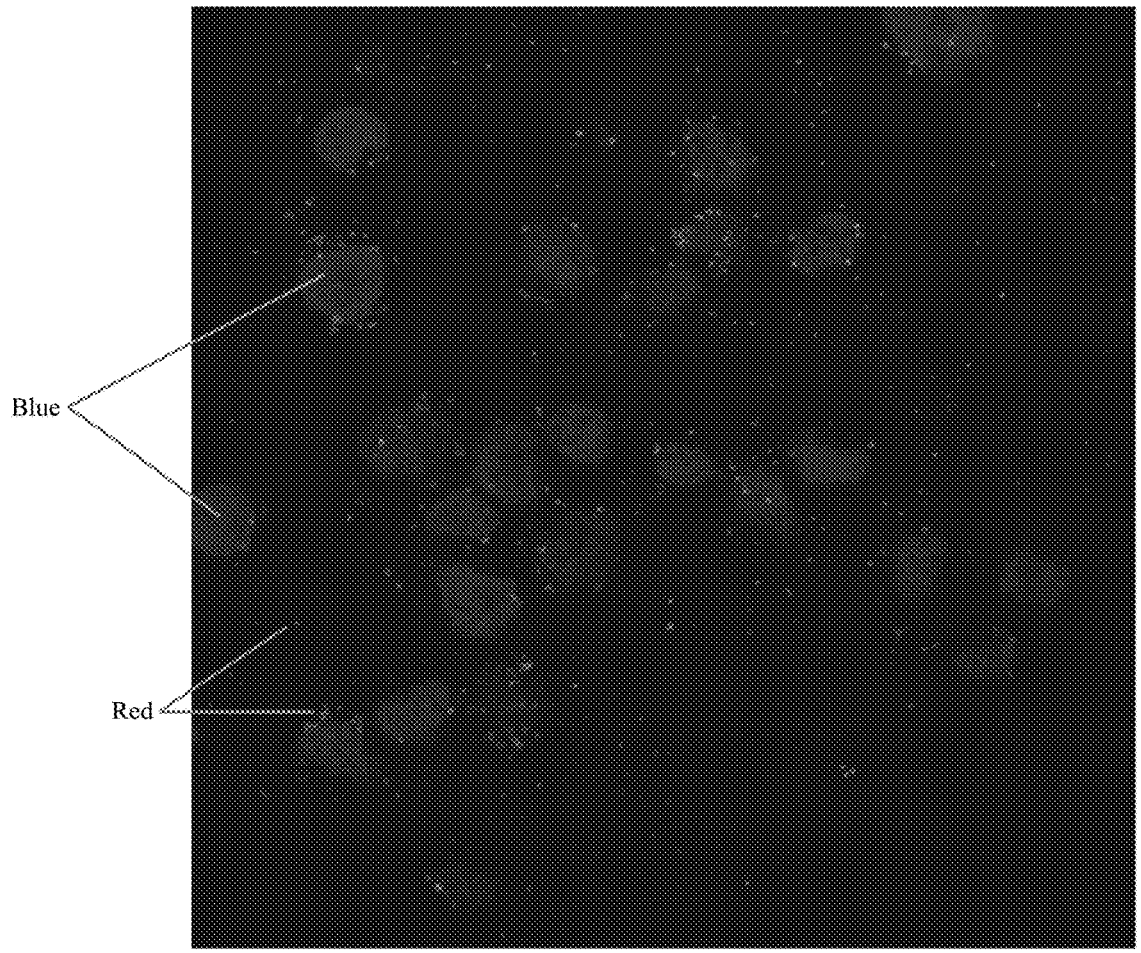
Figure 6B:
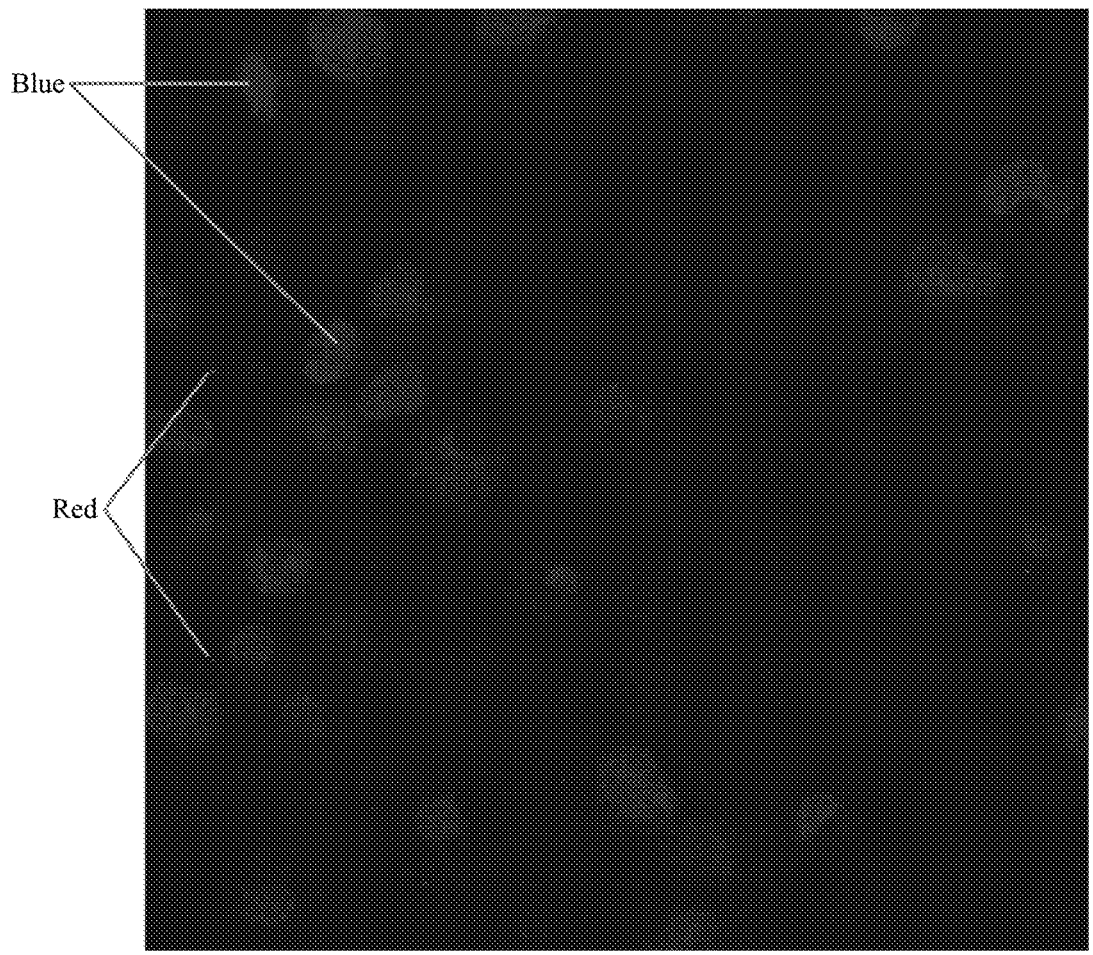

FIGS. 6A and 6B show results of ALK-Grb2 PLA in H3122 cells. PLAs have also been generated for detecting interactions between ALK and Grb2. H3122 cells harboring an ELM4-ALK gene fusion were examined using primary antibodies against the ALK receptor tyrosine kinase and Grb2. The negative control consisted of the same assay but leaving out the Grb2 antibody. In FIG. 6A, the small red foci are identified, indicative of ALK-Grb2 interactions, while no foci are observed in the negative contro (FIG. 6B). This indicates the PLAs can be generated to identify tumors driven by other receptor tyrosine kinases (beyond EGFR), including EML4-ALK transformed lung cancers.

Figure 7:
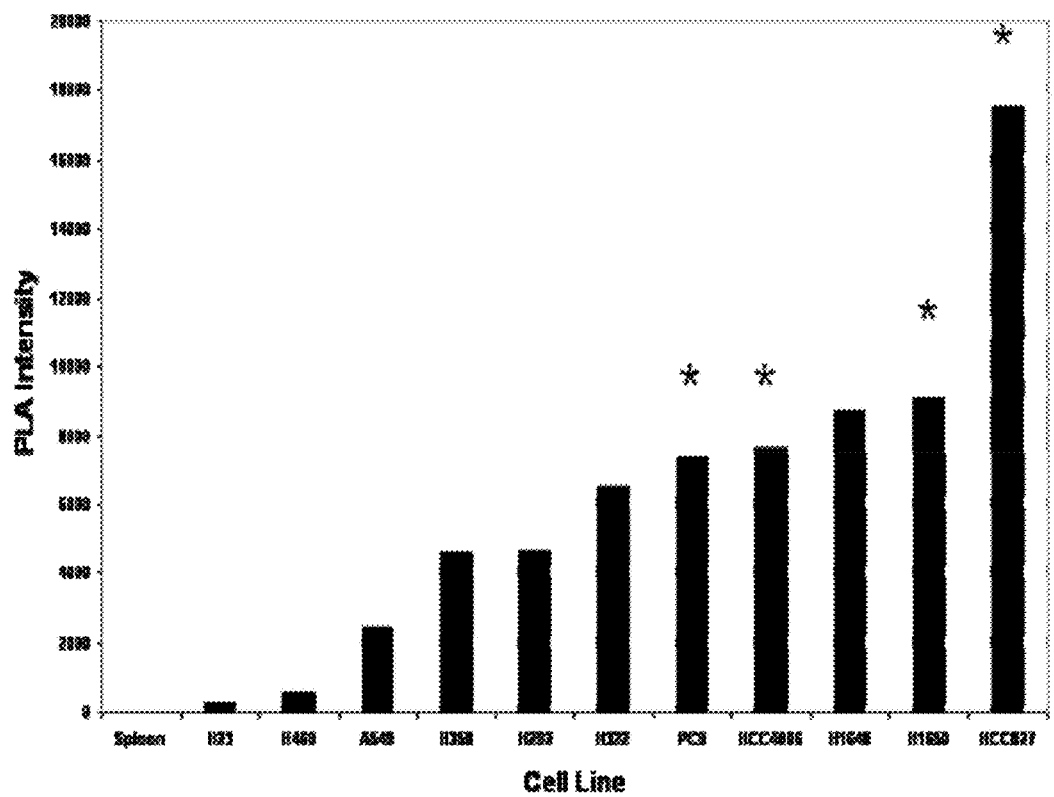

FIG. 7 shows results of examination of lung cancer cell lines and spleen tissue for EGFR:Grb2 PLA signals related to EGFR mutation status and drug sensitivity. This included cells harboring EGFR mutation (HCC827, PC9, H4006, H1650). All these cells had high levels of EGFR:Grb2 PLA signal. H1648, H322, H358, and H292 cells also demonstrated intermediate to higher levels of PLA signal; these cells have wildtype EGFR yet have some degree of sensitivity to EGFR TKI (erlotinib). Finally, A549, H23, and H460 cells are resistant to EGFR TKI (erlotinib) and have the weakest signals amongst the lung cancer cell lines studied. These data indicate that not only does EGFR:Grb2 PLA signal correspond to presence of EGFR mutation status but it also may correlate with or predict sensitivity to EGFR TKI.

Figure 8:
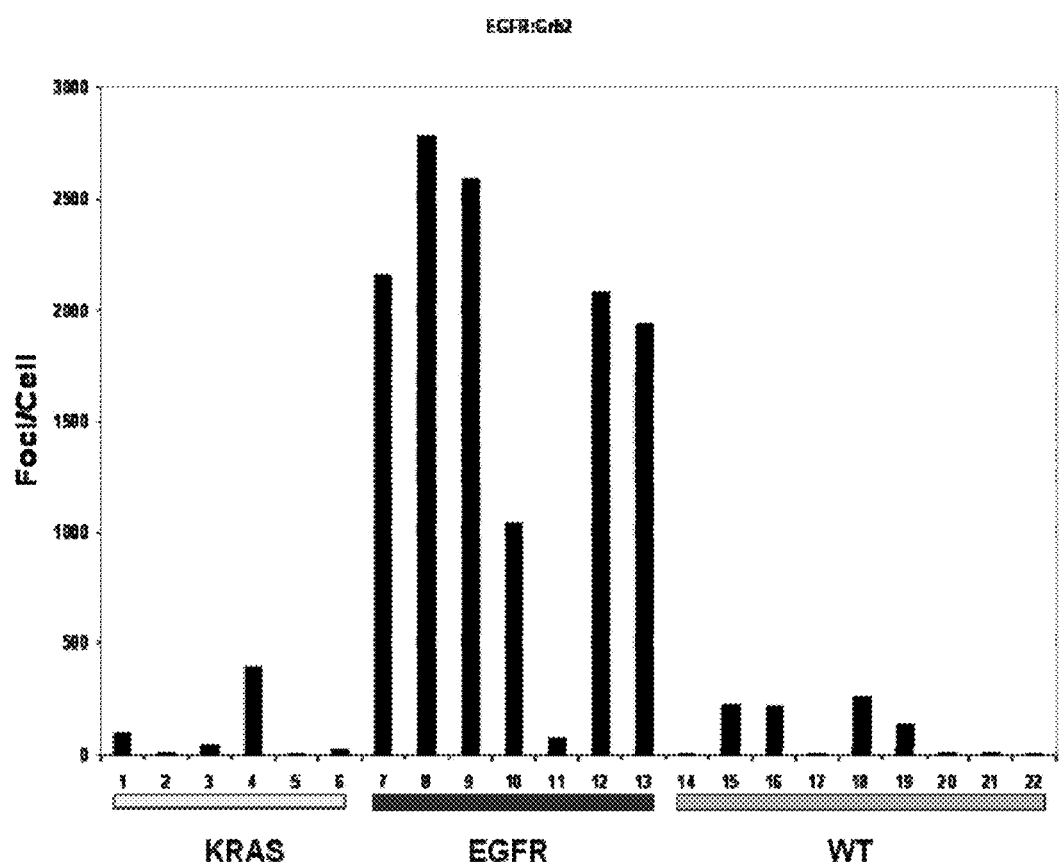

FIG. 8 shows results of PLA examination of a tissue microarray (TMA) that was produced from 21 FFPE lung cancer tumors, 14 without EGFR mutations and 7 with activating EGFR mutations. Included in this array was normal spleen tissue as a negative control. Tissues were examined using EGFR:Grb2 PLA. Of the 7 tumors with EGFR mutation, 6 had the strongest signals across the sample set. One tumor with EGFR mutation that lacked EGFR:Grb2 signal also has a corresponding PIK3CA mutation leading to enhanced PIK3CA activity. The 14 cases without EGFR mutation had lower degrees of signal compared to the 6 positive cases with EGFR mutation. Assuming a signal/noise cutoff of 10 (noise level=zero background of spleen tissue), 6 of the 14 cases had positive levels of EGFR:Grb2 PLA signal. This indicates a group of tumors lacking EGFR mutation that nonetheless may have EGFR pathway activation.

Figure 9A:
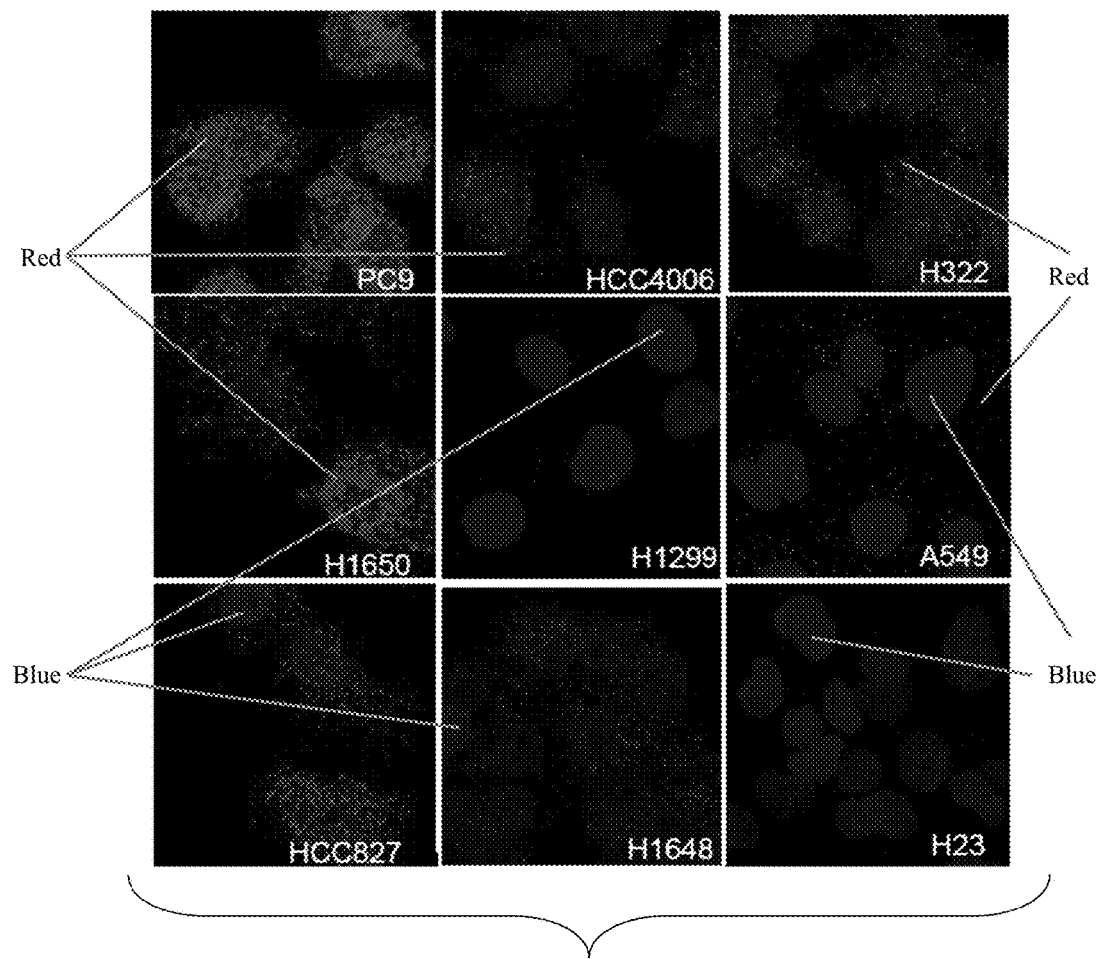
Figure 9B:
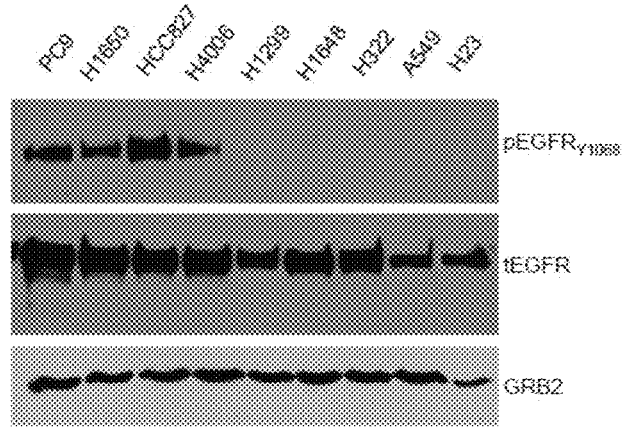

FIGS. 9A and 9B show results of PLA assays revealing that EGFR-GRB2 interactions are independent of expression and generally correlated with EGFR phosphorylation. PLA assays were performed across 9 non-small cell lung cancer (NSCLC) cell lines (PC9, H1650, HCC827, H4006, H1299, H1648, H322, A549, and H23) and analyzed by confocal microscopy at 400× magnification (FIG. 9A). Images represent maximum projections of 12×0.76 μm z-slices. Foci are imaged in the far-red spectrum (Cy5) and nuclei were imaged in the UV region with DAPI. Foci were detected in all EGFR mutant cell lines, while several cell lines (H1299 and H23) have nearly undetectable levels foci and serve as biological negative controls demonstrating the specificity of PLA. Intermediate levels of foci were detected in H322 and H1648, both of which exhibit some degree of erlotinib sensitivity. These results show that EGFR-GRB2 foci correlate with drug sensitivity. Immunoblot analysis of the 9 NSCLC cell lines (50 μg each) showed that all cells expressed detectable levels of both EGFR and GRB2, while phosphorylation of tyrosine 1068 of EGFR was detected only in EGFR mutant cell lines. These results demonstrate that the presence of the EGFR and GRB2 is necessary but not sufficient for interaction. The detection of signal (visible foci) in drug sensitivity further supports the use of PPI as a biomarker of drug sensitivity.

Figure 10:
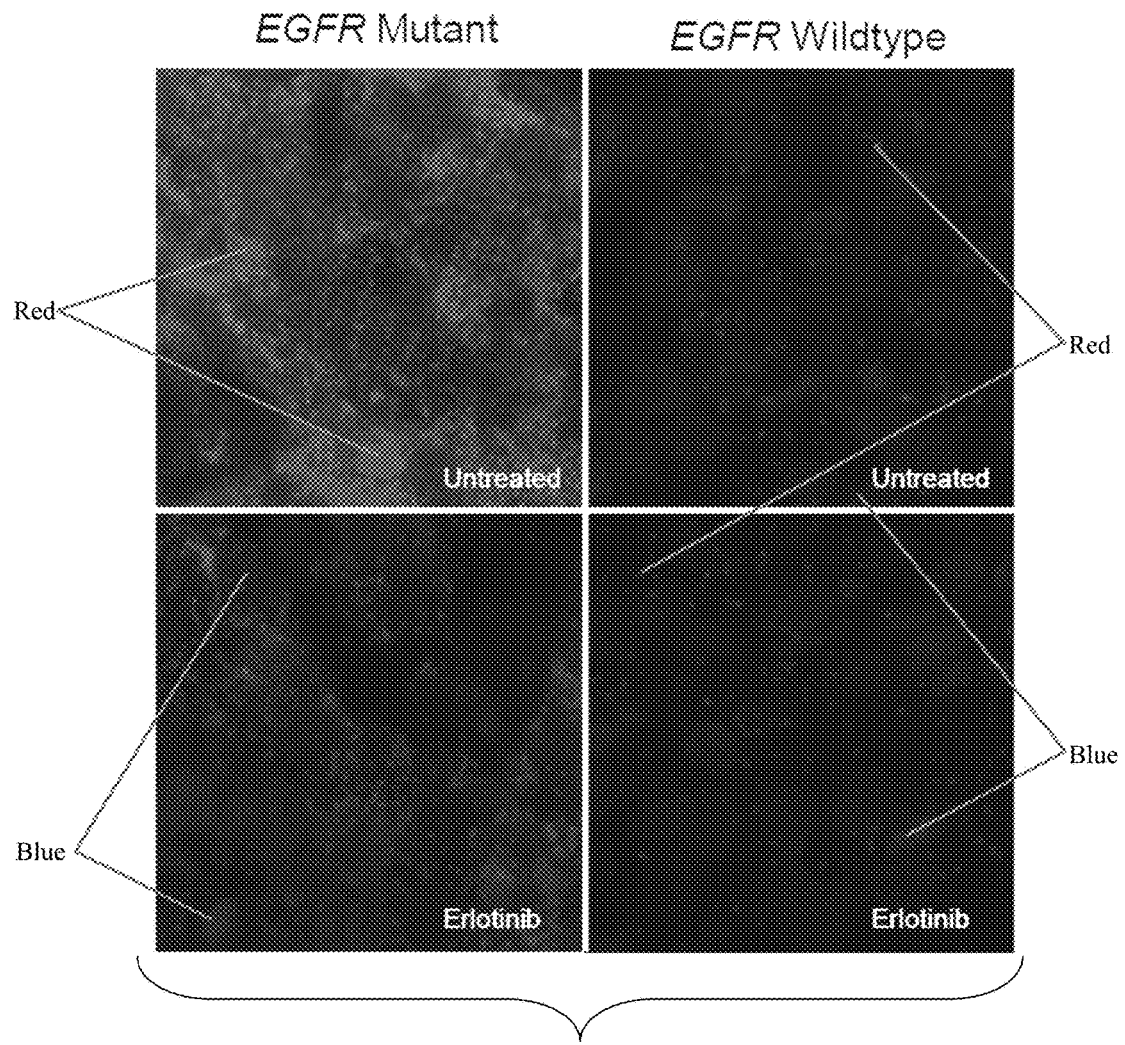

FIG. 10 shows PLA results revealing that EGFR-GRB2 interactions correlate with mutational status and are abrogated with TKI treatment in vivo. Patient-derived xenografts were grown in nude mice and treated with erlotinib for 28 days or with vehicle control. Slides were prepared from excised tumor tissue (verified by pathologist) and analyzed by PLA using 200× magnification. Foci are imaged in the far-red spectrum (Cy5) and nuclei were detected in the UV region with DAPI. Tumors derived from patients with an activating EGFR mutation had very high levels of EGFR-GRB2 detectable by PLA, while EGFR wildtype tumors had markedly lower levels. Importantly, PLA signal in the EGFR mutant tumors was considerably reduced after administration of erlotinib. These results indicate that mutation status is correlated with EGFR-GRB2 foci in vivo and that foci are correlated with erlotinib activity.

Figure 11:
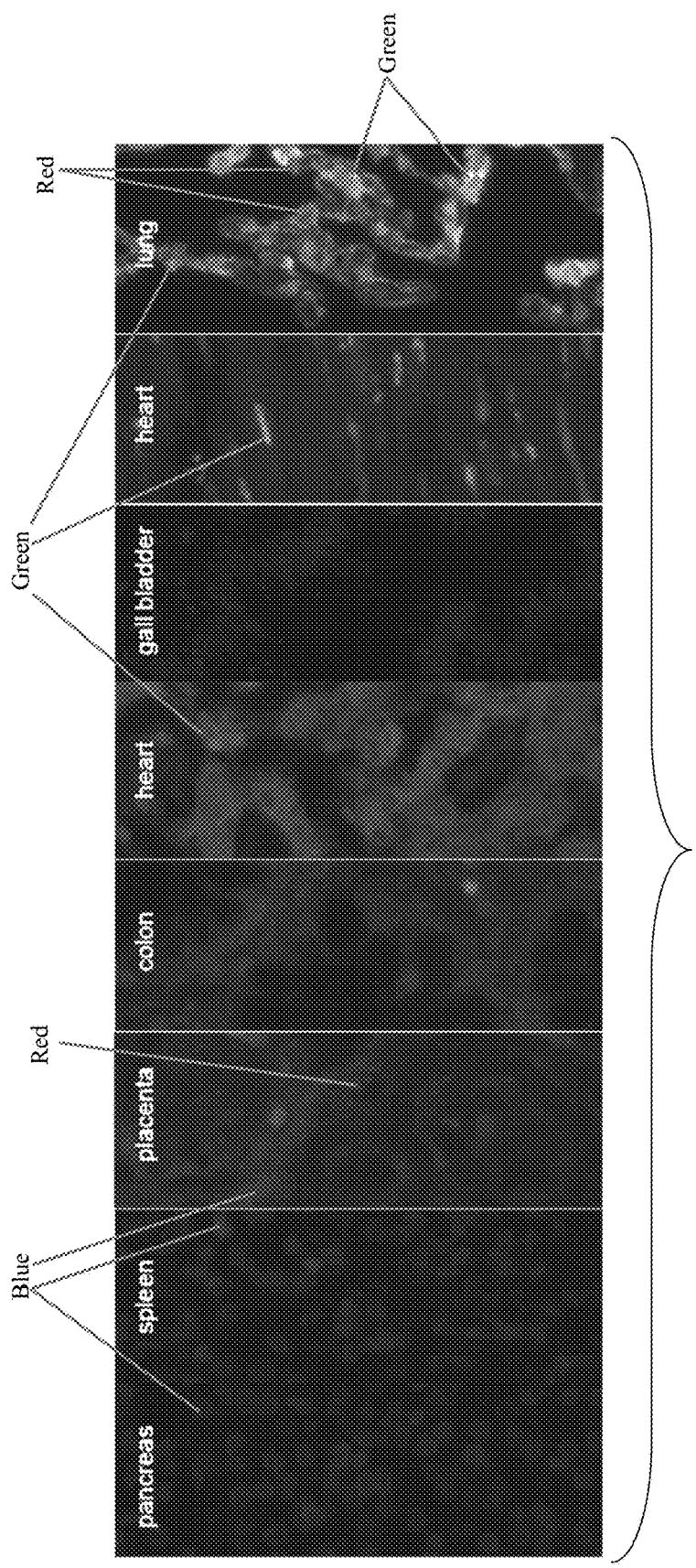

FIG. 11 shows PLA revealing that normal tissues have low to undetectable EGFR-GRB2 interactions. Eight normal tissues were assayed by PLA for EGFR-GRB2 and imaged concordantly with staining for the epithelial-origin marker cytokeratin using (Cy3). As expected, low levels of foci are found in the trophoblasts in placenta and epithelial cells of the gall bladder. Foci were not detected in pancreas, spleen, colon, heart and normal lung. Thus, EGFR-GRB2 interactions are detectable where EGFR is naturally expressed, but at low levels consistent with the growth-arrested state of most normal tissues.

Figures 1, 2, 12C:
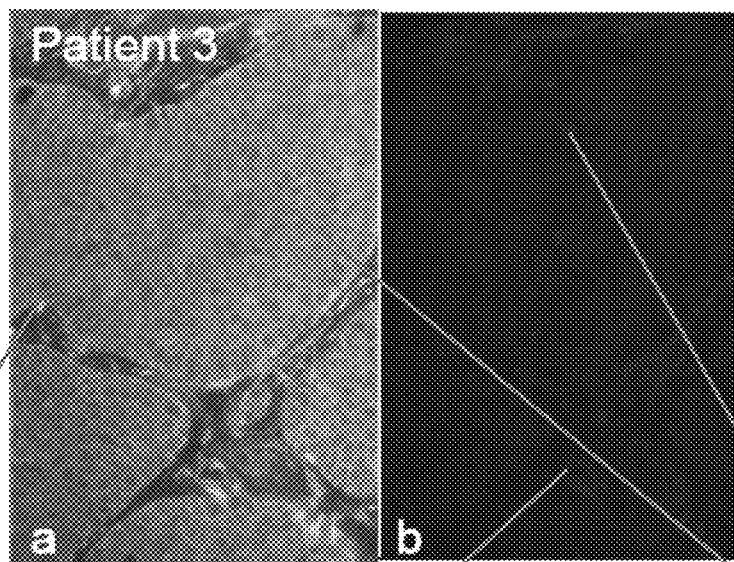
Figures 1, 2, 12D:
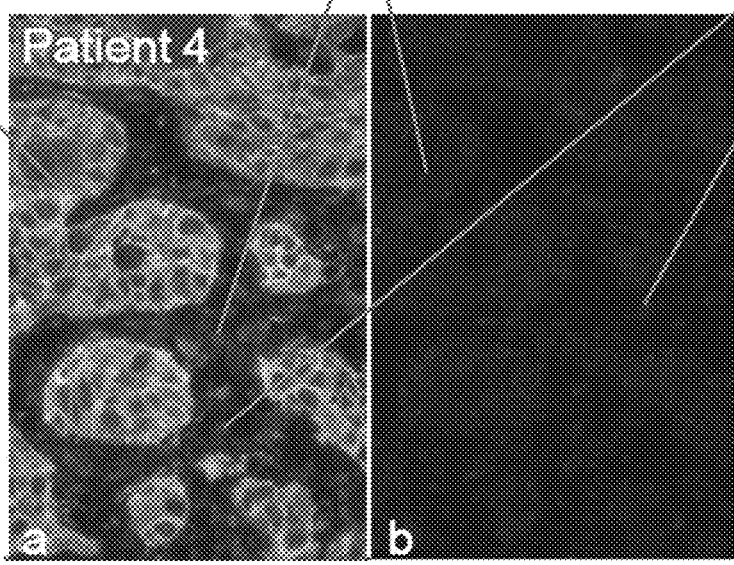

FIGS. 12A-1-12D-2 show PLA results revealing EGFR-GRB2 interactions in lung tumor tissues and co-localization with cytokeratin. Tissues were assayed by PLA in tumor microarray format and analyzed as in FIG. 11. Foci are readily detectable in patient 2 (FIGS. 12B-1 and 12B-2) and patient 4 (FIGS. 12D-1 and 12D-2), and absent in patient 1 (FIGS. 12A-1 and 12A-2) and patient 3 (FIGS. 12C-1 and 12C-2). Importantly, the foci observed in patients 2 and 4 are only found in cytokeratin-positive regions of the specimen, indicating the specificity of PLA in tissues. For each patient, the left panels (FIGS. 12A-1, 12B-1, 12C-1, and 12D-1) show nuclei as blue (DAPI), cytokeratin as green (Cy3) and PLA foci as red (Cy5). In each patient, the right panels (FIGS. 12A-2, 12B-2, 12C-2, and 12D-2) are the same images with the green channel removed for clarity. These results demonstrate that PLA signals are specific for epithelial-derived tissue and provide a tool to quantify signal only within the tumor.

Figures 13A, 13B:
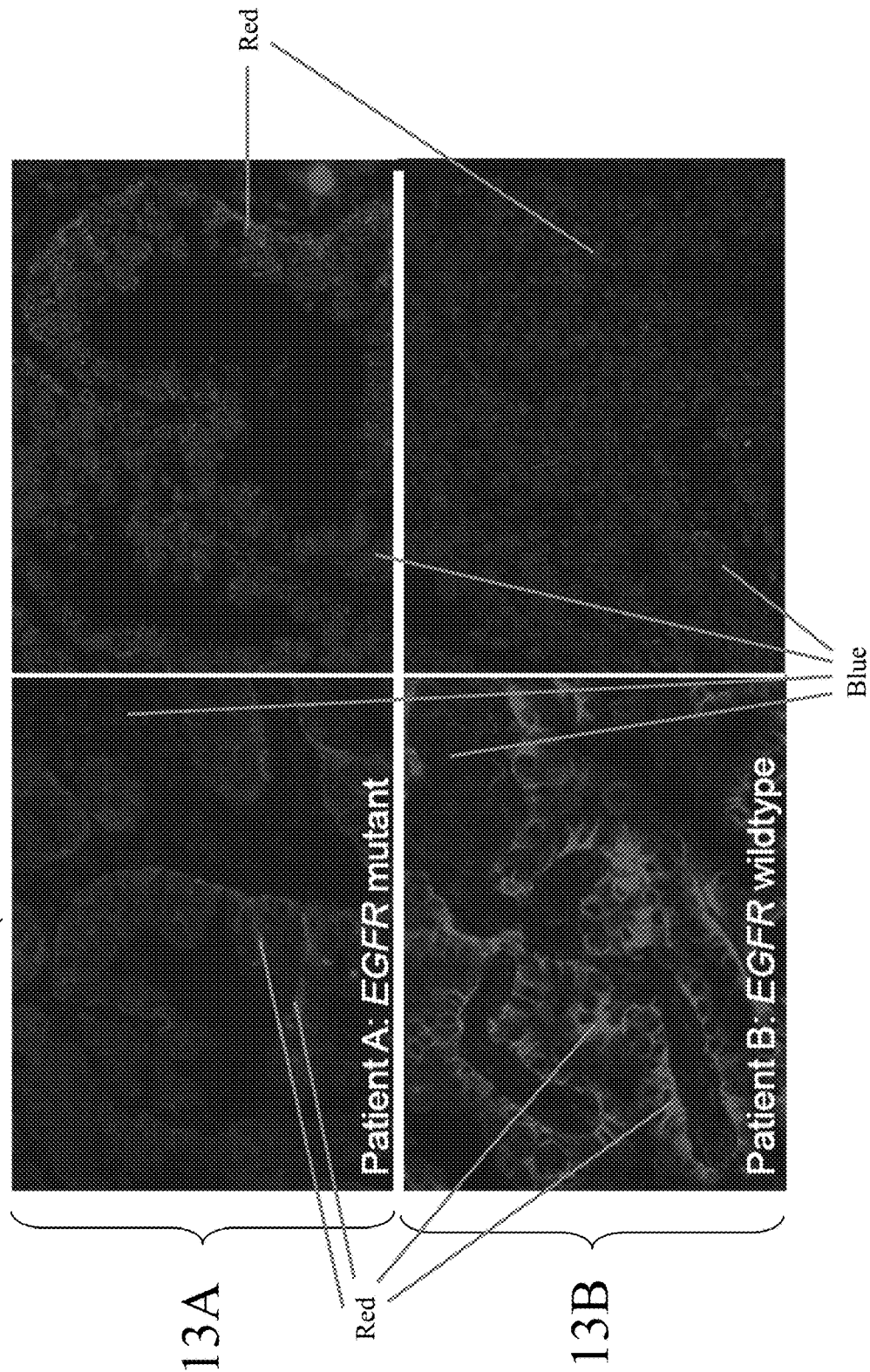

FIGS. 13A and 13B show EGFR-GRB2 PLA demonstrating that PPI are independent of expression levels in lung tumor tissue. PLA were performed and imaged as above on two patients, one harboring an activating mutation in EGFR (FIG. 13A) and the other with wildtype EGFR (FIG. 13B). Both patients express EGFR protein shown on the left, where Cy5-labelled secondary antibodies were used to image EGFR expression by immunofluorescence. Although patient B has higher levels of EGFR protein expression (FIG. 13B), the PLA signal is higher for patient A (FIG. 13A). These data suggest that PLA signal may be a powerful indicator of EGFR signaling activity.

Figure 14B:
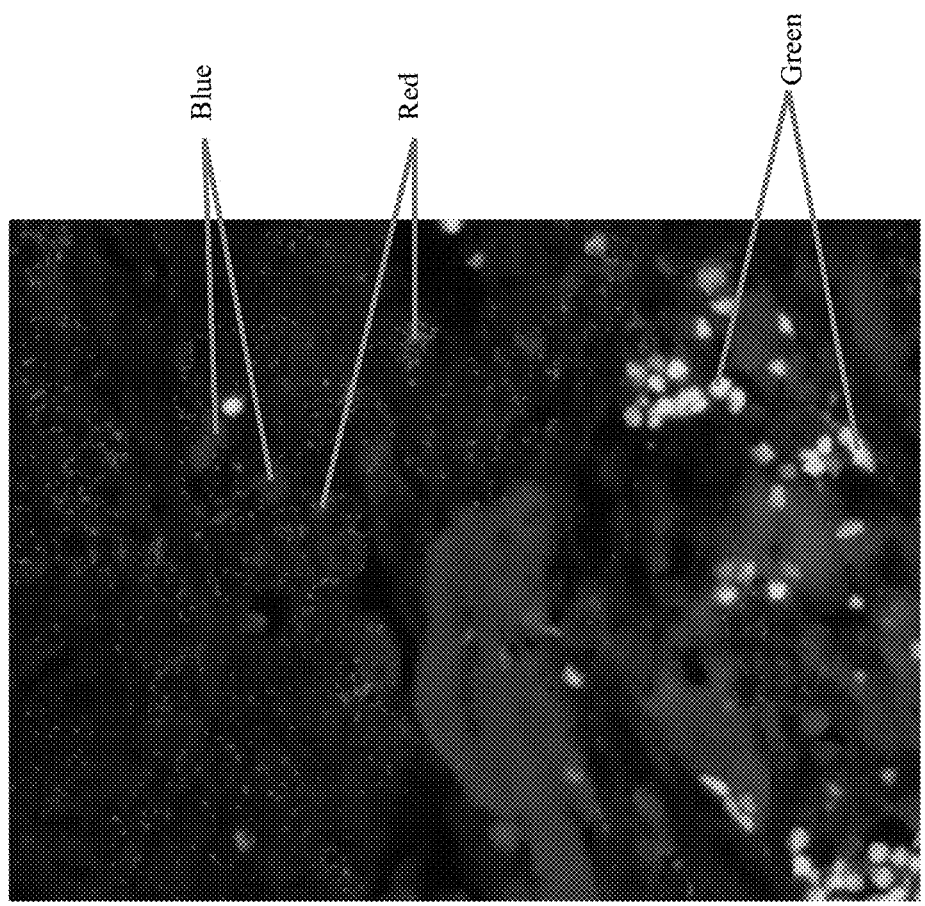
Figure 14A:
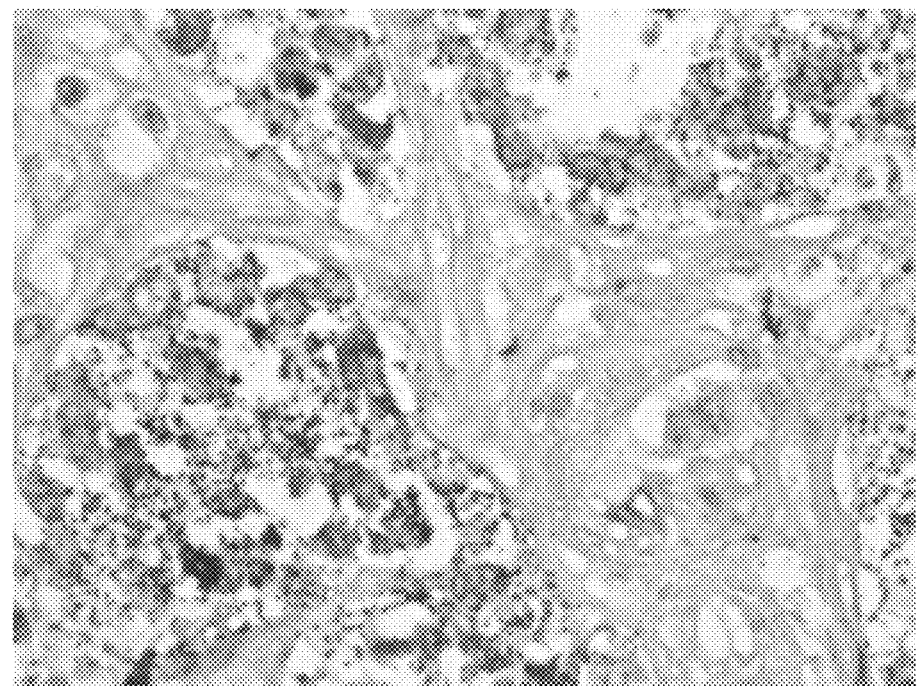

FIGS. 14A and 14B show PLA results demonstrating that PLA foci can be visualized with immuno-fluorescence or brightfield microscopy. PLA were performed on sequential tissue sections and processed at the the same time. FIG. 14A was processed using brightfield detection reagents (horseradish peroxidase-labeled oligonucleotides) and counterstained with hematoxylin. FIG. 14B was processed using immunofluorescence detection reagents (Cy5-labeled oligonucleotides) and nuclei stained with DAPI and tissue autofluorescence imaged on the FITC channel. Images were obtained at 400× magnification on brightfield or immuno-fluorescent platforms, respectively. Similar results were obtained with both methods of detection, indicating that PLA can be performed using only light microscopy.

Figure 15A:
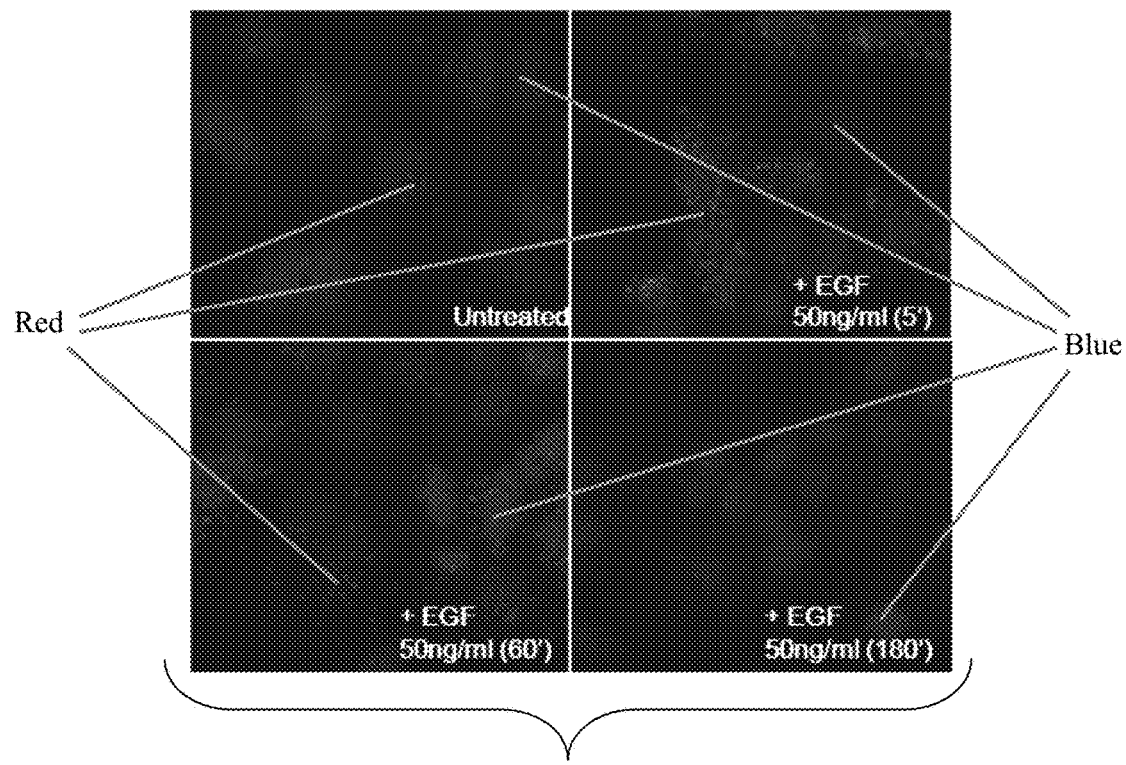
Figures 1, 15A:
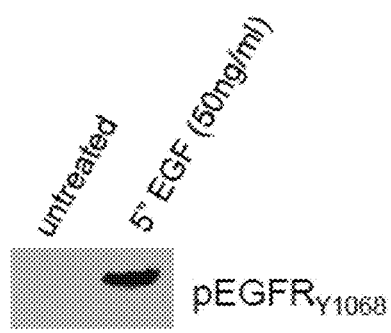

FIGS. 15A-15C show PLA results demonstrating that PLA can be used to monitor phosphorylation status. PLA were performed in three cell lines to assess phosphorylation dynamics as phosphorylation of RTKs is required for binding of downstream effectors. A549 cells were stimulated with 50 ng/ml EGF for various timepoints and phosphorylation of EGFR was monitored by PLA using a single antibody to phosphor-EGFR$_{Y1068}$ (FIG. 15A). Unstimulated A549 cells have low levels of EGFR phosphorylation, which quickly increases before diminishing. PC9 cells were treated for 3 hours with erlotinib and assayed as above (FIG. 15B). 3 hours of erlotinib treatment abolishes the phosphorylation of EGFR. For FIGS. 15A and 15B, immunoblots confirmed the changes in phosphorylation status (FIGS. 15A-1 and 15B-1, respectively). H3122 cells were assayed by PLA using an antibody to ALK and total phosphotyrosine to monitor the change in phosphorylation of ALK in response to crizotinib (FIG. 15C). 3 hours of crizotinib treatment abolishes the phosphorylation of ALK. Importantly, these assays demonstrate that phosphorylation dynamics can be monitored by PLA and that using an RTK antibody paired with a "pan" phosphotyrosine is a viable approach.

Figure 16A:
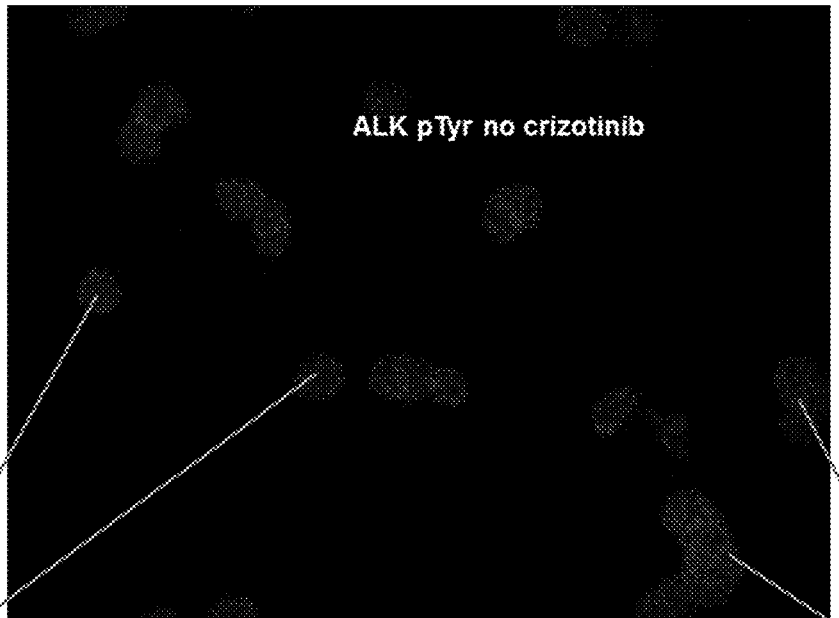
Figure 16B:
Figure 16C:
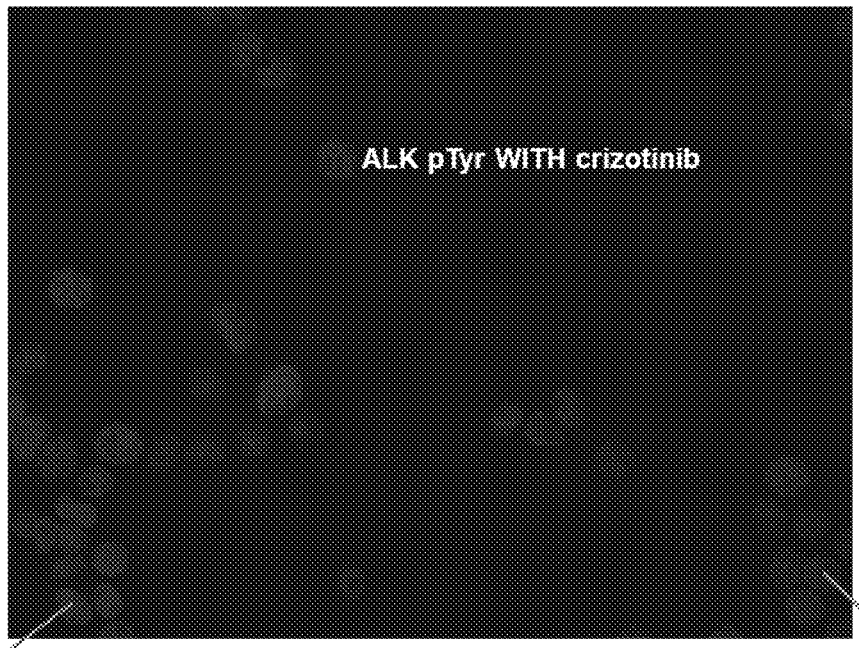
Figure 16D:

FIGS. 16A-16D show results of ALK-Shc1 PLA in EML4-ALK rearranged lung cancer cells. FIGS. 16B and 16D show interaction foci between ALK and Shc1 in EML4-ALK rearranged lung cancer cells that disappear with ALK TKI (crizotinib therapy). FIGS. 16A and 16C show pTyr ALK.

Figure 17:
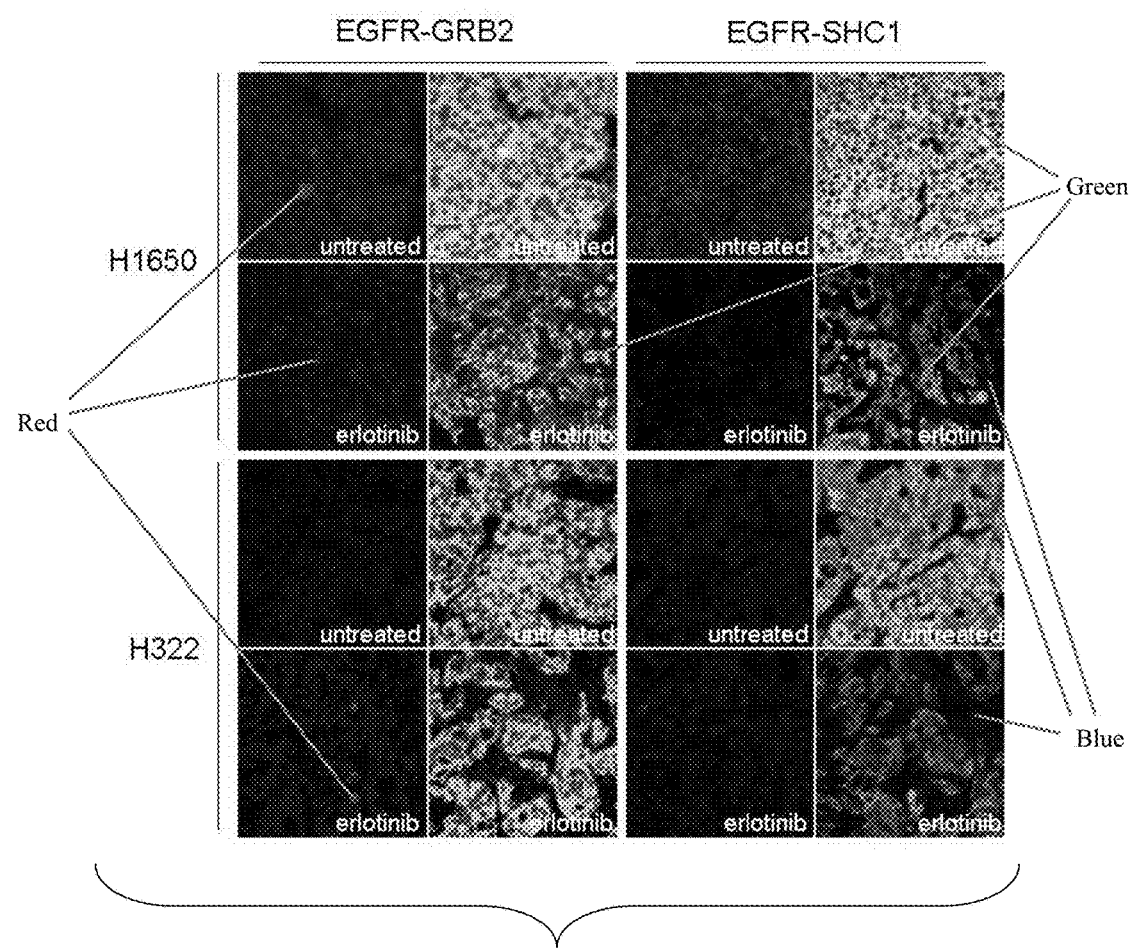

FIG. 17 shows PLA results demonstrating that PLA facilitate the observation of pharmacodynamic effects of kinase inhibitors on signaling networks. Tumor xenografts were established in mice with either H1650 (EGFR mutant) or H322 (EGFR wildtype), treated with or without erlotinib and allowed to grow for 18 days. Formalin-fixed, paraffin-embedded tumor tissue was analyzed by PLA for the interaction of EGFR-GRB2 (left) and EGFR-SHC1 (right). Nuclei are shown in blue, PLA signal is red and cytokeratin is green. For clarity, identical images are shown with and without cytokeratin staining for each tumor. H1650 cells exhibit high levels of EGFR-GRB2 and considerably higher levels of EGFR-Shc1, consistent with the presence of an activating EGFR mutation. H322 cells have lower levels of EGFR interactions, but still show a reduction upon TKI treatment. These data indicate that PLA signal is markedly reduced upon TKI treatment, specifically within the tumor tissues and can be used to evaluate target-specific drug efficacy in vivo.

DETAILED DISCLOSURE OF THE INVENTION

Proximity ligation assay (PLA)-based biomarkers could be an important future direction in personalized medicine. They could be useful for cancer prognosis as well as decision making regarding targeted therapy. The present invention includes assays for protein-protein interactions (PPI) that can be used to determine, for example, when an activated receptor tyrosine protein kinase binds a signal transduction molecule such as GRB2. This assay uses PLAs to quantitatively measure PPI in tissue and cell samples such as that prepared for microscopy. The PLA typically involves primary and secondary antibodies binding two separate proteins in a sample; short nucleic acid strands are attached to the secondary antibodies which are ligated into circles and then amplified and labeled, e.g., with fluorescent probes. The inventors have established in cell lines that EGFR-GRB2 PPIs distinguish populations of lung cancer cells, are independent of EGFR expression level and generally correlate with EGFR phosphorylation. The assay has also been shown to work in FFPE patient tissue samples. The assay can be used to determine if a patient's receptor tyrosine kinase pathway is activated and, therefore, may be a good candidate for intervention with a tyrosine kinase inhibitor.

The assays of the invention represent a platform technology expandable to a larger spectrum of tyrosine kinases and possible signal transduction docking proteins. The assays may be used as a surrogate for tyrosine phosphorylation status, as tyrosine phosphorylation is not easily discerned in FFPE slides without the slides being prepared in a special manner. The assays of the invention can read out pathway activation resulting from mutation, gene amplification, or autocrine factors. Moreover, not all tyrosine kinases have phosphorylation specific antibodies, and it may be easier to make antibodies to the overall tyrosine kinase protein and its adaptor proteins. Given the market of tyrosine kinase inhibitors, both approved and in development, this technology can provide a number of potential biomarker strategies including diagnostics for drug response or companion diagnostics.

One aspect of the invention concerns a method for assessing the sensitivity of a malignancy to a treatment based on PPI. The method for assessing the sensitivity of a malignancy to a treatment comprises comparing a protein-protein interaction (PPI) profile obtained from a sample of the malignancy to a reference PPI profile. The sample PPI profile represents the abundance of target binding partners that are in proximity to each other within the sample. A negative result (lack of PPI) in a sample would indicate a lack of sensitivity to the PPI modulator and be useful clinically to avoid giving patients unnecessary PPI modulator therapy. A positive result (presence of PPI) would indicate that the malignancy is potentially sensitive to the PPI modulator and allow the clinician to give the PPI modulator therapy to those patients who would be most likely to benefit. As a specific example, the method may be used for determining whether there is no EGF signaling in a sample such as spleen tissue, and this kind of a negative result can be useful clinically to avoid giving patients unnecessary EGF receptor inhibitor therapy, or alternatively be used to give the therapy to those patients who would be most likely to benefit.

PPI profiles (e.g., sample PPI profile, and reference PPI profile) may each be expressed as a value representative of the abundance of target binding partners in proximity to each other within the sample. The sample PPI profile and reference PPI profile may be expressed by any method useful for comparison purposes, such as a numeric value, score, cutoff (threshold), or other expression. For example, a negative result in which a PPI profile in a sample does not reach the cutoff would be useful clinically to avoid giving patients unnecessary PPI modulator therapy. A positive result in which a PPI profile in a sample is at or above the cutoff would indicate potential sensitivity and allow the clinician to give the PPI modulator therapy to those patients who would be most likely to benefit.

In some embodiments of the methods and kits of the invention, the target PPI is that of a known cancer signaling network. Binding members of a target PPI may include protein products of oncogenes or tumor suppressor genes, for example. In some embodiments, the sample PPI profile represents the abundance of target binding partners that are in proximity to each other within the sample, wherein at least one of the target binding partners is selected from among EGFR, ALK, MET, IGFR, Src, ErbB3, Mig6, Grb2, Sts1, p85, and Hsp90.

In some embodiments of the methods and kits of the invention, the target binding partners are selected from among EGFR and ErbB3; EGFR and Grb2; EGFR and Mig6; EGFR and Sts1, EGFR and Src; EGFR and Hsp90; ErbB3 and p85; ALK and EML4; MET and Gab1; IGFR and IRS; Hsp90 and Cdc37; ALK and Shc1; and EGFR and Shc1.

In some embodiments of the methods and kits of the invention, the PPI comprises a tyrosine kinase, such as the human tyrosine kinases listed in Tables 3 and 4. In some embodiments, the PPI comprises an interaction between the binding partners listed in Table 5 (human tyrosine kinase interactions).

PLAs can be used to generate biomarkers against receptor tyrosine kinases (RTKs). RTKs are important proteins in cancer and highly "druggable" targets. Approximately twenty different RTK classes have been identified thus far. In some embodiments of the methods and kits of the invention, at least one of the target binding partners is an RTK. In some embodiments of the methods and kits of the invention, at least one of the target binding partners is of an RTK class selected from among RTK class I (EGF receptor family; ErbB family), RTK class II (insulin receptor family), RTK class III (PDGF receptor family), RTK class IV (FGF receptor family) RTK class V (VEGF receptors family), RTK class VI (HGF receptor family), RTK class VII (Trk receptor family), RTK class VIII (Eph receptor family), RTK class IX (AXL receptor family), RTK class X (LTK receptor family), RTK class XI (TIE receptor family), RTK class XII (ROR receptor family), XIII (DDR receptor family), RTK class XIV (RET receptor family), RTK class XV (KLG receptor family), RTK class XVI (RYK receptor family), and RTK class XVII (MuSK receptor family).

In some embodiments of the methods and kits of the invention, one or more of the binding partners of the target PPI have one or more sequence mutations that are known to be associated with occurrence of the malignancy. In other embodiments, the binding partners of the target PPI do not harbor (lack) any sequence mutations known to be associated with occurrence of the malignancy, or with sensitivity to a treatment such as a PPI modulator. In some embodiments, the binding partners of the target PPI and the downstream effectors of the target PPI do not harbor any sequence mutations known to be associated with occurrence of the malignancy, or with sensitivity to a treatment such as a PPI modulator. Such sequence aberrations in a subject or in a sample can be detected using methods known in the art (e.g., mutation analysis). Typically, abnormalities in nucleic acid sequences are identified by comparison to reference sequence data (sequences of normal cells or cancer cells) on databases, such as GenBank and EMBL, and specific data resources such as Cancer Gene Census (mutated genes causally implicated in human cancer), COSMIC (Catalogue of Somatic Mutations in Cancer), and CGP Resequencing Studies (somatic mutations from large scale resequencing of genes in human cancer). Mutations causing or contributing to cancer may be large-scale mutations, involving the deletion or addition of a portion of a chromosome, or small-scale mutations, including point mutations, deletions, insertions, which may occur in the promoter region of a gene and affect its expression, may occur in the coding sequence and alter the stability or function of the gene's protein product.

The sample may be any cell sample potentially harboring the target protein(s). For example, a cytology sample may be obtained from a tissue selected from breast, ovaries, esophagus, stomach, colon, rectum, anus, bile duct, brain, endometrium, lung, liver, skin, prostate, kidney, nasopharynx, pancreas, head and neck, kidney, lymphoma, leukemia, cervix, and bladder. The sample may be a solid or non-solid tumor specimen. The tumor specimen may be a carcinoma. The sample may be a new cancer, recurrent cancer, primary cancer, or metastasized (secondary) cancer.

The sample may be obtained by methods known in the art, such as surgery, biopsy, or from blood (e.g., circulating tumor cells), ascites, or pleural effusion. The sample may be processed using methods known in the art. For example, the sample may be fresh, frozen, or formalin-fixed and paraffin-embedded (FFPE).

Preferably, the treatment against which the sample is being assessed for sensitivity/resistance is a PPI modulator (i.e., a PPI inhibitor or PPI inducer). However, the treatment may be a treatment other than a PPI modulator.

Another aspect of the invention concerns a method for treating a malignancy in a subject, comprising administering a protein-protein interaction (PPI) modulator to the subject, wherein the subject is predetermined to be sensitive to the PPI modulator based on a PPI profile obtained from a sample of the malignancy. In some embodiments, the PPI modulator is an inhibitor of the PPI of the PPI profile (i.e., a PPI inhibitor). In some embodiments, the PPI modulator is an inducer of the PPI of the PPI profile (i.e., a PPI inducer).

Another aspect of the invention concerns a method for treating a malignancy in a subject, comprising:

(a) assessing the sensitivity of a malignancy in the subject, comprising comparing a protein-protein interaction (PPI) profile obtained from a sample of the malignancy to a reference PPI profile; and (b) administering a PPI modulator to the subject if the malignancy is assessed to be sensitive to the PPI modulator; and withholding the PPI modulator from the subject if the malignancy is assessed to be resistant to the PPI modulator. In some embodiments, the PPI modulator is an inhibitor of the PPI of the PPI profile (i.e., a PPI inhibitor). In some embodiments, the PPI modulator is an inducer of the PPI of the PPI profile (i.e., a PPI inducer).

The invention includes also includes kits useful for carrying out methods of the invention, (e.g., methods for the classification of cancers as sensitive or resistant to treatments based on protein-protein interactions, treatment of cancer, identification of biomarkers, identification of protein-protein interaction modulators, and selection of cancer treatments). Thus, one aspect of the invention concerns a kit for detecting the proximity of target binding partners within a cancer protein-protein interaction network, comprising a primary antibody to at least one of the target binding partners, and a proximity probe comprising a secondary antibody (that binds to the primary antibody) with an oligonucleotide conjugated thereto. In preferred embodiments, the kit comprises:

a first primary antibody to a first target binding partner;

a second primary antibody to a second target binding partner;

a first proximity probe comprising a first secondary antibody (that binds to the first primary antibody) with an oligonucleotide conjugated thereto; and a second proximity probe comprising a second secondary antibody (that binds to the second primary antibody) with an oligonucleotide conjugated thereto, wherein when the oligonucleotides of the first and second proximity probes are in sufficient proximity to each other, the oligonucleotides of the proximity probes interact in the presence circle-forming oligonucleotides by enzymatic ligation and form a circular product that is amplified by rolling circle replication, producing an amplification product. Optionally, the kit further comprises a labeled oligonucleotide probe that hybridizes with the amplification product, allowing detection and quantification of the amplification product (representing the association (close proximity) of the target binding partners).

Another aspect of the invention concerns a kit for detecting the proximity of target binding partners within tertiary PPI (a complex having three or more protein binding partners), referred to herein as the "tertiary interaction kit". The target PPI may be within a cancer signaling network, but is not limited to such applications. The tertiary interaction kit can be used to study viruses, for example, in which a viral protein forms an interaction with protein A and protein B in a cell, giving rise to a tertiary complex. Identification of this tertiary PPI may be diagnostic of an active infection or yield important information about the prognosis or predict the correct therapy. In cancer, a tertiary complex may provide important information about the therapeutic efficacy.

The tertiary interaction kit comprises:

a first primary antibody to a first target binding partner of the tertiary interaction;

a second primary antibody to a second target binding partner of the tertiary interaction;

a third primary antibody to a third target binding partner of the tertiary interaction;

a first proximity probe comprising a first secondary antibody (that binds to the first primary antibody) with an oligonucleotide conjugated thereto; and a second proximity probe comprising a second secondary antibody (that binds to the second primary antibody) with an oligonucleotide conjugated thereto;

a third proximity probe comprising a third secondary antibody (that binds to the third primary antibody) with an oligonucleotide conjugated thereto;

wherein when the oligonucleotides of the first and second proximity probes are in sufficient proximity to each other, the oligonucleotides of the first and second proximity probes interact in the presence circle-forming oligonucleotides by enzymatic ligation and form a circular product that is amplified by rolling circle replication, producing a first amplification product; and wherein when the oligonucleotides of the second and third proximity probes are in sufficient proximity to each other, the oligonucleotides of the second and third proximity probes interact in the presence of circle-forming oligonucleotides by enzymatic ligation and form a circular product that is amplified by rolling circle replication, producing a second amplification product. Optionally, the kit detecting proximity of binding partners within a tertiary PPI further comprises a first labeled oligonucleotide probe that hybridizes with the first amplification product, allowing detection and quantification of the first amplification product (representing the association (close proximity) of the first and second target binding partners), and a second labeled oligonucleotide probe that hybridizes with the second amplification product, allowing detection and quantification of the second amplification product (representing the association of the second and third target binding partners). Each primary antibody is of a different species (e.g., mouse, rabbit, and goat, for example). Preferably, the label of the first labeled oligonucleotide yields a signal (e.g., a color) that is distinguishable from that of the second labeled oligonucleotide (red and green, for example). An additional primary antibody, proximity probe, and (optionally) oligonucleotide probe can be included in the kit for each additional target binding partner within the tertiary PPI to be measured. Optionally, images can be constructed for visualization showing each signal with overlay (e.g., red and green overlay).

In the various kits of the invention, each kit can include instructions or packaging materials that describe how to use a compound or composition (e.g., a reagent such as a primary antibody, a secondary antibody, a labeled oligonucleotide probe that hybridizes with the amplification product) of the kit. Within the kit, the secondary antibody may be uncojugated or conjugated to an oligonucleotide (making the secondary antibody a proximity probe). The kits may also comprise, e.g., polymerase (for the amplification reaction), ligase (for the ligation reaction), a buffering agent, a preservative, or a protein stabilizing agent. The kits may also comprise components necessary for detecting the label (e.g., an enzyme or substrate). The kit may also contain a control sample or a series of control samples that can be assayed and compared to a test sample. Each kit can include one or more containers for individually enclosing each component of the kit. Containers of the kits can be of any suitable material, e.g., glass, plastic, metal, etc., and of any suitable size, shape, or configuration. The one or more containers are can be enclosed within outer packaging.

The kits of the invention may be used by contacting the cell-containing sample with the primary antibodies (allowing the primary antibodies to bind to their respective protein targets), contacting the sample with the proximity probes (allowing the proximity probes to bind to their respective antibody targets), allowing the nucleic acid strands (also referred to as arms) of the proximity probes to ligate if binding in close proximity (adding ligase if necessary), amplifying the ligation product (adding polymerase if necessary) to produce an amplification product, and measuring the amplification product corresponding to the interaction of each pair of protein targets within the PPI. Measurement of the amplification product can be made using methods known in the art for detecting and quantifying nucleic acid amplification products, e.g., by adding a labeled oligonucleotide that hybridizes to a sequence of the amplification product, and analyzing the sample by visualizing the amplification product (as represented by the label signal) with an appropriate visualization device, such as a confocal or fluorescence microscope.

Another aspect of the invention concerns a method for measuring protein-protein interactions having three or more binding partners (a tertiary interaction) in a sample, comprising:

contacting the sample with three or more primary antibodies to three or more corresponding target binding partners within a target tertiary interaction;

contacting the sample with three or more proximity probes (first, second, and third proximity probes) comprising a secondary antibody that binds to the corresponding first antibody, wherein each proximity probe has an oligonucleotide conjugated thereto;

wherein when the oligonucleotides of the first and second proximity probes are in sufficient proximity to each other, the oligonucleotides of the first and second proximity probes interact in the presence circle-forming oligonucleotides by enzymatic ligation and form a circular product that is amplified by rolling circle replication, producing a first amplification product; and wherein when the oligonucleotides of the second and third proximity probes are in sufficient proximity to each other, the oligonucleotides of the second and third proximity probes interact in the presence of circle-forming oligonucleotides by enzymatic ligation and form a circular product that is amplified by rolling circle replication, producing a second amplification product; and measuring the first and second amplification products.

In some embodiments, measurement of the first and second amplification products comprises contacting the sample with two or more labeled oligonucleotides, comprising a first labeled oligonucleotide that hybridizes to a sequence of the first amplification product, and a second labeled oligonucleotide that hybridizes to a sequence of the second amplification product, to produce labeled amplification products, wherein the labels are distinguishable from one another; and measuring the PPIs by visualizing the labeled amplification products. An additional primary antibody, proximity probe, and labeled oligonucleotide can be used for each additional target binding partner within the tertiary PPI.

Another aspect of the invention concerns a method for the identification of a biomarker, comprising selecting two or more target binding partners within a cancer sample; generating a PPI profile for the two or more target binding partners; and comparing the PPI profile to the responsiveness of the cancer to a treatment in vitro and/or in vivo (for example, in xenograft animal models or human subjects). Correlation between the PPI profile to the responsiveness of the cancer to a treatment of the cancer in vitro and/or in vivo is indicative of a biomarker for treatment responsiveness for the cancer. In some embodiments, the treatment is a kinase inhibitor (e.g., a tyrosine kinase inhibitor (TKI)). In some embodiments, at least one of the two or more target binding partners comprises a receptor tyrosine kinase (RTK). In some embodiments, RTK is within RTK class I-XVII. Preferably, responsiveness of the treatment to the cancer in vitro, or in vivo with xenograft animal models, is determined with the subject's cancer cells; however, cancer cell lines known to be predictive of responsiveness to the subject's cancer type may be utilized to compare with the PPI profile.

Another aspect of the invention concerns a method for identifying an agent as a PPI modulator, comprising: contacting cancer cells with a candidate agent in vitro or in vivo; and determining whether the candidate agent modulates a selected PPI in a sample of the cancer cells. The candidate agent may be any substance that potentially modulates (increases, decreases, or otherwise alters) the PPI. The candidate agent may be a small molecule, polypeptide, or nucleic acid, for example. Determination of changes in PPI can be made by comparing a first PPI profile of the cancer cells obtained prior to the contacting step to a second PPI profile of the cancer cells obtained after the contacting step, wherein a change in the PPI is indicative of a PPI modulator.

By inhibiting the growth of cells proliferating in an aberrant manner, the methods, PPI modulators, and compositions of the present invention can be used to treat a number of cell proliferation disorders, such as cancers, including, but not limited to, leukemias and lymphomas, such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cells (e.g., cancer cells) in humans and non-human mammals.

In some embodiments, the proliferation disorder to be treated is a cancer producing a tumor characterized by aberrant protein-protein interaction.

The methods of the present invention can be advantageously combined with at least one additional treatment method, including but not limited to, surgery, chemotherapy, radiation therapy, or any other therapy known to those of skill in the art for the treatment and management of proliferation disorders such as cancer.

While PPI modulators can be administered to cells in vitro and in vivo as isolated agents, it is preferred to administer PPI modulators as part of a pharmaceutical composition, in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The PPI modulators utilized in the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds which are substantially the same as another compound but which may have been modified by, for example, adding side groups, oxidation or reduction of the parent structure. Analogs of particular PPIs, and other agents disclosed herein, can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.*, 1997, 7:1623-1628; Honda, T. et al. *Bioorg. Med. Chem. Lett.*, 1998, 8:2711-2714; Konoike, T. et al. *J. Org. Chem.*, 1997, 62:960-966; Honda, T. et al. *J. Med. Chem.*, 2000, 43:4233-4246; each of which are hereby incorporated herein by reference in their entirety). Analogs, fragments, and variants of PPI modulators exhibiting the desired biological activity (such as induction of cell death, cytotoxicity, cytostaticity, induction of cell cycle arrest, etc.) can be identified or confirmed using cellular assays or other in vitro or in vivo assays.

Therapeutic application of the PPI modulators and compositions comprising them can be accomplished by any suitable therapeutic method and technique presently or prospectively known to those skilled in the art.

Active agents such as PPI modulators may be locally administered at one or more anatomical sites, such as sites of unwanted cell growth (such as a tumor site, e.g., injected or topically applied to the tumor), optionally in combination with a pharmaceutically acceptable carrier such as an inert diluent. PPI modulators may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the PPI modulators may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the PPI modulators may be incorporated into sustained-release preparations and devices.

The active agent (e.g., a PPI modulator) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active agent (e.g., PPI modulator) which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the PPI modulators above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, active agents such as PPI modulators may be applied in pure-form, i.e., when they are liquids. However, it will generally be desirable to administer them topically to the skin as compositions, in combination with a dermatologically acceptable carrier, which may be a solid or a liquid.

The PPI modulators can be applied topically to a subject's skin to reduce the size (and may include complete removal) of malignant or benign growths. The PPI modulators can be applied directly to the growth. Preferably, the PPI is applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the active agent can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the active agent to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, pharmaceutical compositions can comprise PPI modulator in combination with a pharmaceutically acceptable carrier. Pharmaceutical compositions adapted for oral, topical or parenteral administration, comprising an amount of an PPI modulator, constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Depending upon the disorder or disease condition to be treated, a suitable dose(s) may be that amount that will reduce proliferation or growth of the target cell(s), or induce cell death. In the context of cancer, a suitable dose(s) is that which will result in a concentration of the active agent (e.g., one or more PPI modulators) in cancer tissue, such as a malignant tumor, which is known to achieve the desired response. The preferred dosage is the amount which results in maximum inhibition of cancer cell growth, without unmanageable side effects. Administration active agents, such as PPI modulators, can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient", "subject", and "individual" are used interchangeably and are intended to include such human and non-human species. Likewise, in vitro methods of the present invention can be carried out on cells of such human and non-human species. In some embodiments, the cells are obtained from a subject. In other embodiments, the cells are cells of a cancer cell line.

Patients in need of treatment using the methods of the present invention can be identified using standard techniques known to those in the medical or veterinary professions, as appropriate.

The terms "cancer" and "malignancy" are used herein interchangeably to refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer;

uterine cancer; cancer of the urinary system, as well as other carcinomas and sarcomas. Examples of cancer types that may potentially be sampled and treated using the kits and methods of the invention are also listed in Table 1.

TABLE 1

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| | Lymphoma, Burkitt's |
| Brain Tumor, Visual Pathway and Hypothalamic Glioma, Childhood | Lymphoma, Cutaneous T-Cell, see Mycosis Fungoides and Sézary Syndrome |
| Brain Tumor, Childhood | Lymphoma, Hodgkin's, Adult |
| Breast Cancer | Lymphoma, Hodgkin's, Childhood |
| Breast Cancer, Childhood | Lymphoma, Hodgkin's During Pregnancy |
| Breast Cancer, Male | Lymphoma, Non-Hodgkin's, Adult |
| Bronchial Adenomas/Carcinoids, Childhood | Lymphoma, Non-Hodgkin's, Childhood |
| | Lymphoma, Non-Hodgkin's During Pregnancy |
| Burkitt's Lymphoma | |
| Carcinoid Tumor, Childhood | Lymphoma, Primary Central Nervous System |
| Carcinoid Tumor, Gastrointestinal | |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, | Oral Cavity Cancer, Lip and |

TABLE 1-continued

Examples of Cancer Types

| | |
|---|---|
| Childhood | Oropharyngeal Cancer |
| Germ Cell Tumor, Extragonadal | Osteosarcoma/Malignant Fibrous |
| Germ Cell Tumor, Ovarian | Histiocytoma of Bone |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and | Pancreatic Cancer, Childhood |
| Hypothalamic | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive |
| Soft Tissue Sarcoma, Childhood | Neuroectodermal Tumors, Childhood |
| Squamous Cell Carcinoma, see Skin | Pituitary Tumor |
| Cancer (non-Melanoma) | Plasma Cell Neoplasm/Multiple Myeloma |
| Squamous Neck Cancer with Occult | Pleuropulmonary Blastoma |
| Primary, Metastatic | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive | Primary Central Nervous System Lymphoma |
| Neuroectodermal Tumors, Childhood | Prostate Cancer |
| T-Cell Lymphoma, Cutaneous, see | Rectal Cancer |
| Mycosis Fungoides and Sézary | Renal Cell (Kidney) Cancer |
| Syndrome | Renal Cell (Kidney) Cancer, Childhood |
| Testicular Cancer | Renal Pelvis and Ureter, Transitional Cell |
| Thymoma, Childhood | Cancer |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal | Salivary Gland Cancer, Childhood |
| Pelvis and Ureter | Sarcoma, Ewing's Family of Tumors |
| Trophoblastic Tumor, Gestational | Sarcoma, Kaposi's |
| Unknown Primary Site, Carcinoma of, | Sarcoma, Soft Tissue, Adult |
| Adult | Sarcoma, Soft Tissue, Childhood |
| Unknown Primary Site, Cancer of, | Sarcoma, Uterine |
| Childhood | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MM), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The treatment methods of the invention can be utilized for early, middle, or late stage disease, and acute or chronic disease.

According to methods of the subject invention, a PPI modulator can be administered to a patient by itself, or co-administered with one or more other agents such as another PPI modulator, or a different agent or agents. Co-administration can be carried out simultaneously (in the same or separate formulations) or consecutively. Furthermore, according to the method of the subject invention, PPI modulators can be administered to a patient as adjuvant therapy. For example, PPI modulators can be administered to a patient in conjunction with chemotherapy, radiation therapy, surgery, or a combination of two or more of the foregoing.

Thus, the PPI modulators, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The PPI modulators can be conjugated to a therapeutic agent, as well.

Additional agents that can be co-administered to target cells in vitro or in vivo, such as in a patient, in the same or as a separate formulation, include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more agents selected from the group consisting of anti-cancer agents, cytotoxic agents, chemotherapeutic agents, anti-signaling agents, and anti-angiogenic agents.

In some embodiments of the methods of the invention, at least one additional anti-cancer agent (e.g., a chemotherapeutic agent) is administered with the PPI modulator. In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor.

Within certain aspects of the present invention, one or more PPI modulators as described herein may be present within a pharmaceutical composition. A pharmaceutical composition comprises one or more PPI modulators in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A PPI modulator may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

Various techniques may be utilized to facilitate delivery of the PPI modulators to the target cells in vitro (including ex vivo) and in vivo (Cellular Drug Delivery: Principles and Practice, edited by Lu, D. R. and Oie, S., Human Press, Totowa, N.J., 2004). Optionally, it may be desirable to facilitate delivery of the PPI modulators through the outer cell membrane. Various carrier molecules may be coupled to the PPI modulators to assist penetration through biological membranes. For example, small regions (e.g., 9-16 amino acids) of proteins called protein transduction domains (PTDs) cell penetrating peptides (CPP) possess the ability to traverse biological membranes through protein transduction (Barnett, E. M. et al., Invest. Opthalmol. Vis. Sci., 2006, 47:2589-2595; Schwarze S. R. et al., Science, 1999, 285 (5433):1569-1572; Wadia, J. S. and Dowdy, S. F., Advanced Drug Delivery Reviews, 2005, 57(4): 579-596; Wadia, J. S. and Dowdy, S. F., Curr. Opin. Biotechnol., 2002, 13(1)52-56; Ho A. et al., Cancer Research, 2001, 61:474-477; Futaki et al., J. Biol. Chem., 2001, February, 276(8):5836-5840; Cao G. et al., J. Neurosci., 2002, 22(13):5423-5431; Becker-Hapk, M. et al., Methods, 2001, 24:247-256; Snyder, E. L. and Dowdy, S. F., Curr. Opin. Mol. Ther., 2001, 3:147-152; Lewin, M. et al., Nat. Biotechnol., 2000, 18:410-414; Tung, C. H. et al., Bioorg. Med. Chem., 2002, 10:3609-3614; Richard, J. P., et al., J. Biol. Chem., Oct. 30, 2002, epub ahead of print). Transduction can occur in a receptor- and transporter-independent fashion that appears to target the lipid bilayer directly. Proteins (peptides) and compounds that are linked to PTDs (e.g., covalently) have the capability to traverse outer cell membranes. Preferably, the delivery peptide is a trans-activating transcriptional activator (TAT) peptide or an Antennapedia (ANT) peptide, or a derivative of either. PTDs can be linked to the active agents for transport across the cell membrane. One well characterized PTD is the human immunodeficient virus (HIV)-1 Tat peptide (see, for example, U.S. Pat. Nos. 5,804,604; 5,747,641; 5,674,980; 5,670,617; and 5,652,122). Peptides such as the homeodomain of Drosophila antennapedia (ANTP) and arginine-rich peptides display similar properties can be employed. VP22, a tegument protein from Herpes simplex virus type 1 (HSV-1), also has the ability to transport proteins across a cell membrane, and may be coupled to some PPIs.

Definitions

The terms "proximity probe" and "PLA probe" are used interchangeably herein to refer to a moiety that binds to a target molecule, such as a protein, in a sample and is detectable using oligonucleotide amplification methods. In some embodiments, a proximity probe comprises a target molecule recognition moiety and an oligonucleotide probe. In some embodiments, a target molecule specific amplification product can be formed when at least two proximity probes specific for the target molecule are bound to the target molecule and the oligonucleotide probe of each proximity probe is ligated to one another to form a ligated probe that is amplified.

Polymerase chain reaction (PCR) is a process for amplifying one or more target nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. The skilled artisan to detect the presence of desired sequence (U.S. Pat. No. 4,683,195) routinely uses polymerase chain reaction.

A specific example of PCR that is routinely performed by the skilled artisan to detect desired sequences is reverse transcript PCR (RT-PCR; Saiki et al., Science, 1985, 230: 1350; Scharf et al., Science, 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

As used herein, the terms "label" and "tag" refer to substances that may confer a detectable signal (e.g., a signal representing the amplification product of a proximity ligation assay). A number of techniques for visualizing or detecting labeled nucleic acids are readily available. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC, spectroscopy, capillary gel electrophoresis, spectroscopy; mass spectroscopy; radiological techniques; and mass balance techniques.

As used herein, the term "ligand" refers to a molecule that contains a structural portion that is bound by specific interaction with a particular receptor protein.

As used herein, the term "PPI" or "protein-protein interaction" refers to refers to the binding of two or more proteins together. PPIs may be binary (two protein binding partners; a dimer) or tertiary (three or more protein binding partners, e.g., a trimer). Proteins within a PPI (i.e., binding partners) may be the same protein (such as a homodimer or homotrimer) or different proteins (such as a heterodimer or heterotrimer). Proteins within a tertiary interaction may be bound to one or more proteins within the PPI. In some embodiments, the PPI comprises a tyrosine kinase, such as the human tyrosine kinases listed in Tables 3 and 4. The PPI may comprise an interaction between the binding partners listed in Table 5 (human tyrosine kinase interactions).

In some embodiments of the methods and kits of the invention, at least one of the target binding partners is of an RTK class selected from among RTK class I (EGF receptor family; ErbB family), RTK class II (insulin receptor family), RTK class III (PDGF receptor family), RTK class IV (FGF receptor family) RTK class V (VEGF receptors family), RTK class VI (HGF receptor family), RTK class VII (Trk receptor family), RTK class VIII (Eph receptor family), RTK class IX (AXL receptor family), RTK class X (LTK receptor family), RTK class XI (TIE receptor family), RTK class XII (ROR receptor family), XIII (DDR receptor family), RTK class XIV (RET receptor family), RTK class XV (KLG receptor family), RTK class XVI (RYK receptor family), and RTK class XVII (MuSK receptor family).

As used herein, the term "PPI profile" or "protein-protein interaction profile" refers to the result or output of an assay that measures the relative abundance of a protein-protein interaction. PPI profiles (e.g., sample PPI profile, and reference PPI profile) may each be expressed as a value representative of the abundance of target binding partners in proximity to each other within the sample. The sample PPI profile and reference PPI profile may be expressed by any method useful for comparison purposes, such as a numeric value, score, cutoff (threshold), or other expression. For example, a negative result in which a PPI profile in a sample does not reach the cutoff would be useful clinically to avoid giving patients unnecessary PPI modulator therapy. A positive result in which a PPI profile in a sample is at or above the cutoff could indicate potential sensitivity and allow the clinician to give the PPI modulator therapy to those patients who would be most likely to benefit. Typically, a reference PPI profile is the PPI profile of a known cancer cell (e.g., cancer cell of a known type or subtype) or of a normal cell (non-cancerous cell) useful for comparison purposes. The reference PPI profile may also be a sample PPI profile obtained at a different time point than the sample PPI profile in question (before or after, to observe changes to the PPI profile of a cancer over time).

As used herein, the term "PPI modulator" refers to an agent (e.g., small molecule, protein, nucleic acid) that directly or indirectly promotes, inhibits, or otherwise alters interaction between two or more proteins. The PPI modulator may be an inducer of the PPI (directly or indirectly promoting interaction), or an inhibitor of the PPI (directly or indirectly inhibiting interaction). For example, a PPI inhibitor may be a kinase inhibitor, which indirectly acts to inhibit PPI.

As used herein, the term "bind" refers to any physical attachment or close association, which may be permanent or temporary. The binding can result from hydrogen bonding, hydrophobic forces, van der Waals forces, covalent, or ionic bonding, for example.

As used herein, the term "antibody" refers to immunoglobulin molecules and immunologically active portions (fragments) of immunoglobulin molecules, i.e., molecules that contain an antibody combining site or paratope. The term is inclusive of monoclonal antibodies and polyclonal antibodies.

As used herein, the terms "administering" or "administer" are used herein to refer the introduction of a substance into cells in vitro or into the body of an individual in vivo by any route (for example, oral, nasal, ocular, rectal, vaginal and parenteral routes). Active agents such as PPI modulators may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN), or orally. For example, active agents such as PPI modulators can be administered by direct injection into or on a tumor, or systemically (e.g., into the circulatory system), to kill circulating tumor cells (CTC).

As used herein, the term "polypeptide" refers to a sequence of two or more amino acids, and is used interchangeably herein with the terms "protein", "gene product", "oligopeptide", and "peptide".

In the context of the instant invention, the terms "oligopeptide", "polypeptide", "peptide" and "protein" can be used interchangeably to refer to amino acid sequences of any length; however, it should be understood that the invention does not relate to the peptides in natural form, that is to say that they are not in their natural environment but that the peptide may have been isolated or obtained by purification from natural sources or obtained from host cells prepared by genetic manipulation (e.g., the peptides, or fragments thereof, are recombinantly produced by host cells, or by chemical synthesis). Peptide PPI modulators may also contain non-natural amino acids, as will be described below. The terms "oligopeptide", "polypeptide", "peptide" and "protein" are also used, in the instant specification, to designate a series of residues of any length, typically L-amino acids, connected one to the other, typically by peptide bonds between the a-amino and carboxyl groups of adjacent amino acids. Linker elements can be joined to the peptides, for example, through peptide bonds or via chemical bonds (e.g., heterobifunctional chemical linker elements) as set forth below. Additionally, the terms "amino acid(s)" and "residue(s)" can be used interchangeably.

As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with active agent such as a PPI modulator may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., proliferation disorder) prior to administration of the PPI modulator.

As used herein, the term "(therapeutically) effective amount" refers to an amount of the PPI modulator or other active agent (e.g., a drug) effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce signaling in the target cells, and/or relieve, to some extent, one or more of the symptoms associated with the cancer. To the extent the administered PPI modulator prevents growth of and/or kills existing cancer cells, it may be cytostatic and/or cytotoxic. For cancer therapy, efficacy can, for example, be measured by assessing the time to disease progression (TTP) and/or determining the response rate (RR).

Treatments can be given in a growth inhibitory amount. As used herein, the term "growth inhibitory amount" of the active agent (e.g., PPI modulator) refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise indicated.

As used herein, the term "sample" refers a biological composition that potentially contains target molecules (e.g., one or more protein binding partners in a protein-protein interaction of interest). Preferably, the sample is a cellular sample (samples of intact cells, e.g., a cytology sample). One or more samples of a malignancy may be obtained from a subject by techniques known in the art, such as biopsy. The type of biopsy utilized is dependent upon the anatomical location from which the sample is to be obtained. Examples include fine needle aspiration (FSA), excisional biopsy, incisional biopsy, colonoscopic biopsy, punch biopsy, and bone marrow biopsy. Depending on the PPI of interest, the sample may be obtained from a pleural effusion or the bloodstream, for example. It should be understood that the methods of the invention may include a step in which a sample is obtained directly from a subject; alternatively, a sample may be obtained or otherwise provided, e.g., by a third party.

A sample may be taken from a subject having or suspected of having cancer. A sample may also comprise proteins isolated from a tissue or cell sample from a subject. In certain aspects, the sample can be, but is not limited to tissue (e.g., biopsy, particularly fine needle biopsy, excision, or punch biopsy), blood, serum, plasma. The sample can be fresh, frozen, fixed (e.g., formalin fixed), or embedded (e.g., paraffin embedded) tissues or cells (e.g., FFPE tissue). In a particular aspect, the sample is a sample of lung cancer cells, colon cancer cells, breast cancer cells, ovarian cancer cells, renal cancer cells, melanoma cells, prostate cancer cells, CNS cancer cells, or leukemia cells, esophageal cancer cells, stomach cancer cells, bile duct cancer cells, liver cancer cells, cancer cells of the rectum or anus, lymphoma, leukemia, cervical cancer cells, bladder cancer cells, or protein from any of the aforementioned cancers. Depending upon the cancer type, the cancer cells may be circulating tumor cells (CTCs).

As used herein, the term "anti-cancer agent" refers to a substance or treatment (e.g., agent or radiation therapy) that inhibits the function of cancer cells, inhibits their growth, formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). Anti-cancer agents include but are not limited to the chemotherapeutic agents listed in Table 2, and other agents disclosed herein, such as erlotinib or other small molecule epidermal growth factor tyrosine kinase inhibitors (EGFR TKI). In the kits and methods of the invention, the treatment or potential treatment may be an anti-cancer agent (for example, a PPI modulator such as a kinase inhibitor or other PPI inhibitor).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with PPI modulators are listed in Table 2. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 2

Examples of Chemotherapeutic Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |

TABLE 2-continued

Examples of Chemotherapeutic Agents

| | |
|---|---|
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| *Erwinia* L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |

TABLE 2-continued

Examples of Chemotherapeutic Agents

| | |
|---|---|
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine | MTC |
| Hydrochlorine | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

As used herein, the term "tumor" refers to all neoplastic cell growth and proliferation, whether malignant or benign, and all pre-cancerous and cancerous cells and tissues. For example, a particular cancer may be characterized by a solid tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The peptide PPI modulators may be capable of inducing apoptosis in tumor cells, reducing tumor size, and/or inhibiting tumor cell growth. The peptides of the invention (or nucleic acids encoding them) can be administered locally at the site of a tumor (e.g., by direct injection) or remotely. The peptide PPI modulators may induce cell death in circulating tumor cells (CTC) in a subject, e.g., by administering the peptides or encoding nucleic acids intravenously. Furthermore, the peptide PPI modulators may prevent or reduce onset of metastasis to other tissues, e.g., to the bone.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

As used herein, the term "pharmaceutically acceptable salt or prodrug" is intended to describe any pharmaceutically acceptable form (such as an ester, phosphate ester, salt of an ester or a related group) of a PPI modulator or other active agent, which, upon administration to a subject, provides the mature or base compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The terms "link" or "join" refers to any method known in the art for functionally connecting peptides, including, without limitation, recombinant fusion, covalent bonding, disulfide bonding, ionic bonding, hydrogen bonding, and electrostatic bonding.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state.

As used in this specification, the singular forms "a", "an", and "the" include plural reference unless the context clearly dictates otherwise. Thus, for example, a reference to "a compound" includes more than one such compound. Reference to "PPI modulator" includes more than one such PPI modulator. A reference to "an antibody" includes more than one such antibody, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Experimental controls are considered fundamental in experiments designed in accordance with the scientific method. It is routine in the art to use experimental controls in scientific experiments to prevent factors other than those being studied from affecting the outcome.

Materials and Methods

Primary Xenograft Mouse Models.

4-6 weeks old female hairless mice Crl:SHO-Prkdc-SCID-Hr-hr mice will be purchased from approved vendors and housed in the institutional animal facilities according to protocols set out by the American Association for Accreditation of Laboratory Animal Care. The inventor has active IACUC protocols for establishing tumor xenografts in mice and to perform drug treatment experiments. Mice will be anesthetized with isofluorane, a small incision and a small subcutaneous pocket will be made in each side of the lower back, and a piece of tumor collected from NSCLC patients will be deposited in each pocket. Animals will be observed until palpable tumors are present and subsequently treated vehicle (31). The mice will be monitored 2-3 times per week. If any mice demonstrate discomfort, i.e., lethargy, abnormal posture, failure to groom, ruffled, matted or soiled hair coat, rapid, shallow and/or labored breathing, have tumors greater than 1.0 cm in diameter, have tumors which interfere with posture, locomotion or feeding, or have tumors abscess through the skin, they will be euthanatized using $CO_2$. Each group of mice will be put in the cleaned and dried chamber, and then the chamber will be slowly filled by compressed carbon dioxide gas. Mice will be quickly euthanatized by carbon dioxide inhalation. Mouse death will be confirmed by verification of cessation of cardiovascular and respiratory movement/activity. This method is consistent with recommendations of the Panel on Euthanasia of the American Veterinary Medical Association. Log entries for complications of either tumor growth or tumor metastasis will be maintained. For tumor harvesting, mice will be euthanized by $CO_2$ inhalation and tumors will be excised and snap frozen in liquid nitrogen.

Cell Line Xenograft Models.

Tumor tissues from subcutaneous mouse models of lung cancer will be used. CD-1 nu/nu mice do not have a thymus and are therefore immunodeficient and unable to produce T-cells. Mice have been selected for these experiments since they are most suitable for xenograft and orthographic studies of lung cancer, are readily available and not endangered, and can be safely maintained in the laboratory animal vivarium. CD-1 nu/nu mice mice will be purchased from approved vendors and housed in institutional animal facilities according to protocols set out by the American Association for Accreditation of Laboratory Animal Care. The inventor currently has active IACUC protocol for establishing subcutaneous tumor xenografts in mice. Both male and female mice of approximately six weeks of age will be used. Mice will be anesthetized in an induction chamber containing 3% isoflurane and 97% oxygen. Mice will be subsequently shaved in the flank area and injected with various human lung cancer cell lines. Animals will be observed until palpable tumors are present and subsequently treated vehicle or compounds in 0.2 ml vehicle containing 0.5% methylcellulose and 0.4% polysorbate 80 (TWEEN 80) (59, 60). The mice will be monitored 2-3 times per week. If any mice demonstrate discomfort, i.e., lethargy, abnormal posture, failure to groom, ruffled, matted or soiled hair coat, rapid, shallow and/or labored breathing, have tumors greater than 1.0 cm in diameter, have tumors which interfere with posture, locomotion or feeding, or have tumors abscess through the skin, they will be euthanatized using CO2. Each group of mice will be put in the cleaned and dried chamber, and then the chamber will be slowly filled by compressed carbon dioxide gas. Mice will be quickly euthanatized by carbon dioxide inhalation. Mouse death will be confirmed by verification of cessation of cardiovascular and respiratory movement/activity. This method is consistent with recommendations of the Panel on Euthanasia of the American Veterinary Medical Association. Log entries for complications of either tumor growth or tumor metastasis will be maintained. For tumor harvesting, mice will be euthanized by CO2 inhalation and tumors will be excised and snap frozen in liquid nitrogen.

Patient consenting process: The TCC protocol was IRB approved in January 2006; since then, 33,000+ patients have prospectively consented to have their tissue collected and agreed to lifetime follow-up. Moffitt expects 100,000 consents within 4 years at 15 partner institutions.

Sample Collection: To date, over 10,000 tumors have been collected. This number will grow exponentially in coming years. TCC collects tumor, blood and urine samples as well as clinical data such as risk factors, therapies and outcomes. All tissues are snap frozen within 15 minutes of resection and 2D bar code labeled. Moffitt has robotic biobanking and every tissue is macrodissected to ≥85% purity.

Pathologic Review of Frozen Tissue Specimens: Each frozen tissue specimen is subjected to comprehensive histopathologic review by Board-certified Pathologists. Each tumor sample is quantified for proportions of the following tissue components: malignant (viable tumor cellularity, tumor necrosis and stroma), normal, abnormal (including inflammation, ulceration, atrophy, hyperplasia etc) and benign neoplastic tissues. In order to achieve the highest possible purity of viable malignant tumor tissue for each specimen, every effort is made to exclude (macrodissect) the latter three components from the tissue processed for subsequent molecular analyses. In order to ensure the highest quality of tissue specimens and to control for pre-analytic variables, the tissue collection and review processes are regulated by specific Standard Operating Procedures (SOPs) and QA/QC protocols.

Gene Expression Profiling: 7,000 samples have been analyzed to date. Identifying molecular signatures is a key component of precision-based personalized medicine. To date, TCC has focused on gene expression but other modalities, including quantitative proteomics, are planned.

Biorepository: All specimens collected under the TCC protocol are stored in a single location at Moffitt in a biobank capable of storing 1,000,000 samples. Currently, tumor specimens are collected from patients with colon, lung, prostate, brain, breast, pancreatic, ovarian, bladder, and renal cancers. As the resource develops, tumor specimens from all disease sites will be acquired from consortium members.

Data Warehouse: Storage is provided for patient records, medical history, registry data, molecular profiles (e.g. gene expression), and clinicopathologic data in compliance with HIPAA requirements. Within 5 years, the warehouse is expected to hold information on primary and metastatic biopsies for over 50,000 patients. Appropriate access is given to the patient, the clinician and researcher to lead to the creation of evidence-based guidelines. Separate web portals are being developed to meet these distinct needs.

Translational research is incorporated along this continuum of care and follow-up. TCC is more than just a registry, cohort study, or tissue bank; the system prospectively consents patients, collects clinical data throughout a patient's lifetime, creates gene expression profiles of all tumors, and enables access to the data for the patient, clinician and researcher. Its capability for in-depth analysis could lead to improving the standard of care addressing each patient's specific needs.

Subjects are being recruited to Total Cancer Care™ (TCC) sites in FL (including the Moffitt Cancer Center (MCC), primary sponsor of the study), NC, SC, CT, KY, LA, IN and NE according to the TCC protocol and consent. The total recruitment expected across all sites is by 2012 is 100,000 patients. Patients ages 18 and older years with newly diagnosed, recurrent or metastatic cancers (stages I-IV) are being recuited. Inclusion criteria are broad to include any willing patient that has visited one of the consortium sites and presented with a cancer diagnosis. Exclusion criteria is any registered patient who is not willing or able to sign the consent for data collection. The TCC study provides for the collection of patient biospecimens and data throughout the patients life in a large prospective study. Tumor samples collected either through resection or biopsy for research studies are comprised of excess tissue not necessary for pathological diagnosis or clinical care and are banked by MCC. No appreciable risks to subjects associated with tissue collection and analysis is anticipated; the patient's surgeon will remove this tissue as part of his or her clinical care, and no additional tissue will be removed for the TCC Study unless specified and consent granted by the patient prior to the procedure. Additional biospecimens, including blood and urine, maybe collected as described in the TCC protocol and consent documents, although these are not used for the study purposes of the proposed research described in this application. If there is a change in protocol procedures or desired biospecimen types an amendment to the protocol and consent are provided to the University of South Florida's Internal Review Board (IRB) for consideration of the benefits to research and the impact on patient care, well being, harm and discomfort. Changes to the TCC protocol at Consortium sites are presented to local IRBs for consideration prior to additional biospecimen collections. Subjects may feel uncomfortable answering personal questions on study questionnaires or knowing that their medical records are being reviewed. Patients will be informed that that they may skip any questions they prefer not to answer. Great care will be taken to protect patient privacy throughout the study in accordance with MCC policies.

The invenor has an active protocol that also allows for patient chart review to gather information necessary for this project as well as access tumor tissue for molecular assays. This study was approved by the University of South Florida IRB and allows access to PHI for research purposes described in this proposal. This allows for chart review by the inventor and his trained staff to identify clinical variables such as age, sex, histology of tumor, stage, response to therapy, and overall survival.

Some of the Figures herein have been labeled with one or more colors to facilitate interpretation when the Figures are viewed in black and white. The lack of a color label on any particular region of a figure should not necessarily be construed as an absence of color in that region.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Epidermal Growth Factor Receptor (EGFR) Protein-Protein Interactions as Biomarkers Cancer is recognized to be a result of changes in cellular genomes resulting in aberrant signaling proteins causing deregulated cell growth, survival, and metastasis. These changes rewire entire signaling 'circuits' resulting in aberrant growth and metastasis. Critical to protein function and signaling is the formation of signaling complexes and networks of signaling proteins that act in concert to produce a physiological signal (1, 2). State of the art mass spectrometry is now able to accurately map protein-protein interaction (PPI) complexes and networks (3, 4). Initially, this was performed in yeast with high impact papers demonstrating the modular organization of PPI and insight into cellular signaling mechanisms (5, 6). However, improvements in mass spectrometry coupled with improved biochemical purification strategies are now enabling PPI mapping in mammalian cells, including cancer cells (7-9). This allows a better understanding of how cancer proteins drive a signaling network to transform cells. The application of network theory to biology may enable a better understanding of cancer, improve ability to classify tumors, and suggest therapeutic approaches against cancer 'hub' proteins or suggest rational combination approaches (10-14). In addition, comprehensive databases (such as www.hprd.org) now list protein interactions based on manually annotated reviews of the literature. Using these databases, groups can construct theoretical PPI that could be important in diseases such as cancer. One group used these databases to demonstrate the importance of deregulated PPI in aggressive cancers (15). Importantly, this network view can produce biomarkers categorized by protein-protein interactions that carry information to guide clinical decision making. Despite the explosion of PPI datasets, most are limited in pre-clinical space and interrogations of PPI in human cancer specimens is lacking. Thus, the present inventors have endeavored to make 'network medicine' a reality (16).

The present inventors have initiated a system wide and global analysis of the PPI driven by hyperactivated epidermal growth factor receptor (EGFR) resulting from somatic mutation in non-small cell lung cancer (NSCLC) (17-19). The inventors' approach has been to combine (i) affinity purification—mass spectrometry (AP-MS) and (ii) phosphotyrosine proteomics. The inventors use cell models that harbor mutant EGFR proteins and are highly sensitive to EGFR TKI. As the network of EGFR is highly dependent on cell context, this approach offers the best chance of recovering pertinent proteins and mechanisms, a potential flaw in using cells other than lung cancer cells driven by mutant EGFR. Tagged versions of EGFR are initially used to identify interactions and second round of AP-MS is performed to more fully construct the network (20, 21). The inventors simultaneously performed tyrosine phosphoproteomics—tyrosine phosphorylated (pTyr) peptides are enriched using an anti-phosphotyrosine antibody and then identified and quantified on an Orbitrap mass spectrometer using published methods (9). Using protein-protein interaction databases, the inventors linked pTyr containing proteins to proteins identified in AP-MS experiments. This produced the final map of nearly 300 proteins (shown in FIGS. 1A-1D). This interaction network allows functional interrogation of targets important in driving mutant EGFR growth and survival signals. In addition, the interactions themselves can be used as biomarkers in human cancer specimens by identifying an EGFR activating state. Thus, the critical question becomes, how can one 'translate' these preclinical mass spectrometry data into human cancer samples?

Translation of these network approaches to tumor samples is hampered by a number of challenges. First, almost all studies have been carried out in engineered mammalian cells that express a tagged version of the protein of interest; this limits the ability to use these modern AP-MS approaches in samples from patients. Second, most samples from patients are formalin fixed and paraffin embedded. This precludes the ability to use fresh frozen tissue for immunoprecipitation and western blotting (IP-WB) to identify protein complexes. IP-WB also requires a large amount of starting material that can be difficult to obtain with needle biopsies.

One solution to mapping networks identified using MS-based proteomics is proximity ligation assays (PLA) (22-27). Briefly, two proteins in complex are each identified with primary antibodies specific for the protein and linked to a conjugated oligonucleotide. A connector oligonucleotide links both proximity probes allowing ligation and formation of a template for PCR amplification. The resulting rolling circular amplification (RCA) serves as a target for hybridized fluorescently labeled detection oligonucleotides allowing distinct and bright spots to be identified and quantified in a fluorescent microscope. See http://www.olink.webbhuset.com/movie.php for an animation describing this technology. This technology has been used to identify in cells in situ Myc-Max interactions, tyrosine phosphorylation of receptor tyrosine kinases, and interactions of proteins in human tissue sections.

As little has been done to establish biomarker systems to measure protein-protein based biomarkers in cancer, it would be advantageous to have an assay (e.g., a PLA) that can quantitatively measure defined protein-protein interactions in cancer specimens (e.g., EGFR protein-protein interactions in lung cancer specimens) and relate expression of these interactions to clinical outcome variables. Lung cancer accounts for over 160,000 deaths per year in the U.S., more than breast, colon, prostate and pancreatic cancer combined (28). The overall five-year survival rate for lung cancer is approximately 15%, and unlike other solid tumors such as colon or breast cancer, little progress has been made in improving survival. There is therefore an important unmet need to better identify key drivers of lung cancer that can be therapeutically exploited. Coupled with this need is the ability to identify patients' subsets driven by drug targets. EGFR is selected as a test case to develop these assays based on (i) its known role in lung cancer pathogenesis, (ii) use of EGFR TKI for treatment of lung cancer, (iii) experimentally derived protein-protein interaction data derived in the inventor's laboratory using mass spectrometry and (iv) availability of antibody reagents (29). The assays are not meant to replace existing clinical assays that predict EGFR kinase inhibitor sensitivity (i.e., EGFR mutation analysis) but are meant to allow a starting point to develop PPI based biomarkers that could be applied to other cancer pathways or drugs. This could allow markers that identify patients benefiting from EGFR TKI whose tumors do not harbor EGFR mutations. Finally, success here can be translated to other signaling systems, such as MET and IGFR, where interactions could be informative (for example, MET with Gab1 and IGFR with IRS proteins) and biomarkers predicting response are unclear (30).

The approach to develop biomarkers based on protein-protein interactions goes one step beyond measurement of protein expression as it determines the binding to two proteins together in tumor tissues. Two proteins may be equally expressed, but because of other nuances in the cancer cell, do not form a signaling complex that drives a signaling cascade. In another tumor cell, these proteins form a complex and drive a signaling cascade. Gene-based approaches that measure mRNA expression or immunohistochemistry approaches that measure protein expression would be unable to discriminate these two cases. One aspect of the invention is a translatable assay system measuring protein-protein interactions driven by hyperactivated forms of EGFR and this approach will be tested in panels of cell lines, animal tumor models, and specimens from lung cancer patients. The inventor builds on the AP-MS mass spectrometry data to build protein-protein interaction networks in lung cancer cell lines driven by activated EGFR and translate these findings into patient based materials. Four aims are described herein.

Aim 1: Establish and validate proximity ligation assays that measure EGFR protein-protein interactions The invention provides assays measuring protein-protein interactions based on proximity ligation assay (PLA) technology. This technology is capable of detecting single protein events such as protein interactions. The assay provides exact spatial information on the location of the events and an objective means of quantifying the events. Experimentally derived mass spectrometry data defining interacting proteins within the EGFR network will guide selection of protein complexes for assay development.

Aim 2: Characterize EGFR protein interactions in cell and tumor models with known EGFR mutation status. Here the hypothesis is that cells and tumors with activating EGFR mutations will demonstrate constitutive complexes with EGFR proteins. This will be tested in both cell lines with known EGFR mutation status and tumor samples from patients with known EGFR mutation status. The inventor will also test the hypothesis that the degree of EGFR complexes is related to sensitivity to EGFR tyrosine kinase inhibitors (TKI).

Aim 3: Characterize changes in EGFR protein-protein interactions in response to EGFR tyrosine kinase inhibitors in primary lung cancer xenograft models and patient samples. EGFR inhibitors are predicted to disrupt signaling complexes on the EGFR protein. The inventor will use primary lung cancer xenograft systems and samples from patients before and after EGFR inhibitor therapy to measure differences in EGFR protein-protein interactions.

Aim 4: Determine if EGFR protein-protein interactions are associated with responses to EGFR tyrosine kinase inhibitors in human lung cancer samples. The inventor hypothesizes that quantitative measurements of EGFR protein-protein interactions could be used as biomarkers to predict activity of EGFR kinase inhibitors in patients with advanced lung cancer. The inventor has developed PLA assays for EGFR protein-protein interactions in lung cancer samples and related these measurements to response to EGFR inhibitors in a group of patients with advanced lung cancer.

Aim 1: Establish Proximity Ligation Assays that Measure EGFR Protein-Protein Interactions.

The mass spectrometry data provides a set of proteins physically interacting with one another that can be translated into assays in tumor material. The initial set of proteins consisting of EGFR, Src, ErbB3, Mig6, Grb2, Sts1, and p85 is based on the MS data and the literature. Aside from EGFR, ErbB3 and p85 were selected as they are important components of mutant EGFR signaling that lead to activation of Akt signaling and lung cancer survival (31, 32). Grb2 was chosen based on its role in activating Ras signaling downstream of EGFR (33, 34). Mig6 and Sts1 were selected based on their ability to negatively regulate EGFR signaling (35-38). Src is intimately involved in EGFR signaling and important in EGFR driven lung cancer (39-41). The inventor will measure the following six interactions: EGFR:ErbB3, EGFR:Grb2, EGFR:Mig6, EGFR:Sts1, EGFR:Src and ErbB3:p85. Guidelines for antibody validation described by David Rimm (42) and summarized below will be followed. Protein extracts from a panel of lung cancer cell lines with and without EGFR mutations will be used to test for antibody specificity using western blots. A panel of cells is examined to avoid reaching conclusions of specificity based on a single cell line. Antibodies that appear specific (dominant single band, few other bands outside MW range of protein) will be selected for further development.

Immunofluorescence (IF) conditions can be optimized for each antibody, including a series of antibody dilutions, different sets of temperatures and incubation times, and different concentrations of secondary antibody conjugated with fluorescence dye. Patterns of IF staining will be examined using fluorescence and confocal microscopy using PC9 cells grown on a 8 or 16 well chamber slides. The antibodies that pass the test in this run of validation have to reach three criteria at the same time: 1) the location of cell compartment must be consistent with those that previous reported (i.e., membrane/cytoplasm/nuclear); 2) antibodies must be sensitive enough to give enough signal intensity above background; 3) Every pair of antibodies must pass the double staining test under the same conditions which is fundamental to the PLA assay. Two antibodies from different species work must well under identical conditions with balanced intensities thus requiring us to screen different pairs of antibodies based on the information from commercial sources and the IF results described above.

Validated antibodies will be used for PLA. An initial experiment was performed (FIGS. 3A-F). PC9 lung cancer cells harboring an activating EGFR mutation were evaluated for EGFR:Grb2 binding based on the MS data. Antibodies were selected and validated with both western blotting and IF as described above. PLA was then tested to measure these interactions in untreated cells and in cells treated with EGFR TKI erlotinib. Additional controls were added such as leaving out either primary antibody or leaving out secondary antibodies. Strong foci were identified indicative of EGFR:Grb2 interactions that are significantly reduced by erlotinib and completely absent in the negative controls. To assess non-specific noise/background in the PLA assays, at least four negative controls will be used in parallel: omit one of the two antibodies in each well, and omit one of two secondary antibodies conjugated with PLUS or MINUS DNA fragments in each well. A positive control is also used in each individual test. Results above used a Leica TCS SP5 AOBS laser scanning confocal microscope. Analysis of labeled foci in the maximum projection images was performed using Image Pro Plus version 6.2 (Media Cybernetics, Inc., Silver Springs, Md.). Regions of interest were derived manually and by image analysis using a click and grow methodology to define cell borders and segment individual cells. Histogram threshholding for the biomarker targeted channels were used to identify the number of foci and determine the mean intensity of the foci for each individual cell. Foci are defined as any Alexa 555 labeled object within the cell that has an area of at least 5 pixels over threshold. Other approaches will be considered. PLA assay creates a perfect fluorescence signal allowing conventional IF to be adapted to the mature AQUA system. The data collection with AQUA includes scanning fluorescence signal in the tissue section with AQUAsition, and transferring image signals into digital numbers with AQUAanlysis software, which is the newest version package, AQUA 2.2. Definiens® Developer v1.2 (Definiens, Munich, Germany) software suite can be used to automatically find individual cells and analyze them. A plasma membrane or whole cytoplasm stain may need to be added to accomplish this task. This will allow for batch processing and increase image analysis throughput significantly, while retaining quality control standards necessary for this project.

Aim 2: Characterize EGFR Protein Interactions in Cell and Tumor Models with Known EGFR Mutation status.

The inventor proposes that cells and tumors with activating EGFR mutations will demonstrate constitutive complexes with EGFR proteins. PLA will be tested to recognize increased protein-protein interactions of EGFR and interacting proteins in a panel of lung cancer cell lines with known EGFR mutation status. This will include cell with activating EGFR mutations (PC9, HCC827, H4006, H1975, H1650, and H820) and wildtype EGFR (H23, A549, H1299, H460, etc) from the Lung SPORE cell line bank (total of nearly 50 NSCLC cell lines). It is expected to find higher degrees of PLA signals in cells with activating EGFR mutations compared to cells without EGFR mutations as these mutant EGFR proteins are constitutively activated and poorly internalized. Also examined will be EGFR PPI PLA signals in lung cancer cells that have wildtype EGFR but nonetheless have some degree of sensitivity to EGFR TKI. This includes H322, H358, H292, and H1648 cells. Intermediate measurements of EGFR PPI using PLA are expected here. This would reflect engagement of the EGFR protein with downstream signaling complexes that occur through mechanisms such as EGFR gene amplification and/or EGFR ligand stimulation.

The initial studies in human samples will measure interactions in patient tumors with and without EGFR mutation tumor sections. For these pilot studies, 20 cases with known EGFR mutation and 20 with wildtype EGFR will be chosen. It is expected to find higher PLA signals in the tumors with mutations and this will provide experience and confidence with human samples. To guide assay refinement in FFPE specimens, control tissue sections from PC9 cell xenografts will be included. Tumors from untreated mice and mice exposed to erlotinib will be collected—the erlotinib treated mice will have EGFR inhibition and loss of protein-protein interactions. Thus, they serve as a control where it is expected to see reduced PLA intensity. This will offer both positive and negative/down-regulated control for the downstream patient tissue samples, and also serve as a materials to optimize conditions for different antibodies for immunohistochemistry (IHC). This is done even if all the antibodies worked well by IF in cell lines.

Aim 3: Characterize Changes in EGFR Protein-Protein Interactions in Response to EGFR Tyrosine Kinase Inhibitors in Primary Lung Cancer Xenograft Models and Patient Samples.

EGFR inhibitors are predicted to disrupt signaling complexes on the EGFR protein. Protein interactions for some of these proteins can be inhibited by EGFR tyrosine kinase inhibitors (erlotinib). For example, the mass spectrometry data found that EGFR no longer bound Grb2, Mig6 or Sts1 with treatment of cells with erlotinib (data not shown). Primary lung cancer xenograft systems and samples from patients before and after EGFR inhibitor therapy will be used to measure differences in EGFR protein-protein interactions. This could allow the development of PLA based assays as pharmacodynamic markers of drug activity. First, primary lung cancer explant models will be used. A series of primary human NSCLC xenograft models from fresh patient tumor samples has been developed. Detailed morphological and molecular studies demonstrated that tumors that grew in the xenograft lines closely resemble the primary tumors, thus, the serially passaged xenografts provide a more clinically relevant model than established cell lines. Of the 11 models, 5 have KRAS mutations and one has a drug sensitive EGFR mutation. Tumors from each mouse will have a core biopsy before and after 7 days of erlotinib (100 mg/kg/day oral gavage). Tumors will be formalin fixed and sectioned for PLA assays. Here it is expected to find reductions in proteins in complex with EGFR as erlotinib would reduce the levels of tyrosine phosphorylated EGFR and disrupt binding of proteins such as Grb2 or Mig6. Second, patient samples treated with EGFR TKI will be used. The inventor just reported a pilot study of gefitinib in early stage NSCLC where patients received 4 weeks of gefitinib prior to having surgical resection of lung cancer (43). This study procured pre-treatment biopsies (FFPE) and post-treatment biopsies (FFPE sample of surgical specimen) for each of 23 patients on the study. Changes in EGFR PPI will be determined using PLA on these tumor samples. Measurements of EGFR PPI using PLA will be analyzed from the pre-treatment sample and again on the post-treatment sample. Here, it is expected that gefitinib will reduce interactions with EGFR.

Aim 4: Determine if EGFR Protein-Protein Interactions are Associated with Responses to EGFR Tyrosine Kinase Inhibitors in Human Lung Cancer Samples.

The inventor proposes that quantitative measurements of EGFR protein-protein interactions can be used as biomarkers to predict activity of EGFR kinase inhibitors in patients with advanced lung cancer. PLA assays for EGFR protein-protein interactions in lung cancer samples will be developed and these measurements will be related to response to EGFR inhibitors in a group of patients with advanced lung cancer. The Moffitt Lung Cancer Program and SPORE has outstanding access to tumor samples for these studies. The inventor has identified 822 patients treated with EGFR TKI at Moffitt in the last 15 years. Of these patients, 193 have tissue available at Moffitt. Tissue microarrays will be created from these samples and used for PLA based assays. The inventor's laboratory has experience with constructing tissue microarrays used for multiple studies of biomarkers related to patient outcomes (44-47). The inventor will correlate PLA biomarkers with response to EGFR TKI. Tumors from patients who received EGFR TKI (erlotinib or gefitinib) will be tested for PLA biomarkers and intensity related to (i) response measured by RECIST and (ii) disease-free survival and (iii) overall survival. It is expected that patients with higher levels of PLA biomarkers to have better responses and better survival with EGFR TKI. To avoid the problem of identifying a prognostic biomarker, a cohort of patients who received cytotoxic chemotherapy as their treatment will also be examined. Here it is expected to find no difference if (i) PLA biomarkers are predictive of outcome for EGFR TKI and (ii) not prognostic in advanced lung cancer. The SPORE is currently producing a second TMA for patients with advanced stage IV non-small cell lung cancer who received chemotherapy at Moffitt. This includes a cohort of nearly 200 cases of patients that had a prior surgical procedure and thus have tissue blocks with adequate tissue to produce tissue arrays. One of the SPORE pathologists is currently building these TMA and clinical data on these patients is being annotated through the SPORE infrastructure. Data elements include age, sex, race, histology, clinical and pathological stage at presentation, sites of metastatic disease, response to therapy (by RECIST) and overall survival times.

Statistical Considerations and Approaches: Proximity ligation assay (PLA) will be used to quantify EGFR protein-protein interactions. PLA's measurement consists of number of foci and signal intensities for each focus. Histograms and boxplots will be used to visualize and examine the sampling distributions of number of foci, total intensities, and mean intensity per focus. Normality of the data will be examined using the Anderson-Darling test. Proper transformation such as log or square root will be explored before applying parametric tests to the data. The goal for specific Aim 2 is to correlate each EGFR protein interaction of interests, quantified using PLA, to the EGFR mutation status of cell lines. After proper transformation, two-sample t-test will be performed to examine whether the signal intensities differ between cell lines with and without EGFR mutations. When the assumption of normality is violated, Mann-Whitney U tests will be applied. Limited attention has been given to the potential of using PLA measurements as biomarkers in the past, and the utility of using the number of foci as potential biomarkers is being explored. After examining the sampling distribution, if appropriate, it will be investigated if the number of foci differs between cell lines with and without EGFR mutations using Poisson regression. Over-dispersion will be examined. With a maximum of 6 proposed interactions in this work, final number of tests (i.e., total number of interactions) will be determined by assay development for Aim 1. The same analysis procedure will be carried out for the data collected from clinical samples. The goal for specific Aim 3 is to assess if there is a difference for each protein interaction, quantified by PLA, before and after EGFR TKI (erloitnib) treatment. The Pre- and post-treatment samples will be taken from the same xenograph mouse. Paired t-tests or Wilcoxon signed-rank tests will be performed to examine the difference of the signal intensities between pre- and post-treatment for each EGFR protein interaction. The same analysis procedure will be performed for the clinical samples. The goal for specific Aim 4 is to identify if each of the EGFR protein-protein interactions is a predictive factor to EGFR tyrosine kinase inhibitors (TKI) but not a general prognostic factor (following the definitions provided by Clark(48, 49). Briefly, a predictive factor has a differential benefit from the TKI treatment that depends on the status of the predictive biomarker while a prognostic factor is thought of as a measure of the natural history of the disease. In statistical terms, a predictive factor could be identified when the interaction term between treatment group and biomarker status in the statistical model is significant. The EGFR protein-protein interactions will be quantified for ~193 human lung cancer samples from patients with advanced stage and about same amount of samples from patients treated with chemotherapy using the tissue microarray arrays (TMAs). The inventor will first examine if there is any spatial heterogeneity visually using heat map as well as analytically using regression models (50, 51). Each EGFR protein-protein interaction will be classified as high- or low-expression group by searching the optimal cut point using the maximal logrank method with adjusted P-values for multiple looks, the association between the overall survival of patients and high- and low-expression groups will be assessed using the Kaplan-Meier curve and log-rank test. Gender, histology, and smoking status will be included along with the treatment group (EGFR TKI vs. chemotherapy) and biomarker status (high vs. low) in the multivariable Cox regression model. The interaction term between treatment group and biomarker status will be tested to determine if the EGFR protein-protein interaction is a predictive marker. Stratified analyses will also be performed and facilitate the visualization of the differential clinical benefit for the patients in different biomarker group using Kaplan Meier curve. For each pair of EGFR protein-protein interaction, one Cox multivariable regression model will first be performed. The assumption of proportional hazards will be evaluated by examining residual plots and by including time-dependent terms in the models. Similar analyses will be performed for the disease free survival. After proper transforming the signal intensity for each EGFR protein-protein interaction, one-way ANOVA will be performed to examine the intensity difference among different response groups (CR/PR, SD, and PD). When parametric assumptions are violated, KruskalWallis test will be performed. The overall goal is to develop and evaluate the proximity ligation assays for each pair of protein interactions to examine if they are effective biomarkers. Multiple hypothesis testing will be addressed using 10% false discovery rate to declare statistical significance. Limited preliminary data are currently available, and no statistical power is calculated for sample size justification. The experiments proposed in this work will give us better estimate of the effective size and sample size for future work. To examine if each protein-protein interaction is a good biomarker to classify disease control (CR/PR/SD) from disease progression (PD), the inventor will evaluate the sensitivity and specificity. ROC analysis will be performed to evaluate the area under the curve (AUC) considering different thresholds. Combination of several markers may lead to a more accurate classification, all selected and quantified biomarkers will be included and examined using several multivariable models such as logistic regression and methods with built-in variable selection procedures such as Hybrid huberized support vector machines (HHSVM) and Bayesian variable selection approach (52, 53).

The rich MS data that has been experimentally generated for protein pairs can be capitalized upon to evaluate and test for interaction. Numerous papers have been published on PLA (23, 25-27, 54). Small interfering RNA (siRNA) molecules can be used to eliminate proteins in PLA assays as another method to develop specific assays (55). The inventor expects that siRNA treated cells will show reduced or absent signaling from PLA assays demonstrating specificity of the assay against the interaction studied. The inventor has substantial experience with AQUA; HistoRx will provide additional expertise and advice, such as providing lists of validated antibodies and help with troubleshooting (46, 47, 56-58).

The SPORE and Moffitt Total Cancer Care initiative have standard operating protocols to minimize these variables. Spatial heterogeneity in interactions measured by PLA could be observed across a tumor. Core to core variation can be examined as it is typical to have 3 cores per tumor for the tissue microarrays. Whole sections of tumors can also be examined to determine spatial variability of PLA signals within the same tumor. The PLA signals may be relatively weak compared to those in conventional AQUA targets detected with IF. However, one advantage of the new version of AQUA is better dynamic range that can distinguish those with higher and lower in PPI signal detected with PLA even with a lower cutoff. Finally, most of the interactions being examined are based on phosphorylation dependent interactions (for example, phosphotyrosine motifs interacting with Src homology-2 (SH2) domains). Thus, some signals could be weak if samples are not prepared well and phosphorylation maintained. The ability exists to examine other signals that are likely more stable based on the MS data (FIGS. 1A-1D); this includes Hsp90:EGFR, Hsp90:Cdc37, and other binary interactions.

FIGS. 3A-F show results of an EGFR-GRB2 PLA in situ. FIGS. 4A-B show results of EGFR-Grb2 PLA in the PC9 lung cancer cell line. FIGS. 5A-B show results of EGFR-Grb2 PLA in lung cancer tumor tissues (in vivo). FIGS. 6A-B show results of ALK-Grb2 PLA in H3122 cells. FIGS. 7 and 8 show, respectively, results of EGFR:Grb2 PLA in cell lines related to EGFR mutation status, and results of EGFR:Grb2 in the 21 tissue microarray related to EGFR and KRAS mutation.

Example 2—Duolink to Test Egfr and Grb2 Interaction

Reagent Information:
Antibody:
  rGRb2 (Rabbit polyclone: C23, SC-255 Santa Cruz),
  mEGFR (mouse monoclonal antibody, LS-C88071/21583, LIFESPAN Biosciences)
  Working dilutions: m-EGFR (1:250)+r-GRb2 (1:100)
  Each well is one square cm, so at least 44 ul/well of PLA solution is needed. But 100 ul for antibodies and 250 ul for washing solutions are applied.

Experimental Procedure:
1. Plate approximately $3 \times 10^4$ cells in 350 □01 media per well of a Lab-Tek II 8-well chamber slide. Grow cells for 36 hours.
2. Aspirate media and add 250 µl 4% paraformaldehyde in PBS per well with a subsequent incubation for 20 minutes at 4°.
3. Aspirate the paraformaldehyde, then go to step 4.
4. 250 µl 0.5% TRITON-X 100 per well from a 10% stock diluted in PBS with a subsequent incubation for 10 minutes at room temperature with gently rocking. Aspirate the TRITON-X 100, wash each well once with 250 µl PBS, and add 250βl 1.5% BSA in PBS (from 10× stock) per well for blocking with gentle rocking for 30 minutes at room temperature.
5. Add the appropriate primary antibodies [m-EGFR (1:250)+r-GRb2 (1:100)] in PBS and incubate at room temperature for 2 hours with gentle rocking.
6. Aspirate the primary antibody solution and wash each well briefly, 3× with 250 µl of 1×PBS.
7. Secondary antibody-PLA probes: Mix and dilute the two PLA probes 1:5 in PBS (9 µl minus +9 µl plus +27 µl PBS=45/well but 44/well, (otherwise the wells could not be covered), incubate the slides in a pre-heated humidity chamber for 1 hour at 37 C.
8. Ligation: Dilute the Ligation stock 1:5 in MQW while waiting (9 µl minus +36 µl MQW=45). Aspirate the PLA probes and wash 2×2 minutes in PBS rocking. Then, add Ligase into ligation solution 1:40 then add 44 µl/well, immediately incubate for 30 minutes at 37 C.
9. Amplification-hybridations-fluorecences probes: Dilute the Amplification stock 1:5 in MQW while waiting (9 µl minus +36 µl MQW=45). Aspirate the Ligation solution and wash 2×2 minutes in PBS rocking, then add Polymerase 1:80 into amplification solution, add polymerase-amplification solution 44 µl/well, incubate for 100 minutes at 37 degrees C. (avoid light).
10. Aspirate the amplification solution wash with 1× Wash Buffer B for 2×10 minutes Wash the slide in 0.1× Wash Buffer B. Let the slides dry at RT in the dark. Mount the slides with Duolink II Mounting Medium. Dry it for overnight (avoid light throughout the step).
11. Observe under confocal microscopy.

Example 3—Duolink to Test Egfr and Grb2 Interaction in Formalin-Fixed Paraffin-Embedded (ffpe) Tissue/Cell Pellets Reagent Information:
Antibodies for FFPE tissues and FFPE cell pellets:
mEGFR (LIFESPAN Bioscie, LS-C88071/21583), 1:50
rGrb2 (Santa Cruz polyclone C23, SC-255), 1:50
Experimental Procedure:
1. Cut slides in 3 um using window type transfer system and adhesive coated slides (Instrumedics). After UV exposure for one minute, peel the tape in TPC solvent, than hydration of tissue/cells section.

2. Put slides in PT4 media and heat with microwave for ten minutes, and then cool down for thirty minutes at room temperature.
3. Add 250 µl 0.5% TRITON-X 100 per well from a 10% stock diluted in PBS with a subsequent incubation for 10 minutes at room temperature with gently rocking. Aspirate the TRITON-X 100, wash each well once with 250 µl PBS, and add 250 µl 1.5% BSA in PBS (from 10× stock) per well for blocking with gentle rocking for thirty minutes at room temperature.
4. Add the appropriate primary antibodies at the pre-determined optimal concentration (see the layout above) in PBS and incubate at room temperature for over night at 4 C with gentle rocking.
5. Aspirate the primary antibody solution and wash the slides briefly three times with 250 µl in PBS.
6. Prepare and incubate secondary antibody-PLA probes: Mix and dilute the two PLA probes 1:5 in PBS (9 µl minus +9 µl plus +27 ul PBS=45/well but 44/squar cm to cover the whole section), add 88 ul Mixed PLA probes/well, incubate the slides in a pre-heated humidity chamber for one hour at 37 degrees C.
7. Ligation: Dilute the Ligation stock 1:5 in MQW while waiting (9 ul minus +36 µMQW=45 µl). Aspirate the PLA probes and wash two times, each for 2 minutes in PBS with gently rocking, Then, add ligase into ligation solution 1:40 then add 44 µl/section, immediately incubate for thirty minutes at 37 degrees C.
8. Prepare and incubate the amplification-hybridization-fluorescence probes: Dilute the amplification stock 1:5 in MQW while waiting (9 µl minus +36 MQW=45). Aspirate the Ligation solution and wash two minutes in PBS rocking two times, then add polymerase 1:80 into amplification solution, add polymerase-amplification solution 44 ul/well, incubate for 100 minutes at 37 degrees C. (avoid light).
9. Aspirate the Amplification solution, wash with 1× Wash Buffer B for 10 minutes for 2 times. Pip the slides in 0.1× Wash Buffer B (Duolink). Then WGA (this step can be omitted) for five minutes (avoid light).
10. Wash with PBS five minutes for three times. Then let the slides dry at room temperature in a dark chamber for twenty minutes. Mount the dried slides with Mounting Medium. Dry the slides for overnight before observation with confocal microscopy.

Example 4—Protein-Protein Interactions for all Human Tyrosine Kinases

Bioinformatic tools were used to identify all reported protein-protein interactions for all human tyrosine kinases (2,848 interactions).
1) 90 of TK (tyrosine kinase) protein were queried from Kinase.com and verified and annotated with gene symbol. Kinase.com is produced by at the Salk Institute and has the full complement of protein kinases in any sequenced genome, including extensive KinBase database, papers and supporting material from Sugen and the Salk Institute.
2) The list of the TK gene symbol was queried with MiMI (Michigan Molecular Interactions) plug from Cytoscape, an open-source software platform for visualizing complex networks and integrating these with any type of attribute data. The network data were save as an Excel file. The NCIBI MiMI is part of the NIH's National Center for Integrative Biomedical Informatics (NCIBI), which provides access to the knowledge and data merged and integrated from numerous protein interactions databases.
3) 90 TK proteins have been reported for interaction with 1,104 proteins, and 2,848 interactions have been reported. The interactions were verified via the following databases: BIND, CCSB, DIP, GRID, HPRD, IntAct, MDC, MINT, reactome and PubMed. The interaction network was rebuilt with Cytoscape.

Some of the resulting data is presented in Tables 3-5. Tables 3 and 4 list ninety human tyrosine kinases, with aliases and accession numbers. Table 5 lists human tyrosine kinase interactions (node 1=tyrosine kinase; node 2=interacting protein).

TABLE 3

Human Tyrosine Kinases (with aliases)

| Gene ♦ | Species↑ | Classification ♦ | Other Names |
|---|---|---|---|
| ABL1 | Human | TK:Abl: | c-ab1, c-ABL, JTK7, p150, ABL1, ABL, v-abl |
| ABL2 | Human | TK:Abl: | ABLL, ARG, ABL2, ABLL |
| ACK | Human | TK:Ack: | ACK1, TNK2, ACK, ACK1, FLJ44758, FLJ45547, p21cdc42Hs |
| ALK | Human | TK:ALK: | ALK, CD246, TFG/ALK |
| AXL | Human | TK:Axl: | UFO, Ark, AXL, UFO |
| BLK | Human | TK:Src:SrcB | MGC10442, BLK, MGC10442 |
| BMX | Human | TK:Tec: | PSCTK3, PSCTK2, ETK, BMX, PSCTK3 |
| BRK | Human | TK:Src:SRM | PTK6, PTK6, BRK, FLJ42088 |
| BTK | Human | TK:Tec: | XLA, PSCTK1, IMD1, BPK, ATK, AGMX1, AT, BTK, MGC126261, MGC126262, XLA |
| CCK4 | Human | TK:CCK4: | PTK7, PTK7, CCK4 |
| CSK | Human | TK:Csk: | CYL, CSK, MGC117393 |
| CTK | Human | TK:Csk: | MGC2101, MGC1708, Lsk, HYL, HHYLTK, DKFZp434N1212, CHK, MATK, CTK, HYLTK, MGC2101 |
| DDR1 | Human | TK:DDR: | trkE, TRKE, RTK6, PTK3A, PTK3, NTRK4, MCK10, EDDR1, DDR, NEP, CAK, DDR1, CD167 |
| DDR2 | Human | TK:DDR: | TYRO10, NTRKR3, TKT, DDR2, MIG20a, TYRO10 |
| EGFR | Human | TK:EGFR: | ERBB1, ERBB, EGFRvIII, EGFR, ERBB1, mENA |
| EphA1 | Human | TK:Eph: | EPHT1, EPHT, EPH, EPHA1, EPHT1, MGC163163 |

TABLE 3-continued

Human Tyrosine Kinases (with aliases)

| Gene | Species | Classification | Other Names |
|---|---|---|---|
| EphA10 | Human | TK:Eph: | EPHA10, FLJ16103, FLJ33655, MGC43817 |
| EphA2 | Human | TK:Eph: | ECK, EPHA2, ECK |
| EphA3 | Human | TK:Eph: | HEK4, HEK, ETK1, TYRO4, ETK, EPHA3, HEK4 |
| EphA4 | Human | TK:Eph: | TYRO1, HEK8, EPHA4, SEK, TYRO1 |
| EphA5 | Human | TK:Eph: | Hs.31092, Hs.194771, HEK7, EPHA5, CEK7, EHK1, TYRO4 |
| EphA6 | Human | TK:Eph: | EPHA6, DKFZp434C1418, EPA6, FLJ35246, PRO57066 |
| EphA7 | Human | TK:Eph: | HEK11, EPHA7, EHK3, HEK11 |
| EphA8 | Human | TK:Eph: | KIAA1459, HEK3, EEK, EPHA8, KIAA1459 |
| EphB1 | Human | TK:Eph: | Hek6, HEK6, EPHT2, ELK, NET, EPHB1, FLJ37986 |
| EphB2 | Human | TK:Eph: | Tyro5, Hek5, HEK5, EPHT3, DRT, ERK, EPHB2, CAPB, MGC87492, PCBC, Tyro5 |
| EphB3 | Human | TK:Eph: | TYRO6, HEK2, ETK2, EPHB3, TYRO6 |
| EphB4 | Human | TK:Eph: | TYRO11, MYK1, HTK, EPHB4, TYRO11 |
| EphB6 | Human | TK:Eph: | HEP, EPHB6, HEP, MGC129910, MGC129911 |
| ErbB2 | Human | TK:EGFR: | c-erbB2, c-erbB-2, TKR1, NGL, Hs.323910, Hs.103992, HER2, HER-2, NEU, ERBB2, HER-2/neu, c-erb B2 |
| ErbB3 | Human | TK:EGFR: | Hs.199067, Hs.167387, Hs.167386, HER3, ERBB3, ErbB-3, MDA-BF-1, MGC88033, c-erbB-3, c-erbB3, erbB3-S, p180-ErbB3, p45-sErbB3, p85-sErbB3 |
| ErbB4 | Human | TK:EGFR: | HER4, ERBB4, HER4, MGC138404, p180erbB4 |
| FAK | Human | TK:FAK: | pp125FAK, FAKpp125, FAK1, FADK, PTK2, FAK, pp125FAK |
| FER | Human | TK:Fer: | TYK3, NCP94, FER, TYK3 |
| FES | Human | TK:Fer: | FPS, FES, FPS |
| FGFR1 | Human | TK:FGFR: | LOC51033, N-SAM, FLT2, FLJ14326, CEK, C-FGR, BFGFR, H5, H4, H3, H2, FLG, FGFR1, CD331, FGFBR, HBGFR, KAL2, N-SAM |
| FGFR2 | Human | TK:FGFR: | TK25, TK14, KGFR, K-SAM, JWS, ECT1, CFD1, CEK3, BFR-1, BEK, FGFR2, CD332, TK25 |
| FGFR3 | Human | TK:FGFR: | FGFR3, ACH, CD333, CEK2, HSFGFR3EX, JTK4 |
| FGFR4 | Human | TK:FGFR: | TKF, JTK2, FGFR4, CD334, MGC20292, TKF |
| FGR | Human | TK:Src:SrcA | SRC2, FGR, FLJ43153, MGC75096, SRC2, c-fgr, c-src2, p55c-fgr, p58c-fgr |
| FLT1 | Human | TK:VEGFR: | VEGFR1, VEGFR-1, FLT-1, FLT, FLT1, VEGFR1 |
| FLT3 | Human | TK:PDGFR: | FLK2, CD135, STK1, FLT3, FLK2 |
| FLT4 | Human | TK:VEGFR: | VEGFR3, PCL, FLT4, FLT41, VEGFR3 |
| FMS | Human | TK:PDGFR: | CSF-1R, CD115, CSF1R, C-FMS, CSFR, FIM2, FMS |
| FRK | Human | TK:Src:Frk | RAK, GTK, FRK, PTK5, RAK |
| FYN | Human | TK:Src:SrcA | MGC45350, SYN, SLK, FYN, MGC45350 |
| HCK | Human | TK:Src:SrcB | p59hck, p56hck, JTK9, HCK |
| IGF1R | Human | TK:InsR: | JTK13, IGF1R, CD221, IGFIR, JTK13, MGC142170, MGC142172, MGC18216 |
| INSR | Human | TK:InsR: | INSR, CD220, HHF5 |
| IRR | Human | TK:InsR: | INSRR, INSRR, IRR |
| ITK | Human | TK:Tec: | LYK, PSCTK2, EMT, ITK, LYK, MGC126257, MGC126258 |
| JAK1 | Human | TK:Jak: | JAK1A, JAK1, JAK1A, JAK1B |
| JAK2 | Human | TK:Jak: | JAK2 |
| JAK3 | Human | TK:Jak: | LJAK, L-JAK, JAKL, JAK3, JAK-3, JAK3_HUMAN, LJAK |
| KDR | Human | TK:VEGFR: | VEGFR2, VEGFR-2, VEGFR, Hs.KDR, Hs.12337, FLK1, FLK-1, KDR, CD309, VEGFR2 |
| KIT | Human | TK:PDGFR: | SCFR, CD117, PBT, KIT, C-Kit, SCFR |
| LCK | Human | TK:Src:SrcB | p56lck, LCK, YT16, p56lck, pp58lck |
| LMR1 | Human | TK:Lmr: | KIAA0641, AATYK, AATK, KIAA0641, LMR1, LMTK1 |
| LMR2 | Human | TK:Lmr: | KIAA1079, LMTK2, AATYK2, BREK, KIAA1079, KPI-2, KPI2, LMR2, cprk |
| LMR3 | Human | TK:Lmr: | LMTK3, KIAA1883, LMR3, TYKLM3 |
| LTK | Human | TK:ALK: | TYK1, LTK, TYK1 |
| LYN | Human | TK:Src:SrcB | JTK8, LYN, FLJ26625, JTK8 |
| MER | Human | TK:Axl: | mer, c-mer, C-MER, MERTK, MER, MGC133349 |
| MET | Human | TK:Met: | HGFR, C-MET, RCCP2, MET, HGFR |
| MUSK | Human | TK:Musk: | MUSK, MGC126323, MGC126324 |
| PDGFRa | Human | TK:PDGFR: | PDGFR2, CD140A, PDGFRA, MGC74795, PDGFR2, Rhe-PDGFRA |
| PDGFRb | Human | TK:PDGFR: | PDGFR1, PDGFR, PDGF-R-beta, JTK12, CD140B, PDGFRB, PDGFR1 |
| PYK2 | Human | TK:FAK: | PTK2B, PKB, CADTK, CAKB, CAK_beta, FAK2, PTK, RAFTK, FADK2, PYK2, RAFTK |
| RET | Human | TK:Ret: | PTC, CDHF12, HSCR1, Hs.168114, Hs.RET, MEN2A, MEN2B, MTC1, RET51, RET, RET-ELE1, RET51 |
| RON | Human | TK:Met: | MST1R, CDw136, CDw136, PTK8, RON |

TABLE 3-continued

Human Tyrosine Kinases (with aliases)

| Gene ◆ | Species ↑ | Classification ◆ | Other Names |
|---|---|---|---|
| ROR1 | Human | TK:Ror: | NTRKR1, dJ537F10.1, ROR1, MGC99659, dJ537F10.1 |
| ROR2 | Human | TK:Ror: | BDB, BDB1, NTRKR2, ROR2, MGC163394, NTRKR2 |
| ROS | Human | TK:Sev: | ROS1, MCF3, MCF3, ROS |
| RYK | Human | TK:Ryk: | D3S3195, RYK1, RYK, JTK5, JTK5A, RYK1 |
| SRC | Human | TK:Src:SrcA | SRC1, ASV, SRC, ASV, c-SRC, p60-Src |
| SRM | Human | TK:Src:SRM | SRMS, C20orf148, SRM, dJ697K14.1 |
| SuRTK106 | Human | TK:TK-Unique: | DKFZp761P1010, DKFZP761P1010, STYK1, NOK, SuRTK106 |
| SYK | Human | TK:Syk: | SYK |
| TEC | Human | TK:Tec: | PSCTK4, TEC, MGC126760, MGC126762, PSCTK4 |
| TIE1 | Human | TK:Tie: | TIE, JTK14, TIE1, JTK14 |
| TIE2 | Human | TK:Tie: | VMCM1, TEK, HPK-6, TIE-2, VMCM, CD202B, TIE2, VMCM1 |
| TNK1 | Human | TK:Ack: | TNK1, MGC46193 |
| TRKA | Human | TK:Trk: | NTRK1, TRK, MTC, TRK-A, DKFZp781I14186, TRK1, TRKA, p140-TrkA |
| TRKB | Human | TK:Trk: | NTRK2, NTRK2, GP145-TrkB, TRKB |
| TRKC | Human | TK:Trk: | NTRK3, NTRK3, TRKC, gp145(trkC) |
| TXK | Human | TK:Tec: | BTKL, PSCTK5, RLK, TKL, TXK, MGC22473, PTK4, TKL |
| TYK2 | Human | TK:Jak: | JTK1, TYK2, JTK1 |
| TYRO3 | Human | TK:Axl: | DTK, RSE, SKY, TIF, TYRO3, BYK, Brt, Tif |
| YES | Human | TK:Src:SrcA | YES1, C-YES, P61-YES, c-yes, HsT441, Yes |
| ZAP70 | Human | TK:Syk: | STD, SRK, ZAP-70, ZAP70, TZK, ZAP-70 |

TABLE 4

Human Tyrosine Kinases (with accession numbers)

| Gene_Symbol | Probeset | Accession | Gene_ID |
|---|---|---|---|
| ABL1 | 202123_s_at | NM_005157 NM_007313 | 25 |
| ABL2 | 231907_at 206411_s_at 226893_at | NM_005158 NM_001168237 NM_001168239 NM_007314 NM_001136000 NM_001168236 NM_001168238 | 27 |
| TNK2 | 203839_s_at 216439_at 1555557_a_at 228279_s_at 203838_s_at | AK225786 NM_001010938 NM_005781 AB209338 | 10188 |
| ALK | 208211_s_at 208212_s_at | NM_004304 | 238 |
| AXL | 202685_s_at 202686_s_at | NM_001699 NM_021913 | 558 |
| BLK | 244394_at 236820_at 206255_at 210934_at | NM_001715 NG_023543 BC038555 | 640 |
| BMX | 206464_at 242967_at | NM_203281 NG_013227 NM_001721 | 660 |
| PTK6 | 1553114_a_at | NM_005975 | 5753 |
| BTK | 205504_at | NM_000061 | 695 |
| PTK7 | 1555324_at 207011_s_at | BC046109 NM_002821 NM_152881 NM_152880 NM_152882 | 5754 |
| CSK | 202329_at | NM_001127190 NM_004383 | 1445 |
| MATK | 206267_s_at | NM_002378 NM_139354 NM_139355 | 4145 |
| DDR1 | 208779_x_at 207169_x_at 210749_x_at 1007_s_at | NM_001202523 NM_001202521 NM_013993 NM_001202522 NM_001954 NM_013994 | 780 |
| DDR2 | 227561_at 205168_at | NM_001014796 NM_006182 AY423733 | 4921 |
| EGFR | 211550_at 210984_x_at 211551_at 211607_x_at 201984_s_at 201983_s_at 1565483_at 1565484_x_at | NM_201284 NM_201282 NM_201283 NM_005228 K03193 | 1956 |
| EPHA1 | 215804_at 205977_s_at | NM_005232 EU826604 | 2041 |
| EPHA10 | 1553371_at 236073_at | NM_001099439 NM_173641 | 284656 |
| EPHA2 | 203499_at | NM_004431 | 1969 |
| EPHA3 | 206071_s_at 206070_s_at 211164_at | NM_182644 NM_005233 | 2042 |
| EPHA4 | 227449_at 228948_at 229374_at 206114_at | NM_004438 | 2043 |
| EPHA5 | 215664_s_at 216837_at 237939_at | L36644 NM_004439 NM_182472 | 2044 |
| EPHA6 | 233184_at 1561396_at | NM_173655 NM_001080448 | 285220 |
| EPHA7 | 1554629_at 229288_at 238533_at 206852_at | NM_004440 BC027940 | 2045 |

TABLE 4-continued

Human Tyrosine Kinases (with accession numbers)

| Gene_Symbol | Probeset | Accession | Gene_ID |
|---|---|---|---|
| EPHA8 | 231796_at 1554069_at | NM_020526 NM_001006943 | 2046 |
| EPHB1 | 230425_at 211898_s_at 210753_s_at | NM_004441 | 2047 |
| EPHB2 | 209588_at 209589_s_at 211165_x_at 210651_s_at | NM_017449 NM_004442 | 2048 |
| EPHB3 | 204600_at 1438_at | NM_004443 | 2049 |
| EPHB4 | 202894_at 216680_s_at | NM_004444 | 2050 |
| EPHB6 | 204718_at | NM_004445 | 2051 |
| ERBB2 | 210930_s_at 216836_s_at | NM_001005862 NM_004448 | 2064 |
| ERBB3 | 1563252_at 202454_s_at 226213_at 1563253_s_at | NM_001982 U88360 | 2065 |
| ERBB4 | 206794_at 241581_at 233494_at 214053_at 233498_at | NM_001042599 AC108220 NM_005235 AK024204 | 2066 |
| PTK2 | 1559529_at 208820_at 207821_s_at 241453_at | NM_153831 NM_005607 AC105009 BC043202 NM_001199649 | 5747 |
| FER | 227579_at 206412_at | AC116428 NM_005246 | 2241 |
| FES | 205418_at | NM_001143783 NM_001143785 NM_002005 NM_001143784 | 2242 |
| FGFR1 | 215404_x_at 207822_at 226705_at 211535_s_at 210973_s_at 207937_x_at | AK024388 NM_023106 NM_015850 M34187 NM_023105 NM_001174067 NM_001174066 NM_001174065 NM_023110 NM_001174063 NM_001174064 | 2260 |
| FGFR2 | 211399_at 203639_s_at 208225_at 208234_x_at 211398_at 211401_s_at 208228_s_at 203638_s_at 211400_at | NM_001144915 NM_001144918 AB030077 NM_001144917 AB030075 M87772 NM_001144916 NM_001144913 NM_022970 NM_001144914 AB030073 NM_001144919 NM_000141 | 2263 |
| FGFR3 | 204380_s_at 204379_s_at | NM_000142 NM_001163213 NM_022965 | 2261 |
| FGFR4 | 1554961_at 211237_s_at 204579_at 1554962_a_at | NM_002011 NM_022963 AF359241 NM_213647 | 2264 |
| FGR | 208438_s_at | NM_001042729 NM_005248 NM_001042747 | 2268 |
| FLT1 | 210287_s_at 226497_s_at 222033_s_at 226498_at | NM_001159920 NM_002019 | 2321 |
| FLT3 | 206674_at | NM_004119 | 2322 |
| FLT4 | 234379_at 210316_at 229902_at | NM_002020 NM_182925 | 2324 |
| CSF1R | 203104_at | NM_005211 | 1436 |
| FRK | 207178_s_at | NM_002031 | 2444 |
| FYN | 217697_at 210105_s_at 216033_s_at | NM_002037 NM_153048 AL109916 NM_153047 | 2534 |
| HCK | 208018_s_at | NM_001172129 NM_001172131 NM_002110 NM_001172130 NM_001172133 NM_001172132 | 3055 |
| IGF1R | 208441_at 243358_at 203627_at 225330_at 238544_at 237377_at 237881_at 203628_at | AF020763 AC055807 NM_000875 | 3480 |
| INSR | 227432_s_at 226450_at 213792_s_at 243002_at 226212_s_at 226216_at 207851_s_at | NM_000208 AB208861 AC010526 NM_001079817 | 3643 |
| INSRR | 215776_at | NM_014215 | 3645 |
| ITK | 211339_s_at | NM_005546 | 3702 |
| JAK1 | 1552611_a_at 239695_at 1552610_a_at 201648_at | NM_002227 BX648044 | 3716 |
| JAK2 | 205842_s_at 205841_at 1562031_at | NM_004972 BC043187 | 3717 |
| JAK3 | 211109_at 211108_s_at 207187_at 227677_at | NM_000215 U31601 | 3718 |
| KDR | 203934_at | NM_002253 | 3791 |
| KIT | 205051_s_at | NM_000222 NM_001093772 | 3815 |
| LCK | 204891_s_at 204890_s_at | NM_001042771 NM_005356 | 3932 |
| AATK | 205986_at | XR_115154 NM_001080395 XR_111752 | 9625 |
| LMTK2 | 235307_at 206223_at 226375_at | NM_014916 NG_013375 | 22853 |
| LMTK3 | 1557103_a_at | NM_001080434 | 114783 |
| LTK | 207106_s_at 217184_s_at | NM_002344 NM_206961 NM_001135685 | 4058 |
| LYN | 202625_at 210754_s_at 202626_s_at | NM_001111097 NM_002350 | 4067 |
| MERTK | 211913_s_at 206028_s_at | NM_006343 | 10461 |
| MET | 213807_x_at 203510_at 211599_x_at 213816_s_at | NM_001127500 NM_000245 | 4233 |
| MUSK | 207632_at 207633_s_at 241122_s_at | NM_001166281 NM_001166280 NM_005592 | 4593 |
| PDGFRA | 211533_at 237696_at 1554828_at 203131_at 215305_at | L25829 AC098587 M22734 BC015186 NM_006206 | 5156 |
| PDGFRB | 202273_at | NM_002609 | 5159 |

TABLE 4-continued

Human Tyrosine Kinases (with accession numbers)

| Gene_Symbol | Probeset | Accession | Gene_ID |
|---|---|---|---|
| PTK2B | 203110_at 203111_s_at | NM_004103 NM_173175 NM_173174 NM_173176 | 2185 |
| RET | 215771_x_at 211421_s_at 205879_x_at | NM_020630 NM_020975 | 5979 |
| MST1R | 205455_at | NM_002447 | 4486 |
| ROR1 | 205805_s_at 211057_at | NM_001083592 NM_005012 | 4919 |
| ROR2 | 231000_at 205578_at | NM_004560 BC051273 | 4920 |
| ROS1 | 207569_at | NM_002944 | 6098 |
| RYK | 214172_x_at 202853_s_at 216976_s_at 238210_at | AC107310 NM_001005861 NM_002958 | 6259 |
| SRC | 1565082_x_at 237103_at 213324_at 1565080_at 221284_s_at 1558211_s_at | NG_023033 NM_198291 NM_005417 | 6714 |
| SRM | 201516_at | NM_003132 | 6723 |
| STYK1 | 221696_s_at 220030_at | NM_018423 | 55359 |
| SYK | 226068_at 209269_s_at 207540_s_at 244023_at | BX647192 NM_001135052 NM_001174168 NM_001174167 NM_003177 | 6850 |
| TEC | 206301_at | NM_003215 | 7006 |
| TIE1 | 1560657_at 204468_s_at | NM_005424 AL833389 | 7075 |
| TEK | 217711_at 206702_at | NM_000459 | 7010 |
| TNK1 | 217149_x_at 205793_x_at | NM_003985 | 8711 |
| NTRK1 | 208605_s_at | NM_001007792 NM_001012331 NM_002529 | 4914 |
| NTRK2 | 214680_at 207152_at 236095_at 221796_at 229463_at 221795_at | NM_006180 NM_001018065 NM_001007097 NM_001018064 BX649001 NM_001018066 | 4915 |
| NTRK3 | 217033_x_at 217377_x_at 215115_x_at 215025_at 206462_s_at 1557795_s_at 228849_at | NM_002530 NM_001012338 NM_001007156 | 4916 |
| TXK | 206828_at | NM_003328 | 7294 |
| TYK2 | 205546_s_at | NM_003331 | 7297 |
| TYRO3 | 211432_s_at 211431_s_at 1566934_at | NM_006293 X72886 | 7301 |
| YES1 | 202932_at 202933_s_at | NM_005433 | 7525 |
| ZAP70 | 1555613_a_at 214032_at | NM_207519 NM_001079 | 7535 |

TABLE 5

Human Tyrosine Kinase Interactions (node 1 = tyrosine kinase; node 2 = interacting protein)

| Node1 | Node2 | int_DataBase |
|---|---|---|
| AATK | STK39 | (GRID) |
| ABL1 | ABI1 | (BIND; GRID; HPRD) |
| ABL1 | ABI2 | (GRID; HPRD; MINT) |
| ABL1 | ABL2 | (BIND; GRID; HPRD) |
| ABL1 | ACTA1 | (HPRD) |
| ABL1 | ADAM15 | (GRID; HPRD) |
| ABL1 | APBB1 | (HPRD) |
| ABL1 | APP | (HPRD) |
| ABL1 | ATM | (DIP; GRID; HPRD; IntAct) |
| ABL1 | ATR | (GRID) |
| ABL1 | BCAR1 | (GRID; HPRD) |
| ABL1 | BCL2L1 | (MINT) |
| ABL1 | BCR | (BIND; GRID; HPRD) |
| ABL1 | BIN1 | (HPRD) |
| ABL1 | BRCA1 | (GRID; HPRD) |
| ABL1 | BTK | (HPRD) |
| ABL1 | C3 | (GRID; HPRD) |
| ABL1 | CABLES1 | (HPRD) |
| ABL1 | CABLES2 | (GRID; HPRD) |
| ABL1 | CASP9 | (HPRD) |
| ABL1 | CAV1 | (HPRD) |
| ABL1 | CBL | (GRID; HPRD; MINT) |
| ABL1 | CD19 | (HPRD) |
| ABL1 | CDC2 | (HPRD) |
| ABL1 | CDK5 | (HPRD) |
| ABL1 | CDKN1B | (HPRD) |
| ABL1 | CREB1 | (GRID) |
| ABL1 | CRK | (BIND; HPRD) |
| ABL1 | CRKL | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| ABL1 | CTNND2 | (GRID; HPRD) |
| ABL1 | DDB1 | (HPRD) |
| ABL1 | DDB2 | (HPRD) |
| ABL1 | DOK1 | (HPRD) |
| ABL1 | DOK3 | (HPRD) |
| ABL1 | EGFR | (MINT) |
| ABL1 | EP300 | (MINT) |
| ABL1 | EPHB2 | (GRID; HPRD) |
| ABL1 | ERBB2 | (MINT) |
| ABL1 | ERBB3 | (MINT) |
| ABL1 | ERBB4 | (MINT) |
| ABL1 | EVL | (GRID; HPRD) |
| ABL1 | GPX1 | (GRID; HPRD) |
| ABL1 | GRB10 | (GRID) |
| ABL1 | GRB2 | (GRID; HPRD) |
| ABL1 | GRIN2D | (HPRD; MINT) |
| ABL1 | HCK | (GRID; HPRD) |
| ABL1 | INPPL1 | (GRID; HPRD) |
| ABL1 | JAK1 | (GRID; HPRD) |
| ABL1 | JAK2 | (HPRD) |
| ABL1 | JUN | (HPRD) |
| ABL1 | KIT | (HPRD) |
| ABL1 | MAP4K1 | (HPRD) |
| ABL1 | MAP4K5 | (GRID; HPRD) |
| ABL1 | MAPT | (HPRD) |
| ABL1 | MDM2 | (GRID; HPRD) |
| ABL1 | MUC1 | (HPRD; MINT) |
| ABL1 | NCF1 | (BIND) |
| ABL1 | NCK1 | (GRID; HPRD) |
| ABL1 | NCSTN | (GRID; HPRD) |
| ABL1 | NEDD9 | (GRID; HPRD) |
| ABL1 | NTRK1 | (GRID; HPRD) |
| ABL1 | PAG1 | (GRID; HPRD) |
| ABL1 | PAK2 | (GRID; HPRD) |
| ABL1 | PDE4D | (BIND) |
| ABL1 | PIK3R1 | (BIND; GRID; HPRD) |
| ABL1 | PLCG1 | (BIND; HPRD) |
| ABL1 | PLSCR1 | (HPRD; MINT) |
| ABL1 | POLR2A | (HPRD) |
| ABL1 | PRKCD | (MINT) |
| ABL1 | PRKD1 | (HPRD) |
| ABL1 | PRKDC | (GRID; HPRD; MINT) |
| ABL1 | PSTPIP1 | (GRID; HPRD) |
| ABL1 | PTPN12 | (HPRD) |
| ABL1 | PTPN18 | (HPRD) |
| ABL1 | PTPN6 | (GRID; HPRD) |
| ABL1 | PXN | (GRID; HPRD) |
| ABL1 | RAD51 | (GRID; HPRD; MINT) |
| ABL1 | RAD52 | (HPRD) |
| ABL1 | RAD9A | (GRID; HPRD) |
| ABL1 | RAN | (GRID; HPRD) |
| ABL1 | RASA1 | (BIND; HPRD) |
| ABL1 | RB1 | (BIND; GRID; HPRD; MINT) |
| ABL1 | RFX1 | (GRID; HPRD) |
| ABL1 | RIN1 | (BIND; GRID; HPRD; IntAct; MINT) |
| ABL1 | ROBO1 | (BIND; HPRD) |
| ABL1 | ROS1 | (GRID; HPRD) |
| ABL1 | RYBP | (GRID) |
| ABL1 | SFN | (HPRD; IntAct) |
| ABL1 | SH3BP1 | (GRID) |
| ABL1 | SH3BP2 | (HPRD) |
| ABL1 | SHD | (GRID; HPRD) |
| ABL1 | SHE | (HPRD) |
| ABL1 | SLC9A2 | (GRID; HPRD) |
| ABL1 | SORBS1 | (GRID; HPRD) |
| ABL1 | SORBS2 | (GRID; HPRD) |
| ABL1 | SOS2 | (HPRD) |
| ABL1 | SRC | (BIND; HPRD) |
| ABL1 | ST5 | (GRID; HPRD) |
| ABL1 | TERT | (HPRD; MINT) |
| ABL1 | TP53 | (GRID; HPRD; MINT) |
| ABL1 | TP73 | (GRID; HPRD; MINT) |
| ABL1 | TRAF6 | (HPRD) |
| ABL1 | TUB | (GRID; HPRD) |
| ABL1 | WASF1 | (BIND; HPRD; MINT) |

TABLE 5-continued

Human Tyrosine Kinase Interactions (node 1 = tyrosine kinase; node 2 = interacting protein)

| Node1 | Node2 | int_DataBase |
|---|---|---|
| ABL1 | WASL | (HPRD) |
| ABL1 | XPO1 | (BIND) |
| ABL1 | XRCC6 | (GRID; HPRD) |
| ABL1 | YTHDC1 | (GRID; HPRD) |
| ABL1 | YWHAB | (HPRD) |
| ABL1 | YWHAE | (HPRD) |
| ABL1 | YWHAG | (HPRD) |
| ABL1 | YWHAH | (BIND; HPRD) |
| ABL1 | YWHAZ | (HPRD) |
| ABL1 | ZAP70 | (GRID; HPRD) |
| ABL1 | ZDHHC16 | (GRID; HPRD) |
| ABL2 | ABI2 | (BIND) |
| ABL2 | BCR | (BIND; HPRD) |
| ABL2 | CAT | (GRID; HPRD) |
| ABL2 | CRK | (BIND; GRID; HPRD; IntAct) |
| ABL2 | EGFR | (MINT) |
| ABL2 | EPHB2 | (HPRD) |
| ABL2 | ERBB2 | (MINT) |
| ABL2 | ERBB3 | (MINT) |
| ABL2 | ERBB4 | (MINT) |
| ABL2 | GPX1 | (HPRD) |
| ABL2 | HCK | (GRID; HPRD) |
| ABL2 | HRAS | (MINT) |
| ABL2 | JAK1 | (GRID) |
| ABL2 | ONECUT1 | (BIND) |
| ABL2 | RIN1 | (BIND; DIP; IntAct; MINT) |
| ABL2 | SIVA1 | (HPRD) |
| ABL2 | SORBS2 | (GRID; HPRD) |
| ALK | CENPF | (IntAct) |
| ALK | EIF4B | (IntAct) |
| ALK | EPHA1 | (IntAct) |
| ALK | EPHB3 | (IntAct) |
| ALK | HSP90AA1 | (GRID) |
| ALK | HSPD1 | (IntAct) |
| ALK | IRS1 | (GRID; HPRD; IntAct) |
| ALK | JAK3 | (GRID; HPRD) |
| ALK | MAP3K1 | (IntAct) |
| ALK | MAP3K3 | (IntAct; MINT) |
| ALK | MDK | (HPRD) |
| ALK | NPM1 | (HPRD) |
| ALK | PLCG1 | (GRID; HPRD) |
| ALK | PTN | (DIP; GRID; HPRD) |
| ALK | PTPRZ1 | (HPRD) |
| ALK | RASA1 | (GRID) |
| ALK | SHC1 | (GRID; HPRD) |
| ALK | SHC3 | (GRID; HPRD) |
| ALK | SOCS5 | (IntAct) |
| ALK | STAT3 | (IntAct) |
| ALK | TNFRSF8 | (HPRD) |
| ALK | ZC3HC1 | (HPRD) |
| AXL | ADAM10 | (HPRD) |
| AXL | CBL | (HPRD) |
| AXL | CSK | (BIND) |
| AXL | GAS6 | (GRID; HPRD; MINT) |
| AXL | GRB2 | (BIND; CCSB; GRID; HPRD) |
| AXL | IL15RA | (HPRD) |
| AXL | IL2RG | (HPRD) |
| AXL | LCK | (BIND; CCSB; GRID; HPRD) |
| AXL | NCK2 | (BIND; HPRD) |
| AXL | PIK3R1 | (BIND; HPRD) |
| AXL | PIK3R2 | (BIND; GRID; HPRD) |
| AXL | PIK3R3 | (BIND; HPRD) |
| AXL | PLCG1 | (BIND; HPRD) |
| AXL | PTPN11 | (HPRD) |
| AXL | RANBP9 | (BIND; HPRD) |
| AXL | SHC1 | (BIND; CCSB; GRID; HPRD) |
| AXL | SHC3 | (HPRD) |
| AXL | SOCS1 | (BIND; HPRD) |
| AXL | SRC | (CCSB; GRID; HPRD) |
| AXL | TENC1 | (BIND; GRID; HPRD) |
| BLK | BCAS2 | (GRID; HPRD) |
| BLK | BCL2 | (GRID; HPRD) |
| BLK | BCR | (GRID; HPRD) |
| BLK | CBL | (GRID; HPRD; MINT) |
| BLK | CD79A | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| BLK | CD79B | (GRID; HPRD) |
| BLK | CTR9 | (GRID; HPRD) |
| BLK | EGFR | (MINT) |
| BLK | ERBB2 | (MINT) |
| BLK | FCGR2A | (GRID; HPRD) |
| BLK | FCGR2B | (HPRD) |
| BLK | MAX | (BIND) |
| BLK | MYC | (BIND) |
| BLK | PLCG2 | (GRID; HPRD) |
| BLK | TAF1 | (BIND) |
| BLK | UBE3A | (GRID; HPRD) |
| BMX | BTK | (HPRD) |
| BMX | CASP3 | (CCSB; GRID; HPRD) |
| BMX | CAV1 | (CCSB; GRID: HPRD) |
| BMX | EGFR | (MINT) |
| BMX | ERBB2 | (MINT) |
| BMX | ITK | (HPRD) |
| BMX | KDR | (HPRD) |
| BMX | PAK1 | (GRID; HPRD) |
| BMX | PIM1 | (IntAct) |
| BMX | PTK2 | (CCSB; GRID; HPRD) |
| BMX | PTPN21 | (GRID; HPRD) |
| BMX | RAP1A | (HPRD) |
| BMX | RUFY1 | (BIND; CCSB; GRID; HPRD) |
| BMX | RUFY2 | (HPRD) |
| BMX | SRC | (CCSB; GRID; HPRD) |
| BMX | STAT1 | (CCSB; GRID; HPRD) |
| BMX | STAT3 | (CCSB; GRID; HPRD) |
| BMX | STAT5A | (CCSB; GRID; HPRD) |
| BMX | TEC | (HPRD) |
| BMX | TNFRSF1B | (HPRD) |
| BMX | TP53 | (IntAct) |
| BTK | ARID3A | (GRID; HPRD) |
| BTK | BLNK | (GRID; HPRD; MINT) |
| BTK | CAV1 | (GRID; HPRD) |
| BTK | CBL | (BIND; GRID; HPRD) |
| BTK | CD19 | (HPRD) |
| BTK | CMTM3 | (HPRD) |
| BTK | DAPP1 | (HPRD) |
| BTK | EWSR1 | (GRID; HPRD) |
| BTK | FAS | (GRID; HPRD) |
| BTK | FCER1G | (IntAct) |
| BTK | GNA12 | (GRID; HPRD) |
| BTK | GNAQ | (GRID; HPRD) |
| BTK | GNG2 | (HPRD) |
| BTK | GTF2I | (GRID; HPRD; IntAct) |
| BTK | HCK | (GRID; HPRD) |
| BTK | IBTK | (GRID; HPRD) |
| BTK | IRAK1 | (HPRD) |
| BTK | ITK | (HPRD) |
| BTK | JAK1 | (GRID; HPRD) |
| BTK | KHDRBS1 | (GRID; HPRD) |
| BTK | KIT | (HPRD) |
| BTK | LYN | (GRID; HPRD) |
| BTK | MAPK1 | (HPRD) |
| BTK | MYD88 | (HPRD) |
| BTK | PIK3AP1 | (HPRD) |
| BTK | PIP4K2A | (HPRD) |
| BTK | PIP4K2B | (HPRD) |
| BTK | PIP4K2C | (HPRD) |
| BTK | PIP5K1A | (HPRD) |
| BTK | PIP5K1B | (HPRD) |
| BTK | PIP5K1C | (HPRD) |
| BTK | PLCG1 | (HPRD) |
| BTK | PLCG2 | (HPRD) |
| BTK | PRKCA | (HPRD) |
| BTK | PRKCB1 | (HPRD) |
| BTK | PRKCE | (HPRD) |
| BTK | PRKCQ | (HPRD; IntAct) |
| BTK | PRKCZ | (HPRD) |
| BTK | PRKD1 | (BIND; GRID; HPRD) |
| BTK | RELA | (HPRD) |
| BTK | SH2B2 | (HPRD) |
| BTK | SH3BP5 | (GRID; HPRD; IntAct) |
| BTK | STAT5A | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| BTK | SYK | (HPRD) |
| BTK | TAF1 | (BIND) |
| BTK | TEC | (HPRD) |
| BTK | TIRAP | (HPRD) |
| BTK | TLR4 | (HPRD) |
| BTK | TLR6 | (HPRD) |
| BTK | TLR8 | (HPRD) |
| BTK | TLR9 | (HPRD) |
| BTK | TNFRSF10A | (HPRD) |
| BTK | VAV1 | (GRID; HPRD) |
| BTK | WAS | (GRID; HPRD) |
| BTK | WASF2 | (GRID; HPRD) |
| CSF1R | CBL | (GRID; HPRD) |
| CSF1R | CSF1 | (GRID; HPRD) |
| CSF1R | FYN | (GRID; HPRD) |
| CSF1R | GRAP2 | (GRID; HPRD) |
| CSF1R | GRB2 | (GRID; HPRD) |
| CSF1R | INPP5D | (BIND; HPRD) |
| CSF1R | INPPL1 | (BIND; HPRD) |
| CSF1R | LYN | (GRID; HPRD) |
| CSF1R | PIK3R1 | (BIND; GRID; HPRD) |
| CSF1R | PIK3R2 | (GRID; HPRD) |
| CSF1R | RASA1 | (GRID; HPRD) |
| CSF1R | RUNX1 | (BIND) |
| CSF1R | SHC1 | (HPRD) |
| CSF1R | SOCS1 | (BIND; GRID; HPRD) |
| CSF1R | SOCS3 | (GRID; HPRD) |
| CSF1R | SOS1 | (HPRD) |
| CSF1R | THOC5 | (HPRD) |
| CSF1R | YES1 | (GRID; HPRD) |
| CSK | ADRB2 | (HPRD) |
| CSK | ARRB1 | (GRID; HPRD) |
| CSK | CAV1 | (GRID; HPRD) |
| CSK | CBL | (GRID) |
| CSK | CD247 | (GRID; HPRD) |
| CSK | CD44 | (GRID; HPRD) |
| CSK | CDH5 | (BIND; HPRD) |
| CSK | CREBBP | (GRID; HPRD) |
| CSK | DAB2 | (GRID; HPRD) |
| CSK | DOK1 | (HPRD) |
| CSK | DOK3 | (HPRD) |
| CSK | EGFR | (BIND; GRID; MINT) |
| CSK | ERBB3 | (BIND; GRID; MINT) |
| CSK | FGR | (HPRD) |
| CSK | FYN | (GRID; HPRD) |
| CSK | GJA1 | (HPRD; MINT) |
| CSK | GSN | (HPRD) |
| CSK | HCK | (HPRD) |
| CSK | HNF4A | (BIND) |
| CSK | HNRPK | (GRID; HPRD) |
| CSK | IGF1R | (BIND; GRID; HPRD; MINT) |
| CSK | INSR | (BIND; GRID; HPRD) |
| CSK | LAIR1 | (HPRD) |
| CSK | LCK | (HPRD) |
| CSK | LYN | (HPRD) |
| CSK | MAPK15 | (HPRD) |
| CSK | PAG1 | (GRID; HPRD) |
| CSK | PARD3 | (MINT) |
| CSK | PECAM1 | (GRID; HPRD) |
| CSK | PLD2 | (GRID; HPRD) |
| CSK | PRKACA | (HPRD) |
| CSK | PTK2 | (GRID; HPRD) |
| CSK | PTPN12 | (GRID; HPRD) |
| CSK | PTPN18 | (GRID; HPRD) |
| CSK | PTPN22 | (HPRD) |
| CSK | PXN | (GRID; HPRD) |
| CSK | RASA1 | (GRID; HPRD) |
| CSK | RB1 | (HPRD) |
| CSK | RGS16 | (BIND; HPRD) |
| CSK | SDC3 | (GRID; HPRD) |
| CSK | SHC1 | (GRID; HPRD) |
| CSK | SIT1 | (GRID; HPRD) |
| CSK | SRC | (GRID; HPRD) |
| CSK | YES1 | (HPRD) |
| CSK | YTHDC1 | (GRID) |

TABLE 5-continued

Human Tyrosine Kinase Interactions (node 1 = tyrosine kinase; node 2 = interacting protein)

| Node1 | Node2 | int_DataBase |
|---|---|---|
| DDR1 | C1orf165 | (HPRD; IntAct) |
| DDR1 | COL11A1 | (GRID; HPRD) |
| DDR1 | COL2A1 | (GRID; HPRD) |
| DDR1 | COL3A1 | (GRID; HPRD) |
| DDR1 | COL5A2 | (GRID; HPRD) |
| DDR1 | FRS2 | (GRID; HPRD) |
| DDR1 | NCK2 | (HPRD; MINT) |
| DDR1 | PLCG1 | (GRID; HPRD) |
| DDR1 | PTPN11 | (HPRD; MINT) |
| DDR1 | RGS2 | (HPRD; IntAct; MDC; MINT) |
| DDR1 | SHC1 | (GRID; HPRD) |
| DDR1 | SNAPIN | (HPRD; IntAct; MDC; MINT) |
| DDR1 | TM4SF1 | (HPRD; IntAct; MDC; MINT) |
| DDR1 | TTR | (HPRD; IntAct; MDC; MINT) |
| DDR1 | WDR57 | (HPRD; IntAct; MDC; MINT) |
| DDR2 | COL1A1 | (GRID; HPRD) |
| DDR2 | COL3A1 | (GRID; HPRD) |
| DDR2 | SHC1 | (GRID; HPRD; MINT) |
| DDR2 | SRC | (GRID; HPRD; MINT) |
| EGFR | ACTA1 | (HPRD) |
| EGFR | ADAM10 | (reactome) |
| EGFR | ADAM12 | (reactome) |
| EGFR | ADAM17 | (reactome) |
| EGFR | ADRBK1 | (MINT) |
| EGFR | AGTR1 | (HPRD) |
| EGFR | ALCAM | (HPRD) |
| EGFR | AMH | (GRID; HPRD) |
| EGFR | ANKS1A | (MINT) |
| EGFR | ANXA1 | (HPRD; MINT) |
| EGFR | APBA3 | (MINT) |
| EGFR | APBB1 | (MINT) |
| EGFR | APBB2 | (MINT) |
| EGFR | APBB3 | (MINT) |
| EGFR | APPL1 | (MINT) |
| EGFR | AR | (GRID; HPRD) |
| EGFR | AREG | (DIP; GRID; HPRD) |
| EGFR | ARF4 | (GRID; HPRD) |
| EGFR | ATP1A1 | (HPRD) |
| EGFR | ATP1B1 | (HPRD) |
| EGFR | ATP5C1 | (HPRD; IntAct; MDC; MINT) |
| EGFR | BTC | (DIP; GRID; HPRD) |
| EGFR | CALM1 | (BIND; HPRD) |
| EGFR | CALM2 | (HPRD) |
| EGFR | CALM3 | (HPRD) |
| EGFR | CAMK2A | (HPRD) |
| EGFR | CAMK2G | (HPRD) |
| EGFR | CAMLG | (GRID; HPRD) |
| EGFR | CASP1 | (GRID; HPRD) |
| EGFR | CAV1 | (GRID; HPRD) |
| EGFR | CAV2 | (HPRD) |
| EGFR | CAV3 | (GRID; HPRD) |
| EGFR | CBL | (BIND; HPRD; IntAct; MINT) |
| EGFR | CBLB | (GRID; HPRD) |
| EGFR | CBLC | (GRID; HPRD) |
| EGFR | CD44 | (BIND; GRID; HPRD) |
| EGFR | CD59 | (IntAct) |
| EGFR | CD82 | (GRID; HPRD) |
| EGFR | CDC25A | (GRID; HPRD) |
| EGFR | CDH1 | (BIND; GRID; HPRD) |
| EGFR | CEACAM1 | (HPRD) |
| EGFR | CEBPB | (GRID; HPRD) |
| EGFR | CISH | (MINT) |
| EGFR | CLTA | (BIND; HPRD) |
| EGFR | CLTCL1 | (HPRD) |
| EGFR | COX2 | (HPRD) |
| EGFR | CRK | (BIND; GRID; HPRD; MINT) |
| EGFR | CRKL | (MINT) |
| EGFR | CTNNB1 | (GRID; HPRD) |
| EGFR | CTNND1 | (GRID; HPRD) |
| EGFR | DCN | (GRID; HPRD) |
| EGFR | DEGS1 | (GRID; HPRD) |
| EGFR | DOK2 | (GRID; HPRD) |
| EGFR | DOK4 | (MINT) |
| EGFR | DOK5 | (MINT) |
| EGFR | DOK6 | (MINT) |

TABLE 5-continued

Human Tyrosine Kinase Interactions (node 1 = tyrosine kinase; node 2 = interacting protein)

| Node1 | Node2 | int_DataBase |
|---|---|---|
| EGFR | EGF | (BIND; DIP; GRID; HPRD; IntAct; MINT; reactome) |
| EGFR | ELF3 | (HPRD) |
| EGFR | EPB41 | (HPRD) |
| EGFR | EPHA2 | (HPRD) |
| EGFR | EPPK1 | (GRID; HPRD) |
| EGFR | EPS15 | (GRID; HPRD) |
| EGFR | EPS8 | (GRID; HPRD) |
| EGFR | ERBB2 | (BIND; GRID; HPRD; IntAct; MINT) |
| EGFR | ERBB3 | (GRID; HPRD; IntAct) |
| EGFR | ERBB4 | (HPRD; IntAct) |
| EGFR | EREG | (GRID; HPRD) |
| EGFR | ERRFI1 | (GRID; HPRD) |
| EGFR | ESR1 | (GRID; HPRD) |
| EGFR | EZR | (HPRD) |
| EGFR | FAS | (HPRD) |
| EGFR | FER | (GRID; HPRD) |
| EGFR | FES | (MINT) |
| EGFR | FRS2 | (HPRD) |
| EGFR | GAB1 | (GRID; HPRD) |
| EGFR | GAB2 | (IntAct) |
| EGFR | GAPDH | (HPRD) |
| EGFR | GNAI2 | (GRID; HPRD) |
| EGFR | GRB10 | (BIND; GRID; HPRD; MINT) |
| EGFR | GRB14 | (GRID; HPRD) |
| EGFR | GRB2 | (BIND; DIP; GRID; HPRD) |
| EGFR | GRB7 | (GRID; HPRD) |
| EGFR | HBEGF | (GRID; HPRD) |
| EGFR | HGS | (HPRD) |
| EGFR | HIST3H3 | (HPRD) |
| EGFR | HOXC10 | (HPRD) |
| EGFR | HSP90AA1 | (BIND) |
| EGFR | HTT | (GRID; HPRD) |
| EGFR | ICAM1 | (HPRD) |
| EGFR | INPPL1 | (GRID; HPRD) |
| EGFR | IRS1 | (MINT) |
| EGFR | IRS4 | (MINT) |
| EGFR | ITGA5 | (GRID; HPRD) |
| EGFR | JAK2 | (HPRD; MINT) |
| EGFR | JUP | (GRID) |
| EGFR | KRT17 | (GRID; HPRD) |
| EGFR | KRT18 | (GRID; HPRD) |
| EGFR | KRT7 | (GRID; HPRD) |
| EGFR | KRT8 | (GRID; HPRD) |
| EGFR | LRSAM1 | (GRID) |
| EGFR | LYN | (HPRD) |
| EGFR | MAP2K1 | (HPRD) |
| EGFR | MAP3K14 | (GRID; HPRD) |
| EGFR | MAP4K1 | (GRID; HPRD) |
| EGFR | MAPK1 | (HPRD) |
| EGFR | MAPK8IP1 | (MINT) |
| EGFR | MAPK8IP2 | (MINT) |
| EGFR | MET | (HPRD) |
| EGFR | MIST | (MINT) |
| EGFR | MUC1 | (BIND; GRID; HPRD; MINT) |
| EGFR | NCK1 | (GRID; HPRD; MINT) |
| EGFR | NCK2 | (GRID; HPRD) |
| EGFR | NRG1 | (GRID) |
| EGFR | NUMB | (MINT) |
| EGFR | NUMBL | (MINT) |
| EGFR | PAK1 | (BIND; HPRD) |
| EGFR | PDGFRB | (GRID; HPRD) |
| EGFR | PIK3C2A | (IntAct) |
| EGFR | PIK3C2B | (GRID; HPRD; IntAct) |
| EGFR | PIK3R1 | (BIND; HPRD; MINT) |
| EGFR | PIK3R2 | (BIND; HPRD; MINT) |
| EGFR | PITPNA | (GRID; HPRD) |
| EGFR | PKIA | (HPRD) |
| EGFR | PLCG1 | (BIND; GRID; HPRD; MINT) |
| EGFR | PLCG2 | (MINT) |
| EGFR | PLD1 | (HPRD) |
| EGFR | PLD2 | (BIND; GRID; HPRD) |
| EGFR | PLEC1 | (GRID; HPRD) |
| EGFR | PLSCR1 | (GRID; HPRD; MINT) |
| EGFR | PRKACA | (GRID; HPRD) |
| EGFR | PRKAR1A | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| EGFR | PRKCA | (GRID; HPRD) |
| EGFR | PRKCD | (HPRD) |
| EGFR | PRKD1 | (HPRD) |
| EGFR | PTK2 | (BIND; GRID; HPRD) |
| EGFR | PTK2B | (GRID; HPRD) |
| EGFR | PTK6 | (GRID; HPRD; MINT) |
| EGFR | PTPN1 | (GRID; HPRD) |
| EGFR | PTPN11 | (BIND; GRID; HPRD; MINT) |
| EGFR | PTPN2 | (HPRD) |
| EGFR | PTPN6 | (GRID; HPRD) |
| EGFR | PTPRJ | (GRID; HPRD) |
| EGFR | PTPRS | (HPRD) |
| EGFR | RASA1 | (BIND; GRID; HPRD; MINT) |
| EGFR | RGS16 | (GRID; HPRD) |
| EGFR | RIN2 | (MINT) |
| EGFR | RIPK1 | (GRID; HPRD) |
| EGFR | S100A7 | (HPRD) |
| EGFR | S100A9 | (HPRD) |
| EGFR | SCAMP1 | (BIND; HPRD) |
| EGFR | SCAMP3 | (BIND; HPRD) |
| EGFR | SEC13 | (HPRD) |
| EGFR | SFN | (HPRD) |
| EGFR | SGSM2 | (HPRD; MDC) |
| EGFR | SH2B3 | (MINT) |
| EGFR | SH2D1A | (MINT) |
| EGFR | SH2D2A | (MINT) |
| EGFR | SH2D3A | (GRID; HPRD) |
| EGFR | SH3BGRL | (GRID; MINT) |
| EGFR | SH3BGRL3 | (BIND) |
| EGFR | SH3GL2 | (HPRD) |
| EGFR | SH3KBP1 | (HPRD) |
| EGFR | SHC1 | (BIND; DIP; GRID; HPRD; IntAct; MINT) |
| EGFR | SHC2 | (MINT) |
| EGFR | SHC3 | (GRID; HPRD; MINT) |
| EGFR | SLC3A2 | (HPRD) |
| EGFR | SNRPD2 | (GRID; HPRD) |
| EGFR | SNX1 | (DIP; GRID; HPRD) |
| EGFR | SNX2 | (GRID; HPRD) |
| EGFR | SNX4 | (GRID; HPRD) |
| EGFR | SNX6 | (GRID; HPRD) |
| EGFR | SOCS1 | (GRID; HPRD) |
| EGFR | SOCS3 | (GRID; HPRD) |
| EGFR | SOS1 | (GRID; HPRD) |
| EGFR | SOS2 | (GRID; HPRD) |
| EGFR | SRC | (GRID; HPRD; reactome) |
| EGFR | STAM2 | (HPRD) |
| EGFR | STAT1 | (GRID; HPRD) |
| EGFR | STAT3 | (BIND; GRID; HPRD) |
| EGFR | STAT5A | (GRID; HPRD) |
| EGFR | STAT5B | (BIND; GRID; HPRD; MINT) |
| EGFR | SYK | (MINT) |
| EGFR | TGFA | (DIP; GRID; HPRD; IntAct) |
| EGFR | TJP1 | (GRID; HPRD) |
| EGFR | TLN1 | (MINT) |
| EGFR | TLR2 | (MINT) |
| EGFR | TLR4 | (MINT) |
| EGFR | TNC | (GRID; HPRD) |
| EGFR | TNK2 | (GRID; HPRD) |
| EGFR | TNS4 | (MINT) |
| EGFR | TUBA4A | (HPRD) |
| EGFR | UBB | (HPRD) |
| EGFR | VAV1 | (GRID; HPRD) |
| EGFR | VAV2 | (BIND; GRID; HPRD) |
| EGFR | VAV3 | (GRID; HPRD) |
| EGFR | XPO6 | (HPRD) |
| EGFR | XRCC6 | (GRID; HPRD) |
| EGFR | YWHAZ | (BIND; HPRD) |
| EGFR | ZAP70 | (MINT) |
| EGFR | ZNF259 | (GRID; HPRD) |
| EPHA1 | EFNA1 | (BIND; GRID; HPRD) |
| EPHA1 | HNF4A | (BIND) |
| EPHA1 | ONECUT1 | (BIND) |
| EPHA1 | SMURF2 | (BIND; HPRD) |
| EPHA2 | ACP1 | (GRID; HPRD) |
| EPHA2 | CBL | (HPRD) |

TABLE 5-continued

Human Tyrosine Kinase Interactions (node 1 = tyrosine kinase; node 2 = interacting protein)

| Node1 | Node2 | int_DataBase |
| --- | --- | --- |
| EPHA2 | CDH5 | (HPRD) |
| EPHA2 | CLDN4 | (HPRD) |
| EPHA2 | EFNA1 | (BIND; DIP; GRID; HPRD) |
| EPHA2 | EFNA2 | (GRID; HPRD) |
| EPHA2 | EFNA3 | (BIND; GRID; HPRD) |
| EPHA2 | EFNA4 | (BIND; GRID; HPRD) |
| EPHA2 | EFNA5 | (BIND; GRID; HPRD) |
| EPHA2 | GRB2 | (GRID; HPRD) |
| EPHA2 | HNF4A | (BIND) |
| EPHA2 | PAX3 | (BIND) |
| EPHA2 | PIK3R1 | (GRID) |
| EPHA2 | PIK3R2 | (HPRD) |
| EPHA2 | PTK2 | (GRID; HPRD) |
| EPHA2 | PTPN11 | (GRID; HPRD) |
| EPHA2 | RASA1 | (HPRD) |
| EPHA2 | SHC1 | (GRID; HPRD) |
| EPHA2 | SLA | (GRID; HPRD) |
| EPHA2 | TIAM1 | (HPRD) |
| EPHA2 | TNFAIP1 | (GRID; HPRD) |
| EPHA3 | ADAM10 | (HPRD) |
| EPHA3 | CRK | (GRID; HPRD) |
| EPHA3 | E2F4 | (BIND) |
| EPHA3 | EFNA1 | (HPRD) |
| EPHA3 | EFNA2 | (GRID; HPRD) |
| EPHA3 | EFNA5 | (GRID; HPRD) |
| EPHA3 | EFNB2 | (GRID; HPRD) |
| EPHA3 | RUFY1 | (GRID; HPRD) |
| EPHA3 | RUFY2 | (GRID; HPRD) |
| EPHA3 | TP53 | (GRID) |
| EPHA4 | ARHGEF15 | (CCSB; GRID; HPRD) |
| EPHA4 | EFNA1 | (BIND; CCSB; GRID; HPRD) |
| EPHA4 | EFNA3 | (BIND; GRID; HPRD) |
| EPHA4 | EFNA4 | (BIND; GRID; HPRD) |
| EPHA4 | EFNA5 | (BIND; HPRD) |
| EPHA4 | EFNB2 | (BIND; GRID; HPRD) |
| EPHA4 | EFNB3 | (GRID; HPRD) |
| EPHA4 | FGFR1 | (HPRD) |
| EPHA4 | FGFR2 | (HPRD) |
| EPHA4 | FGFR3 | (HPRD) |
| EPHA4 | FGFR4 | (HPRD) |
| EPHA4 | FYN | (CCSB; GRID; HPRD) |
| EPHA4 | NGEF | (CCSB; GRID; HPRD) |
| EPHA4 | PAX3 | (BIND) |
| EPHA5 | EFNA1 | (BIND; GRID; HPRD) |
| EPHA5 | EFNA2 | (GRID; HPRD) |
| EPHA5 | EFNA3 | (BIND; GRID; HPRD) |
| EPHA5 | EFNA4 | (BIND; HPRD) |
| EPHA5 | EFNA5 | (BIND; GRID; HPRD) |
| EPHA5 | STAT3 | (GRID) |
| EPHA6 | EFNA1 | (BIND; GRID; HPRD) |
| EPHA6 | EFNA3 | (BIND) |
| EPHA6 | EFNA4 | (BIND; HPRD) |
| EPHA6 | EFNA5 | (BIND) |
| EPHA7 | EFNA1 | (BIND: CCSB; GRID; HPRD) |
| EPHA7 | EFNA3 | (BIND; HPRD) |
| EPHA7 | EFNA4 | (BIND; HPRD) |
| EPHA7 | EFNA5 | (BIND; HPRD) |
| EPHA7 | MLLT4 | (BIND; GRID; HPRD; MINT) |
| EPHA7 | SDCBP | (BIND) |
| EPHA8 | EFNA1 | (HPRD) |
| EPHA8 | EFNA4 | (HPRD) |
| EPHA8 | EFNA5 | (GRID; HPRD) |
| EPHA8 | FYN | (CCSB; GRID; HPRD) |
| EPHA8 | PIK3CG | (CCSB; GRID; HPRD) |
| EPHB1 | ACP1 | (BIND; GRID; HPRD) |
| EPHB1 | EFNA1 | (HPRD) |
| EPHB1 | EFNA5 | (GRID; HPRD) |
| EPHB1 | EFNB1 | (BIND; GRID; HPRD) |
| EPHB1 | EFNB2 | (BIND; GRID; HPRD) |
| EPHB1 | EPHB6 | (GRID; HPRD) |
| EPHB1 | GRB10 | (BIND; HPRD; IntAct) |
| EPHB1 | GRB2 | (BIND; GRID; HPRD) |
| EPHB1 | NCK1 | (GRID; HPRD) |
| EPHB1 | PDGFRB | (BIND) |
| EPHB1 | PXN | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| EPHB2 | ACP1 | (BIND; GRID; HPRD) |
| EPHB2 | ADAM17 | (GRID) |
| EPHB2 | AQP1 | (HPRD) |
| EPHB2 | ARHGEF6 | (HPRD) |
| EPHB2 | BCL2 | (GRID) |
| EPHB2 | EFNA5 | (HPRD) |
| EPHB2 | EFNB1 | (BIND; GRID; HPRD) |
| EPHB2 | EFNB2 | (BIND; GRID; HPRD) |
| EPHB2 | ERF | (HPRD) |
| EPHB2 | FOS | (HPRD) |
| EPHB2 | GRB2 | (HPRD) |
| EPHB2 | GRIN1 | (HPRD) |
| EPHB2 | GRIN2B | (HPRD) |
| EPHB2 | ITSN1 | (GRID; HPRD) |
| EPHB2 | KALRN | (HPRD) |
| EPHB2 | MLLT4 | (BIND; GRID; HPRD; MINT) |
| EPHB2 | NCK1 | (GRID; HPRD) |
| EPHB2 | PICK1 | (HPRD) |
| EPHB2 | PTK2 | (HPRD) |
| EPHB2 | RASA1 | (GRID; HPRD) |
| EPHB2 | RRAS | (HPRD) |
| EPHB2 | RYK | (GRID; HPRD) |
| EPHB2 | SDC2 | (HPRD) |
| EPHB2 | SDCBP | (HPRD) |
| EPHB2 | SH2D3C | (HPRD) |
| EPHB2 | SRC | (GRID; HPRD) |
| EPHB2 | SYNJ1 | (HPRD) |
| EPHB2 | VAV2 | (HPRD) |
| EPHB3 | CRK | (GRID; HPRD) |
| EPHB3 | EFNB3 | (GRID; HPRD) |
| EPHB3 | FYN | (GRID; HPRD) |
| EPHB3 | HNRPA3 | (BIND) |
| EPHB3 | MLLT4 | (BIND; GRID; HPRD; MINT) |
| EPHB3 | RASA1 | (GRID; HPRD) |
| EPHB3 | RYK | (GRID; HPRD) |
| EPHB4 | EFNB2 | (GRID; HPRD) |
| EPHB4 | GRIN1 | (HPRD) |
| EPHB4 | SDC3 | (HPRD) |
| EPHB6 | CBL | (GRID; HPRD) |
| EPHB6 | CRK | (HPRD) |
| EPHB6 | CRKL | (HPRD) |
| EPHB6 | EFNB2 | (GRID; HPRD) |
| EPHB6 | GRB2 | (HPRD) |
| EPHB6 | HDHD2 | (HPRD) |
| EPHB6 | HNRPA3 | (BIND) |
| EPHB6 | MLLT4 | (BIND; GRID; HPRD; MINT) |
| EPHB6 | SAT1 | (HPRD; IntAct; MDC; MINT) |
| ERBB2 | ACPP | (HPRD) |
| ERBB2 | ANKS1A | (MINT) |
| ERBB2 | APBB1 | (MINT) |
| ERBB2 | APBB3 | (MINT) |
| ERBB2 | BLNK | (MINT) |
| ERBB2 | BTC | (GRID; HPRD) |
| ERBB2 | CAV1 | (GRID; HPRD) |
| ERBB2 | CBL | (BIND) |
| ERBB2 | CD82 | (GRID; HPRD) |
| ERBB2 | CDC37 | (BIND) |
| ERBB2 | CHN1 | (MINT) |
| ERBB2 | CISH | (MINT) |
| ERBB2 | CRK | (MINT) |
| ERBB2 | CRKL | (MINT) |
| ERBB2 | CTNNB1 | (GRID; HPRD) |
| ERBB2 | DAB1 | (MINT) |
| ERBB2 | DLG4 | (GRID; HPRD) |
| ERBB2 | DOK1 | (MINT) |
| ERBB2 | DOK4 | (MINT) |
| ERBB2 | DOK6 | (MINT) |
| ERBB2 | EGF | (GRID; HPRD) |
| ERBB2 | ERBB2IP | (GRID; HPRD) |
| ERBB2 | ERBB3 | (GRID; HPRD; IntAct) |
| ERBB2 | ERBB4 | (IntAct) |
| ERBB2 | ERRFI1 | (BIND; GRID; HPRD) |
| ERBB2 | ESR1 | (HPRD) |
| ERBB2 | FER | (MINT) |
| ERBB2 | FGR | (MINT) |

TABLE 5-continued

Human Tyrosine Kinase Interactions (node 1 = tyrosine kinase; node 2 = interacting protein)

| Node1 | Node2 | int_DataBase |
|---|---|---|
| ERBB2 | GRAP2 | (MINT) |
| ERBB2 | GRB2 | (BIND; GRID; HPRD) |
| ERBB2 | GRB7 | (GRID; HPRD; MINT) |
| ERBB2 | H3F3A | (BIND) |
| ERBB2 | HLA-A | (GRID; HPRD) |
| ERBB2 | HSP90AA1 | (BIND; GRID; HPRD) |
| ERBB2 | HSP90B1 | (GRID; HPRD) |
| ERBB2 | HSPA8 | (BIND) |
| ERBB2 | IL6ST | (GRID; HPRD) |
| ERBB2 | IRS1 | (MINT) |
| ERBB2 | IRS4 | (MINT) |
| ERBB2 | ITGA5 | (HPRD) |
| ERBB2 | ITGB4 | (GRID; HPRD) |
| ERBB2 | ITK | (MINT) |
| ERBB2 | JAK1 | (MINT) |
| ERBB2 | JAK2 | (GRID; HPRD) |
| ERBB2 | JUP | (GRID; HPRD) |
| ERBB2 | MAPK8IP1 | (MINT) |
| ERBB2 | MAPK8IP2 | (MINT) |
| ERBB2 | MATK | (GRID; HPRD; MINT) |
| ERBB2 | MIST | (MINT) |
| ERBB2 | MMP16 | (BIND) |
| ERBB2 | MUC1 | (GRID; HPRD) |
| ERBB2 | MUC4 | (HPRD) |
| ERBB2 | NCK2 | (MINT) |
| ERBB2 | NCOA3 | (BIND) |
| ERBB2 | NCOR1 | (BIND) |
| ERBB2 | NF2 | (HPRD) |
| ERBB2 | NRG1 | (DIP; GRID; MINT) |
| ERBB2 | PAK1 | (GRID; HPRD) |
| ERBB2 | PICK1 | (GRID; HPRD) |
| ERBB2 | PIK3C2A | (IntAct) |
| ERBB2 | PIK3C2B | (IntAct) |
| ERBB2 | PIK3R1 | (GRID; HPRD; MINT) |
| ERBB2 | PIK3R2 | (GRID; HPRD; MINT) |
| ERBB2 | PLCG1 | (GRID; HPRD; MINT) |
| ERBB2 | PLCG2 | (MINT) |
| ERBB2 | PTK2 | (GRID; HPRD) |
| ERBB2 | PTK2B | (GRID; HPRD) |
| ERBB2 | PTPN11 | (BIND; GRID; MINT) |
| ERBB2 | PTPN18 | (HPRD) |
| ERBB2 | RASA1 | (MINT) |
| ERBB2 | RIN1 | (MINT) |
| ERBB2 | RIN2 | (MINT) |
| ERBB2 | SERPINA3 | (GRID; HPRD) |
| ERBB2 | SH2B2 | (MINT) |
| ERBB2 | SH2B3 | (MINT) |
| ERBB2 | SH2D1B | (MINT) |
| ERBB2 | SH2D2A | (MINT) |
| ERBB2 | SH3BGRL | (GRID) |
| ERBB2 | SH3BGRL3 | (BIND; MINT) |
| ERBB2 | SH3BP2 | (MINT) |
| ERBB2 | SHC1 | (BIND; GRID; HPRD; MINT) |
| ERBB2 | SHC2 | (MINT) |
| ERBB2 | SHC3 | (MINT) |
| ERBB2 | SLA2 | (MINT) |
| ERBB2 | SOCS1 | (MINT) |
| ERBB2 | SOS1 | (GRID; HPRD) |
| ERBB2 | SRC | (BIND; GRID; HPRD) |
| ERBB2 | STAT1 | (MINT) |
| ERBB2 | STAT3 | (MINT) |
| ERBB2 | STUB1 | (GRID; HPRD) |
| ERBB2 | SUPT6H | (MINT) |
| ERBB2 | SYK | (MINT) |
| ERBB2 | TAF1 | (BIND) |
| ERBB2 | TEC | (MINT) |
| ERBB2 | TGFA | (HPRD) |
| ERBB2 | TLN1 | (MINT) |
| ERBB2 | TOB1 | (GRID; HPRD) |
| ERBB2 | TP53RK | (BIND) |
| ERBB2 | TXK | (MINT) |
| ERBB2 | UBB | (HPRD) |
| ERBB2 | VAV2 | (MINT) |
| ERBB2 | VAV3 | (MINT) |
| ERBB3 | AGTR2 | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| ERBB3 | CD82 | (CCSB; GRID; HPRD) |
| ERBB3 | CDK5 | (HPRD) |
| ERBB3 | CHN2 | (MINT) |
| ERBB3 | CRK | (MINT) |
| ERBB3 | CRKL | (MINT) |
| ERBB3 | DAB1 | (MINT) |
| ERBB3 | DAPP1 | (MINT) |
| ERBB3 | EGF | (GRID; HPRD) |
| ERBB3 | EGR1 | (GRID) |
| ERBB3 | ERBB4 | (HPRD; IntAct) |
| ERBB3 | FER | (MINT) |
| ERBB3 | FGFR1 | (MINT) |
| ERBB3 | FLYWCH1 | (HPRD; MDC) |
| ERBB3 | GRB2 | (BIND; GRID; HPRD) |
| ERBB3 | GRB7 | (CCSB; GRID; HPRD; MINT) |
| ERBB3 | HCK | (MINT) |
| ERBB3 | HNF4A | (BIND) |
| ERBB3 | IL6ST | (GRID; HPRD) |
| ERBB3 | ITK | (MINT) |
| ERBB3 | JAK2 | (MINT) |
| ERBB3 | JAK3 | (MINT) |
| ERBB3 | MUC1 | (GRID: HPRD) |
| ERBB3 | NCK1 | (MINT) |
| ERBB3 | NCK2 | (MINT) |
| ERBB3 | NRG1 | (BIND; CCSB; DIP; GRID; HPRD; MINT) |
| ERBB3 | NRG2 | (GRID; HPRD) |
| ERBB3 | ODF2L | (HPRD; MDC) |
| ERBB3 | PA2G4 | (CCSB; GRID; HPRD; IntAct) |
| ERBB3 | PIK3R1 | (GRID; HPRD; IntAct; MINT) |
| ERBB3 | PIK3R2 | (BIND; GRID; MINT) |
| ERBB3 | PLCG1 | (MINT) |
| ERBB3 | PTGES3 | (CCSB; GRID; HPRD) |
| ERBB3 | PTK2 | (CCSB; GRID; HPRD) |
| ERBB3 | PTK2B | (HPRD) |
| ERBB3 | PTK6 | (GRID; HPRD; MINT) |
| ERBB3 | RASA1 | (MINT) |
| ERBB3 | RASA4 | (HPRD; IntAct; MDC; MINT) |
| ERBB3 | RGS4 | (CCSB; GRID; HPRD) |
| ERBB3 | RIN1 | (MINT) |
| ERBB3 | RNF41 | (HPRD) |
| ERBB3 | RPN1 | (GRID) |
| ERBB3 | SH2B3 | (MINT) |
| ERBB3 | SH2D1A | (MINT) |
| ERBB3 | SHC1 | (BIND; CCSB; GRID; HPRD; MINT) |
| ERBB3 | SHC3 | (MINT) |
| ERBB3 | SOS1 | (GRID; HPRD; MINT) |
| ERBB3 | SRC | (MINT) |
| ERBB3 | SYK | (MINT) |
| ERBB3 | TNS4 | (MINT) |
| ERBB3 | TXK | (MINT) |
| ERBB3 | VAV2 | (MINT) |
| ERBB3 | VAV3 | (MINT) |
| ERBB3 | ZAP70 | (MINT) |
| ERBB3 | ZNF207 | (GRID) |
| ERBB4 | ADAM17 | (HPRD) |
| ERBB4 | ANKS1A | (MINT) |
| ERBB4 | BTC | (GRID; HPRD) |
| ERBB4 | CD44 | (GRID; HPRD) |
| ERBB4 | CRK | (BIND; GRID) |
| ERBB4 | CRKL | (MINT) |
| ERBB4 | CTGF | (GRID; HPRD) |
| ERBB4 | DLG1 | (GRID; HPRD) |
| ERBB4 | DLG2 | (BIND; GRID; HPRD; IntAct) |
| ERBB4 | DLG3 | (BIND; GRID; HPRD; IntAct) |
| ERBB4 | DLG4 | (BIND; GRID; HPRD; IntAct; MINT) |
| ERBB4 | EREG | (GRID; HPRD) |
| ERBB4 | GRB2 | (BIND; GRID) |
| ERBB4 | GRIN1 | (IntAct) |
| ERBB4 | HBEGF | (GRID; HPRD) |
| ERBB4 | MUC1 | (GRID; HPRD) |
| ERBB4 | NCK1 | (GRID) |
| ERBB4 | NCK2 | (BIND; MINT) |
| ERBB4 | NRG1 | (DIP; GRID; HPRD; MINT) |
| ERBB4 | NRG2 | (GRID; HPRD) |
| ERBB4 | NRG3 | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| ERBB4 | NRG4 | (HPRD) |
| ERBB4 | PIK3R2 | (BIND; GRID; MINT) |
| ERBB4 | PTPN11 | (BIND; GRID; MINT) |
| ERBB4 | RASA1 | (MINT) |
| ERBB4 | RNF41 | (GRID; HPRD) |
| ERBB4 | SHC1 | (BIND; GRID; MINT) |
| ERBB4 | SNTB2 | (BIND; GRID; HPRD; IntAct) |
| ERBB4 | STAT5A | (GRID; HPRD) |
| ERBB4 | STAT5B | (BIND; MINT) |
| ERBB4 | SYK | (MINT) |
| ERBB4 | TGFA | (HPRD) |
| ERBB4 | YAP1 | (GRID; HPRD) |
| FER | CALM1 | (HPRD) |
| FER | CTNNB1 | (HPRD) |
| FER | CTNND1 | (GRID; HPRD) |
| FER | CTTN | (GRID; HPRD) |
| FER | IRS1 | (HPRD) |
| FER | JAK1 | (HPRD) |
| FER | JUP | (HPRD) |
| FER | STAT3 | (GRID; HPRD) |
| FER | TMF1 | (GRID; HPRD) |
| FER | YWHAB | (HPRD) |
| FES | BCAR1 | (GRID; HPRD) |
| FES | BCR | (GRID; HPRD) |
| FES | CSF2RB | (HPRD) |
| FES | DOK1 | (HPRD) |
| FES | DPYSL5 | (CCSB; GRID; HPRD) |
| FES | HSH2D | (GRID; HPRD) |
| FES | IL4R | (GRID; HPRD) |
| FES | IRS1 | (HPRD) |
| FES | IRS2 | (HPRD) |
| FES | JAK1 | (HPRD) |
| FES | JAK2 | (HPRD) |
| FES | JAK3 | (HPRD) |
| FES | PIK3R1 | (GRID; HPRD) |
| FES | PLXNA1 | (HPRD) |
| FES | PSMD13 | (GRID) |
| FES | RASA1 | (CCSB; GRID; HPRD) |
| FES | RASA3 | (GRID; HPRD) |
| FES | STAT3 | (CCSB; GRID; HPRD) |
| FGFR1 | ATF2 | (BIND) |
| FGFR1 | BNIP2 | (BIND; CCSB; GRID; HPRD) |
| FGFR1 | CBL | (reactome) |
| FGFR1 | CREBBP | (HPRD) |
| FGFR1 | CRK | (HPRD) |
| FGFR1 | FDPS | (CCSB; GRID; HPRD) |
| FGFR1 | FGF1 | (CCSB; DIP; GRID; HPRD; MINT; reactome) |
| FGFR1 | FGF17 | (HPRD; reactome) |
| FGFR1 | FGF18 | (HPRD) |
| FGFR1 | FGF2 | (DIP; GRID; HPRD; IntAct; reactome) |
| FGFR1 | FGF20 | (reactome) |
| FGFR1 | FGF23 | (reactome) |
| FGFR1 | FGF3 | (HPRD) |
| FGFR1 | FGF4 | (HPRD; reactome) |
| FGFR1 | FGF5 | (DIP; GRID; HPRD; reactome) |
| FGFR1 | FGF6 | (HPRD; reactome) |
| FGFR1 | FGF7 | (HPRD) |
| FGFR1 | FGF8 | (HPRD; reactome) |
| FGFR1 | FGF9 | (HPRD; reactome) |
| FGFR1 | FGFR2 | (BIND) |
| FGFR1 | FRS2 | (CCSB; GRID; HPRD; reactome) |
| FGFR1 | FRS3 | (BIND; GRID; HPRD; reactome) |
| FGFR1 | GRB14 | (GRID; HPRD) |
| FGFR1 | GRB2 | (CCSB; GRID; HPRD; reactome) |
| FGFR1 | IL17RD | (HPRD) |
| FGFR1 | JUN | (BIND) |
| FGFR1 | KL | (reactome) |
| FGFR1 | KPNB1 | (GRID; HPRD) |
| FGFR1 | MMP2 | (HPRD) |
| FGFR1 | NCAM1 | (GRID; HPRD) |
| FGFR1 | NCK2 | (BIND; HPRD) |
| FGFR1 | NRP1 | (HPRD) |
| FGFR1 | PIK3R1 | (HPRD) |
| FGFR1 | PIK3R2 | (BIND; HPRD) |
| FGFR1 | PLCG1 | (BIND; HPRD) |

TABLE 5-continued

Human Tyrosine Kinase Interactions (node 1 = tyrosine kinase; node 2 = interacting protein)

| Node1 | Node2 | int_DataBase |
|---|---|---|
| FGFR1 | RPS6KA1 | (BIND; HPRD) |
| FGFR1 | RTN1 | (BIND) |
| FGFR1 | RTN3 | (BIND; HPRD) |
| FGFR1 | SH3BP2 | (BIND; HPRD) |
| FGFR1 | SHB | (BIND; GRID) |
| FGFR1 | SHC1 | (CCSB; GRID; HPRD) |
| FGFR1 | SLA | (BIND; HPRD) |
| FGFR1 | SOS1 | (HPRD) |
| FGFR1 | TENC1 | (BIND; HPRD) |
| FGFR2 | CACNA1D | (GRID; HPRD) |
| FGFR2 | CBL | (reactome) |
| FGFR2 | FGF1 | (DIP; GRID; HPRD; IntAct; MINT; reactome) |
| FGFR2 | FGF10 | (DIP; GRID; HPRD; IntAct; MINT; reactome) |
| FGFR2 | FGF16 | (reactome) |
| FGFR2 | FGF17 | (HPRD; reactome) |
| FGFR2 | FGF18 | (HPRD; reactome) |
| FGFR2 | FGF2 | (DIP; GRID; IntAct; reactome) |
| FGFR2 | FGF20 | (reactome) |
| FGFR2 | FGF22 | (reactome) |
| FGFR2 | FGF23 | (HPRD; reactome) |
| FGFR2 | FGF3 | (DIP; HPRD; reactome) |
| FGFR2 | FGF4 | (HPRD; reactome) |
| FGFR2 | FGF5 | (GRID; HPRD; reactome) |
| FGFR2 | FGF6 | (DIP; HPRD; reactome) |
| FGFR2 | FGF7 | (DIP; GRID; HPRD; reactome) |
| FGFR2 | FGF8 | (HPRD; reactome) |
| FGFR2 | FGF9 | (DIP; GRID; HPRD; reactome) |
| FGFR2 | FRS2 | (reactome) |
| FGFR2 | FRS3 | (reactome) |
| FGFR2 | FYN | (HPRD) |
| FGFR2 | GRB2 | (reactome) |
| FGFR2 | ITGA5 | (HPRD) |
| FGFR2 | PAK4 | (HPRD) |
| FGFR2 | PLCG1 | (GRID; HPRD) |
| FGFR2 | UQCRB | (BIND) |
| FGFR3 | ATF3 | (HPRD; IntAct; MDC) |
| FGFR3 | C13orf34 | (HPRD; IntAct; MDC) |
| FGFR3 | C6orf47 | (GRID; HPRD) |
| FGFR3 | CBL | (reactome) |
| FGFR3 | CCDC17 | (HPRD; IntAct; MDC) |
| FGFR3 | CENTD2 | (HPRD; IntAct; MDC) |
| FGFR3 | CHGB | (HPRD; IntAct; MDC) |
| FGFR3 | CTSK | (HPRD; IntAct; MDC) |
| FGFR3 | FGF1 | (DIP; GRID; HPRD; IntAct; reactome) |
| FGFR3 | FGF16 | (reactome) |
| FGFR3 | FGF17 | (HPRD; reactome) |
| FGFR3 | FGF18 | (HPRD; reactome) |
| FGFR3 | FGF2 | (DIP; HPRD; reactome) |
| FGFR3 | FGF20 | (reactome) |
| FGFR3 | FGF23 | (HPRD; reactome) |
| FGFR3 | FGF3 | (HPRD) |
| FGFR3 | FGF4 | (DIP; HPRD; reactome) |
| FGFR3 | FGF5 | (DIP; HPRD; reactome) |
| FGFR3 | FGF6 | (HPRD) |
| FGFR3 | FGF7 | (DIP; HPRD) |
| FGFR3 | FGF8 | (GRID; HPRD; reactome) |
| FGFR3 | FGF9 | (GRID; HPRD; reactome) |
| FGFR3 | FGFR2 | (BIND) |
| FGFR3 | FRS2 | (reactome) |
| FGFR3 | FRS3 | (reactome) |
| FGFR3 | GPSM3 | (BIND; HPRD; IntAct; MINT) |
| FGFR3 | GRB2 | (GRID; HPRD; reactome) |
| FGFR3 | GTF3C1 | (HPRD; MDC) |
| FGFR3 | HBZ | (HPRD; IntAct; MDC) |
| FGFR3 | HNRNPL | (HPRD; IntAct; MDC) |
| FGFR3 | KIAA1377 | (HPRD; IntAct; MDC) |
| FGFR3 | KRT8 | (HPRD; IntAct; MDC) |
| FGFR3 | NDUFS6 | (HPRD; IntAct; MDC) |
| FGFR3 | POLA2 | (HPRD; IntAct; MDC) |
| FGFR3 | PTPN11 | (GRID) |
| FGFR3 | RADIL | (HPRD; MDC) |
| FGFR3 | RNF130 | (HPRD; IntAct; MDC) |
| FGFR3 | RPL8 | (HPRD; IntAct; MDC) |
| FGFR3 | SH2B1 | (GRID; HPRD) |
| FGFR3 | SLC25A6 | (HPRD; IntAct; MDC) |

TABLE 5-continued

Human Tyrosine Kinase Interactions (node 1 = tyrosine kinase; node 2 = interacting protein)

| Node1 | Node2 | int_DataBase |
|---|---|---|
| FGFR3 | SMA4 | (IntAct) |
| FGFR3 | SMG7 | (HPRD; MDC) |
| FGFR3 | STAT1 | (HPRD) |
| FGFR3 | STAT3 | (HPRD) |
| FGFR4 | ADH6 | (BIND) |
| FGFR4 | ATF2 | (BIND) |
| FGFR4 | ATP5H | (BIND) |
| FGFR4 | CALM1 | (BIND) |
| FGFR4 | CBL | (reactome) |
| FGFR4 | CDH2 | (HPRD) |
| FGFR4 | COX6C | (BIND) |
| FGFR4 | COX7B | (BIND) |
| FGFR4 | DPM2 | (BIND) |
| FGFR4 | E2F4 | (BIND) |
| FGFR4 | EIF3E | (BIND) |
| FGFR4 | FBP1 | (BIND) |
| FGFR4 | FGA | (BIND) |
| FGFR4 | FGF1 | (DIP; GRID; HPRD; reactome) |
| FGFR4 | FGF16 | (reactome) |
| FGFR4 | FGF17 | (HPRD; reactome) |
| FGFR4 | FGF18 | (HPRD; reactome) |
| FGFR4 | FGF19 | (BIND; DIP; GRID; HPRD; reactome) |
| FGFR4 | FGF2 | (DIP; GRID; HPRD; reactome) |
| FGFR4 | FGF20 | (reactome) |
| FGFR4 | FGF23 | (reactome) |
| FGFR4 | FGF3 | (HPRD) |
| FGFR4 | FGF4 | (HPRD; reactome) |
| FGFR4 | FGF5 | (HPRD) |
| FGFR4 | FGF6 | (GRID; HPRD; reactome) |
| FGFR4 | FGF7 | (HPRD) |
| FGFR4 | FGF8 | (GRID; HPRD; reactome) |
| FGFR4 | FGF9 | (HPRD; reactome) |
| FGFR4 | FN1 | (BIND) |
| FGFR4 | FRS2 | (reactome) |
| FGFR4 | FRS3 | (reactome) |
| FGFR4 | GJC1 | (BIND) |
| FGFR4 | GLRX | (BIND) |
| FGFR4 | GPT | (BIND) |
| FGFR4 | GRB2 | (reactome) |
| FGFR4 | GSTO1 | (BIND) |
| FGFR4 | HNRNPC | (BIND) |
| FGFR4 | LDLRAP1 | (BIND) |
| FGFR4 | PLCG1 | (HPRD) |
| FGFR4 | POLR2I | (BIND) |
| FGFR4 | PPIA | (BIND) |
| FGFR4 | PSMA4 | (BIND) |
| FGFR4 | RPLP2 | (BIND) |
| FGFR4 | SF3B4 | (BIND) |
| FGFR4 | STAT1 | (HPRD) |
| FGFR4 | STAT3 | (HPRD) |
| FGFR4 | TLR4 | (BIND) |
| FGR | ARRB1 | (GRID; HPRD) |
| FGR | CBL | (GRID; HPRD) |
| FGR | CCR3 | (GRID; HPRD) |
| FGR | CD24 | (GRID; HPRD) |
| FGR | DAB2 | (GRID; HPRD) |
| FGR | DOK1 | (HPRD) |
| FGR | HCLS1 | (HPRD) |
| FGR | HSP90AA1 | (DIP) |
| FGR | INPP5D | (GRID; HPRD) |
| FGR | NCOA6 | (GRID) |
| FGR | PLAUR | (DIP) |
| FGR | PTK2 | (GRID; HPRD) |
| FGR | SLAMF1 | (GRID; HPRD) |
| FGR | SNCA | (HPRD) |
| FGR | SRC | (HPRD) |
| FGR | SYK | (GRID; HPRD; MINT) |
| FGR | VDR | (HPRD) |
| FGR | WAS | (GRID; HPRD; MINT) |
| FGR | YWHAQ | (GRID; HPRD) |
| FLT1 | ATR | (GRID; HPRD) |
| FLT1 | CRK | (HPRD) |
| FLT1 | CTNNB1 | (HPRD) |
| FLT1 | FYN | (HPRD) |
| FLT1 | GRB2 | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| FLT1 | KDR | (GRID; HPRD) |
| FLT1 | NCK1 | (BIND; HPRD) |
| FLT1 | NRP1 | (HPRD) |
| FLT1 | NRP2 | (HPRD) |
| FLT1 | PGF | (DIP; GRID; HPRD; IntAct) |
| FLT1 | PIK3R1 | (BIND) |
| FLT1 | PLCG1 | (BIND; HPRD) |
| FLT1 | PLCG2 | (GRID; HPRD) |
| FLT1 | PTK2 | (HPRD) |
| FLT1 | PTPN11 | (BIND; HPRD) |
| FLT1 | SHC1 | (GRID; HPRD) |
| FLT1 | SHC2 | (MINT) |
| FLT1 | STAT1 | (HPRD) |
| FLT1 | STAT3 | (HPRD) |
| FLT1 | VEGFA | (BIND; DIP; GRID; HPRD; IntAct) |
| FLT1 | VEGFB | (GRID; HPRD) |
| FLT1 | YES1 | (HPRD) |
| FLT3 | CBLB | (GRID; HPRD) |
| FLT3 | FIZ1 | (HPRD) |
| FLT3 | FLT3LG | (GRID; HPRD) |
| FLT3 | GRB2 | (GRID; HPRD) |
| FLT3 | INPP5D | (HPRD) |
| FLT3 | NCK1 | (HPRD) |
| FLT3 | PTPN12 | (HPRD) |
| FLT3 | PTPN6 | (HPRD) |
| FLT3 | SH3BP2 | (HPRD) |
| FLT3 | SHC1 | (GRID; HPRD) |
| FLT3 | SOCS1 | (GRID; HPRD) |
| FLT4 | ATF7IP | (BIND; HPRD) |
| FLT4 | FIGF | (DIP; GRID; HPRD) |
| FLT4 | GRB2 | (GRID; HPRD) |
| FLT4 | ITGA5 | (HPRD) |
| FLT4 | ITGB1 | (GRID; HPRD) |
| FLT4 | KDR | (HPRD; IntAct) |
| FLT4 | PTK2 | (HPRD) |
| FLT4 | PTPN11 | (HPRD) |
| FLT4 | SHC1 | (GRID; HPRD) |
| FLT4 | SHC3 | (HPRD) |
| FLT4 | VEGFC | (BIND; DIP; GRID; HPRD) |
| FRK | HNF4A | (BIND) |
| FRK | RB1 | (BIND; CCSB; GRID; HPRD) |
| FYN | ACP1 | (HPRD) |
| FYN | ADAM15 | (CCSB; GRID; HPRD; MINT) |
| FYN | ADD2 | (GRID; HPRD) |
| FYN | ATXN1 | (HPRD; IntAct; MINT) |
| FYN | BCAR1 | (GRID; HPRD) |
| FYN | BCL3 | (GRID; HPRD) |
| FYN | CASP3 | (HPRD) |
| FYN | CASP8 | (HPRD) |
| FYN | CAV1 | (HPRD) |
| FYN | CBL | (BIND; GRID; HPRD; MINT) |
| FYN | CBLB | (HPRD) |
| FYN | CD19 | (GRID; HPRD) |
| FYN | CD2 | (BIND; CCSB; GRID; HPRD; MINT) |
| FYN | CD226 | (GRID; HPRD) |
| FYN | CD247 | (BIND; CCSB; GRID; HPRD) |
| FYN | CD2AP | (GRID; HPRD; MINT) |
| FYN | CD36 | (GRID; HPRD) |
| FYN | CD44 | (CCSB; GRID; HPRD) |
| FYN | CD48 | (CCSB; GRID) |
| FYN | CD5 | (HPRD) |
| FYN | CD55 | (CCSB; GRID; HPRD) |
| FYN | CD79A | (HPRD) |
| FYN | CD79B | (HPRD) |
| FYN | CDC2 | (CCSB; GRID; HPRD) |
| FYN | CDK5 | (HPRD) |
| FYN | CNN1 | (HPRD) |
| FYN | CNN3 | (HPRD) |
| FYN | CNTN1 | (GRID; HPRD) |
| FYN | CNTNAP1 | (HPRD) |
| FYN | CRK | (HPRD) |
| FYN | CSF2RB | (HPRD) |
| FYN | CTLA4 | (GRID; HPRD) |
| FYN | CTNNB1 | (HPRD) |
| FYN | CTNND1 | (GRID) |

TABLE 5-continued

Human Tyrosine Kinase Interactions (node 1 = tyrosine kinase; node 2 = interacting protein)

| Node1 | Node2 | int_DataBase |
|---|---|---|
| FYN | CTNND2 | (HPRD) |
| FYN | DCC | (BIND) |
| FYN | DLG4 | (GRID; HPRD) |
| FYN | DOK1 | (HPRD) |
| FYN | DOK3 | (HPRD) |
| FYN | DOK4 | (BIND; HPRD) |
| FYN | EVL | (CCSB; GRID; HPRD) |
| FYN | FAS | (CCSB; GRID; HPRD) |
| FYN | FASLG | (GRID; HPRD) |
| FYN | FCER2 | (BIND; CCSB; GRID; HPRD) |
| FYN | FCGR2A | (HPRD) |
| FYN | FLOT1 | (HPRD) |
| FYN | FLOT2 | (HPRD) |
| FYN | FN1 | (HPRD) |
| FYN | FNBP4 | (CCSB; GRID; HPRD) |
| FYN | FYB | (GRID; HPRD; MINT) |
| FYN | GAB3 | (GRID; HPRD) |
| FYN | GNB2L1 | (CCSB; GRID; HPRD) |
| FYN | GP6 | (GRID; HPRD) |
| FYN | GRAP | (HPRD) |
| FYN | GRB10 | (GRID; HPRD) |
| FYN | GRIN2A | (GRID; HPRD) |
| FYN | GRIN2B | (GRID; HPRD) |
| FYN | HNRPK | (BIND; CCSB; GRID; HPRD) |
| FYN | HRAS | (HPRD; MINT) |
| FYN | HTR6 | (IntAct) |
| FYN | IL2RB | (HPRD) |
| FYN | IL7R | (BIND; GRID; HPRD) |
| FYN | IRS1 | (HPRD) |
| FYN | ITGAV | (HPRD) |
| FYN | ITGB4 | (HPRD) |
| FYN | ITGB6 | (HPRD) |
| FYN | ITK | (GRID; HPRD) |
| FYN | ITPR1 | (HPRD) |
| FYN | JAK2 | (GRID; HPRD) |
| FYN | JUP | (HPRD) |
| FYN | KDR | (HPRD; MINT) |
| FYN | KHDRBS1 | (GRID; HPRD; IntAct; MINT) |
| FYN | KIT | (HPRD) |
| FYN | LCP2 | (HPRD) |
| FYN | LYN | (HPRD) |
| FYN | MAG | (GRID; HPRD) |
| FYN | MAP2 | (HPRD; MINT) |
| FYN | MAPT | (HPRD) |
| FYN | MCAM | (GRID; HPRD) |
| FYN | MS4A1 | (CCSB; GRID; HPRD) |
| FYN | NCAM1 | (GRID; HPRD) |
| FYN | NCK1 | (MINT) |
| FYN | NEDD9 | (GRID; HPRD) |
| FYN | NMT1 | (HPRD) |
| FYN | NPHS1 | (GRID; HPRD) |
| FYN | NTRK2 | (GRID; HPRD) |
| FYN | PAG1 | (GRID; HPRD) |
| FYN | PDE4D | (BIND) |
| FYN | PDGFRB | (CCSB; GRID; HPRD) |
| FYN | PECAM1 | (GRID; HPRD) |
| FYN | PIK3R1 | (BIND; GRID; HPRD) |
| FYN | PIK3R2 | (GRID; HPRD) |
| FYN | PLAUR | (CCSB; GRID; HPRD) |
| FYN | PLCG1 | (GRID; HPRD) |
| FYN | PLCG2 | (CCSB; GRID; HPRD) |
| FYN | PLD2 | (GRID; HPRD) |
| FYN | PRKCD | (HPRD; IntAct) |
| FYN | PRKCE | (HPRD) |
| FYN | PRKCH | (HPRD) |
| FYN | PRKCQ | (GRID; HPRD) |
| FYN | PRKCZ | (HPRD) |
| FYN | PTK2 | (GRID; HPRD) |
| FYN | PTPN11 | (CCSB; GRID; HPRD) |
| FYN | PTPN5 | (GRID; HPRD) |
| FYN | PTPRA | (CCSB; GRID; HPRD) |
| FYN | PTPRC | (GRID; HPRD) |
| FYN | PTPRE | (HPRD) |
| FYN | PTPRF | (HPRD) |
| FYN | PTPRZ1 | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| FYN | PXN | (GRID; HPRD) |
| FYN | RAF1 | (CCSB; GRID; HPRD) |
| FYN | RICS | (GRID; HPRD) |
| FYN | SDC3 | (CCSB; GRID; HPRD) |
| FYN | SH2B2 | (HPRD) |
| FYN | SH2D1A | (GRID; HPRD; MINT) |
| FYN | SH3BP2 | (HPRD) |
| FYN | SHC1 | (HPRD; MINT) |
| FYN | SIT1 | (GRID; HPRD) |
| FYN | SKAP1 | (GRID; HPRD) |
| FYN | SKAP2 | (CCSB; GRID; HPRD) |
| FYN | SLAMF1 | (CCSB; GRID; HPRD) |
| FYN | SNCA | (GRID; HPRD) |
| FYN | SNX26 | (HPRD) |
| FYN | SOCS1 | (BIND; GRID; HPRD) |
| FYN | SOS1 | (GRID; HPRD) |
| FYN | SPHK1 | (IntAct) |
| FYN | SPHK2 | (IntAct) |
| FYN | SPN | (GRID; HPRD) |
| FYN | SRC | (MINT) |
| FYN | STAT1 | (HPRD) |
| FYN | SYK | (CCSB; GRID; HPRD) |
| FYN | TEK | (HPRD) |
| FYN | THY1 | (CCSB; GRID; HPRD) |
| FYN | TNK2 | (CCSB; GRID; HPRD) |
| FYN | TOM1L1 | (HPRD) |
| FYN | TRAT1 | (HPRD) |
| FYN | TRPC6 | (GRID; HPRD) |
| FYN | TRPV4 | (GRID; HPRD) |
| FYN | TUBA1B | (CCSB; GRID; HPRD) |
| FYN | TUBA3C | (CCSB; GRID; HPRD) |
| FYN | TUBA4A | (CCSB; GRID; HPRD) |
| FYN | TXK | (HPRD) |
| FYN | TYK2 | (CCSB; GRID; HPRD) |
| FYN | TYRO3 | (GRID; HPRD) |
| FYN | UNC119 | (CCSB; GRID; HPRD) |
| FYN | VAV1 | (CCSB; GRID; HPRD) |
| FYN | WAS | (CCSB; GRID; HPRD; MINT) |
| FYN | WASF1 | (GRID; HPRD) |
| FYN | WASF2 | (GRID; HPRD) |
| FYN | YTHDC1 | (GRID; HPRD) |
| FYN | ZAP70 | (CCSB; GRID; HPRD) |
| HCK | ACTB | (HPRD) |
| HCK | ADAM15 | (CCSB; GRID; HPRD; MINT) |
| HCK | AGK | (HPRD; MDC) |
| HCK | ARRB1 | (HPRD) |
| HCK | BCAR1 | (GRID; HPRD) |
| HCK | BCR | (GRID; HPRD) |
| HCK | C14orf4 | (HPRD) |
| HCK | C2orf44 | (HPRD; IntAct) |
| HCK | CBL | (GRID; HPRD) |
| HCK | CCR3 | (GRID; HPRD) |
| HCK | CD2AP | (HPRD; IntAct) |
| HCK | CSF2RB | (HPRD) |
| HCK | CSF3R | (GRID; HPRD) |
| HCK | DDEF1 | (HPRD; IntAct) |
| HCK | DNM2 | (HPRD; IntAct) |
| HCK | DOK1 | (HPRD) |
| HCK | ELMO1 | (GRID; HPRD; IntAct; MINT) |
| HCK | EVL | (HPRD; IntAct) |
| HCK | FCGR1A | (CCSB; GRID; HPRD) |
| HCK | FCGR2A | (CCSB; GRID; HPRD) |
| HCK | GALNAC4S-6ST | (GRID; HPRD) |
| HCK | HNRPK | (HPRD) |
| HCK | IL6ST | (GRID; HPRD) |
| HCK | INPP5D | (HPRD) |
| HCK | KHDRBS1 | (BIND; HPRD; IntAct) |
| HCK | KIT | (HPRD) |
| HCK | LCP2 | (HPRD; IntAct) |
| HCK | PECAM1 | (GRID; HPRD) |
| HCK | PIK3CB | (HPRD) |
| HCK | PIK3R1 | (HPRD; IntAct) |
| HCK | PIK3R2 | (HPRD; IntAct) |
| HCK | PLAUR | (CCSB; DIP; GRID; HPRD) |
| HCK | PLCG1 | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| HCK | PLCG2 | (HPRD) |
| HCK | RAPGEF1 | (GRID; HPRD) |
| HCK | RASA1 | (CCSB; GRID; HPRD) |
| HCK | RASA3 | (GRID; HPRD) |
| HCK | SF3B3 | (HPRD; IntAct) |
| HCK | SH3BP1 | (HPRD; IntAct) |
| HCK | SH3KBP1 | (HPRD; IntAct) |
| HCK | SKAP2 | (CCSB; GRID; HPRD) |
| HCK | SOS1 | (HPRD; IntAct) |
| HCK | STAT3 | (HPRD) |
| HCK | TRPV4 | (GRID; HPRD) |
| HCK | TSG101 | (HPRD; IntAct) |
| HCK | UNC119 | (CCSB; GRID; HPRD) |
| HCK | VAV1 | (HPRD) |
| HCK | WAS | (HPRD; IntAct; MINT) |
| HCK | WIPF1 | (CCSB; GRID; HPRD; IntAct; MINT) |
| IGF1R | ARHGEF12 | (GRID; HPRD; MINT) |
| IGF1R | CRK | (HPRD) |
| IGF1R | CRKL | (HPRD) |
| IGF1R | DOK4 | (HPRD) |
| IGF1R | DOK5 | (HPRD) |
| IGF1R | EHD1 | (BIND; GRID; HPRD) |
| IGF1R | ESR1 | (HPRD) |
| IGF1R | GIGYF1 | (GRID; HPRD) |
| IGF1R | GIPC1 | (HPRD) |
| IGF1R | GNAI1 | (GRID; HPRD) |
| IGF1R | GNAI2 | (GRID; HPRD) |
| IGF1R | GNB2L1 | (BIND; GRID; HPRD) |
| IGF1R | GRB10 | (BIND; GRID; HPRD; MINT) |
| IGF1R | GYS1 | (BIND) |
| IGF1R | HNF1A | (BIND) |
| IGF1R | IGF1 | (BIND; DIP; GRID; HPRD) |
| IGF1R | IGF2 | (GRID; HPRD) |
| IGF1R | IGFBP3 | (GRID; HPRD) |
| IGF1R | INS | (BIND; GRID; HPRD) |
| IGF1R | INSR | (HPRD) |
| IGF1R | IRS1 | (BIND; GRID; HPRD) |
| IGF1R | IRS2 | (GRID; HPRD; MINT) |
| IGF1R | IRS4 | (HPRD) |
| IGF1R | ITGB1 | (BIND; HPRD) |
| IGF1R | JAK1 | (BIND; GRID; HPRD) |
| IGF1R | JAK2 | (HPRD) |
| IGF1R | KRT27 | (HPRD) |
| IGF1R | MAP3K5 | (HPRD) |
| IGF1R | MDM2 | (HPRD) |
| IGF1R | NEDD4 | (GRID; HPRD) |
| IGF1R | PBEF1 | (BIND) |
| IGF1R | PIK3R1 | (DIP; GRID; HPRD) |
| IGF1R | PIK3R2 | (BIND; HPRD) |
| IGF1R | PIK3R3 | (GRID; HPRD) |
| IGF1R | PRKCD | (BIND; HPRD) |
| IGF1R | PRKD1 | (BIND; HPRD) |
| IGF1R | PTPN1 | (GRID; HPRD) |
| IGF1R | PTPN11 | (DIP; GRID; HPRD) |
| IGF1R | RASA1 | (GRID; HPRD) |
| IGF1R | SHC1 | (BIND; DIP; GRID; HPRD; IntAct) |
| IGF1R | SNAP29 | (GRID) |
| IGF1R | SOCS1 | (BIND; GRID; HPRD; MINT) |
| IGF1R | SOCS2 | (BIND; GRID; HPRD; MINT) |
| IGF1R | SOCS3 | (BIND; GRID; HPRD; MINT) |
| IGF1R | SRC | (HPRD) |
| IGF1R | STAT3 | (HPRD) |
| IGF1R | TAF1 | (BIND) |
| IGF1R | VAV3 | (GRID; HPRD) |
| IGF1R | WISP2 | (HPRD) |
| IGF1R | YWHAB | (BIND; GRID; HPRD; IntAct; MINT) |
| IGF1R | YWHAE | (BIND; GRID; HPRD; MINT) |
| IGF1R | YWHAG | (GRID; HPRD; MINT) |
| IGF1R | YWHAZ | (BIND; GRID; HPRD) |
| INSR | ACP1 | (HPRD) |
| INSR | ADRB2 | (HPRD) |
| INSR | AHSG | (GRID; HPRD) |
| INSR | ARF1 | (BIND; HPRD) |
| INSR | ARHGAP26 | (HPRD) |
| INSR | CALM1 | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| INSR | CALM2 | (HPRD) |
| INSR | CALM3 | (HPRD) |
| INSR | CASP7 | (BIND) |
| INSR | CAV1 | (GRID; HPRD) |
| INSR | CAV3 | (HPRD) |
| INSR | CBL | (HPRD) |
| INSR | CEACAM1 | (HPRD) |
| INSR | CRK | (HPRD) |
| INSR | CRKL | (HPRD; IntAct) |
| INSR | DOK1 | (HPRD; reactome) |
| INSR | DOK4 | (HPRD) |
| INSR | DOK5 | (HPRD) |
| INSR | ENPP1 | (GRID; HPRD) |
| INSR | FABP4 | (HPRD) |
| INSR | FRS2 | (GRID; HPRD) |
| INSR | GAB1 | (GRID; HPRD) |
| INSR | GNB2L1 | (HPRD) |
| INSR | GRB10 | (BIND; GRID; HPRD; MINT; reactome) |
| INSR | GRB14 | (GRID; HPRD; MINT) |
| INSR | GRB2 | (reactome) |
| INSR | GRB7 | (GRID; HPRD) |
| INSR | HMGA1 | (BIND) |
| INSR | HNF1A | (BIND) |
| INSR | HRAS | (GRID; HPRD) |
| INSR | IGF2 | (GRID; HPRD) |
| INSR | IMPDH2 | (BIND) |
| INSR | INS | (DIP; GRID; HPRD; reactome) |
| INSR | INSRR | (GRID; HPRD) |
| INSR | IRS1 | (BIND; DIP; GRID; HPRD; IntAct; MINT; reactome) |
| INSR | IRS2 | (GRID; HPRD; MINT; reactome) |
| INSR | JAK1 | (BIND; HPRD) |
| INSR | JAK2 | (HPRD) |
| INSR | KHDRBS1 | (HPRD) |
| INSR | KRT27 | (HPRD) |
| INSR | MAD2L1 | (HPRD; MINT) |
| INSR | MAPK3 | (GRID; HPRD) |
| INSR | PBEF1 | (BIND) |
| INSR | PIK3CA | (reactome) |
| INSR | PIK3CB | (reactome) |
| INSR | PIK3R1 | (BIND; DIP; HPRD; reactome) |
| INSR | PIK3R2 | (reactome) |
| INSR | PIK3R3 | (GRID; HPRD) |
| INSR | PLCG1 | (HPRD) |
| INSR | PRKCA | (HPRD) |
| INSR | PRKCD | (GRID; HPRD) |
| INSR | PTK2 | (HPRD) |
| INSR | PTPN1 | (GRID; HPRD; MINT) |
| INSR | PTPN11 | (DIP; GRID; HPRD) |
| INSR | PTPN12 | (GRID; HPRD) |
| INSR | PTPN2 | (HPRD) |
| INSR | PTPN6 | (GRID; HPRD) |
| INSR | PTPRC | (HPRD) |
| INSR | PTPRF | (GRID; HPRD) |
| INSR | RAF1 | (GRID; HPRD) |
| INSR | RASA1 | (GRID; HPRD) |
| INSR | SH2B1 | (GRID; HPRD) |
| INSR | SH2B2 | (HPRD) |
| INSR | SHC1 | (BIND; DIP; GRID; HPRD; IntAct; reactome) |
| INSR | SMAD2 | (GRID; HPRD) |
| INSR | SNX1 | (GRID; HPRD) |
| INSR | SNX2 | (GRID; HPRD) |
| INSR | SNX4 | (GRID; HPRD) |
| INSR | SNX6 | (GRID; HPRD) |
| INSR | SOCS1 | (BIND; HPRD) |
| INSR | SOCS2 | (HPRD) |
| INSR | SOCS3 | (GRID; HPRD) |
| INSR | SOCS6 | (BIND; HPRD) |
| INSR | SORBS1 | (GRID; HPRD) |
| INSR | SOS1 | (reactome) |
| INSR | SRC | (HPRD) |
| INSR | STAT5A | (HPRD) |
| INSR | STAT5B | (HPRD) |
| INSR | SYNCRIP | (GRID; HPRD) |
| INSR | VAV1 | (GRID; HPRD) |
| INSR | VAV3 | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| INSR | YWHAB | (HPRD; IntAct) |
| INSRR | KRT27 | (HPRD) |
| ITK | BLNK | (GRID; HPRD) |
| ITK | CBL | (GRID; HPRD) |
| ITK | CD28 | (GRID; HPRD) |
| ITK | GRB2 | (GRID; HPRD) |
| ITK | HNRPK | (BIND; GRID; HPRD) |
| ITK | KHDRBS1 | (GRID; HPRD) |
| ITK | KPNA2 | (BIND; GRID; HPRD) |
| ITK | LAT | (BIND; GRID; HPRD) |
| ITK | LCK | (HPRD) |
| ITK | LCP2 | (BIND; GRID; HPRD; MINT) |
| ITK | PLCG1 | (BIND; GRID; HPRD) |
| ITK | PLCG2 | (HPRD) |
| ITK | PPIA | (GRID; HPRD) |
| ITK | SH2D2A | (HPRD) |
| ITK | SMAD4 | (BIND; HPRD) |
| ITK | SOCS1 | (BIND; GRID; HPRD) |
| ITK | TGFBR1 | (BIND; HPRD) |
| ITK | WAS | (GRID; HPRD) |
| JAK1 | ARRB1 | (GRID) |
| JAK1 | ATIC | (GRID) |
| JAK1 | BRCA1 | (GRID; HPRD; MINT) |
| JAK1 | CCR1 | (HPRD) |
| JAK1 | CCR5 | (HPRD) |
| JAK1 | CSF2RB | (HPRD) |
| JAK1 | CSF3R | (GRID; HPRD) |
| JAK1 | CXCR4 | (HPRD) |
| JAK1 | ELF3 | (GRID) |
| JAK1 | ELP2 | (GRID; HPRD) |
| JAK1 | GHR | (GRID; HPRD) |
| JAK1 | GNB2L1 | (BIND; GRID; HPRD; MINT) |
| JAK1 | GRB2 | (DIP; GRID; HPRD) |
| JAK1 | IFNAR1 | (DIP) |
| JAK1 | IFNAR2 | (BIND; HPRD; MINT) |
| JAK1 | IFNGR1 | (GRID; HPRD) |
| JAK1 | IL10RA | (BIND; GRID; HPRD) |
| JAK1 | IL21R | (GRID; HPRD) |
| JAK1 | IL2RB | (BIND; DIP; GRID; HPRD) |
| JAK1 | IL2RG | (HPRD) |
| JAK1 | IL3RA | (HPRD) |
| JAK1 | IL4R | (BIND; GRID; HPRD) |
| JAK1 | IL5RA | (GRID; HPRD) |
| JAK1 | IL6R | (MINT) |
| JAK1 | IL6ST | (DIP; GRID; HPRD) |
| JAK1 | IL7R | (HPRD) |
| JAK1 | IL9R | (GRID; HPRD) |
| JAK1 | INPP5D | (HPRD) |
| JAK1 | IRS1 | (HPRD) |
| JAK1 | IRS2 | (GRID; HPRD) |
| JAK1 | JAK3 | (GRID; HPRD) |
| JAK1 | JAKMIP1 | (BIND; HPRD) |
| JAK1 | LRPPRC | (MINT) |
| JAK1 | MDK | (GRID; HPRD) |
| JAK1 | OSMR | (GRID; HPRD) |
| JAK1 | PDGFRA | (HPRD) |
| JAK1 | PDGFRB | (HPRD) |
| JAK1 | PIK3R1 | (GRID; HPRD) |
| JAK1 | PLA2G4A | (HPRD) |
| JAK1 | PLAUR | (BIND; DIP; GRID; HPRD) |
| JAK1 | PLCG2 | (HPRD) |
| JAK1 | PRKCZ | (HPRD) |
| JAK1 | PRMT5 | (GRID; HPRD) |
| JAK1 | PTPN11 | (GRID; HPRD) |
| JAK1 | PTPN2 | (HPRD) |
| JAK1 | PTPN6 | (HPRD) |
| JAK1 | PTPRC | (HPRD) |
| JAK1 | RAF1 | (GRID; HPRD) |
| JAK1 | SH2B2 | (HPRD) |
| JAK1 | SHB | (GRID; HPRD) |
| JAK1 | SOCS1 | (GRID; HPRD) |
| JAK1 | SOCS3 | (HPRD) |
| JAK1 | STAM | (HPRD) |
| JAK1 | STAM2 | (GRID; HPRD; MINT) |
| JAK1 | STAT1 | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| JAK1 | STAT2 | (HPRD) |
| JAK1 | STAT3 | (GRID; HPRD; MINT) |
| JAK1 | STAT5A | (GRID HPRD) |
| JAK1 | STAT6 | (HPRD) |
| JAK1 | SYK | (GRID; HPRD) |
| JAK1 | TAF1 | (BIND) |
| JAK1 | TEC | (GRID; HPRD) |
| JAK1 | TNFRSF1A | (GRID; HPRD) |
| JAK1 | TSHR | (GRID; HPRD) |
| JAK1 | TYK2 | (GRID; HPRD) |
| JAK2 | AGTR1 | (GRID; HPRD) |
| JAK2 | BCR | (GRID; HPRD) |
| JAK2 | BRCA1 | (GRID; HPRD, MINT) |
| JAK2 | CCR2 | (GRID; HPRD) |
| JAK2 | CCR5 | (GRID; HPRD) |
| JAK2 | CRLF2 | (HPRD) |
| JAK2 | CSF2RB | (GRID; HPRD) |
| JAK2 | CSF3R | (GRID; HPRD) |
| JAK2 | CTLA4 | (BIND; GRID, HPRD) |
| JAK2 | CXCR4 | (GRID; HPRD) |
| JAK2 | DNAJA3 | (BIND; GRID, HPRD) |
| JAK2 | ELP2 | (GRID; HPRD) |
| JAK2 | EPOR | (GRID; HPRD) |
| JAK2 | GHR | (GRID; HPRD) |
| JAK2 | GRB10 | (GRID; HPRD) |
| JAK2 | GRB2 | (GRID; HPRD) |
| JAK2 | GTF2I | (HPRD) |
| JAK2 | HES1 | (HPRD) |
| JAK2 | HES5 | (HPRD) |
| JAK2 | HSPA8 | (GRID; HPRD) |
| JAK2 | HTR2A | (GRID; HPRD) |
| JAK2 | IFNGR1 | (HPRD) |
| JAK2 | IFNGR2 | (GRID; HPRD) |
| JAK2 | IL12RB2 | (BIND; GRID; HPRD) |
| JAK2 | IL23R | (HPRD) |
| JAK2 | IL3RA | (HPRD) |
| JAK2 | IL4R | (HPRD) |
| JAK2 | IL5RA | (GRID; HPRD) |
| JAK2 | IRS1 | (HPRD) |
| JAK2 | IRS2 | (HPRD) |
| JAK2 | JAK3 | (HPRD) |
| JAK2 | KIT | (GRID; HPRD) |
| JAK2 | LEPR | (GRID; HPRD; IntAct) |
| JAK2 | LYN | (GRID; HPRD) |
| JAK2 | MDK | (GRID; HPRD) |
| JAK2 | MPL | (HPRD) |
| JAK2 | MST1R | (HPRD) |
| JAK2 | NFKBIA | (HPRD) |
| JAK2 | OSMR | (GRID; HPRD) |
| JAK2 | PDGFRB | (HPRD) |
| JAK2 | PIK3R1 | (GRID; HPRD) |
| JAK2 | PKD1 | (HPRD) |
| JAK2 | PLCG2 | (HPRD) |
| JAK2 | PPIA | (GRID; HPRD) |
| JAK2 | PPP2CA | (HPRD) |
| JAK2 | PPP2R1B | (GRID; HPRD) |
| JAK2 | PPP2R5A | (GRID; HPRD) |
| JAK2 | PRLR | (GRID; HPRD) |
| JAK2 | PRMT5 | (GRID; HPRD) |
| JAK2 | PTK2 | (GRID; HPRD) |
| JAK2 | PTPN1 | (GRID; HPRD) |
| JAK2 | PTPN11 | (GRID; HPRD) |
| JAK2 | PTPN12 | (GRID; HPRD) |
| JAK2 | PTPN6 | (GRID; HPRD) |
| JAK2 | PTPRC | (HPRD) |
| JAK2 | RAF1 | (GRID; HPRD) |
| JAK2 | SH2B1 | (GRID; HPRD) |
| JAK2 | SH2B2 | (HPRD) |
| JAK2 | SHC1 | (GRID; HPRD) |
| JAK2 | SIRPA | (GRID; HPRD) |
| JAK2 | SOCS1 | (GRID; HPRD) |
| JAK2 | SOCS3 | (GRID; HPRD) |
| JAK2 | STAM | (GRID; HPRD) |
| JAK2 | STAM2 | (GRID; HPRD) |
| JAK2 | STAP2 | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| JAK2 | STAT1 | (HPRD) |
| JAK2 | STAT2 | (HPRD) |
| JAK2 | STAT3 | (GRID; HPRD) |
| JAK2 | STAT5A | (GRID; HPRD) |
| JAK2 | STAT5B | (HPRD) |
| JAK2 | TEC | (GRID; HPRD) |
| JAK2 | TNFRSF1A | (GRID; HPRD) |
| JAK2 | TSHR | (GRID; HPRD) |
| JAK2 | TUB | (GRID; HPRD) |
| JAK2 | TYK2 | (HPRD) |
| JAK2 | UBASH3B | (HPRD) |
| JAK2 | VAV1 | (GRID; HPRD) |
| JAK2 | VCP | (GRID; HPRD) |
| JAK2 | YES1 | (GRID; HPRD) |
| JAK3 | CD247 | (CCSB; GRID; HPRD) |
| JAK3 | CD40 | (HPRD) |
| JAK3 | CXCR4 | (CCSB; GRID; HPRD) |
| JAK3 | IL2RB | (CCSB; GRID; HPRD) |
| JAK3 | IL2RG | (CCSB; DIP; GRID; HPRD) |
| JAK3 | IL4R | (GRID; HPRD) |
| JAK3 | IL6ST | (HPRD) |
| JAK3 | IL7R | (HPRD) |
| JAK3 | INPP5D | (HPRD) |
| JAK3 | IRS1 | (GRID; HPRD) |
| JAK3 | IRS2 | (GRID; HPRD) |
| JAK3 | KHDRBS1 | (HPRD; IntAct) |
| JAK3 | LCK | (CCSB; GRID; HPRD) |
| JAK3 | PIK3R1 | (HPRD) |
| JAK3 | PRMT5 | (GRID; HPRD) |
| JAK3 | PTPN2 | (HPRD) |
| JAK3 | PTPN6 | (HPRD) |
| JAK3 | PTPRC | (GRID; HPRD) |
| JAK3 | SH2B2 | (HPRD) |
| JAK3 | SHB | (GRID; HPRD) |
| JAK3 | SOCS1 | (GRID; HPRD) |
| JAK3 | SOCS3 | (HPRD) |
| JAK3 | STAM | (CCSB; GRID; HPRD) |
| JAK3 | STAM2 | (CCSB; GRID; HPRD) |
| JAK3 | STAT3 | (CCSB; GRID; HPRD) |
| JAK3 | STAT5A | (CCSB; GRID; HPRD) |
| JAK3 | TIAF1 | (GRID; HPRD) |
| KDR | ACP1 | (GRID; HPRD) |
| KDR | ANXA5 | (GRID; HPRD) |
| KDR | ATR | (HPRD) |
| KDR | CAV1 | (HPRD) |
| KDR | CBL | (HPRD) |
| KDR | CDH5 | (GRID; HPRD; MINT) |
| KDR | COL18A1 | (GRID; HPRD) |
| KDR | CRK | (HPRD) |
| KDR | CSF2RB | (HPRD) |
| KDR | CTNNB1 | (HPRD) |
| KDR | DNM2 | (HPRD) |
| KDR | FIGF | (DIP; GRID; HPRD) |
| KDR | FRS2 | (HPRD) |
| KDR | GNA11 | (HPRD) |
| KDR | GNAQ | (HPRD) |
| KDR | GRB10 | (GRID; HPRD) |
| KDR | GRB2 | (GRID; HPRD) |
| KDR | HSP90AA1 | (HPRD) |
| KDR | IQGAP1 | (HPRD) |
| KDR | ITGB3 | (HPRD) |
| KDR | NCK1 | (HPRD; MINT) |
| KDR | NRP1 | (HPRD; MINT) |
| KDR | P2RY2 | (HPRD) |
| KDR | PLCG1 | (BIND; HPRD) |
| KDR | PLCG2 | (GRID; HPRD) |
| KDR | PLXNA1 | (GRID) |
| KDR | PTPN11 | (HPRD) |
| KDR | PTPN6 | (HPRD) |
| KDR | RASA1 | (HPRD) |
| KDR | SH2D2A | (BIND; HPRD) |
| KDR | SHB | (GRID; HPRD) |
| KDR | SHC1 | (GRID; HPRD; MINT) |
| KDR | SHC2 | (BIND; GRID; HPRD; MINT) |
| KDR | SRC | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| KDR | STAT1 | (HPRD) |
| KDR | SYNGAP1 | (HPRD) |
| KDR | TIMP3 | (HPRD) |
| KDR | VEGFA | (BIND; DIP; GRID; HPRD; MINT) |
| KDR | VEGFC | (BIND; GRID; HPRD) |
| KDR | YES1 | (HPRD) |
| KIT | BCR | (GRID) |
| KIT | CBL | (HPRD) |
| KIT | CBLB | (HPRD) |
| KIT | CD63 | (GRID) |
| KIT | CD81 | (GRID; HPRD) |
| KIT | CD9 | (GRID; HPRD) |
| KIT | CISH | (HPRD) |
| KIT | CLTC | (GRID; HPRD) |
| KIT | CRK | (HPRD) |
| KIT | CRKL | (GRID; HPRD) |
| KIT | CSF2RA | (HPRD) |
| KIT | CSF2RB | (HPRD) |
| KIT | DOK1 | (GRID; HPRD) |
| KIT | EPOR | (GRID; HPRD) |
| KIT | GRAP | (GRID; HPRD) |
| KIT | GRAP2 | (GRID; HPRD) |
| KIT | GRB10 | (GRID; HPRD) |
| KIT | GRB2 | (BIND; DIP; GRID; HPRD) |
| KIT | GRB7 | (GRID; HPRD) |
| KIT | INPP5D | (HPRD) |
| KIT | KITLG | (GRID; HPRD) |
| KIT | LCK | (GRID; HPRD) |
| KIT | LYN | (BIND; GRID; HPRD) |
| KIT | MATK | (GRID; HPRD) |
| KIT | MPDZ | (GRID; HPRD) |
| KIT | PIK3CG | (HPRD) |
| KIT | PIK3R1 | (BIND; GRID; HPRD) |
| KIT | PIK3R2 | (BIND; GRID; HPRD) |
| KIT | PLCE1 | (HPRD) |
| KIT | PLCG1 | (BIND; GRID; HPRD) |
| KIT | PRKCA | (HPRD) |
| KIT | PRKCB1 | (HPRD) |
| KIT | PTPN11 | (BIND; GRID; HPRD) |
| KIT | PTPN6 | (GRID; HPRD) |
| KIT | PTPRO | (GRID; HPRD) |
| KIT | PTPRU | (HPRD) |
| KIT | RASA1 | (HPRD) |
| KIT | SH2B2 | (HPRD) |
| KIT | SH2B3 | (HPRD) |
| KIT | SOCS1 | (BIND; GRID; HPRD) |
| KIT | SOCS5 | (HPRD) |
| KIT | SOCS6 | (HPRD) |
| KIT | SPRED1 | (HPRD) |
| KIT | SPRED2 | (HPRD) |
| KIT | SRC | (HPRD) |
| KIT | STAP1 | (HPRD) |
| KIT | STAT1 | (BIND; GRID; HPRD) |
| KIT | STAT5A | (HPRD) |
| KIT | STAT5B | (HPRD) |
| KIT | TEC | (GRID; HPRD) |
| KIT | YES1 | (HPRD) |
| LCK | ACP1 | (HPRD) |
| LCK | ADAM15 | (CCSB; GRID; HPRD; MINT) |
| LCK | AP2A1 | (reactome) |
| LCK | AP2A2 | (reactome) |
| LCK | AP2B1 | (reactome) |
| LCK | AP2M1 | (reactome) |
| LCK | AP2S1 | (reactome) |
| LCK | ATP6V1H | (reactome) |
| LCK | BCAR1 | (GRID; HPRD) |
| LCK | CAMLG | (BIND) |
| LCK | CBL | (GRID; HPRD; MINT) |
| LCK | CCR5 | (GRID; HPRD) |
| LCK | CD2 | (CCSB; GRID; HPRD; MINT) |
| LCK | CD247 | (HPRD; MINT) |
| LCK | CD28 | (GRID; HPRD) |
| LCK | CD38 | (BIND; CCSB; GRID; HPRD) |
| LCK | CD3E | (GRID; HPRD) |
| LCK | CD4 | (CCSB; GRID; HPRD; MINT; reactome) |

TABLE 5-continued

Human Tyrosine Kinase Interactions (node 1 = tyrosine kinase; node 2 = interacting protein)

| Node1 | Node2 | int_DataBase |
|---|---|---|
| LCK | CD44 | (CCSB; GRID; HPRD) |
| LCK | CD48 | (CCSB; GRID; HPRD) |
| LCK | CD5 | (DIP; GRID; HPRD) |
| LCK | CD55 | (CCSB; GRID; HPRD) |
| LCK | CD79A | (HPRD) |
| LCK | CD79B | (HPRD) |
| LCK | CD8A | (HPRD) |
| LCK | CD8B | (BIND) |
| LCK | CDC25C | (CCSB; GRID; HPRD) |
| LCK | CSF2RB | (HPRD) |
| LCK | CSF3R | (HPRD) |
| LCK | CTLA4 | (GRID; HPRD) |
| LCK | CTNND1 | (GRID) |
| LCK | CTNND2 | (GRID; HPRD) |
| LCK | DAPP1 | (HPRD) |
| LCK | DEF6 | (HPRD) |
| LCK | DLG1 | (GRID; HPRD) |
| LCK | DNM2 | (BIND) |
| LCK | DOK1 | (HPRD) |
| LCK | DOK2 | (CCSB; GRID; HPRD) |
| LCK | DOK3 | (HPRD) |
| LCK | ESR1 | (HPRD) |
| LCK | ESR2 | (HPRD) |
| LCK | EZR | (HPRD) |
| LCK | FAS | (CCSB; GRID; HPRD) |
| LCK | FASLG | (GRID; HPRD) |
| LCK | FCGR3A | (CCSB; GRID; HPRD) |
| LCK | GAB2 | (HPRD) |
| LCK | GRAP | (HPRD) |
| LCK | HSP90AA1 | (DIP; MINT) |
| LCK | IFNAR1 | (HPRD) |
| LCK | IL2RB | (CCSB; GRID; HPRD) |
| LCK | KHDRBS1 | (BIND; GRID; HPRD; IntAct; MINT) |
| LCK | KIR2DL3 | (HPRD) |
| LCK | LAT | (HPRD) |
| LCK | LAX1 | (HPRD) |
| LCK | LCP2 | (HPRD; MINT) |
| LCK | LIME1 | (HPRD) |
| LCK | LYN | (HPRD) |
| LCK | MAPK1 | (HPRD; MINT) |
| LCK | MAPK3 | (HPRD) |
| LCK | MS4A1 | (HPRD) |
| LCK | MUC1 | (HPRD) |
| LCK | NEDD9 | (GRID; HPRD) |
| LCK | NFKBIA | (BIND; HPRD) |
| LCK | NOTCH1 | (GRID; HPRD) |
| LCK | NR3C1 | (MINT) |
| LCK | NXF1 | (IntAct) |
| LCK | PAG1 | (GRID; HPRD) |
| LCK | PECAM1 | (GRID; HPRD) |
| LCK | PIK3CA | (GRID; HPRD) |
| LCK | PIK3R1 | (GRID; HPRD; MINT) |
| LCK | PLCG1 | (GRID; HPRD) |
| LCK | PLCG2 | (HPRD) |
| LCK | PLD2 | (GRID; HPRD) |
| LCK | PRKACA | (HPRD) |
| LCK | PRKCA | (HPRD) |
| LCK | PRKCD | (HPRD) |
| LCK | PRKCQ | (HPRD) |
| LCK | PTK2 | (HPRD) |
| LCK | PTPN11 | (CCSB; GRID; HPRD) |
| LCK | PTPN6 | (CCSB; GRID; HPRD) |
| LCK | PTPRC | (GRID; HPRD; IntAct) |
| LCK | PTPRF | (HPRD) |
| LCK | PTPRH | (HPRD) |
| LCK | PXN | (GRID; HPRD) |
| LCK | RAF1 | (CCSB; GRID; HPRD) |
| LCK | RASA1 | (HPRD) |
| LCK | SH2B3 | (CCSB; GRID; HPRD) |
| LCK | SH2D1A | (HPRD; MINT) |
| LCK | SH2D2A | (HPRD; IntAct) |
| LCK | SH3BP2 | (HPRD) |
| LCK | SHC1 | (HPRD) |
| LCK | SIT1 | (GRID; HPRD) |
| LCK | SKAP1 | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| LCK | SQSTM1 | (CCSB; GRID; HPRD) |
| LCK | STAT1 | (HPRD) |
| LCK | STAT3 | (CCSB; GRID; HPRD) |
| LCK | STAT5A | (HPRD) |
| LCK | SYK | (CCSB; GRID; HPRD; MINT) |
| LCK | TEK | (GRID; HPRD) |
| LCK | THY1 | (CCSB; GRID; HPRD) |
| LCK | TRAT1 | (HPRD) |
| LCK | TRPV4 | (GRID; HPRD) |
| LCK | TUB | (GRID; HPRD) |
| LCK | UNC119 | (CCSB; GRID; HPRD) |
| LCK | VAV1 | (HPRD) |
| LCK | WASL | (IntAct) |
| LCK | ZAP70 | (CCSB; GRID; HPRD; MINT) |
| LMTK2 | CDK5 | (GRID) |
| LMTK2 | CDK5R1 | (GRID; HPRD) |
| LMTK2 | PPP1R2 | (GRID; HPRD) |
| LMTK3 | ZBTB16 | (MDC) |
| LTK | CBL | (GRID; HPRD) |
| LTK | PIK3C2B | (GRID; HPRD) |
| LTK | PLCG1 | (HPRD) |
| LTK | PTPN1 | (GRID; HPRD) |
| LTK | SHC1 | (GRID; HPRD) |
| LYN | ACTB | (HPRD) |
| LYN | ADAM15 | (MINT) |
| LYN | BANK1 | (GRID; HPRD) |
| LYN | BCAR1 | (GRID; HPRD) |
| LYN | CASP3 | (HPRD) |
| LYN | CASP7 | (HPRD) |
| LYN | CASP9 | (HPRD) |
| LYN | CBL | (BIND; DIP; GRID; HPRD; MINT) |
| LYN | CBLC | (GRID; HPRD) |
| LYN | CD19 | (GRID; HPRD) |
| LYN | CD22 | (GRID; HPRD; IntAct) |
| LYN | CD24 | (GRID; HPRD) |
| LYN | CD36 | (GRID; HPRD) |
| LYN | CD79A | (HPRD) |
| LYN | CD79B | (HPRD) |
| LYN | CDAN3 | (GRID) |
| LYN | CDC2 | (GRID; HPRD) |
| LYN | CDK2 | (GRID; HPRD) |
| LYN | CDK4 | (GRID) |
| LYN | CDKN1B | (HPRD) |
| LYN | CRKL | (HPRD) |
| LYN | CSF2RA | (HPRD) |
| LYN | CSF2RB | (GRID; HPRD) |
| LYN | CSF3R | (GRID; HPRD) |
| LYN | CSNK2B | (BIND; GRID; HPRD; IntAct; MINT) |
| LYN | CTLA4 | (GRID; HPRD) |
| LYN | DAPP1 | (HPRD) |
| LYN | DLG4 | (GRID; HPRD) |
| LYN | DOK1 | (HPRD) |
| LYN | DOK3 | (HPRD) |
| LYN | EPOR | (GRID; HPRD) |
| LYN | EVL | (GRID; HPRD) |
| LYN | FCAR | (GRID; HPRD) |
| LYN | FCER1G | (GRID; HPRD) |
| LYN | FCGR2A | (HPRD) |
| LYN | FCGR2B | (HPRD) |
| LYN | FOLR1 | (GRID; HPRD) |
| LYN | GAB2 | (GRID; HPRD) |
| LYN | GAB3 | (GRID; HPRD) |
| LYN | GALNAC4S-6ST | (GRID; HPRD) |
| LYN | GP6 | (GRID; HPRD) |
| LYN | GRIA3 | (GRID; HPRD) |
| LYN | HCLS1 | (GRID; HPRD; MINT) |
| LYN | HNRPK | (HPRD) |
| LYN | IL2RB | (HPRD) |
| LYN | IL7R | (GRID; HPRD) |
| LYN | INPP5D | (GRID; HPRD) |
| LYN | ITPR1 | (HPRD) |
| LYN | KHDRBS1 | (HPRD; IntAct; MINT) |
| LYN | LCP2 | (BIND; GRID; HPRD) |
| LYN | LIME1 | (HPRD) |
| LYN | MAP3K3 | (IntAct; MINT) |

TABLE 5-continued

Human Tyrosine Kinase Interactions (node 1 = tyrosine kinase; node 2 = interacting protein)

| Node1 | Node2 | int_DataBase |
|---|---|---|
| LYN | MAP4K1 | (HPRD) |
| LYN | MAPK3 | (GRID; HPRD) |
| LYN | MATK | (HPRD) |
| LYN | MME | (GRID; HPRD) |
| LYN | MS4A1 | (HPRD) |
| LYN | MS4A2 | (GRID; HPRD) |
| LYN | MUC1 | (GRID) |
| LYN | NEDD9 | (GRID; HPRD) |
| LYN | NMT1 | (GRID; HPRD) |
| LYN | NPHS1 | (GRID; HPRD) |
| LYN | PAG1 | (GRID; HPRD) |
| LYN | PDE4A | (GRID; HPRD) |
| LYN | PDE4D | (BIND) |
| LYN | PECAM1 | (GRID; HPRD) |
| LYN | PIK3CG | (GRID; HPRD) |
| LYN | PILRB | (HPRD) |
| LYN | PLAUR | (DIP) |
| LYN | PLCG1 | (GRID; HPRD) |
| LYN | PLCG2 | (HPRD) |
| LYN | PPP1R15A | (BIND; GRID; HPRD) |
| LYN | PPP1R8 | (GRID; HPRD) |
| LYN | PRAM1 | (GRID; HPRD) |
| LYN | PRKCD | (HPRD) |
| LYN | PRKCQ | (GRID; HPRD) |
| LYN | PRKDC | (GRID; HPRD) |
| LYN | PTK2 | (HPRD; MINT) |
| LYN | PTPN6 | (GRID; HPRD) |
| LYN | PTPRC | (HPRD) |
| LYN | RASA1 | (HPRD) |
| LYN | RGS16 | (BIND; HPRD) |
| LYN | SH2B2 | (HPRD) |
| LYN | SHC1 | (GRID; HPRD; MINT) |
| LYN | SKAP1 | (GRID; HPRD) |
| LYN | SKAP2 | (GRID; HPRD) |
| LYN | SLC4A1 | (HPRD) |
| LYN | SNCA | (HPRD) |
| LYN | SPHK2 | (IntAct) |
| LYN | SYK | (DIP; GRID; HPRD; MINT) |
| LYN | TEC | (HPRD) |
| LYN | TEK | (HPRD) |
| LYN | TRAT1 | (HPRD) |
| LYN | TRPV4 | (GRID; HPRD) |
| LYN | TYK2 | (GRID; HPRD) |
| LYN | UBB | (BIND; HPRD) |
| LYN | UNC119 | (GRID; HPRD) |
| LYN | YES1 | (HPRD) |
| MATK | CD36 | (GRID; HPRD) |
| MATK | EWSR1 | (CCSB; GRID; HPRD; IntAct) |
| MATK | NTRK1 | (GRID; HPRD) |
| MATK | PXN | (GRID; HPRD) |
| MATK | SRC | (CCSB; GRID; HPRD) |
| MERTK | BMPR2 | (HPRD) |
| MERTK | GAS6 | (GRID; HPRD; reactome) |
| MERTK | GRB2 | (GRID; HPRD) |
| MERTK | LMO4 | (BIND; HPRD) |
| MERTK | PROS1 | (reactome) |
| MERTK | VAV1 | (HPRD) |
| MET | BAG1 | (GRID; HPRD) |
| MET | CASP3 | (HPRD) |
| MET | CBL | (BIND; GRID; HPRD; MINT) |
| MET | CDH1 | (GRID) |
| MET | CNR1 | (HPRD) |
| MET | CTNNB1 | (GRID; HPRD) |
| MET | CTTN | (HPRD) |
| MET | DAPK3 | (HPRD) |
| MET | DNAJA3 | (HPRD) |
| MET | FAS | (HPRD) |
| MET | GAB1 | (BIND; GRID; HPRD; MINT) |
| MET | GLMN | (GRID; HPRD) |
| MET | GRB2 | (GRID; HPRD) |
| MET | HGF | (BIND; GRID; HPRD; IntAct) |
| MET | HGFAC | (DIP) |
| MET | HGS | (GRID; HPRD) |
| MET | INPP5D | (BIND; HPRD) |
| MET | INPPL1 | (BIND; HPRD) |

TABLE 5-continued

Human Tyrosine Kinase Interactions (node 1 = tyrosine kinase; node 2 = interacting protein)

| Node1 | Node2 | int_DataBase |
|---|---|---|
| MET | ITGB4 | (HPRD) |
| MET | MUC20 | (HPRD) |
| MET | PCBD2 | (HPRD) |
| MET | PIK3R1 | (BIND; HPRD) |
| MET | PLCG1 | (HPRD) |
| MET | PLXNB1 | (HPRD; MINT) |
| MET | POLR2A | (BIND) |
| MET | PTPN11 | (GRID; HPRD) |
| MET | PTPRB | (HPRD) |
| MET | PTPRJ | (HPRD) |
| MET | RANBP10 | (GRID; HPRD) |
| MET | RANBP9 | (GRID; HPRD; MINT) |
| MET | SH3KBP1 | (GRID) |
| MET | SHC1 | (GRID; HPRD) |
| MET | SMC1A | (HPRD) |
| MET | SNAPIN | (HPRD) |
| MET | SNX2 | (HPRD) |
| MET | SPSB1 | (HPRD) |
| MET | SRC | (GRID; HPRD) |
| MET | STAT3 | (GRID; HPRD) |
| MET | TAF1 | (BIND) |
| MET | VAV1 | (HPRD) |
| MST1R | AKT1 | (HPRD) |
| MST1R | EPOR | (HPRD) |
| MST1R | GAB1 | (HPRD) |
| MST1R | GRB2 | (GRID; HPRD) |
| MST1R | HYAL2 | (GRID; HPRD) |
| MST1R | MAX | (BIND) |
| MST1R | MST1 | (DIP; GRID; HPRD) |
| MST1R | MYC | (BIND) |
| MST1R | PIK3R1 | (GRID; HPRD) |
| MST1R | PLCG1 | (GRID; HPRD) |
| MST1R | RELA | (HPRD) |
| MST1R | SFN | (HPRD) |
| MST1R | SHC1 | (GRID; HPRD) |
| MST1R | SRC | (GRID; HPRD) |
| MST1R | YES1 | (HPRD) |
| MST1R | YWHAB | (HPRD) |
| MST1R | YWHAE | (HPRD) |
| MST1R | YWHAH | (HPRD) |
| MST1R | YWHAQ | (HPRD) |
| MST1R | YWHAZ | (HPRD) |
| MUSK | COLQ | (HPRD) |
| MUSK | DOK7 | (HPRD) |
| MUSK | RAPSN | (GRID; HPRD) |
| MUSK | SYNE1 | (GRID; HPRD) |
| NTRK1 | ADCYAP1 | (reactome) |
| NTRK1 | ADCYAP1R1 | (reactome) |
| NTRK1 | ADORA2A | (reactome) |
| NTRK1 | BRAF | (reactome) |
| NTRK1 | CAV1 | (GRID; HPRD) |
| NTRK1 | CCNA2 | (BIND) |
| NTRK1 | CPSF4 | (BIND) |
| NTRK1 | CRK | (HPRD; reactome) |
| NTRK1 | DNAJA3 | (HPRD) |
| NTRK1 | DYNLL1 | (HPRD) |
| NTRK1 | FRS2 | (BIND; GRID; HPRD; reactome) |
| NTRK1 | FRS3 | (BIND; GRID; HPRD) |
| NTRK1 | GIPC1 | (BIND; GRID; HPRD) |
| NTRK1 | GRB2 | (GRID; HPRD) |
| NTRK1 | HIST3H3 | (BIND) |
| NTRK1 | HIST4H4 | (BIND) |
| NTRK1 | HRAS | (reactome) |
| NTRK1 | IRS1 | (HPRD) |
| NTRK1 | IRS2 | (HPRD) |
| NTRK1 | KIDINS220 | (HPRD; reactome) |
| NTRK1 | KRAS | (reactome) |
| NTRK1 | MAPK3 | (HPRD) |
| NTRK1 | NEDD4L | (HPRD) |
| NTRK1 | NGF | (BIND; DIP; GRID; HPRD; reactome) |
| NTRK1 | NGFR | (DIP; GRID; HPRD) |
| NTRK1 | NRAS | (reactome) |
| NTRK1 | PIK3R1 | (HPRD) |
| NTRK1 | PLCG1 | (GRID; HPRD; reactome) |
| NTRK1 | PTPN1 | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| NTRK1 | PTPN11 | (HPRD) |
| NTRK1 | RAF1 | (reactome) |
| NTRK1 | RAP1A | (GRID; HPRD; reactome) |
| NTRK1 | RAPGEF1 | (reactome) |
| NTRK1 | RASA1 | (HPRD) |
| NTRK1 | RICS | (GRID; HPRD) |
| NTRK1 | RIT1 | (reactome) |
| NTRK1 | RIT2 | (reactome) |
| NTRK1 | RUSC1 | (HPRD) |
| NTRK1 | SH2B1 | (HPRD) |
| NTRK1 | SH2B2 | (HPRD) |
| NTRK1 | SHC1 | (BIND; HPRD; reactome) |
| NTRK1 | SHC2 | (HPRD; reactome) |
| NTRK1 | SHC3 | (GRID; HPRD; reactome) |
| NTRK1 | SQSTM1 | (HPRD) |
| NTRK1 | STAT3 | (reactome) |
| NTRK1 | UBB | (HPRD) |
| NTRK1 | YWHAB | (reactome) |
| NTRK2 | ADCYAP1 | (reactome) |
| NTRK2 | ADCYAP1R1 | (reactome) |
| NTRK2 | ADORA2A | (reactome) |
| NTRK2 | ATP5O | (BIND) |
| NTRK2 | BDNF | (DIP; GRID; HPRD) |
| NTRK2 | DOK5 | (HPRD) |
| NTRK2 | DYNLL1 | (GRID; HPRD) |
| NTRK2 | FRS3 | (GRID; HPRD) |
| NTRK2 | GIPC1 | (GRID; HPRD) |
| NTRK2 | KIDINS220 | (HPRD) |
| NTRK2 | NCK1 | (GRID; HPRD) |
| NTRK2 | NCK2 | (GRID; HPRD) |
| NTRK2 | NGFR | (HPRD) |
| NTRK2 | NTF3 | (GRID; HPRD) |
| NTRK2 | NTF4 | (BIND; GRID; HPRD) |
| NTRK2 | PLCG1 | (HPRD) |
| NTRK2 | PTPN1 | (GRID; HPRD) |
| NTRK2 | PTPN11 | (HPRD) |
| NTRK2 | SH2B1 | (HPRD) |
| NTRK2 | SH2B2 | (HPRD) |
| NTRK2 | SH2D1A | (MINT) |
| NTRK2 | SHC1 | (HPRD) |
| NTRK2 | SHC2 | (HPRD) |
| NTRK2 | SHC3 | (GRID; HPRD) |
| NTRK2 | SQSTM1 | (GRID; HPRD) |
| NTRK2 | TNFRSF1A | (BIND) |
| NTRK2 | TRAF2 | (BIND) |
| NTRK2 | UBB | (HPRD) |
| NTRK3 | CYP2D6 | (BIND) |
| NTRK3 | DOK5 | (HPRD) |
| NTRK3 | DYNLL1 | (HPRD) |
| NTRK3 | FOS | (MINT) |
| NTRK3 | HTR2A | (HPRD) |
| NTRK3 | IRAK1 | (GRID; HPRD) |
| NTRK3 | JUN | (MINT) |
| NTRK3 | KIDINS220 | (HPRD) |
| NTRK3 | MAPK1 | (HPRD; MINT) |
| NTRK3 | MAPK3 | (HPRD) |
| NTRK3 | NGFR | (GRID; HPRD) |
| NTRK3 | NGFRAP1 | (CCSB; GRID; HPRD) |
| NTRK3 | NTF3 | (DIP; GRID; HPRD; MINT) |
| NTRK3 | PLCG1 | (GRID; HPRD) |
| NTRK3 | PMAIP1 | (BIND) |
| NTRK3 | PTPN1 | (CCSB; GRID; HPRD) |
| NTRK3 | SH2D1A | (MINT) |
| NTRK3 | SHC1 | (CCSB; GRID; HPRD) |
| NTRK3 | SHC2 | (HPRD) |
| NTRK3 | SQSTM1 | (CCSB; GRID; HPRD) |
| NTRK3 | TNFRSF1A | (BIND) |
| NTRK3 | TRAF2 | (BIND) |
| PDGFRA | CAV1 | (CCSB; GRID; HPRD) |
| PDGFRA | CBL | (GRID) |
| PDGFRA | CRK | (CCSB; GRID; HPRD) |
| PDGFRA | CRKL | (GRID; HPRD) |
| PDGFRA | GRB14 | (GRID; HPRD) |
| PDGFRA | ITGAV | (GRID; HPRD) |
| PDGFRA | ITGB3 | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| PDGFRA | PDGFA | (DIP; GRID; HPRD) |
| PDGFRA | PDGFB | (CCSB; DIP; GRID; HPRD) |
| PDGFRA | PDGFC | (GRID; HPRD) |
| PDGFRA | PDGFRB | (CCSB; GRID; HPRD) |
| PDGFRA | PIK3R1 | (HPRD) |
| PDGFRA | PLCG1 | (GRID; HPRD) |
| PDGFRA | PTPN11 | (CCSB; GRID; HPRD) |
| PDGFRA | RAPGEF1 | (GRID; HPRD) |
| PDGFRA | SHB | (GRID; HPRD) |
| PDGFRA | SHF | (HPRD) |
| PDGFRA | SLC9A3R1 | (GRID; HPRD) |
| PDGFRA | SNX2 | (GRID; HPRD) |
| PDGFRA | SNX4 | (CCSB; GRID; HPRD) |
| PDGFRA | SNX6 | (GRID; HPRD) |
| PDGFRA | STAT1 | (HPRD) |
| PDGFRA | STAT3 | (HPRD) |
| PDGFRA | STAT5A | (HPRD) |
| PDGFRA | STAT5B | (HPRD) |
| PDGFRB | ARAF | (HPRD) |
| PDGFRB | BAG1 | (CCSB; GRID; HPRD) |
| PDGFRB | CBL | (BIND; HPRD) |
| PDGFRB | CBLC | (HPRD) |
| PDGFRB | COPA | (GRID; HPRD) |
| PDGFRB | COPB1 | (CCSB; GRID; HPRD) |
| PDGFRB | CRK | (BIND; CCSB; GRID; HPRD) |
| PDGFRB | EDG1 | (CCSB; GRID; HPRD) |
| PDGFRB | EIF2AK2 | (GRID; HPRD) |
| PDGFRB | GAB1 | (HPRD) |
| PDGFRB | GRB10 | (GRID; HPRD) |
| PDGFRB | GRB14 | (GRID; HPRD) |
| PDGFRB | GRB2 | (CCSB; DIP; GRID; HPRD) |
| PDGFRB | GRB7 | (HPRD) |
| PDGFRB | ITGB3 | (GRID; HPRD) |
| PDGFRB | KRTAP4-12 | (CCSB; GRID; HPRD; IntAct) |
| PDGFRB | NCK1 | (BIND; CCSB; GRID; HPRD) |
| PDGFRB | NCK2 | (CCSB; GRID; HPRD) |
| PDGFRB | PDAP1 | (CCSB; GRID; HPRD) |
| PDGFRB | PDGFB | (CCSB; DIP; GRID; HPRD) |
| PDGFRB | PDGFD | (HPRD) |
| PDGFRB | PIK3C2B | (IntAct) |
| PDGFRB | PIK3CA | (HPRD) |
| PDGFRB | PIK3R1 | (BIND; DIP; GRID; HPRD) |
| PDGFRB | PIK3R2 | (BIND; HPRD) |
| PDGFRB | PIK3R3 | (BIND; CCSB; GRID; HPRD) |
| PDGFRB | PLAUR | (BIND) |
| PDGFRB | PLCG1 | (BIND; DIP; GRID; HPRD) |
| PDGFRB | PRDX2 | (HPRD) |
| PDGFRB | PTEN | (MINT) |
| PDGFRB | PTK2 | (CCSB; GRID; HPRD) |
| PDGFRB | PTPN1 | (HPRD) |
| PDGFRB | PTPN11 | (BIND; CCSB; GRID; HPRD) |
| PDGFRB | PTPN2 | (HPRD) |
| PDGFRB | PTPRJ | (HPRD) |
| PDGFRB | RAF1 | (CCSB; GRID; HPRD) |
| PDGFRB | RASA1 | (BIND; CCSB; DIP; GRID; HPRD) |
| PDGFRB | SH3KBP1 | (CCSB; GRID) |
| PDGFRB | SHB | (BIND) |
| PDGFRB | SHC1 | (BIND; CCSB; GRID; HPRD) |
| PDGFRB | SLC9A3R1 | (GRID; HPRD; MINT) |
| PDGFRB | SLC9A3R2 | (MINT) |
| PDGFRB | SNX1 | (CCSB; GRID; HPRD) |
| PDGFRB | SNX2 | (GRID; HPRD) |
| PDGFRB | SNX4 | (GRID; HPRD) |
| PDGFRB | SOCS1 | (BIND; HPRD) |
| PDGFRB | SRC | (BIND; CCSB; GRID; HPRD) |
| PDGFRB | STAT1 | (HPRD) |
| PDGFRB | STAT3 | (HPRD) |
| PDGFRB | STAT5A | (DIP; HPRD) |
| PDGFRB | STAT5B | (HPRD) |
| PDGFRB | SYNGAP1 | (HPRD) |
| PDGFRB | TYK2 | (HPRD) |
| PDGFRB | YES1 | (HPRD) |
| PTK2 | ACTN1 | (HPRD) |
| PTK2 | APC | (GRID; HPRD) |
| PTK2 | ARHGAP26 | (GRID; HPRD) |

TABLE 5-continued

Human Tyrosine Kinase Interactions (node 1 = tyrosine kinase; node 2 = interacting protein)

| Node1 | Node2 | int_DataBase |
| --- | --- | --- |
| PTK2 | ATG12 | (CCSB; GRID; HPRD; MINT) |
| PTK2 | BCAR1 | (BIND; GRID; HPRD; MINT) |
| PTK2 | BIN1 | (GRID; HPRD) |
| PTK2 | BIRC4 | (reactome) |
| PTK2 | CASP3 | (reactome) |
| PTK2 | CASP7 | (reactome) |
| PTK2 | CCR5 | (GRID; HPRD) |
| PTK2 | CD4 | (CCSB; GRID) |
| PTK2 | CD47 | (CCSB; GRID; HPRD) |
| PTK2 | CD79B | (HPRD) |
| PTK2 | CIB1 | (GRID; HPRD) |
| PTK2 | CRK | (GRID; HPRD) |
| PTK2 | CRKL | (GRID) |
| PTK2 | CSPG4 | (GRID; HPRD) |
| PTK2 | CXCR4 | (HPRD) |
| PTK2 | DCC | (BIND; GRID) |
| PTK2 | DDEF1 | (GRID; HPRD) |
| PTK2 | DIABLO | (reactome) |
| PTK2 | DLGAP3 | (HPRD) |
| PTK2 | DNM2 | (BIND; HPRD) |
| PTK2 | EFS | (CCSB; GRID; HPRD) |
| PTK2 | EZR | (CCSB; GRID; HPRD) |
| PTK2 | GIT1 | (GRID: HPRD) |
| PTK2 | GRB2 | (BIND; CCSB; GRID; HPRD) |
| PTK2 | GRB7 | (CCSB; GRID; HPRD) |
| PTK2 | GSK3B | (CCSB; GRID; HPRD) |
| PTK2 | GZMB | (HPRD) |
| PTK2 | HNF4A | (BIND) |
| PTK2 | IGHM | (HPRD) |
| PTK2 | IRS1 | (GRID; HPRD) |
| PTK2 | ITGAV | (GRID; HPRD) |
| PTK2 | ITGB1 | (BIND; CCSB; GRID; HPRD) |
| PTK2 | ITGB2 | (CCSB; GRID; HPRD) |
| PTK2 | ITGB3 | (BIND; GRID; HPRD) |
| PTK2 | ITGB4 | (HPRD) |
| PTK2 | ITGB5 | (BIND) |
| PTK2 | KCNMA1 | (HPRD) |
| PTK2 | MAPK8IP3 | (GRID; HPRD) |
| PTK2 | MICAL1 | (GRID; HPRD) |
| PTK2 | NCAM1 | (HPRD) |
| PTK2 | NCK2 | (CCSB; GRID; HPRD) |
| PTK2 | NEDD8 | (HPRD) |
| PTK2 | NEDD9 | (GRID; HPRD) |
| PTK2 | NEO1 | (BIND) |
| PTK2 | PIAS1 | (HPRD) |
| PTK2 | PIK3R1 | (GRID; HPRD) |
| PTK2 | PKD1 | (BIND; GRID; HPRD) |
| PTK2 | PLCG1 | (GRID; HPRD) |
| PTK2 | PPP1CB | (CCSB; GRID; HPRD) |
| PTK2 | PTEN | (GRID) |
| PTK2 | PTPN1 | (HPRD) |
| PTK2 | PTPN11 | (CCSB; GRID; HPRD) |
| PTK2 | PTPN12 | (GRID; HPRD) |
| PTK2 | PTPRH | (GRID; HPRD) |
| PTK2 | PXN | (BIND; GRID; HPRD; MINT) |
| PTK2 | RB1CC1 | (GRID; HPRD) |
| PTK2 | RET | (HPRD) |
| PTK2 | RIPK1 | (BIND; HPRD; MINT) |
| PTK2 | ROCK1 | (HPRD) |
| PTK2 | SELE | (GRID; HPRD) |
| PTK2 | SHC1 | (BIND; CCSB; GRID; HPRD) |
| PTK2 | SOCS2 | (CCSB; GRID; HPRD; MINT) |
| PTK2 | SORBS1 | (HPRD) |
| PTK2 | SRC | (BIND; CCSB; GRID; HPRD; IntAct; MINT) |
| PTK2 | STAT1 | (CCSB; GRID; HPRD) |
| PTK2 | SYK | (CCSB; GRID; HPRD) |
| PTK2 | TGFB1I1 | (CCSB; GRID; HPRD) |
| PTK2 | TLN1 | (GRID; HPRD) |
| PTK2 | TNFRSF1A | (HPRD) |
| PTK2 | TNS1 | (HPRD) |
| PTK2 | TP53 | (HPRD) |
| PTK2 | TRIO | (HPRD) |
| PTK2 | TRIP6 | (CCSB; GRID; HPRD) |
| PTK2 | VCL | (BIND; HPRD) |
| PTK2B | ANXA6 | (HPRD) |

TABLE 5-continued

Human Tyrosine Kinase Interactions (node 1 = tyrosine kinase; node 2 = interacting protein)

| Node1 | Node2 | int_DataBase |
| --- | --- | --- |
| PTK2B | ARHGAP21 | (HPRD) |
| PTK2B | ARHGAP5 | (HPRD) |
| PTK2B | BCAR1 | (GRID; HPRD) |
| PTK2B | CBL | (GRID; HPRD) |
| PTK2B | CCR5 | (GRID; HPRD) |
| PTK2B | CD2AP | (GRID) |
| PTK2B | CRK | (GRID; HPRD) |
| PTK2B | DCC | (GRID) |
| PTK2B | DDEF1 | (HPRD) |
| PTK2B | DDEF2 | (GRID; HPRD) |
| PTK2B | DLG3 | (GRID; HPRD) |
| PTK2B | DLG4 | (GRID; HPRD) |
| PTK2B | DLGAP3 | (HPRD) |
| PTK2B | EFS | (GRID; HPRD) |
| PTK2B | EWSR1 | (GRID; HPRD) |
| PTK2B | FGFR2 | (HPRD) |
| PTK2B | FGFR3 | (HPRD) |
| PTK2B | FLT1 | (HPRD) |
| PTK2B | FYN | (GRID; HPRD) |
| PTK2B | GNA13 | (GRID; HPRD) |
| PTK2B | GRB2 | (GRID; HPRD) |
| PTK2B | GRIN2A | (GRID; HPRD) |
| PTK2B | GSN | (GRID; HPRD) |
| PTK2B | IL7R | (HPRD) |
| PTK2B | ITGB2 | (GRID; HPRD) |
| PTK2B | ITGB3 | (GRID; HPRD) |
| PTK2B | JAK1 | (GRID; HPRD) |
| PTK2B | JAK2 | (GRID; HPRD) |
| PTK2B | JAK3 | (GRID; HPRD) |
| PTK2B | KCNA2 | (GRID; HPRD) |
| PTK2B | LCK | (GRID; HPRD) |
| PTK2B | LPXN | (GRID; HPRD; MINT) |
| PTK2B | LYN | (GRID; HPRD) |
| PTK2B | MAP3K4 | (HPRD; MINT) |
| PTK2B | MATK | (GRID; HPRD) |
| PTK2B | MCAM | (GRID; HPRD) |
| PTK2B | NEDD9 | (GRID; HPRD) |
| PTK2B | NPHP1 | (GRID; HPRD) |
| PTK2B | PDPK1 | (HPRD) |
| PTK2B | PIK3R1 | (GRID; HPRD) |
| PTK2B | PITPNM1 | (GRID; HPRD) |
| PTK2B | PITPNM2 | (GRID; HPRD) |
| PTK2B | PITPNM3 | (GRID; HPRD) |
| PTK2B | PRKCD | (GRID; HPRD) |
| PTK2B | PTK2 | (HPRD) |
| PTK2B | PTPN11 | (GRID; HPRD) |
| PTK2B | PTPN12 | (GRID; HPRD) |
| PTK2B | PTPN6 | (GRID; HPRD) |
| PTK2B | PXN | (GRID; HPRD) |
| PTK2B | RASA1 | (GRID; HPRD) |
| PTK2B | RB1CC1 | (GRID; HPRD) |
| PTK2B | SH2D3C | (HPRD) |
| PTK2B | SHC1 | (GRID; HPRD) |
| PTK2B | SLC2A1 | (GRID; HPRD) |
| PTK2B | SNCA | (HPRD) |
| PTK2B | SORBS1 | (GRID) |
| PTK2B | SORBS2 | (BIND; GRID; HPRD) |
| PTK2B | SRC | (GRID; HPRD) |
| PTK2B | STAP1 | (HPRD) |
| PTK2B | STAT3 | (HPRD) |
| PTK2B | SYK | (GRID; HPRD) |
| PTK2B | TGFB1I1 | (BIND; GRID; HPRD) |
| PTK2B | TLN1 | (GRID; HPRD) |
| PTK2B | VAV1 | (GRID; HPRD) |
| PTK2B | ZAP70 | (GRID; HPRD) |
| PTK6 | IRS1 | (BIND) |
| PTK6 | IRS4 | (BIND) |
| PTK6 | KHDRBS1 | (GRID; HPRD) |
| PTK6 | STAP2 | (GRID; HPRD) |
| PTK7 | E2F4 | (BIND) |
| PTK7 | HNF4A | (BIND) |
| RET | AKAP5 | (HPRD) |
| RET | CBL | (HPRD; MINT) |
| RET | CBLB | (HPRD) |
| RET | CRK | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| RET | DOK1 | (GRID; HPRD) |
| RET | DOK2 | (CCSB; GRID; HPRD) |
| RET | DOK3 | (HPRD) |
| RET | DOK4 | (GRID; HPRD) |
| RET | DOK5 | (GRID; HPRD) |
| RET | DOK6 | (GRID; HPRD) |
| RET | FAU | (MINT) |
| RET | FRS2 | (BIND; CCSB; GRID; HPRD) |
| RET | GAB1 | (GRID; HPRD) |
| RET | GDNF | (GRID; HPRD) |
| RET | GFRA1 | (CCSB; GRID; HPRD) |
| RET | GFRA4 | (HPRD) |
| RET | GRB10 | (GRID; HPRD) |
| RET | GRB2 | (BIND; CCSB; GRID; HPRD) |
| RET | GRB7 | (CCSB; GRID; HPRD) |
| RET | HIST2H4A | (HPRD) |
| RET | JUN | (BIND) |
| RET | MAPK1 | (HPRD) |
| RET | MAPK14 | (HPRD) |
| RET | MAPK3 | (HPRD) |
| RET | MAPK8 | (HPRD) |
| RET | MAPK9 | (HPRD) |
| RET | NRTN | (GRID; HPRD) |
| RET | PDLIM7 | (GRID; HPRD) |
| RET | PIK3R1 | (GRID; HPRD) |
| RET | PLCG1 | (BIND; GRID; HPRD) |
| RET | PRKAR2A | (HPRD) |
| RET | PTPN11 | (HPRD) |
| RET | PTPRF | (GRID) |
| RET | SHC1 | (BIND; CCSB; GRID; HPRD; MINT) |
| RET | SHC3 | (BIND; HPRD) |
| RET | SRC | (CCSB; GRID; HPRD) |
| RET | STAT3 | (CCSB; GRID; HPRD) |
| ROR1 | NGF | (DIP) |
| ROR2 | FZD2 | (HPRD) |
| ROR2 | FZD5 | (HPRD) |
| ROR2 | MAGED1 | (GRID; HPRD) |
| ROR2 | WNT5A | (HPRD) |
| ROS1 | LPHN1 | (HPRD) |
| ROS1 | PTPN6 | (GRID; HPRD) |
| ROS1 | VAV3 | (GRID; HPRD) |
| RYK | FZD8 | (BIND; HPRD) |
| RYK | WNT1 | (BIND; HPRD) |
| RYK | WNT3A | (BIND; HPRD) |
| SRC | ACTN1 | (IntAct) |
| SRC | ADAM12 | (GRID; HPRD) |
| SRC | ADAM15 | (CCSB; GRID; HPRD; MINT) |
| SRC | ADRB2 | (HPRD) |
| SRC | ADRB3 | (GRID; HPRD) |
| SRC | ADRBK1 | (CCSB; GRID; HPRD) |
| SRC | AFAP1 | (CCSB; GRID; HPRD) |
| SRC | AFAP1L2 | (HPRD) |
| SRC | AKT1 | (HPRD) |
| SRC | ANKRD11 | (GRID; HPRD) |
| SRC | ANXA1 | (HPRD) |
| SRC | ANXA2 | (CCSB; GRID; HPRD) |
| SRC | AR | (GRID) |
| SRC | ARHGAP1 | (CCSB; GRID; HPRD) |
| SRC | ARR3 | (CCSB; GRID; HPRD) |
| SRC | ARRB1 | (MINT) |
| SRC | ATP2B4 | (HPRD) |
| SRC | BCAR1 | (BIND; GRID; HPRD) |
| SRC | BCR | (BIND; HPRD) |
| SRC | CAV1 | (GRID; HPRD; MINT) |
| SRC | CAV2 | (HPRD) |
| SRC | CBL | (BIND; GRID; HPRD; MINT) |
| SRC | CBLC | (HPRD) |
| SRC | CCNA2 | (DIP) |
| SRC | CCND1 | (DIP) |
| SRC | CD2AP | (GRID; HPRD; MINT) |
| SRC | CD33 | (HPRD) |
| SRC | CD36 | (GRID; HPRD) |
| SRC | CD46 | (CCSB; GRID; HPRD) |
| SRC | CD59 | (CCSB; GRID; HPRD) |
| SRC | CDCP1 | (BIND; HPRD) |

TABLE 5-continued

Human Tyrosine Kinase Interactions (node 1 = tyrosine kinase; node 2 = interacting protein)

| Node1 | Node2 | int_DataBase |
|---|---|---|
| SRC | CDH1 | (GRID) |
| SRC | CDH5 | (HPRD) |
| SRC | CDK5 | (HPRD) |
| SRC | CEACAM1 | (HPRD) |
| SRC | CEACAM3 | (HPRD) |
| SRC | CHUK | (HPRD) |
| SRC | CNTNAP1 | (HPRD) |
| SRC | COL1A1 | (reactome) |
| SRC | COL1A2 | (reactome) |
| SRC | CTNNB1 | (HPRD) |
| SRC | CTNND1 | (HPRD) |
| SRC | CTTN | (HPRD) |
| SRC | DAB1 | (HPRD) |
| SRC | DAB2 | (CCSB; GRID; HPRD) |
| SRC | DAG1 | (HPRD) |
| SRC | DAPP1 | (HPRD) |
| SRC | DDEF1 | (GRID; HPRD) |
| SRC | DGKA | (HPRD) |
| SRC | DGKZ | (HPRD) |
| SRC | DNM1 | (HPRD; MINT) |
| SRC | DNM2 | (MINT) |
| SRC | DOK1 | (HPRD) |
| SRC | DOK4 | (BIND; HPRD) |
| SRC | DRD4 | (BIND) |
| SRC | E2F4 | (BIND) |
| SRC | EFNB1 | (CCSB; GRID; HPRD) |
| SRC | EFNB2 | (HPRD) |
| SRC | EGF | (reactome) |
| SRC | EPS8 | (CCSB; GRID; HPRD) |
| SRC | ESR1 | (GRID; HPRD) |
| SRC | ESR2 | (GRID; HPRD) |
| SRC | ETS1 | (BIND; HPRD) |
| SRC | ETS2 | (BIND; HPRD) |
| SRC | EVL | (CCSB; GRID; HPRD) |
| SRC | FARP2 | (HPRD) |
| SRC | FASLG | (GRID; HPRD) |
| SRC | FCER1G | (reactome) |
| SRC | FHIT | (HPRD) |
| SRC | FOXO1 | (GRID; HPRD) |
| SRC | FRS2 | (HPRD) |
| SRC | FYB | (HPRD) |
| SRC | GAB2 | (GRID; HPRD) |
| SRC | GAB3 | (GRID; HPRD) |
| SRC | GFAP | (CCSB; GRID; HPRD) |
| SRC | GIT1 | (GRID; HPRD) |
| SRC | GJA1 | (BIND; CCSB; GRID; HPRD; reactome) |
| SRC | GJB1 | (BIND; HPRD) |
| SRC | GNB2L1 | (BIND; CCSB; GRID; HPRD) |
| SRC | GP2 | (HPRD) |
| SRC | GP6 | (reactome) |
| SRC | GRB10 | (HPRD) |
| SRC | GRB2 | (CCSB; GRID; HPRD) |
| SRC | GRIN2A | (GRID; HPRD) |
| SRC | GRIN2B | (GRID; HPRD) |
| SRC | GRLF1 | (HPRD) |
| SRC | GTF2I | (HPRD) |
| SRC | GUCY2C | (HPRD; MINT) |
| SRC | HLA-A | (HPRD) |
| SRC | HLA-B | (HPRD) |
| SRC | HNF1A | (GRID; HPRD) |
| SRC | HNRPK | (BIND; CCSB; GRID; HPRD) |
| SRC | HRAS | (HPRD; MINT; reactome) |
| SRC | HSP90AA1 | (CCSB; DIP; GRID; HPRD) |
| SRC | IKBKB | (HPRD; IntAct) |
| SRC | IKBKG | (HPRD; IntAct) |
| SRC | IL6R | (GRID; HPRD) |
| SRC | INPPL1 | (HPRD) |
| SRC | ITGB3 | (HPRD) |
| SRC | JUP | (HPRD) |
| SRC | KCNA5 | (HPRD) |
| SRC | KCNB1 | (HPRD) |
| SRC | KCNQ5 | (HPRD) |
| SRC | KHDRBS1 | (BIND; GRID; HPRD; IntAct; MDC; MINT) |
| SRC | KIFAP3 | (CCSB; GRID; HPRD) |
| SRC | KRAS | (reactome) |

TABLE 5-continued

Human Tyrosine Kinase Interactions (node 1 = tyrosine kinase; node 2 = interacting protein)

| Node1 | Node2 | int_DataBase |
|---|---|---|
| SRC | LCT | (MINT) |
| SRC | LRP1 | (HPRD) |
| SRC | MAPK15 | (HPRD) |
| SRC | MPZL1 | (CCSB; GRID; HPRD) |
| SRC | MUC1 | (BIND; GRID; HPRD; MINT) |
| SRC | MYLK | (GRID; HPRD) |
| SRC | NCOA6 | (GRID) |
| SRC | ND2 | (GRID; HPRD) |
| SRC | NDUFS1 | (BIND) |
| SRC | NFKBIA | (HPRD) |
| SRC | NMT1 | (HPRD) |
| SRC | NOS2A | (HPRD) |
| SRC | NPHS1 | (GRID; HPRD) |
| SRC | NRAS | (reactome) |
| SRC | P2RY2 | (HPRD) |
| SRC | PAK2 | (HPRD) |
| SRC | PDE4D | (BIND) |
| SRC | PDE6G | (GRID; HPRD) |
| SRC | PDPK1 | (HPRD) |
| SRC | PECAM1 | (GRID; HPRD) |
| SRC | PELP1 | (GRID; HPRD) |
| SRC | PGR | (HPRD) |
| SRC | PIK3R1 | (GRID; HPRD) |
| SRC | PKD1 | (GRID; HPRD) |
| SRC | PLCG1 | (GRID; HPRD) |
| SRC | PLSCR1 | (GRID) |
| SRC | PPARD | (HPRD) |
| SRC | PRKACA | (HPRD) |
| SRC | PRKCA | (HPRD) |
| SRC | PRKCD | (HPRD; MINT) |
| SRC | PRKCE | (GRID; HPRD) |
| SRC | PRKCH | (HPRD) |
| SRC | PRKCI | (HPRD) |
| SRC | PRKCZ | (CCSB; GRID; HPRD) |
| SRC | PRKD1 | (HPRD) |
| SRC | PTPN1 | (HPRD) |
| SRC | PTPN11 | (HPRD) |
| SRC | PTPN18 | (HPRD) |
| SRC | PTPN2 | (BIND; HPRD) |
| SRC | PTPN21 | (GRID; HPRD) |
| SRC | PTPN6 | (HPRD) |
| SRC | PTPRA | (HPRD) |
| SRC | PTPRE | (HPRD) |
| SRC | PXN | (GRID; HPRD) |
| SRC | RAF1 | (CCSB; GRID; HPRD) |
| SRC | RALA | (reactome) |
| SRC | RALB | (reactome) |
| SRC | RALGDS | (reactome) |
| SRC | RASA1 | (CCSB; GRID; HPRD) |
| SRC | RGS16 | (BIND; HPRD) |
| SRC | RICS | (BIND; GRID; HPRD) |
| SRC | SH2D2A | (BIND) |
| SRC | SH2D3C | (HPRD) |
| SRC | SH3BP1 | (CCSB; GRID; HPRD) |
| SRC | SH3PXD2A | (GRID; HPRD) |
| SRC | SHB | (BIND; GRID; HPRD) |
| SRC | SHC1 | (BIND; CCSB; GRID; HPRD) |
| SRC | SKAP1 | (GRID; HPRD) |
| SRC | SLC9A2 | (GRID; HPRD) |
| SRC | SMARCB1 | (GRID; HPRD) |
| SRC | SMARCE1 | (GRID; HPRD) |
| SRC | SNURF | (GRID) |
| SRC | SPTAN1 | (HPRD) |
| SRC | SRF | (GRID; HPRD) |
| SRC | STAP2 | (HPRD) |
| SRC | STAT1 | (CCSB; GRID: HPRD) |
| SRC | STAT3 | (CCSB; GRID; HPRD) |
| SRC | STAT5A | (CCSB; GRID; HPRD) |
| SRC | STAT5B | (HPRD) |
| SRC | STAT6 | (HPRD) |
| SRC | SUPT4H1 | (BIND) |
| SRC | SYK | (CCSB; GRID; HPRD; reactome) |
| SRC | SYN1 | (GRID; HPRD) |
| SRC | TERT | (HPRD) |
| SRC | TIAM1 | (GRID; HPRD) |

TABLE 5-continued

Human Tyrosine Kinase Interactions (node 1 = tyrosine kinase; node 2 = interacting protein)

| Node1 | Node2 | int_DataBase |
| --- | --- | --- |
| SRC | TLR3 | (MINT) |
| SRC | TNFRSF11A | (HPRD) |
| SRC | TNFSF11 | (HPRD) |
| SRC | TRAF1 | (HPRD) |
| SRC | TRAF3 | (HPRD) |
| SRC | TRAF6 | (CCSB; GRID; HPRD) |
| SRC | TRAT1 | (HPRD) |
| SRC | TRIP6 | (CCSB; GRID; HPRD) |
| SRC | TRPC6 | (GRID; HPRD) |
| SRC | TRPV4 | (GRID; HPRD) |
| SRC | TUB | (GRID; HPRD) |
| SRC | TXK | (HPRD) |
| SRC | TYRO3 | (GRID; HPRD) |
| SRC | VCL | (HPRD) |
| SRC | VIL1 | (HPRD) |
| SRC | WAS | (CCSB; GRID; HPRD) |
| SRC | WBP11 | (HPRD) |
| SRC | WT1 | (HPRD) |
| SRC | YTHDC1 | (GRID; HPRD) |
| SRC | YWHAB | (CCSB; GRID; HPRD) |
| SRC | YWHAE | (CCSB; GRID; HPRD) |
| SRC | YWHAG | (CCSB; GRID; HPRD) |
| SRC | YWHAH | (GRID; HPRD) |
| SRM | MAX | (BIND) |
| SYK | BLNK | (CCSB; GRID; HPRD) |
| SYK | CBL | (BIND; GRID; HPRD; MINT) |
| SYK | CBLB | (BIND; CCSB; GRID; HPRD) |
| SYK | CD19 | (GRID; HPRD) |
| SYK | CD22 | (GRID; HPRD; IntAct) |
| SYK | CD3E | (GRID; HPRD) |
| SYK | CD79A | (GRID; HPRD) |
| SYK | CD79B | (HPRD) |
| SYK | COL1A1 | (reactome) |
| SYK | COL1A2 | (reactome) |
| SYK | CRKL | (BIND; GRID; HPRD) |
| SYK | CSF2RB | (HPRD) |
| SYK | CSF3R | (GRID; HPRD) |
| SYK | CTTN | (CCSB; GRID; HPRD) |
| SYK | DBNL | (HPRD) |
| SYK | DTYMK | (BIND) |
| SYK | DUSP3 | (HPRD) |
| SYK | EPOR | (GRID; HPRD) |
| SYK | EZR | (BIND; CCSB; GRID) |
| SYK | FCER1G | (GRID; HPRD; IntAct; reactome) |
| SYK | FCGR1A | (CCSB; GRID; HPRD) |
| SYK | FCGR2A | (HPRD) |
| SYK | GAB2 | (HPRD) |
| SYK | GP6 | (reactome) |
| SYK | GRB2 | (CCSB; GRID; HPRD) |
| SYK | HCLS1 | (HPRD) |
| SYK | HMGCS2 | (BIND) |
| SYK | HNRNPU | (GRID; HPRD) |
| SYK | IL15RA | (HPRD) |
| SYK | IL2RB | (HPRD) |
| SYK | ITGB2 | (HPRD; IntAct) |
| SYK | JUN | (BIND) |
| SYK | LAT | (CCSB; GRID; HPRD) |
| SYK | LAX1 | (HPRD) |
| SYK | LCP2 | (CCSB; GRID; HPRD) |
| SYK | MAP4K1 | (HPRD) |
| SYK | MAPK3 | (HPRD) |
| SYK | MAX | (BIND) |
| SYK | MS4A2 | (GRID; HPRD) |
| SYK | MSN | (BIND) |
| SYK | MYC | (BIND) |
| SYK | NFAM1 | (HPRD) |
| SYK | NFKBIB | (BIND) |
| SYK | PAG1 | (GRID; HPRD) |
| SYK | PIK3AP1 | (HPRD) |
| SYK | PIK3R1 | (HPRD; MINT) |
| SYK | PIK3R2 | (HPRD; MINT) |
| SYK | PLCG1 | (DIP; GRID; HPRD) |
| SYK | PLCG2 | (HPRD; reactome) |
| SYK | POU2AF1 | (IntAct) |
| SYK | PRKCA | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| SYK | PRKD1 | (HPRD) |
| SYK | PTPN6 | (CCSB; GRID; HPRD) |
| SYK | PXN | (GRID; HPRD) |
| SYK | RASA1 | (HPRD) |
| SYK | RPS6KA1 | (HPRD) |
| SYK | RPS6KA2 | (DIP) |
| SYK | SELPLG | (HPRD) |
| SYK | SH2B2 | (HPRD) |
| SYK | SH3BP2 | (GRID; HPRD) |
| SYK | SHC1 | (HPRD) |
| SYK | SIT1 | (GRID; HPRD) |
| SYK | SLA | (CCSB; GRID; HPRD) |
| SYK | SLC4A1 | (HPRD) |
| SYK | SNCA | (HPRD) |
| SYK | STAT1 | (BIND; HPRD) |
| SYK | STAT3 | (CCSB; GRID; HPRD) |
| SYK | STAT5A | (CCSB; GRID; HPRD) |
| SYK | TAF1 | (BIND) |
| SYK | TLR4 | (HPRD) |
| SYK | TRAF6 | (CCSB; GRID; HPRD) |
| SYK | TUBA1A | (CCSB; GRID; HPRD) |
| SYK | TUBA4A | (HPRD) |
| SYK | TYROBP | (HPRD) |
| SYK | UBB | (BIND; CCSB; GRID; HPRD) |
| SYK | UCP2 | (BIND) |
| SYK | VAV1 | (CCSB; GRID; HPRD) |
| SYK | VAV2 | (HPRD) |
| TEC | DOK1 | (HPRD) |
| TEC | EPOR | (HPRD) |
| TEC | GNA12 | (GRID; HPRD) |
| TEC | IL3RA | (HPRD) |
| TEC | PIK3R1 | (HPRD) |
| TEC | PIK3R3 | (GRID; HPRD) |
| TEC | PIP4K2A | (HPRD) |
| TEC | PIP5K1A | (HPRD) |
| TEC | PLCG1 | (HPRD) |
| TEC | PLCG2 | (HPRD) |
| TEC | PLK4 | (GRID; HPRD) |
| TEC | PRLR | (GRID; HPRD) |
| TEC | PTPN18 | (HPRD) |
| TEC | PTPN21 | (GRID; HPRD) |
| TEC | SHC1 | (HPRD) |
| TEC | SOCS1 | (GRID; HPRD) |
| TEC | STAP1 | (HPRD) |
| TEC | VAV1 | (GRID; HPRD) |
| TEC | WAS | (GRID; HPRD) |
| TEK | ANGPT1 | (DIP; GRID; HPRD) |
| TEK | ANGPT2 | (BIND; DIP; GRID; HPRD) |
| TEK | ANGPT4 | (BIND; GRID; HPRD) |
| TEK | ANGPTL1 | (BIND; GRID; HPRD) |
| TEK | DOK2 | (GRID; HPRD) |
| TEK | DOK4 | (HPRD) |
| TEK | GRB14 | (GRID; HPRD) |
| TEK | GRB2 | (GRID; HPRD) |
| TEK | GRB7 | (GRID; HPRD) |
| TEK | PIK3R1 | (GRID; HPRD) |
| TEK | PTPN11 | (GRID; HPRD) |
| TEK | PTPRB | (HPRD) |
| TEK | SHC1 | (HPRD) |
| TEK | SOCS1 | (BIND; GRID; HPRD) |
| TEK | STAT5A | (HPRD) |
| TEK | STAT5B | (HPRD) |
| TEK | TIE1 | (GRID; HPRD) |
| TEK | TNIP2 | (HPRD) |
| TIE1 | PIK3R1 | (GRID; HPRD) |
| TIE1 | PTPN11 | (CCSB; GRID; HPRD) |
| TNK1 | PLCG1 | (GRID; HPRD) |
| TNK1 | SFN | (GRID) |
| TNK2 | ARSE | (HPRD; MDC) |
| TNK2 | CDC42 | (CCSB; GRID; HPRD) |
| TNK2 | CLTC | (GRID; HPRD) |
| TNK2 | CSPG4 | (GRID; HPRD) |
| TNK2 | GRB2 | (CCSB; GRID; HPRD) |
| TNK2 | HSH2D | (GRID; HPRD) |
| TNK2 | HSP90AB2P | (HPRD) |

TABLE 5-continued

Human Tyrosine Kinase Interactions (node 1 = tyrosine kinase; node 2 = interacting protein)

| Node1 | Node2 | int_DataBase |
|---|---|---|
| TNK2 | ITFG2 | (HPRD; MDC) |
| TNK2 | MCF2 | (GRID; HPRD) |
| TNK2 | MERTK | (HPRD) |
| TNK2 | NCK1 | (CCSB; GRID; HPRD) |
| TNK2 | RASGEF1C | (HPRD; MDC) |
| TNK2 | RASGRF1 | (GRID; HPRD) |
| TNK2 | RPL18A | (HPRD; MDC) |
| TNK2 | SEZ6 | (HPRD; MDC) |
| TNK2 | SFRS5 | (HPRD; MDC) |
| TNK2 | SNX9 | (HPRD) |
| TNK2 | VTI1B | (HPRD; MDC) |
| TNK2 | WWOX | (HPRD) |
| TXK | CCR5 | (GRID; HPRD) |
| TXK | CTLA4 | (HPRD) |
| TXK | LCP2 | (HPRD) |
| TXK | SH2D2A | (HPRD) |
| TXK | TH1L | (HPRD) |
| TXK | YTHDC1 | (GRID; HPRD) |
| TYK2 | CBL | (BIND; GRID; HPRD) |
| TYK2 | CRKL | (GRID; HPRD) |
| TYK2 | GHR | (GRID; HPRD) |
| TYK2 | GNB2L1 | (BIND; CCSB; GRID; HPRD; MINT) |
| TYK2 | IFNAR1 | (BIND; CCSB; DIP; GRID; HPRD; MINT) |
| TYK2 | IFNAR2 | (BIND; HPRD) |
| TYK2 | IL12RB1 | (BIND) |
| TYK2 | IL13RA1 | (CCSB; GRID; HPRD) |
| TYK2 | IL6ST | (DIP; GRID; HPRD) |
| TYK2 | IRS1 | (GRID; HPRD) |
| TYK2 | IRS2 | (GRID; HPRD) |
| TYK2 | JAKMIP1 | (BIND; HPRD) |
| TYK2 | MAX | (BIND) |
| TYK2 | MYC | (BIND) |
| TYK2 | PIK3R1 | (GRID; HPRD) |
| TYK2 | PLAUR | (BIND; DIP; HPRD) |
| TYK2 | PRMT5 | (GRID; HPRD) |
| TYK2 | PTAFR | (HPRD) |
| TYK2 | PTPN1 | (CCSB; GRID; HPRD) |
| TYK2 | PTPN6 | (CCSB; GRID; HPRD) |
| TYK2 | PTPRC | (HPRD) |
| TYK2 | STAM2 | (CCSB; GRID; HPRD) |
| TYK2 | STAT1 | (GRID; HPRD; MINT) |
| TYK2 | STAT2 | (HPRD) |
| TYK2 | TAF1 | (BIND) |
| TYK2 | VAV1 | (CCSB; GRID; HPRD) |
| TYK2 | XRCC5 | (GRID; HPRD) |
| TYRO3 | GAS6 | (GRID; HPRD) |
| TYRO3 | PIK3R1 | (GRID; HPRD) |
| TYRO3 | PROS1 | (GRID; HPRD) |
| TYRO3 | YES1 | (GRID; HPRD) |
| YES1 | ADAM12 | (GRID; HPRD) |
| YES1 | ADAM15 | (MINT) |
| YES1 | CD2AP | (GRID; HPRD; MINT) |
| YES1 | CD36 | (GRID; HPRD) |
| YES1 | CD46 | (GRID; HPRD) |
| YES1 | CDCP1 | (BIND) |
| YES1 | CKAP4 | (IntAct) |
| YES1 | DLG4 | (GRID; HPRD) |
| YES1 | DOK1 | (HPRD) |
| YES1 | GP2 | (HPRD) |
| YES1 | GP6 | (HPRD) |
| YES1 | ITGB4 | (HPRD) |
| YES1 | NPHS1 | (GRID; HPRD) |
| YES1 | OCLN | (GRID; HPRD) |
| YES1 | PECAM1 | (GRID; HPRD) |
| YES1 | PTPRE | (HPRD) |
| YES1 | RASA1 | (GRID; HPRD) |
| YES1 | RPL10 | (GRID; HPRD) |
| YES1 | TAF1 | (BIND) |
| YES1 | TP53BP2 | (GRID; HPRD) |
| YES1 | TRPV4 | (GRID; HPRD) |
| YES1 | YAP1 | (GRID) |
| YES1 | ZNF512B | (BIND; MINT) |
| ZAP70 | ACP1 | (CCSB; GRID; HPRD) |
| ZAP70 | CARD11 | (HPRD) |
| ZAP70 | CBL | (GRID; HPRD) |

TABLE 5-continued

Human Tyrosine Kinase Interactions (node 1 = tyrosine kinase; node 2 = interacting protein)

| Node1 | Node2 | int_DataBase |
|---|---|---|
| ZAP70 | CBLB | (CCSB; GRID; HPRD) |
| ZAP70 | CD247 | (BIND; CCSB; GRID; HPRD) |
| ZAP70 | CD3E | (GRID; HPRD) |
| ZAP70 | CD5 | (GRID; HPRD) |
| ZAP70 | CD79B | (HPRD) |
| ZAP70 | CRK | (BIND; CCSB; GRID; HPRD) |
| ZAP70 | CRKL | (BIND) |
| ZAP70 | DBNL | (CCSB; GRID; HPRD) |
| ZAP70 | DEF6 | (HPRD) |
| ZAP70 | DUSP3 | (HPRD) |
| ZAP70 | FCGR3A | (CCSB; GRID; HPRD) |
| ZAP70 | FCRL3 | (GRID; HPRD) |
| ZAP70 | GAB2 | (GRID; HPRD) |
| ZAP70 | GRB2 | (HPRD) |
| ZAP70 | HSP90AA1 | (MINT) |
| ZAP70 | IFNAR1 | (HPRD) |
| ZAP70 | LAT | (HPRD; MINT) |
| ZAP70 | LAX1 | (HPRD) |
| ZAP70 | LCP2 | (HPRD) |
| ZAP70 | MUC1 | (HPRD) |
| ZAP70 | NFAM1 | (HPRD) |
| ZAP70 | PAG1 | (GRID; HPRD) |
| ZAP70 | PLCG1 | (GRID; HPRD) |
| ZAP70 | PRLR | (GRID; HPRD) |
| ZAP70 | PTPN3 | (HPRD) |
| ZAP70 | PTPN6 | (CCSB; GRID; HPRD) |
| ZAP70 | PTPRC | (GRID; HPRD) |
| ZAP70 | RASA1 | (CCSB; GRID; HPRD) |
| ZAP70 | SH2B3 | (HPRD) |
| ZAP70 | SH3BP2 | (GRID; HPRD) |
| ZAP70 | SHB | (GRID; HPRD) |
| ZAP70 | SHC1 | (BIND; CCSB; GRID; HPRD) |
| ZAP70 | SIT1 | (GRID; HPRD) |
| ZAP70 | SLA | (CCSB; GRID; HPRD) |
| ZAP70 | SLA2 | (GRID; HPRD) |
| ZAP70 | SLAMF6 | (GRID; HPRD) |
| ZAP70 | SOS1 | (GRID; HPRD) |
| ZAP70 | TUBA4A | (CCSB; GRID; HPRD) |
| ZAP70 | TUBB | (HPRD) |
| ZAP70 | TUBB2A | (HPRD) |
| ZAP70 | TYROBP | (HPRD) |
| ZAP70 | UBE2L3 | (HPRD) |
| ZAP70 | VAV1 | (CCSB; GRID; HPRD) |
| ZAP70 | WIPF1 | (HPRD) |

A list of the interacting proteins of Table 5 followed by their accession numbers (in parenthesis) are as follows:

AATK (205986_at), ABI1 (209027_s_at 209028_s_at), ABI2 (225098_at 209856_x_at 207268_x_at 225112_at 211793_s_at), ABL1 (202123_s_at), ABL2 (231907_at 206411_s_at 226893_at), ACP1 (1554808_at 201630_s_at 215227_x_at 201629_s_at), ACPP (237030_at 231711_at 204393_s_at), ACTA1 (203872_at), ACTB (AFFX-HSAC07/X00351_3_at 213867_x_at AFFX-HSAC07/X00351_M_at AFFX-HSAC07/X00351_5_at 224594_x_at 200801_x_at), ACTN1 (208637_x_at 208636_at), ADAM10 (202604_x_at 233538_s_at 214895_s_at), ADAM12 (202952_s_at 213790_at 204943_at), ADAM15 (217007_s_at 1555896_a_at), ADAM17 (205746_s_at 205745_x_at), ADCYAP1 (230237_at 206281_at), ADCYAP1R1 (207151_at 236373_at 226690_at 242547_at), ADD2 (205268_s_at 237336_at 206807_s_at), ADH6 (214261_s_at 207544_s_at), ADORA2A (205013_s_at), ADRB2 (206170_at), ADRB3 (206812_at 217303_s_at), ADRBK1 (201401_s_at), AFAP1 (203563_at), AFAP1L2 (226829_at), AGK (1555610_at 222132_s_at 218568_at), AGTR1 (205357_s_at 208016_s_at), AGTR2 (207293_s_at 222321_at 207294_at), AHSG (210929_s_at 204551_s_at), AKAP5 (230846_at 207800_at), AKT1 (207163_s_at), ALCAM (1569362_at 240655_at 201951_at 201952_at), ALK (208211_s_at 208212_s_at), AMH (206516_at), ANGPT1 (241119_at 1552939_at 205609_at 205608_s_at), ANGPT2 (237261_at 205572_at 236034_at 211148_s_at), ANGPT4 (221134_at), ANGPTL1 (239183_at 231773_at 224339_s_at), ANKRD11 (238538_at 234701_at 227661_at 219437_s_at 228356_at 231999_at), ANKS1A (212747_at), ANXA1 (201012_at), ANXA2 (210427_x_at 208816_x_at 213503_x_at 201590_x_at 1568126_at), ANXA5 (200782_at), ANXA6 (200982_s_at), AP2A1 (234068_s_at 223237_x_at 229617_x_at), AP2A2 (212159_x_at 211779_x_at 215764_x_at 212161_at), AP2B1 (200615_s_at 200612_s_at), AP2M1 (200613_at), AP2S1 (202120_x_at 211047_x_at 208074_s_at), APBA3 (205146_x_at 215148_s_at), APBB1 (202652_at), APBB2 (213419_at 212972_x_at 212985_at 216747_at 216750_at 40148_at 212970_at), APBB3 (204650_s_at), APC (215310_at 203526_s_at 203525_s_at 203527_s_at 216933_x_at), APP (200602_at 211277_x_at 237571_at 214953_s_at 243314_at), APPL1 (222538_s_at 218158_s_at), AQP1 (209047_at 207542_s_at), AR (211621_at 211110_s_at), ARAF (201895_at), AREG (205239_at), ARF1 (208750_s_at 200065_s_at 244504_x_at), ARF4 (201096_s_at 201097_s_at), ARHGAP1 (216689_x_at 241419_at 217153_at 202117_at), ARHGAP21 (241701_at 224764_at), ARHGAP26 (226576_at 205069_s_at 205068_s_at 215955_x_at), ARHGAP5 (233849_s_at 217936_at 235635_at 1552627_a_at), ARHGEF12 (237398_at 234541_s_at 233620_at 233621_s_at 201335_s_at 234129_at 201333_s_at 201334_s_at), ARHGEF15 (217348_x_at 205507_at), ARHGEF6 (209539_at), ARID3A (205865_at), ARR3 (207136_at), ARRB1 (228444_at 222912_at 49111_at 222756_s_at 43511_s_at 218832_x_at 221861_at), ARSE (205894_at), ATF2 (1555146_at 205446_s_at), ATF3 (1554420_at 1554980_a_at 202672_s_at), ATF7IP (231825_x_at 218987_at 216197_at 216198_at), ATG12 (213930_at 213026_at 204833_at), ATIC (208758_at), ATM (1554631_at 210858_x_at 208442_s_at 212672_at 1570352_at 1553387_at), ATP1A1 (220948_s_at), ATP1B1 (227556_at 201243_s_at 201242_s_at), ATP2B4 (212136_at 205410_s_at 212135_s_at), ATP5C1 (205711_x_at 208870_x_at 213366_x_at), ATP5H (210149_s_at 1555998_at), ATP5O (1564482_at 200818_at), ATP6V1H (1557585_at 1557586_s_at 221504_s_at), ATR (209902_at 233288_at 209903_s_at), ATXN1 (236404_at 1559249_at 203232_s_at 203231_s_at 242230_at 230507_at 236802_at), AXL (202685_s_at 202686_s_at), BAG1 (202387_at 229720_at 211475_s_at), BANK1 (1558662_s_at 222915_s_at 219667_s_at), BCAR1 (223116_at), BCAS2 (203053_at), BCL2 (203685_at 207005_s_at 207004_at 203684_s_at 237837_at), BCL2L1 (215037_s_at 212312_at 206665_s_at), BCL3 (204908_s_at 204907_s_at), BCR (226602_s_at 202315_s_at 217223_s_at), BDNF (239367_at 244503_at 206382_s_at), BIN1 (214643_x_at 202931_x_at 214439_x_at 210202_s_at 210201_x_at), XIAP (225858_s_at 235222_x_at 206536_s_at 225859_at 243026_x_at 228363_at), BLK (244394_at 236820_at 206255_at 210934_at), BLNK (244172_at 207655_s_at 243867_at), BMPR2 (238516_at 225144_at 210214_s_at 209920_at 231873_at), BMX (206464_at 242967_at), BNIP2 (209308_s_at), BRAF (206044_s_at 243829_at), BRCA1 (211851_x_at 204531_s_at), BTC (241412_at 207326_at), BTK (205504_at), C13orf34 (219544_at), C14orf4 (not found), BENDS (219670_at), C2orf44 (219120_at), C3 (217767_at), C6orf47 (204968_at), CABLES1 (225531_at 225532_at), CABLES2 (226004_at), CACNA1D (207998_s_at 210108_at), CALM1 (213710_s_at 213688_at 211985_s_at 211984_at 209563_x_at 200653_s_at 200655_s_at), CALM2 (207243_s_at), CALM3 (1563431_x_at 200622_x_at 200623_s_at), CAMK2A (213108_at 207613_s_at), CAMK2G (212669_at 212757_s_at), CAMLG (203538_at), CARD11 (223514_at), CASP1 (211366_x_at 209970_x_at 211368_s_at 211367_s_at 1552703_s_at), CASP3 (202763_at), CASP7 (207181_s_at), CASP8 (207686_s_at 1553306_at 213373_s_at), CASP9 (237451_x_at 240437_at 203984_s_at 210775_x_at), CAT (201432_at 211922_s_at), CAV1 (212097_at 203065_s_at), CAV2 (213426_s_at 203323_at 203324_s_at), CAV3 (208204_s_at), CBL (225231_at 229010_at 206607_at 243475_at 225234_at), CBLB (208348_s_at 209682_at 227900_at), CBLC (220638_s_at 223668_at), CCDC17 (236320_at), CCNA2 (213226_at 203418_at), CCND1 (208712_at 208711_s_at), CCR1 (205099_s_at 205098_at), CCR2 (207794_at 206978_at), CCR3 (208304_s_at), CCR5 (206991_s_at), CD19 (206398_s_at), CD2 (205831_at), CD22 (220674_at 204581_at 38521_at 217422_s_at), CD226 (207315_at), CD24 (216379_x_at 208651_x_at 209771_x_at 266_s_at 209772_s_at 208650_s_at), CD247 (210031_at), CD28 (206545_at 211856_x_at 211861_x_at), CD2AP (203593_at 236257_at), CD33 (206120_at), CD36 (228766_at 209554_at 206488_s_at 209555_s_at), CD38 (234187_at 205692_s_at), CD3E (205456_at), CD4 (216424_at 203547_at), CD40 (205153_s_at 35150_at 222292_at 215346_at), CD44 (1565868_at 212014_x_at 229221_at 212063_at 209835_x_at 217523_at 1557905_s_at 210916_s_at 204490_s_at 216056_at 204489_s_at), CD46 (208783_s_at 211574_s_at 207549_x_at), CD47 (213856_at 213055_at 213857_s_at 226016_at 211075_s_at 242974_at 227259_at), CD48 (237759_at 204118_at), CD5 (230489_at 206485_at), CD55 (1555950_a_at 201925_s_at 201926_s_at), CD59 (228748_at 200983_x_at 212463_at 200984_s_at 200985_s_at), CD63 (200663_at), CD79A (205049_s_at 1555779_a_at), CD79B (205297_s_at 1555748_x_at 1555746_at), CD81 (200675_at), CD82 (228910_at 203904_x_at), CD8A (205758_at), CD8B (230037_at 215332_s_at 207979_s_at), CD9 (201005_at), CDAN3 (not found), CDK1 (231534_at 203214_x_at 210559_s_at 203213_at), CDC25A (1555772_a_at 204696_s_at 204695_at), CDC25C (217010_at 205167_s_at), CDC37 (209953_s_at), CDC42 (210232_at 214230_at 208728_s_at 208727_s_at), CDCP1 (218451_at 1554110_at 234932_s_at), CDH1 (201131_s_at 201130_s_at), CDH2 (203440_at 203441_s_at), CDH5 (204677_at), CDK2 (211804_s_at 204252_at 211803_at), CDK4 (202246_s_at), CDK5 (204247_s_at), CDK5R1 (204996_s_at 204995_at), CDKN1B (209112_at), CEACAM1 (211889_x_at 209498_at 206576_s_at 210610_at 211883_x_at), CEACAM3 (208052_x_at 210789_x_at), CEBPB (212501_at), CENPF (207828_s_at 209172_s_at), ARAP1 (34206_at 212516_at), CHGB (204260_at), CHN1 (212624_s_at), CHN2 (207486_x_at 213385_at 211419_s_at), CHUK (209666_s_at), CIB1 (201953_at), CISH (221223_x_at 223377_x_at 223961_s_at), CKAP4 (200998_s_at 200999_s_at 226526_s_at), CLDN4 (201428_at), CLTA (1560434_x_at 200960_x_at 1560433_at 216295_s_at 204050_s_at), CLTC (200614_at), CLTCL1 (205944_s_at), CMTM3 (1555704_at 1555705_a_at 224733_at), CNN1 (203951_at), CNN3 (201445_at), CNR1 (213436_at 208243_s_at 207940_s_at), CNTN1 (241190_at 211203_s_at 227202_at), CNTNAP1 (219400_at), COL11A1 (229271_x_at 37892_at 204320_at), COL18A1 (209082_s_at 209081_s_at), COL1A1 (1556499_s_at 202310_s_at 202312_s_at 217430_x_at 202311_s_at), COL1A2 (202404_s_at 202403_s_at), COL2A1 (217404_s_at 213492_at), COL3A1 (211161_s_at 215076_s_at 201852_x_at), COL5A2 (221729_at 221730_at), COLO (206073_at), COPA (214336_s_at 1559862_at 208684_at), COPB1 (201359_at 201358_s_at), PTGS2 (204748_at 1554997_a_at), COX6C (201754_at), COX7B (202110_at), CPSF4 (206688_s_at), CREB1 (204313_s_at 225565_at 214513_s_at 204314_s_at 237289_at 243625_at 204312_x_at 225572_at), CREBBP (211808_s_at 202160_at 228177_at 237239_at), CRK (202224_at 202226_s_at), CRKL (206184_at 212180_at), CRLF2 (208303_s_at), CSF1 (211839_s_at 210557_x_at 207082_at 209716_at), CSF1R (203104_at), CSF2RA (210340_s_at 211287_x_at 211286_x_at 207085_x_at), CSF2RB (205159_at), CSF3R (203591_s_at 1553297_a_at), CSK (202329_at), CSNK2B (201390_s_at), CSPG4 (214297_at 204736_s_at), CTGF (209101_at), CTLA4 (221331_x_at 231794_at 234895_at 236341_at 234362_s_at), CTNNB1 (1554411_at 201533_at), CTNND1 (211240_x_at 208862_s_at 208407_s_at 1557944_s_at), CTNND2 (209617_s_at 209618_at), CTR9 (202060_at), CTSK (202450_s_at), CTTN (201059_at 214782_at 214074_s_at), CXCR4 (211919_s_at 217028_at 209201_x_at), CYP2D6 (207498_s_at 217468_at 215809_at), DAB1 (228329_at 220611_at), DAB2 (210757_x_at 201278_at 232898_at 201279_s_at 201280_s_at), DAG1 (212128_s_at 205417_s_at), DAPK3 (203891_s_at 228681_x_at 203890_s_at), DAPP1 (222859_s_at 222858_s_at 219290_x_at), DBNL (222429_at), DCC (238914_at 206939_at), DCN (239786_at 201893_x_at 211896_s_at 211813_x_at 209335_at 229554_at), DDB1 (208619_at), DDB2 (203409_at), ASAP1 (231205_at 237082_at 224790_at 224791_at 236533_at 221039_s_at 224796_at), ASAP2 (206414_s_at), DDR1 (208779_x_at 207169_x_at 210749_x_at 1007_s_at), DDR2 (227561_at 205168_at), DEF6 (221293_s_at 226659_at), DEGS1 (207431_s_at 209250_at), DGKA (211272_s_at 203385_at), DGKZ (207556_s_at 239342_at), DIABLO (219350_s_at), DLG1 (229703_at 202515_at 215988_s_at 217208_s_at 202516_s_at 202514_at), DLG2 (228973_at 206253_at), DLG3 (241839_at 207732_s_at 212729_at 212727_at 212728_at), DLG4 (204592_at 210684_s_at), DLGAP3 (231151_at), DNAJA3 (205963_s_at 1554078_s_at), DNM1 (215116_s_at 217341_at), DNM2 (202253_s_at 216024_at), DOK1 (216835_s_at 211121_at), DOK2 (214054_at), DOK3 (223553_s_at 220320_at), DOK4 (207747_s_at 209690_s_at 209691_s_at), DOK5 (214844_at 1554863_s_at), DOK6 (236290_at 242867_x_at 241729_at 231980_at), DOK7 (240633_at), DPM2 (209391_at), DPYSL5 (224100_s_at 222797_at), DRD4 (208215_x_at), DTYMK (1553984_s_at 203270_at), DUSP3 (201537_s_at 201536_at 201538_s_at), DYNLL1 (200703_at), E2F4 (38707_r_at 202248_at), S1PR1 (239401_at 204642_at 244422_at), EFNA1 (202023_at), EFNA2 (208256_at 1553573_s_at), EFNA3 (210132_at), EFNA4 (205107_s_at), EFNA5 (227955_s_at 214036_at 207301_at 233814_at), EFNB1 (202711_at), EFNB2 (202669_s_at 202668_at), EFNB3 (210883_x_at 205031_at), EFS (210880_s_at 204400_at), EGF (206254_at), EGFR (211550_at 210984_x_at 211551_at 211607_x_at 201984_s_at 201983_s_at 1565483_at 1565484_x_at), EGR1 (201694_s_at 201693_s_at 227404_s_at), EHD1 (222221_x_at 209039_x_at 209038_s_at 209037_s_at 208112_x_at), EIF2AK2 (204211_x_at), EIF3E (236989_at 208697_s_at 235429_at), EIF4B (211938_at 219599_at 211937_at), ELF3 (229842_at 201510_at 210827_s_at), ELMO1 (204513_s_at), ELP2 (231713_s_at 232503_at), ENPP1 (228952_at 229088_at 205066_s_at 205065_at), EP300 (213579_at 202221_s_at), EPB41 (207793_s_at 214530_x_at 225051_at 1554481_a_at), EPHA1 (215804_at 205977_s_at), EPHA2 (203499_at), EPHA3 (206071_s_at 206070_s_at 211164_at), EPHA4 (227449_at 228948_at 229374_at 206114_at), EPHA5 (215664_s_at 216837_at 237939_at), EPHA6 (233184_at 1561396_at), EPHA7 (1554629_at 229288_at 238533_at 206852_at), EPHA8 (231796_at 1554069_at), EPHB1 (230425_at 211898_s_at 210753_s_at), EPHB2 (209588_at 209589_s_at 211165_x_at 210651_s_at), EPHB3 (204600_at 1438_at), EPHB4 (202894_at 216680_at), EPHB6 (204718_at), EPOR (209962_at 216999_at 209963_s_at 396_f_at 3798_at 215054_at), EPPK1 (232164_at 208156_x_at 232165_at), EPS15 (217886_at 234277_at 217887_at 234278_at), EPS8 (202609_at), ERBB2 (210930_s_at 216836_s_at), ERBB2IP (217941_s_at 222473_s_at), ERBB3 (1563252_at 202454_s_at 226213_at 1563253_s_at), ERBB4 (206794_at 241581_at 233494_at 214053_at 233498_at), EREG (1569583_at 205767_at), ERF (203643_at), ERRFI1 (224657_at), ESR1 (217163_at 211627_x_at 205225_at 215552_s_at 211233_x_at 211235_s_at 211234_x_at), ESR2 (211120_x_at 211119_at 240777_at 211117_x_at 211118_x_at 210780_at), ETS1 (224833_at 1555355_a_at 241435_at 214447_at), ETS2 (242784_at 201329_s_at 201328_at), EVL (244375_at 217838_s_at 227232_at), EWSR1 (217622_at 210011_s_at 210012_s_at 229966_at 209214_s_at), EZR (217234_s_at 208622_s_at 208621_s_at 217230_at 208623_s_at), FABP4 (203980_at), FARP2 (1558855_at 1554337_at 204511_at), FAS (216252_x_at 215719_x_at 204780_s_at 204781_s_at), FASLG (211333_s_at 210865_at), FAU (200019_s_at), FBP1 (209696_at), FCAR (211306_s_at 211816_x_at 211305_x_at 207674_at 211307_s_at), FCER1G (204232_at 1554899_s_at), FCER2 (206759_at 206760_s_at), FCGR1A (214511_x_at 216950_at 216951_at), FCGR2A (211395_x_at 210992_x_at 203561_at 1565674_at 1565673_at), FCGR2B (211395_x_at 210889_s_at), FCGR3A (204007_at 204006_s_at), FCRL3 (231093_at 1553196_a_at), FDPS (201275_at), FER (227579_at 206412_at), FES (205418_at), FGA (205650_s_at 205649_s_at), FGF1 (205117_at 208240_s_at 1552721_a_at), FGF10 (231762_at), FGF16 (221374_at), FGF17 (221376_at), FGF18 (231382_at 211485_s_at 206987_x_at 211029_x_at), FGF19 (223761_at), FGF2 (204422_s_at 204421_s_at), FGF20 (220394_at), FGF22 (221315_s_at), FGF23 (221166_at), FGF3 (214571_at), FGF4 (1552982_a_at), FGF5 (210310_s_at 210311_at 208378_x_at), FGF6 (208417_at), FGF7 (1555103_s_at 205782_at 1555102_at 1554741_s_at), FGF8 (208449_s_at), FGF9 (239178_at 206404_at), FGFR1 (215404_x_at 207822_at 226705_at 211535_s_at 210973_s_at 207937_x_at), FGFR2 (211399_at 203639_s_at 208225_at 208234_x_at 211398_at 211401_s_at 208228_s_at 203638_s_at 211400_at), FGFR3 (204380_s_at 204379_s_at), FGFR4 (1554961_at 211237_s_at 204579_at 1554962_a_at), FGR (208438_s_at), FHIT (206492_at), FIGF (206742_at), FIZ1 (228663_x_at 226967_at), FLOT1 (210142_x_at 208749_at 208748_at), FLOT2 (201350_at 211299_s_at), FLT1 (210287_s_at 226497_s_at 222033_s_at 226498_at), FLT3 (206674_at), FLT3LG (206980_s_at 210607_at), FLT4 (234379_at 210316_at 229902_at), FLYWCH1 (223950_s_at 234106_s_at 225952_at), FN1 (211719_x_at 235629_at 214702_at 214701_s_at 212464_s_at 1558199_at 216442_at 210495_x_at), FNBP4 (235101_at 212232_at), FOLR1 (204437_s_at), FOS (209189_at), FOXO1 (228484_s_at 239728_at 202724_s_at 202723_s_at), FRK (207178_s_at), FRS2 (226045_at 221308_at 238486_at), FRS3 (219907_at), FYB (224148_at 211795_s_at 205285_s_at 211794_at 227266_s_at), FYN (217697_at 210105_s_at 216033_s_at), FZD2 (210220_at 238129_s_at), FZD5 (221245_s_at 206136_at), FZD8 (216587_s_at 224325_at 227405_s_at), GAB1 (225998_at 214987_at 229114_at 1560382_at 226002_at 207112_s_at), GAB2 (203853_s_at), GAB3 (241259_at 228410_at), CHST15 (244874_at 203066_at), GAPDH (AFFX-HUMGAPDH/M33197_3_at AFFX-HUMGAPDH/M33197_5_at AFFX-HUMGAPDH/M33197_M_at 212581_x_at 217398_x_at 213453_x_at), GAS6 (202177_at 1598_g_at), GDNF (221359_at 230090_at), GFAP (203539_s_at 229259_at 203540_at), GFRA1 (205696_s_at 227550_at 230163_at), GFRA4 (234868_s_at 221199_at), GHR (241584_at 205498_at), GIGYF1 (228755_at 226768_at 236447_at), GIPC1 (207525_s_at), GIT1 (218030_at), GJA1 (201667_at), GJB1 (204973_at), GJC1 (228563_at 208460_at 228776_at 243502_at), GLMN (207153_s_at), GLRX (206662_at 20927_s_at), GNA11 (214679_x_at 40562_at 204248_at 564_at 213944_x_at 213766_x_at 221955_at), GNA12 (221737_at 224681_at), GNA13 (224761_at 227539_at 206917_at), GNAI1 (209576_at 227692_at), GNAI2 (201040_at), GNAQ (211426_x_at), GNB2L1 (200651_at), GNG2 (223943_s_at 224965_at 224964_s_at 1555766_a_at), GP2 (208473_s_at 214324_at 206681_x_at), GP6 (220336_s_at), GPSM3 (204265_s_at 214847_s_at), GPT (206709_x_at), GPX1 (200736_s_at), GRAP (229726_at 206620_at), GRAP2 (208406_s_at), GRB10 (209410_s_at 215248_at 209409_at 210999_s_at), GRB14 (206204_at), GRB2 (223049_at 215075_s_at), GRB7 (210761_s_at), GRIA3 (1569290_s_at 208032_s_at 206730_at 230144_at), GRIN1 (205914_s_at 205915_x_at 211125_x_at 210781_x_at 210782_x_at), GRIN2A (231384_at 206534_at 242286_at), GRIN2B (237933_at 210411_s_at 210412_at), GRIN2D (229883_at 207036_x_at), GRLF1 (202044_at 229394_s_at 202045_at 239456_at 202046_s_at), GSK3B (242336_at 209945_s_at 226191_at), GSN (214040_s_at 200696_s_at 234240_at 227957_at 234431_at 227958_s_at), GSTO1 (1557915_s_at 201470_at), GTF2I (210891_s_at 239649_at 229896_at 210892_s_at 201065_s_at), GTF3C1 (202320_at 35671_at), GUCY2C (206312_at), GYS1 (201673_s_at), GZMB (210164_at), H3F3A (200080_s_at 213828_x_at 208755_x_at 213826_s_at 211940_x_at), HBEGF (38037_at 203821_at 222076_at), HBZ (206647_at), HCK (208018_s_at), HCLS1 (202957_at), HDHD2 (223155_at), HES1 (203395_s_at 203394_s_at 237115_at), HES5 (239230_at), HGF (210997_at 209960_at 210998_s_at 210755_at 209961_s_at), HGFAC (207027_at), HGS (232627_at 210428_s_at), HIST2H4A (207046_at 230795_at), HIST3H3 (208572_at), HIST1H4I (214634_at), HLA-A (221875_x_at 217436_x_at 215313_x_at 211911_x_at 204806_x_at 208729_x_at), HLA-B (216526_x_at 211911_x_at 214459_x_at 209140_x_at 208729_x_at), HMGA1 (206074_s_at 210457_x_at), HMGCS2 (204607_at 240110_at), HNF1A (210515_at), HNF4A (214832_at 230914_at 208429_x_at 216889_s_at), HNRNPC (214737_x_at 200751_s_at 200014_s_at 212626_x_at 227110_at), HNRNPL (35201_at 202072_at), HNRNPU (225805_at 200594_x_at 200593_s_at 235603_at 216855_s_at), HNRNPA3P1 (211931_s_at 206809_s_at 211933_s_at 206808_at), HNRNPK (200097_s_at 200775_s_at), HOXC10 (218959_at), HRAS (212983_at), HSH2D (1552623_at), HSP9OAA1 (214328_s_at 211969_at 210211_s_at 211968_s_at), HSP90AB2P (1557910_at 214359_s_at), HSP90B1 (216449_x_at 200598_at 200599_s_at), HSPA8 (210338_s_at 221891_x_at 224187_x_at 208687_x_at), HSPD1 (200806_s_at 200807_s_at), HTR2A (211616_s_at 244130_at 207135_at), HTR6 (1552857_a_at), HTT (202389_s_at 202390_s_at), HYAL2 (206855_s_at), IBTK (210970_s_at), ICAM1 (202637_s_at 215485_s_at 202638_s_at), IFNAR1 (225661_at 225669_at 204191_at), IFNAR2 (204785_x_at 230735_at 204786_s_at), IFNGR1 (202727_s_at 242903_at 211676_s_at), IFNGR2 (201642_at), IGF1 (211577_s_at 209542_at 209541_at 209540_at), IGF1R (208441_at 243358_at 203627_at 225330_at 238544_at 237377_at 237881_at 203628_at), IGF2 (210881_s_at 202410_x_at 202409_at), IGFBP3 (210095_s_at 212143_s_at), IGHM (212827_at), IKBKB (209342_s_at 209341_s_at 211027_s_at), IKBKG (209929_s_at 36004_at), IL10RA (204912_at), IL12RB1 (206890_at 239522_at 1552584_at), IL12RB2 (206999_at), IL13RA1 (210904_s_at 201888_s_at 211612_s_at 201887_at), IL15RA (207375_s_at), IL17RD (227997_at 229263_at), IL21R (237753_at 221658_s_at 219971_at), IL23R (1561853_a_at 1552912_a_at), IL2RB (205291_at), IL2RG (204116_at), IL3RA (206148_at), IL4R (203233_at), IL5RA (211516_at 211517_s_at 207902_at 210744_s_at), IL6R (205945_at 217489_s_at), IL6ST (211000_s_at 212196_at 234474_x_at 214077_x_at 204863_s_at 212195_at 234967_at 204864_s_at), IL7R (226218_at 205798_at), IL9R (217212_s_at 208164_s_at), IMPDH2 (201892_s_at), INPP5D (1568943_at 233545_at 203331_s_at 203332_s_at), INPPL1 (201598_s_at), INS (206598_at), INSR (227432_s_at 226450_at 213792_s_at 243002_at 226212_s_at 226216_at 207851_s_at), INSRR (215776_at), IQGAP1 (213446_s_at 210840_s_at 200791_s_at), IRAK1 (201587_s_at 1555784_s_at), IRS1 (238933_at 242979_at 239463_at 235392_at 204686_at), IRS2 (236338_at 209185_s_at 209184_s_at), IRS4 (207403_at), ITFG2 (226295_at 220589_s_at), ITGA5 (201389_at), ITGAV (202351_at), ITGB1 (1553530_a_at 211945_s_at 1553678_a_at 215879_at 216190_x_at 216178_x_at), ITGB2 (1555349_a_at 202803_s_at), ITGB3 (204625_s_at 204627_at 216261_at 211579_at 215240_at 204628_s_at 204626_s_at), ITGB4 (204989_s_at 214292_at 230704_s_at 211905_s_at 204990_s_at), ITGB5 (201125_s_at 214021_x_at), ITGB6 (208084_at 208083_s_at), ITK (211339_s_at), ITPR1 (1562373_at 203710_at 231329_at 216944_s_at 244090_at 211323_s_at), ITSN1 (2092979_at 209298_s_at 210713_at 35776_at 207322_at), JAK1 (1552611_a_at 239695_at 1552610_a_at 201648_at), JAK2 (205842_s_at 205841_at 1562031_at), JAK3 (211109_at 211108_s_at 207187_at 227677_at), JAKMIP1 (238600_at), JUN (201466_s_at 201464_x_at 213281_at 201465_s_at), JUP (201015_s_at), KALRN (232717_at 206078_at 227750_at 236651_at 205635_at), KCNA2 (239118_at 208564_at), KCNA5 (206762_at), KCNB1 (211006_s_at), KCNMA1 (221584_s_at 228414_at 221583_s_at 214921_at), KCNQS (244623_at 223891_at), KDR (203934_at), KHDRBS1 (200040_at 201488_x_at), KIAA1377 (232166_at 236325_at 235956_at), KIDINS220 (1557246_at 214932_at 212163_at 212162_at), KIFAP3 (203333_at), KIR2DL3 (211410_x_at 211397_x_at 216907_x_at 211532_x_at 207314_x_at 208122_x_at 208203_x_at 216552_x_at 211688_x_at 208179_x_at 211687_x_at 207313_x_at 216676_x_at 208198_x_at 210890_x_at), KIT (205051_s_at), KITLG (211124_s_at 226534_at 207029_at), KL (205978_at), KPNA2 (201088_at 211762_s_at), KPNB1 (217027_x_at 208975_s_at 213507_s_at 208974_x_at), KRAS (1559204_x_at 1559203_s_at 204009_s_at 214352_s_at), KRT17 (212236_x_at 205157_s_at), KRT18 (201596_x_at), KRT27 (240388_at), KRT7 (1558394_s_at 209016_s_at), KRT8 (216568_x_at 230116_at 209008_x_at), KRTAP4-12 (224269_at), LAIR1 (210644_s_at 208071_s_at), LAT (209881_s_at 211005_at), LAX1 (207734_at), LCK (204891_s_at 204890_s_at), LCP2 (205270_s_at 205269_at), LCT (206945_at), LDLRAP1 (221790_s_at 57082_at), LEPR (209894_at 1556919_at 211356_x_at 211354_s_at 207255_at 211355_x_at), LIME1 (219541_at), LMO4 (229537_at 241922_at 209204_at 227155_at 209205_s_at), LMTK2 (235307_at 206223_at 226375_at), LMTK3 (1557103_a_at), LPHN1 (219145_at 47560_at 203488_at), LPXN (216250_s_at 242778_at), LRP1 (200785_s_at 1555353_at 200784_s_at), LRPPRC (211615_s_at 211971_s_at 230194_at 1557360_at 230594_at), LRSAM1 (227675_at 235449_at), LTK (207106_s_at 217184_s_at), LYN (202625_at 210754_s_at 202626_s_at), MAD2L1 (1554768_a_at 203362_s_at), MAG (217447_at 216617_s_at), MAGED1 (209014_at 244878_at), MAP2 (241044_x_at 210015_s_at 225540_at), MAP2K1 (202670_at), MAP3K1 (225927_at 214786_at), MAP3K14 (205192_at), MAP3K3 (227131_at 203514_at), MAP3K4 (204089_x_at 216199_s_at), MAP3K5 (203837_at 203836_s_at), MAP4K1 (214339_s_at 214219_x_at 206296_x_at), MAP4K5 (211081_s_at 203553_s_at 203552_at), MAPK1 (208351_s_at 224621_at 1552264_a_at 1552263_at 229847_at 212271_at), MAPK14 (202530_at 210449_x_at 211561_x_at 211087_x_at), MAPK15 (241357_at), MAPK3 (212046_x_at), MAPK8 (226046_at 226048_at 210671_x_at 210477_x_at), MAPK8IP1 (213014_at 213013_at), MAPK8IP2 (208603_s_at 205050_s_at), MAPK8IP3 (216139_s_at 213177_at 230162_s_at 213178_s_at 232085_at 216137_s_at), MAPK9 (210570_x_at 225781_at 203218_at), MAPT (203929_s_at 203930_s_at 225379_at 206401_s_at 203928_x_at), MATK (206267_s_at), MAX (209331_s_at 209332_s_at 210734_x_at 208403_x_at 214108_at), MCAM (210869_s_at 209086_x_at 211340_s_at 209087_x_at), MCF2 (1555313_a_at 217004_s_at 208017_s_at), MDK (209035_at), MDM2 (217542_at 229711_s_at 225160_x_at 217373_x_at 244616_x_at 205386_s_at 211832_s_at), MERTK (211913_s_at 206028_s_at), MET (213807_x_at 203510_at 211599_x_at 213816_s_at), MICAL1 (218376_s_at), CLNK (1570239_a_at 1562587_at), MLLT4 (238871_at 230622_at 208512_s_at), MME (203434_s_at 203435_s_at), MMP16 (207012_at 223614_at 208167_s_at 208166_at 207013_s_at), MMP2 (201069_at), MPDZ (205079_s_at 213306_at), MPL (211903_s_at 216825_s_at 207550_at), MPZL1 (210594_x_at 201874_at 210210_at 201875_s_at 210087_s_at 231621_at), MS4A1 (228592_at 228599_at 210356_x_at 217418_x_at), MS4A2 (207497_s_at 207496_at), MSN (200600_at 240960_at), MST1 (216320_x_at 205614_x_at 213380_x_at), MST1R (205455_at), MUC1 (211695_x_at 207847_s_at 213693_s_at), MUC20 (231941_s_at 230043_at 226622_at), MUC4 (204895_x_at 235055_x_at 217109_at 217110_s_at), MUSK (207632_at 207633_s_at 241122_s_at), MYC (202431_s_at), MYD88 (209124_at), MYLK (1568770_at 1563466_at 2248239_at 202555_s_at), NCAM1 (214952_at 209968_s_at 229799_s_at 227394_at 217359_s_at 212843_at), NCF1 (204961_s_at 214084_x_at), NCK1 (211063_s_at 204725_s_at 229895_s_at), NCK2 (203315_at), NCOA3 (207700_s_at 209061_at 211352_s_at 209062_x_at 209060_x_at), NCOA6 (208979_at 1568874_at), NCOR1 (234313_at 200854_at 200856_x_at 200855_at 200857_s_at), NCSTN (237076_at 208759_at), ND2 (not found), NDUFS1 (203039_s_at 229647_at 236356_at), NDUFS6 (203606_at), NEDD4 (213012_at), NEDD4L (226974_at 212445_s_at 241396_at 212448_at 236490_at), NEDD8 (243733_at 201840_at), NEDD9 (1569020_at 202150_s_at 202149_at), NEO1 (204321_at 229877_at 225270_at), NF2 (204991_s_at 238618_at 217150_s_at 211091_s_at 210767_at 218915_at 211092_s_at 211017_s_at), NFAM1 (243099_at 230322_at), NFKBIA (201502_s_at), NFKBIB (214448_x_at 228388_at 214062_x_at), NGEF (227240_at 243556_at), NGF (206814_at), NGFR (205858_at), NGFRAP1 (217963_s_at), NMT1 (201159_s_at 201157_s_at 201158_at), NOS2 (210037_s_at), NOTCH1 (218902_at), NPHP1 (206285_at 238844_s_at 238843_at), NPHS1 (207673_at 241181_x_at), NPM1 (200063_s_at 221923_at 221691_x_at), NR3C1 (201866_s_at 232431_at 216321_s_at 201865_x_at 211671_s_at), NRAS (224985_at 202647_s_at), NRG1 (208231_at 208232_x_at 208241_at 208230_s_at 206237_s_at 206343_s_at), NRG2 (242303_at 208062_s_at 206879_s_at), NRG3 (229233_at), NRG4 (242426_at), NRP1 (210510_s_at 212298_at), NRP2 (223510_at 211844_s_at 210842_at 229225_at 1555468_at 230410_at 210841_s_at 214632_at 228102_at 225566_at 228103_s_at), NRTN (210683_at), NTF3 (206706_at), NTF4 (not found), NTRK1 (208605_s_at), NTRK2 (214680_at 207152_at 236095_at 221796_at 229463_at 221795_at), NTRK3 (217033_x_at 217377_x_at 215115_x_at 215025_at 206462_s_at 1557795_s_at 228849_at), NUMB (209073_s_at 230462_at 207545_s_at), NUMBL (242195_x_at 224059_s_at), NXF1 (208922_s_at), OCLN (235937_at 209925_at), ODF2L (230926_s_at 237420_at 228577_x_at), ONECUT1 (2107459_at), OSMR (1554008_at 226621_at 205729_at), P2RY2 (206277_at), PA2G4 (214794_at 208676_s_at), PAG1 (225626_at 227354_at 225622_at), PAK1 (226507_at 209615_s_at), PAK2 (208878_s_at 208877_at 208876_s_at 236283_x_at 208875_s_at 205962_at 1559052_s_at 244268_x_at), PAK4 (203154_s_at 33814_at 215326_at), PARD3 (221526_x_at 221527_s_at 221280_s_at 210094_s_at), PAX3 (207679_at 231490_at 231666_at 216059_at 207680_x_at), NAMPT (217739_s_at 217738_at 1555167_s_at), PCBD2 (1554894_a_at 223712_at), PDAP1 (202290_at 217624_at), PDE4A (211901_s_at 211591_s_at 204735_at 211447_s_at), PDE4D (228962_at 1554717_a_at 243586_at 204491_at 222322_at 210837_s_at 210836_x_at 211840_s_at), PDE6G (210060_at), PDGFA (229830_at 216867_s_at 205463_s_at), PDGFB (204200_s_at 216061_x_at 217112_at), PDGFC (242171_at 222719_s_at 218718_at), PDGFD (222860_s_at 219304_s_at), PDGFRA (211533_at 237696_at 1554828_at 203131_at 215305_at), PDGFRB (202273_at), PDLIM7 (203369_x_at 214266_s_at 214121_x_at 203370_s_at 214122_at), PDPK1 (221244_s_at 232050_at 204524_at 32029_at 224986_s_at 222260_at), PECAM1 (1558397_at 208983_s_at 208982_at 208981_at), PELP1 (215354_s_at), PGF (209652_s_at), PGR (208305_at 228554_at), PIAS1 (217864_s_at 222371_at), PICK1 (204746_s_at), PIK3AP1 (1554508_at 226459_at), PIK3C2A (1569022_a_at 235792_x_at 1553694_a_at 213070_at 1569021_at 226094_at), PIK3C2B (204484_at), PIK3CA (204369_at), PIK3CB (212688_at 217620_s_at), PIK3CG (206369_s_at 206370_at), PIK3R1 (212240_s_at 212249_at 212239_at), PIK3R2 (229392_s_at 207105_s_at 1568629_s_at), PIK3R3 (202743_at 211580_s_at), PILRB (225321_s_at 220954_s_at), PIM1 (209193_at), PIP4K2A (205570_at 229713_at 212829_at), PIP4K2B (1553047_at 201081_s_at 1553048_a_at 201080_at), PIP4K2C (218942_at), PIP5K1A (210256_s_at 207391_s_at 211205_x_at), PIP5K1B (205632_s_at), PIP5K1C (212518_at), PITPNA (241974_at 201191_at 239124_at 201192_s_at 201190_s_at 237424_at), PITPNM1 (203826_s_at), PITPNM2 (1552923_a_at 1552924_at 232950_s_at), PITPNM3 (221254_at 230076_at), PKD1 (216949_s_at 202327_at 202328_s_at), PKIA (204612_at), PLA2G4A (210145_at), PLAUR (210845_s_at 214866_at 211924_s_at), PLCE1 (205112_at 205111_s_at), PLCG1

(216551_x_at 202789_at), PLCG2 (204613_at), PLD1 (215723_s_at 226636_at 177_at 205203_at 1557126_a_at 215724_at), PLD2 (209643_s_at), PLEC (216971_s_at 201373_at 238083_at), PLK4 (204887_s_at 204886_at 211088_s_at), PLSCR1 (202446_s_at 202430_s_at), PLXNA1 (1558140_at 221537_at 221538_s_at), PLXNB1 (215807_s_at 215668_s_at), PMAIP1 (204286_s_at 204285_s_at), POLA2 (204441_s_at), POLR2A (202725_at 217420_s_at 217415_at), POLR2I (212955_s_at), POU2AF1 (205267_at), PPARD (210636_at 37152_at 208044_s_at), PPIA (217602_at 211378_x_at 211978_x_at 211765_x_at 201293_x_at 226336_at 212661_x_at), PPP1CB (201409_s_at 201408_at 201407_s_at 228222_at), PPP1R15A (37028_at 202014_at), PPP1R2 (202165_at 202166_s_at 213774_s_at), PPP1R8 (207830_s_at), PPP2CA (208652_at), PPP2R1B (202886_s_at 202885_s_at 202883_s_at 202884_s_at 222351_at), PPP2R5A (202187_s_at), PRAM1 (241742_at), PRDX2 (215067_x_at 39729_at), PRKACA (202801_at 216234_s_at), PRKAR1A (242482_at 200604_s_at 200605_s_at 200603_at), PRKAR2A (204842_x_at 204843_s_at), PRKCA (213093_at 1560074_at 215195_at 206923_at 215194_at), PRKCB (227817_at 209685_s_at 207957_s_at 230437_s_at 228795_at 227824_at), PRKCD (202545_at), PRKCE (206248_at 226101_at), PRKCH (218764_at 206099_at), PRKCI (213518_at 209678_s_at 209677_at), PRKCQ (210039_s_at 210038_at), PRKCZ (202178_at), PRKD1 (205880_at 217705_at), PRKDC (208694_at 210543_s_at), PRLR (211917_s_at 231981_at 243755_at 216638_s_at 227629_at 210476_s_at 206346_at), PRMT5 (1564520_s_at 1564521_x_at 217786_at), PROS1 (207808_s_at), PSMA4 (203396_at), PSMD13 (201233_at 201232_s_at), PSTPIP1 (211178_s_at), PTAFR (206278_at 211661_x_at 227184_at), PTEN (233314_at 233254_x_at 211711_s_at 225363_at 227469_at 217492_s_at 204054_at 204053_x_at), PTGES3 (200627_at), PTK2 (1559529_at 208820_at 207821_s_at 241453_at), PTK2B (203110_at 203111_s_at), PTK6 (1553114_a_at), PTK7 (1555324_at 207011_s_at), PTN (211737_x_at 209466_x_at 209465_x_at), PTPN1 (202716_at 240260_at 239526_x_at 217689_at), PTPN11 (209895_at 209896_s_at 205867_at 212610_at 205868_s_at 241930_x_at 1552637_at), PTPN12 (216915_s_at 202006_at 216884_at 244356_at), PTPN18 (203555_at 213521_at 1569552_at), PTPN2 (213136_at 204935_at 213137_s_at), PTPN21 (205438_at 226380_at 222092_at 40524_at 1320_at), PTPN22 (236539_at 208010_s_at 206060_s_at), PTPN3 (227944_at 203997_at), PTPNS (236456_at 233471_at), PTPN6 (206687_s_at), PTPRA (213799_s_at 213795_s_at), PTPRB (205846_at 217177_s_at 230250_at), PTPRC (212587_s_at 207238_s_at 1552480_s_at 1569830_at 212588_at), PTPRE (221840_at 1559018_at), PTPRF (215066_at 200637_s_at 200636_s_at 200635_s_at), PTPRH (208300_at), PTPRJ (210173_at 214137_at 227396_at), PTPRO (208121_s_at 1554199_at), PTPRS (1555666_at 210823_s_at 229465_s_at 226571_s_at), PTPRU (211320_s_at), PTPRZ1 (204469_at), PXN (211823_s_at 201087_at), RAD51 (205023_at 205024_s_at), RAD52 (205647_at 210630_s_at 211904_x_at), RAD9A (204828_at 1562022_s_at), RADIL (223693_s_at), RAF1 (201244_s_at), RALA (214435_x_at 224880_at), RALB (202101_s_at 202100_at), RALGDS (209050_s_at 209051_s_at), RAN (200750_s_at), RANBP10 (53987_at 221809_at 1558773_s_at), RANBP9 (202582_s_at 216125_s_at 202583_s_at), RAP1A (1555339_at 202362_at 1555340_x_at), RAPGEF1 (225738_at 226389_s_at 204543_at), RAPSN (211570_s_at), RASA1 (210621_s_at 202677_at), RASA3 (225562_at 206221_at 206220_s_at), RASA4 (212706_at 208534_s_at 212707_s_at), RASGEF1C (236748_at), RASGRF1 (214905_at 215688_at 1554992_at 210550_s_at), RB1 (203132_at 211540_s_at), RB1CC1 (202033_s_at 237626_at 202034_x_at), RELA (230202_at 201783_s_at 209878_s_at), RET (215771_x_at 211421_s_at 205879_x_at), RFX1 (206321_at 226786_at), RGS16 (209324_s_at 209325_s_at), RGS2 (202388_at), RGS4 (204337_at 204339_s_at 204338_s_at), ARHGAP32 (242196_at 203431_s_at 210791_s_at 229648_at), RIN1 (205211_s_at), RIN2 (209684_at 233811_at), RIPK1 (209941_at 226551_at), RIT1 (239843_at 243463_s_at 209882_at), RIT2 (206984_s_at), RNF130 (217865_at), RNF41 (201961_s_at 201962_s_at), ROBO1 (213194_at 240558_at), ROCK1 (235854_x_at 214578_s_at 230239_at 213044_at), ROR1 (205805_s_at 211057_at), ROR2 (231000_at 205578_at), ROS1 (207569_at), RPL10 (200724_at 221989_at 200725_x_at), RPL18A (200869_at), RPL8 (200936_at), RPLP2 (200908_s_at 200909_s_at), RPN1 (201011_at), RPS6KA1 (203379_at), RPS6KA2 (240720_at 236658_at 212912_at 204906_at 1557970_s_at), RRAS (212647_at), RTN1 (210222_s_at 203485_at), RTN3 (219549_s_at 224564_s_at), RUFY1 (218243_at 233380_s_at), RUFY2 (1554133_at 238550_at 1569630_a_at 233192_s_at 235345_at), RUNX1 (236114_at 209359_x_at 211182_x_at 211181_x_at 209360_s_at 210805_x_at 211180_x_at 208129_x_at 211620_x_at 210365_at), RUSC1 (206949_s_at), RYBP (201846_s_at 242719_at 201844_s_at 237456_at 201845_s_at), RYK (214172_x_at 202853_s_at 216976_s_at 238210_at), S100A7 (205916_at), S100A9 (203535_at), SAT1 (210592_s_at 213988_s_at 203455_s_at), SCAMP1 (212425_at 1552978_a_at 206668_s_at 212416_at 206667_s_at 212417_at), SCAMP3 (201771_at), SDC2 (212154_at 212158_at 212157_at), SDC3 (1554864_a_at 202898_at), SDCBP (200958_s_at), SEC13 (207707_s_at), SELE (206211_at), SELPLG (209879_at 209880_s_at), SERPINA3 (202376_at), SEZ6 (243430_at 229651_at), SF3B3 (200688_at 200687_s_at), SF3B4 (209044_x_at), SFN (33323_r_at 33322_i_at 209260_at), SRSF5 (210077_s_at 203380_x_at 212266_s_at), SGSM2 (212319_at 36129_at), SH2B1 (209322_s_at 40149_at), SH2B2 (205367_at), SH2B3 (203320_at), SH2D1A (211210_x_at 211209_x_at 211211_x_at 210116_at), SH2D1B (1553177_at 1553176_at), SH2D2A (207351_s_at), SH2D3A (219513_s_at 222169_x_at), SH2D3C (226673_at 1552667_a_at), SH3BGRL (201312_s_at 201311_s_at), SH3BGRL3 (221269_s_at), SH3BP1 (215799_at 213633_at), SH3BP2 (211250_s_at 209370_s_at 209371_s_at), SH3BP5 (201811_x_at 201810_s_at), SH3GL2 (205751_at), SH3KBP1 (1554168_a_at 235692_at 223082_at), SH3PXD2A (224817_at 213252_at 207661_s_at), SHB (204657_s_at 230459_s_at 204656_at 1557458_s_at 243595_at), SHC1 (201469_s_at 214853_s_at), SHC2 (213464_at), SHC3 (243881_at 206330_s_at 229824_at), SHD (227845_s_at), SHE (229910_at), SHF (228922_at), SIRPA (202897_at 202896_s_at 202895_s_at 217024_x_at), SIT1 (205484_at), SIVA1 (210792_x_at 203489_at), SKAP1 (205790_at), SKAP2 (216899_s_at 204362_at 204361_s_at 225639_at), SLA (203761_at 203760_s_at), SLA2 (232234_at 1555688_at), SLAMF1 (1555626_a_at 206181_at), SLAMF6 (1552497_a_at), SLC25A6 (212085_at 212826_s_at), SLC2A1 (235633_at 201250_s_at

201249_at), SLC3A2 (200924_s_at), SLC4A1 (205592_at 1552713_a_at), SLC9A2 (211116_at), SLC9A3R1 (201349_at), SLC9A3R2 (209830_s_at), SMN1 (242495_at 203852_s_at), SMAD2 (239271_at 226563_at 243895_x_at 203076_s_at 203075_at 235598_at 203077_s_at), SMAD4 (1565702_at 202527_s_at 235725_at 202526_at 235622_at), SMARCB1 (212167_s_at), SMARCE1 (229511_at 211989_at 211988_at), SMC1A (1555677_s_at 239688_at 217555_at 201589_at), SMG7 (242575_at 217189_s_at 201793_x_at 201794_s_at), SMURF2 (232020_at 230820_at 227489_at 205596_s_at), SNAP29 (239084_at 222597_at 218327_s_at), SNAPIN (223066_at), SNCA (211546_x_at 207827_x_at 236081_at 204467_s_at 204466_s_at), SNRPD2 (200826_at), SNTB2 (227312_at 226685_at 213814_s_at 205314_x_at 238925_at 205315_s_at), SNURF (206042_x_at 201522_x_at), SNX1 (213364_s_at 201716_at 214531_s_at 216357_at), SNX2 (202113_s_at 202114_at), ARHGAP33 (233885_at 215256_x_at 213827_at), SNX4 (205329_s_at 212652_s_at), SNX6 (217789_at 222410_s_at), SNX9 (223028_s_at 223027_at), SOCSC1 (210001_s_at 209999_x_at 210000_s_at 213337_s_at), SOCS2 (203373_at 203372_s_at), SOCS3 (214105_at 206360_s_at 206359_at 227697_at), SOCS5 (208127_s_at 209648_x_at 209647_s_at), SOCS6 (227542_at 206020_at 214462_at), SORBS1 (237026_at 211705_s_at 211819_s_at 222513_s_at 218087_s_at), SORBS2 (1558815_at 237285_at 241104_at 225728_at 240120_at 204288_s_at 220858_at), SOS1 (1557354_at 212777_at 242018_at 242682_at 229261_at 227426_at 212780_at), SOS2 (217575_s_at 217644_s_at 217576_x_at 212870_at 211665_s_at), SPHK1 (219257_s_at), SPHK2 (209857_s_at 40273_at), SPN (216980_s_at 216981_x_at 206057_x_at 206056_x_at 1568964_x_at), SPRED1 (244439_at 235074_at 226837_at), SPRED2 (212466_at 212458_at 214026_s_at), SPSB1 (226075_at 219677_at), SPTAN1 (214926_at 215235_at 214925_s_at 208611_s_at), SQSTM1 (217252_at 244804_at 201471_s_at 217255_at 213112_s_at), SRC (1565082_x_at 237103_at 213324_at 1565080_at 221284_s_at 1558211_s_at), SRF (202401_s_at 202400_s_at), SRM (201516_at), ST5 (202440_s_at), STAM (203544_s_at), STAM2 (228254_at 215044_s_at 208194_s_at 242569_at 209649_at), STAP1 (220059_at 1554343_a_at), STAP2 (221610_s_at), STAT1 (AFFX-HUMISGF3A/M97935_5_at AFFX-HUMISGF3A/ M97935_3_at 200887_s_at AFFX-HUMISGF3A/ M97935_MB at AFFX-HUMISGF3A/M97935_MA at 209969_s_at), STAT2 (225636_at 205170_at 217199_s_at), STAT3 (208991_at 225289_at 208992_s_at 243213_at), STAT5A (203010_at), STAT5B (1555086_at 212550_at 205026_at 1555088_x_at 212549_at), STATE (201332_s_at 201331_s_at), STK39 (202786_at), STUB1 (217934_x_at 233049_x_at 227625_s_at), SUPT4H1 (201484_at 201483_s_at), SUPT6H (208830_s_at 208420_x_at 1554311_a_at 208831_x_at), SYK (226068_at 209269_s_at 207540_s_at 244023_at), SYN1 (221914_at 1553264_a_at), SYNCRIP (217834_s_at 209025_s_at 209024_s_at 217833_at 217832_at 1555427_s_at), SYNE1 (244070_at 215350_at 209447_at 244144_at), SYNGAP1 (230297_x_at 234285_at), SYNJ1 (212990_at 232993_at 207594_s_at), TAF1 (227205_at 216955_at 216711_s_at), TEC (206301_at), TEK (217711_at 206702_at), TENC1 (212494_at), TERT (207199_at 1555271_a_at), TGFA (211258_s_at 205016_at 205015_s_at), TGFB1I1 (209651_at), TGFBR1 (224793_at 206943_at), TH1L (225006_x_at 225865_at 225261_s_at 220607_s_at), THOC5 (209418_s_at 209419_at), THY1 (213869_x_at 208850_s_at 208851_s_at), TIAF1 (202039_at), TIAM1 (213135_at 206409_at), TIE1 (1560657_at 204468_s_at), TIMP3 (201149_s_at 201150_s_at 201147_s_at 201148_s_at), TIRAP (1554091_a_at 239796_x_at 236687_at 1552360_a_at 1552804_a_at), TJP1 (214168_s_at 202011_at), TLN1 (203254_s_at), TLR2 (204924_at), TLR3 (206271_at 239587_at), TLR4 (221060_s_at 1552798_a_at 224341_x_at 232068_s_at), TLR6 (239021_at 207446_at), TLR8 (220832_at 229560_at), TLR9 (223903_at), TM4SF1 (209387_s_at 238168_at 209386_at 215033_at 215034_s_at), TMF1 (215855_s_at 227685_at 214948_s_at 235566_at 213024_at), TNC (201645_at), TNFAIP1 (201208_s_at 201207_at), TNFRSF10A (1552648_a_at), TNFRSF11A (207037_at 238846_at), TNFRSF1A (207643_s_at), TNFRSF1B (203508_at), TNFRSF8 (206729_at), TNFSF11 (211153_s_at 241248_at 210643_at), TNIP2 (48531_at 218335_x_at 232160_s_at), TNK1 (217149_x_at 205793_x_at), TNK2 (203839_s_at 216439_at 1555557_a_at 228279_s_at 203838_s_at), TNS1 (221748_s_at 218863_s_at 221246_x_at 221747_at 218864_at), TNS4 (230398_at 222265_at), TOB1 (228834_at 202704_at), TOM1L1 (240261_at 204485_s_at), TP53 (211300_s_at 201746_at), TP53BP2 (203120_at), TP53RK (225402_at 235192_at), TP73 (1554379_a_at 232546_at 220804_s_at), TRAF1 (235116_at 205599_at), TRAF2 (204413_at), TRAF3 (208315_x_at 221571_at), TRAF6 (205558_at), TRAT1 (217147_s_at), TRIO (240399_at 209010_s_at 209011_at 209012_at 244527_at 209013_x_at 240773_at 208178_x_at), TRIP6 (209129_at), TRPC6 (217287_s_at 241558_at 206528_at), TRPV4 (219516_at), TSG101 (230176_at 201758_at), TSHR (215443_at 215442_s_at 210055_at), TTR (209660_at), TUB (208431_s_at 228882_at 210737_at), TUBA1A (211072_x_at 211058_x_at 201090_x_at 209118_s_at 211750_x_at 212639_x_at 209251_x_at 213646_x_at), TUBA1B (211072_x_at 211058_x_at 201090_x_at 211750_x_at 212639_x_at 209251_x_at 213646_x_at), TUBA3C (210527_x_at 216323_x_at), TUBA4A (212242_at), TUBB (212320_at 211714_x_at 209026_x_at), TUBB2A (213476_x_at 204141_at 209372_x_at), TXK (206828_at), TYK2 (205546_s_at), TYRO3 (211432_s_at 211431_s_at 1566934_at), TYROBP (204122_at), UBASH3B (244068_at 240387_at 238587_at 238462_at 228353_x_at 228359_at), UBB (200633_at 242300_at), UBE2L3 (200684_s_at 200683_s_at 200682_s_at 200676_s_at), UBE3A (211575_s_at 213128_s_at 211285_s_at 213291_s_at 212278_x_at), UCP2 (208998_at 208997_s_at), UNC119 (203271_s_at), UQCRB (209066_x_at 209065_at 205849_s_at 244293_at), VAV1 (206219_s_at), VAV2 (205537_s_at 226063_at 205536_at), VAV3 (218806_s_at 224221_s_at 218807_at), VCL (200930_s_at 200931_s_at), VCP (208649_s_at 228442_at 208648_at), VDR (204255_s_at 204254_s_at 204253_s_at 213692_s_at), VEGFA (212171_x_at 211527_s_at 210512_s_at 210513_s_at), VEGFB (203683_s_at), VEGFC (209946_at), VIL1 (1554943_at 1554945_x_at 205506_at), VTI1B (209452_s_at 225926_at), WAS (205400_at 38964_r_at), WASF1 (204165_at), WASF2 (224563_at 224562_at 221725_at), WASL (224813_at 205810_s_at 230340_s_at 205809_s_at), WBP11 (217822_at 217821_s_at), SNRNP40 (215905_s_at), WIPF1 (202664_at 231182_at 202665_s_at 202663_at), WISP2 (205792_at), WNT1 (208570_s_at), WNT3A (not found), WNT5A (213425_at 205990_s_at 231227_s_at), WT1 (216953_s_at 206067_s_at), WWOX (237035_at 223868_s_at 219077_s_at 221147_x_at 210695_s_at 242099_at 223747_x_at), XPO1 (208775_at), XPO6 (211982_x_at 214784_x_at), XRCC5 (208643_s_at 208642_s_at), XRCC6 (200792_at), YAP1 (224895_at 224894_at 213342_at), YES1 (202932_at 202933_s_at).

Example 5—Proximity Ligation Assay for Egfr and Grb2 Interaction In Cell Lines Using Intracellular Egfr EpitopE Updated Methods
Reagent Information:
Antibodies:
  mGRb2 (Mouse monoclonal, clone 81 (Cat#610112, BD Biosciences)
  rEGFR (Rabbit monoclonal, clone D38B1 (Cat#4267, Cell Signaling)
  Working dilutions: m-EGFR (1:50)+r-GRb2 (1:50)
Solutions:
  $_{MQ}H_2O$
  PBS
Kit Components:
  Secondary antibody-PLA probes (plus and minus)
  Ligation reagents
  Amplification ligation reagents
  1× Wash Buffer B
  0.01×Wash Buffer B
  Mounting media (w/DAPI)
Experimental Procedure:
  1. Plate cells in chamber wells 24 h before processing. For most cell lines, $50 \times 10^4$ per well (0.8 cm²) is sufficient. This number should be adjusted for longer culture times and different-sized chamber wells.
  2. Wash each well with PBS (2×2 m).
  3. Fix cells by adding 400 µl 10% Buffered formalin per well. Incubate 20 m RT with gentle rocking.
  4. Wash each well with PBS (3×2 m).
  5. Permabilize cells by adding 0.5% TRITON X: 100 (diluted in PBS). Incubate 10 m RT, no rocking.
  6. Wash each well with PBS (3×2 m).
  7. Remove chamber from slide. Note that excess silicone adhesive should be removed with a scalpel to ensure that it does not interfere with coverslipping later.
  8. Add 1.5% BSA (diluted in PBS) using a volume sufficient to fully cover each well. For 8-well slides (0.8 cm²), a volume of 50 µl is sufficient. A grease pen can be used to ensure a hydrophopic barrier exists between wells, but is usually not necessary. Incubate 30 m RT in humidity chamber.
  9. Primary antibodies: Add 50 µl per well appropriate primary antibody solution [r-EGFR and m-GRb2] diluted in PBS. Incubate ON in humidity chamber 4° C. with gentle rocking.
  a. Record start time
  b. Incubation time should be 16-18 hours
  10. Next day: Tap off primary antibody solution. Wash 2 times with sequential immersion in PBS in Coplin jars. Wash 2×5 m RT with gentle rocking.
  11. PLA probes (secondary antibody-DNA conjugates): Mix and dilute the two PLA probes 1:5 (diluted in PBS) (use 8 µl minus probe and 8 µl probe plus and 24 µl PBS=40 µl/cm²). Ensure complete coverage of tissue area. Incubate slides 1 h 37° C. in pre-heated humidity chamber.
  12. Tap off PLA probes and wash. Wash 2×5 m with PBS, RT with gentle rocking. Thaw 5× ligation mix at beginning of washes.
  13. PLA probe ligation: Dilute ligation stock 1:5 in $_{MQ}H_2O$ while waiting, saving room for ligase (e.g., 8 µl 5× ligation mix and 31 µl $_{MQ}H_2O$=39 µl). Add Ligase into ligation solution 1:40 during final wash above. Cover tissue area completely using 40 µl/cm². Incubate for 30 m 37° C. in pre-warmed humidity chamber.
  14. Tap off ligation solution and wash. Wash 2×2 m RT with gentle rocking (PBS). Thaw 5× amplification mix at beginning of washes (avoiding light).
  15. PLA probe amplification-hybridization-fluorescence: Dilute Amplification stock 1:5 in MQH2O while waiting (8 µl and 31.5 µl $_{MQ}H_2O$=39 µl). Add Polymerase 1:80 into amplification solution then add polymerase-amplification solution. Cover tissue area completely using 40 µl/cm². Incubate 2 h 37° C. pre-warmed humidity chamber (avoid light).
  16. Tap off amplification solution and wash 2×10 m RT with 1× Wash Buffer B. Rinse slide in 0.01× Wash Buffer B.
  17. Allow slides to dry for ~10 m in dark. Mount with Invitrogen Prolong Gold with DAPI. Add mounting media to cover slip and gently press down onto tissue area. Allow to dry overnight and image by confocal microscopy next day. Note that Prolong Gold is an aqueous-based mounting media and will not cure. Care should be taken to avoid moving coverslip, once mounted. Store slides at 4° after initial overnight dry.
  18. Confocal Microscopy: Use the Leica TCS SP5 laser scanning confocal microscope. Place slide on scope and find best in-focus plane. Take care to avoid imaging along edges of tissue, whenever possible. Note that Cy5 foci cannot be seen through the confocal eyepiece due to the far red wavelength. Use 40× oil objective and begin with voltage settings of ~450 for the 405 laser line (DAPI) and ~580 for the 633 laser line (Cy5). Use 1024×1024 image size and acquire at 200 Hz.
  19. Use the "live" scan to observe foci. Use the z-plane wheel to scroll above and below the focus plane until foci disappear and only DAPI remains, set upper and lower limits. Generally, 12 z-slices at 0.76 µm provides sufficient coverage of all foci.
  20. Do not adjust 633 laser line between samples. DAPI can be adjusted and will vary among cell types. Keep DAPI relatively dim as the merged images may be overexposed if DAPI is too intense.
  21. After collecting samples (2-3 fields of view for each sample), process each series as a maximum projection. These images can then be exported as TIFF files.

Example 6—Duolink Assay for Egfr and Grb2 Interaction from FFPE Tissues With Cytokeratin Counterstaining Reagent Information
Antibodies:
  GRB2 (Mouse monoclonal, clone 81 (Cat#610112, BD Biosciences)
  EGFR (Rabbit monoclonal, clone D38B1 (Cat#4267, Cell Signaling)
  Cytokeratin, pan (Guinea Pig polyclonal (Cat#9 9097-48B 097-48B, US Biological)
  AlexFluor555, goat anti-guinea pig (Invitrogen, Cat#A-21435)
  Working dilutions: m-EGFR (1:100)+r-gRb2 (1:100)+gp-CK (1:100)
Solutions:
  AR Buffer (PT4) (10 mM Tris Base, 1 mM EDTA, 0.05% TWEEN 20, pH9)

PBS
$_{MQ}H_2O$
0.05% PBST (1 L PBS+500 µL TWEEN 20)
Kit Components:
Secondary antibody-PLA probes (plus and minus)
Ligation reagents
Amplification ligation reagents
1× Wash Buffer B
0.01× Wash Buffer B
Mounting media (w/DAPI)
Experimental Procedure:
1. Antigen Retrieval: Deparrafinize/Rehydrate slides. Perform successive washes in Xylenes and Ethanol Gradient as Follows:
  a. 10 m Xylene
  b. 10 m Xylene (use fresh xylene for this wash, can rotate forward)
  c. 10 m 50:50 Xylene:Ethanol
  d. 5 m 100% ethanol* Begin setup of pressure cooker here
  e. 5 m 100% ethanol
  f. 5 m 95% ethanol
  g. 5 m 70% ethanol
  h. 5 m 50% ethanol
  i. H2O; can hold here if pressure cooker not ready
2. Antigen retrieval (HIER method, using pressure cooker). Bring 3 L of 1× PT4 (TE, pH9) [Use a metal slide holder placed within an eppendorf tube jar] to a low boil in pressure cooker. Place slide rack in eppendorf tube jar, seal and boil for 20 m. Remove from heat and let cool for 20 min.
3. Wash slide with PBS briefly and use grease pen to trace along edges of TMA or tissue. Work as quickly as possible aspirating area around spots in order to delineate area without spots drying.
  a. Record approximate area in cm$^2$
4. Rinse briefly in PB ST (0.05%) and add 1.5% BSA using a volume sufficient to fully cover delineated area. Ensure that hydrophopic barrier created by grease pen is maintained. Incubate 30 m RT in humidity chamber.
5. Primary antibodies: Add 200-300 µl/slide appropriate primary antibodies [r-EGFR and m-GRb2] in 0.15% BSA (diluted in 0.05% PBST) Incubate ON in humidity chamber 4° C. with gentle rocking.
  a. Record start time
  b. Incubation time should be 16-18 h
6. Next day: Tap off primary antibody solution. Wash 2 times with sequential immersion in 0.05% PBST in Coplin jars. Wash 2×5 m RT with gentle rocking (0.05% PBST).
7. PLA probes (secondary antibody-DNA conjugates): Mix and dilute the two PLA probes 1:5 in 0.15% BSA (diluted in 0.05% PBST) (use 8 µl minus probe and 8 µl probe plus and 24 µl PBS=40 µl/cm$^2$). Ensure complete coverage of tissue area. Incubate slides 1 h 37° C. in pre-heated humidity chamber.
8. Tap off PLA probes and wash. Wash 2×5 m RT with gentle rocking (0.05% PBST). Thaw 5× ligation mix at beginning of washes.
9. PLA probe ligation: Dilute ligation stock 1:5 in $_{MQ}H_2O$ while waiting, saving room for ligase (e.g., 8 µl 5× ligation mix and 31 µl $_{MQ}H_2O$=39 µl). Add Ligase into ligation solution 1:40 during final wash above. Cover tissue area completely using 40 µl/cm$^2$. Incubate for 30 m 37° C. in pre-warmed humidity chamber.
10. Tap off ligation solution and wash. Wash 2×2 m RT with gentle rocking (0.05% PBST). Thaw 5× amplification mix at beginning of washes (avoiding light).
11. PLA probe amplification-hybridization-fluorescence: Dilute Amplification stock 1:5 in $_{MQ}H_2O$ while waiting (8 µl and 31.5 µl $_{MQ}H_2O$=39 µl). Add Polymerase 1:80 into amplification solution then add polymerase-amplification solution. Cover tissue area completely using 40 µl/cm$^2$. Incubate 2 h 37° C. pre-warmed humidity chamber (avoid light).
12. Tap off amplification solution and rinse slides with PBS. Incubate with antipan cytokeratin (diluted 1:100) in PBS. Incubate 1 h 37° C.
13. Tap of antibody solution, wash twice with PBS (2×5 m RT with gentle rocking).
14. Add Alexa-Fluor555, diluted 1:500 in PBS. Incubate 30 m at 37° C.
15. Tap off antibody solution and wash 2×10 m RT with 1× Wash Buffer B. Rinse slide in 0.01× Wash Buffer B.
16. Allow slides to dry for ~10 m in dark. Mount with Invitrogen Prolong Gold with DAPI. Add mounting media to cover slip and gently press down onto tissue area. Allow to dry overnight and image by confocal microscopy next day. Note that Prolong Gold is an aqueous-based mounting media and will not cure. Care should be taken to avoid moving coverslip, once mounted. Store slides at 4° after initial overnight dry.
17. Confocal Microscopy: Use the Leica TCS SP5 laser scanning confocal microscope. Place slide on scope and find best in-focus plane. Take care to avoid imaging along edges of tissue, whenever possible. Note that Cy5 foci cannot be seen through the confocal eyepiece due to the far red wavelength. Use 40× oil objective and begin with voltage settings of ~450 for the 405 laser line (DAPI), ~600 for the 543 laser line (Cy3) and ~580 for the 633 laser line (Cy5). Use 1024×1024 image size and acquire at 200 Hz.
18. Use the "live" scan to observe foci. Use the z-plane wheel to scroll above and below the focus plane until foci disappear and only DAPI remains, set upper and lower limits. Generally, 12 z-slices at 76 µm provides sufficient coverage of all foci.
19. Do not adjust 633 laser line between samples. DAPI and Cy3 can be adjusted and will vary among cell types. Keep DAPI relatively dim as the merged images may be overexposed if DAPI is too intense.
20. After collecting samples (2-3 fields of view for each sample), process each series as a maximum projection. These images can then be exported as TIFF files.

Example 7—Proximity Ligation Assay for Phosphorylated RTKS in Cell Lines

Antibodies (Varies):
  pEGFRY1068 (Rabbit monoclonal, clone D38B1 Cat#4267, Cell Signaling)
  ALK (rabbit monoclonal, clone D5F3 Cat #3633, Cell Signaling)
  P-Tyr-100 (mouse monoclonal, Cat#9411, Cell Signaling)
  Working dilutions: pEGFRY1068 (1:50), ALK (1:50), P-Tyr-100 (1:1000)
Solutions:
  $_{MQ}H_2O$
  PBS
  Kit Components:
  Secondary antibody-PLA probes (plus and minus)
  Ligation reagents
  Amplification ligation reagents
  1× Wash Buffer B
  0.01× Wash Buffer B
  Mounting media (w/DAPI)

Experimental Procedure:
1. Plate cells in chamber wells 24 h before processing. For most cell lines, 50×10$^4$ per well (0.8 cm$^2$) is sufficient. This number should be adjusted for longer culture times and different-sized chamber wells.
2. Wash each well with PBS (2×2 m).
3. Fix cells by adding 400 µl 10% Buffered formalin per well. Incubate 20 m RT with gentle rocking.
4. Wash each well with PBS (3×2 m).
5. Permabilize cells by adding 0.5% TRITON-X 100 (diluted in PBS). Incubate 10 m RT, no rocking.
6. Wash each well with PBS (3×2 m).
7. Remove chamber from slide. Note that excess silicone adhesive should be removed with a scalpel to ensure that it does not interfere with coverslipping later.
8. Add 1.5% BSA (diluted in PBS) using a volume sufficient to fully cover each well. For 8-well slides (0.8 cm$^2$), a volume of 50 µl is sufficient. A grease pen can be used to ensure a hydrophobic barrier exists between wells, but is usually not necessary. Incubate 30 m RT in humidity chamber.
9. Primary antibodies: Add 50 µl per well appropriate primary antibody solution diluted in PBS. Here, can use either a single antibody or double (depends on epitope availability and goals of experiment). Incubate ON in humidity chamber 4° C. with gentle rocking.
  a. Record start time
  b. Incubation time should be 16-18 h
10. Next day: Tap off primary antibody solution. Wash 2 times with sequential immersion in PBS in Coplin jars. Wash 2×5 m RT with gentle rocking.
11. PLA probes (secondary antibody-DNA conjugates): Note: if performing single recognition experiment ensure that a plus and minus probe from the same species as primary antibody are used. Mix and dilute the two PLA probes 1:5 (diluted in PBS) (use 8µl minus probe and 8 µl probe plus and 24 µl PBS=40 µl/cm$^2$). Ensure complete coverage of tissue area. Incubate slides 1 h 37° C. in pre-heated humidity chamber.
12. Tap off PLA probes and wash. Wash 2×5 m with PBS, RT with gentle rocking. Thaw 5× ligation mix at beginning of washes.
13. PLA probe ligation: Dilute ligation stock 1:5 in $_{MQ}$H$_2$O while waiting, saving room for ligase (e.g., 8 µl 5× ligation mix and 31 µl $_{MQ}$H$_2$O=39 µl). Add Ligase into ligation solution 1:40 during final wash above. Cover tissue area completely using 40 µl/cm$^2$. Incubate for 30 m 37° C. in pre-warmed humidity chamber.
14. Tap off ligation solution and wash. Wash 2×2 m RT with gentle rocking (PBS). Thaw 5× amplification mix at beginning of washes (avoiding light).
15. PLA probe amplification-hybridization-fluorescence: Dilute Amplification stock 1:5 in $_{MQ}$H$_2$O while waiting (8 µl and 31.5 µl $_{MQ}$H$_2$O=39 µl). Add Polymerase 1:80 into amplification solution then add polymerase-amplification solution. Cover tissue area completely using 40 µl/cm$^2$. Incubate 2 h 37° C. pre-warmed humidity chamber (avoid light).
16. Tap off amplification solution and wash 2×10 m RT with 1× Wash Buffer B. Rinse slide in 0.01× Wash Buffer B.
17. Allow slides to dry for 10 m in dark. Mount with Invitrogen Prolong Gold with DAPI. Add mounting media to cover slip and gently press down onto tissue area. Allow to dry overnight and image by confocal microscopy next day. Note that Prolong Gold is an aqueous-based mounting media and will not cure. Care should be taken to avoid moving coverslip, once mounted. Store slides at 4° after initial overnight dry.
18. Confocal Microscopy: Use the Leica TCS SP5 laser scanning confocal microscope. Place slide on scope and find best in-focus plane. Take care to avoid imaging along edges of tissue, whenever possible. Note that Cy5 foci cannot be seen through the confocal eyepiece due to the far red wavelength. Use 40× oil objective and begin with voltage settings of ~450 for the 405 laser line (DAPI) and ~580 for the 633 laser line (Cy5). Use 1024×1024 image size and acquire at 200 Hz.
19. Use the "live" scan to observe foci. Use the z-plane wheel to scroll above and below the focus plane until foci disappear and only DAPI remains, set upper and lower limits. Generally, 12 z-slices at 0.76 µm provides sufficient coverage of all foci.
20. Do not adjust 633 laser line between samples. DAPI can be adjusted and will vary among cell types. Keep DAPI relatively dim as the merged images may be overexposed if DAPI is too intense.
21. After collecting samples (2-3 fields of view for each sample), process each series as a maximum projection. These images can then be exported as TIFF files.

Example 8—Dulink Assay for Egfr and Grb2 Interaction from FFPE Tissues With Brightfield Detection Reagent Information:
Antibodies:
  GRB2 (Mouse monoclonal, clone 81 (Cat#610112, BD Biosciences)
  EGFR (Rabbit monoclonal, clone D38B1 (Cat#4267, Cell Signaling)
  Working dilutions: m-EGFR (1:100)+r-GRb2 (1:100)
Solutions:
  AR Buffer (PT4) (10 mM Tris Base, 1 mM EDTA, 0.05% TWEEN 20, pH9)
  PBS
  $_{MQ}$H$_2$O
  0.05% PBST (1 L PBS+500 µL Tween20)
Kit Components:
  Secondary antibody-PLA probes (plus and minus)
  Ligation reagents
  Amplification reagents
  Detection reagents
  Counterstain reagents
  1× Wash Buffer B
  0.01× Wash Buffer B
  Mounting media (w/DAPI)
Experimental Procedure:
21. Antigen Retrieval: Deparraffinize/Rehydrate slides. Perform successive washes in Xylenes and Ethanol Gradient as Follows:
  a. 10 m Xylene
  b. 10 m Xylene (use fresh xylene for this wash, can rotate forward)
  c. 10 m 50:50 Xylene:Ethanol
  d. 5 m 100% ethanol* Begin setup of pressure cooker here
  e. 5 m 100% ethanol
  f. 5 m 95% ethanol
  g. 5 m 70% ethanol
  h. 5 m 50% ethanol
  i. H2O; can hold here if pressure cooker not ready
22. Antigen retrieval (HIER method, using pressure cooker). Bring 3 L of 1× PT4 (TE, pH9) [Use a metal slide holder placed within an eppendorf tube jar] to a low boil in pressure cooker. Place slide rack in eppendorf tube jar, seal and boil for 20 m. Remove from heat and let cool for 20 min.

23. Wash slide with PBS briefly and use grease pen to trace along edges of TMA or tissue. Work as quickly as possible aspirating area around spots in order to delineate area without spots drying.
   a. Record approximate area in $cm^2$ 24. Rinse briefly in PB ST (0/05%) and 25. Add 1.5% BSA using a volume sufficient to fully cover delineated area. Ensure that hydrophopic barrier created by grease pen is maintained. Incubate 30 m RT in humidity chamber.

26. Primary antibodies: Add 200-300 µl/slide appropriate primary antibodies [r-EGFR and m-GRb2] in 0.15% BSA (diluted in 0.05% PBST) Incubate ON in humidity chamber 4° C. with gentle rocking.
   a. Record start time
   b. Incubation time should be 16-18 h 27. Next day: Tap off primary antibody solution. Wash 2 times with sequential immersion in 0.05% PBST in Coplin jars. Wash 2×5 m RT with gentle rocking (0.05% PB ST).

28. PLA probes (secondary antibody-DNA conjugates): Mix and dilute the two PLA probes 1:5 in 0.15% BSA (diluted in 0.05% PBST) (use 8 µl minus probe and 8 µl probe plus and 24 µl PBS=40 µl/$cm^2$). Ensure complete coverage of tissue area. Incubate slides 1 h 37° C. in pre-heated humidity chamber.

29. Tap off PLA probes and wash. Wash 2×5 m RT with gentle rocking (0.05% PBST). Thaw 5× ligation mix at beginning of washes.

30. PLA probe ligation: Dilute ligation stock 1:5 in $_{MQ}H_2O$ while waiting, saving room for ligase (e.g., 8 µl 5× ligation mix and 31 µl $_{MQ}H_2O$=39 µl). Add Ligase into ligation solution 1:40 during final wash above. Cover tissue area completely using 40 µl/$cm^2$. Incubate for 30 m 37° C. in pre-warmed humidity chamber.

31. Tap off ligation solution and wash. Wash 2×2 m RT with gentle rocking (0.05% PBST). Thaw 5× amplification mix at beginning of washes.

32. PLA probe amplification: Dilute Amplification stock 1:5 in $_{MQ}H_2O$ while waiting (8 µl and 31.5 µl $_{MQ}H_2O$=39 µl). Add Polymerase 1:80 into amplification solution then add polymerase-amplification solution. Cover tissue area completely using 40 µl/$cm^2$. Incubate 2 h 37° C. pre-warmed humidity chamber.

33. Tap off amplification solution and wash. Wash 2×2 m RT with gentle rocking (0.05% PBST). Thaw 5× detection mix at beginning of washes (avoiding light).

34. Dilute 5× detection reagent in $H_2O$ and add to slides. Incubate 1 h 37° C.

35. Rinse 2×5 m in PBST, then add detection reagents (A, B, C, D) and incubate 10 m.

36. Rinse 2×2 m in $H_2O$ and add hematoxylin nuclei stain dropwise. Incubate 2 m RT. Rinse for 10 m under running tap water.

37. Dehydrate slides by incubating in increasing concentrations of ethanol and then incubate in two changes of xylene (reversal of step 1 in the protocol). Allow slides to dry in fume hood.

38. Mount slides in toluene-based mounting media and allow to cure overnight.

39. Brightfield Microscopy: Observe slides under light microscopy at 200×, 400×, 630× or 1000×. Alternatively, slides may be scanned on a slide scanner.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Sordella R, Bell D W, Haber D A, Settleman J. Gefitinib-sensitizing EGFR mutations in lung cancer activate anti-apoptotic pathways. Science 2004; 305: 1163-7.
2. Faber A C, Li D, Song Y, et al. Differential induction of apoptosis in HER2 and EGFR addicted cancers following PI3K inhibition. Proc Natl Acad Sci USA 2009; 106: 19503-8.
3. Glatter T, Wepf A, Aebersold R, Gstaiger M. An integrated workflow for charting the human interaction proteome: insights into the PP2A system. Mol Syst Biol 2009; 5: 237.
4. Gstaiger M, Aebersold R. Applying mass spectrometry-based proteomics to genetics, genomics and network biology. Nat Rev Genet 2009; 10: 617-27.
5. Gavin A C, Aloy P, Grandi P, et al. Proteome survey reveals modularity of the yeast cell machinery. Nature 2006; 440: 631-6.
6. Gavin A C, Bosche M, Krause R, et al. Functional organization of the yeast proteome by systematic analysis of protein complexes. Nature 2002; 415: 141-7.
7. Burckstummer T, Bennett K L, Preradovic A, et al. An efficient tandem affinity purification procedure for inter-action proteomics in mammalian cells. Nature methods 2006; 3: 1013-9.
8. Henney A, Superti-Furga G. A network solution. Nature 2008; 455: 730-1.
9. Li J, Rix U, Fang B, et al. A chemical and phosphoproteomic characterization of dasatinib action in lung cancer. Nat Chem Biol; 6: 291-9.
10. Yildirim M A, Goh K I, Cusick M E, Barabasi A L, Vidal M. Drug-target network. Nat Biotechnol 2007; 25: 1119-26.
11. Barabasi A L. Network medicine—from obesity to the "diseasome". N Engl J Med 2007; 357: 404-7.
12. Goh K I, Cusick M E, Valle D, Childs B, Vidal M, Barabasi A L. The human disease network. Proc Natl Acad Sci USA 2007; 104: 8685-90.
13. Lim J, Hao T, Shaw C, et al. A protein-protein interaction network for human inherited ataxias and disorders of Purkinje cell degeneration. Cell 2006; 125: 801-14.
14. Barabasi A L, Oltvai Z N. Network biology: understanding the cell's functional organization. Nat Rev Genet 2004; 5: 101-13.
15. Taylor I W, Linding R, Warde-Farley D, et al. Dynamic modularity in protein interaction networks predicts breast cancer outcome. Nat Biotechnol 2009; 27: 199-204.
16. Pawson T, Linding R. Network medicine. FEBS Lett 2008; 582: 1266-70.
17. Lynch T J, Bell D W, Sordella R, et al. Activating mutations in the epidermal growth factor receptor underlying responsiveness of non-small-cell lung cancer to gefitinib. N Engl J Med 2004; 350: 2129-39.

18. Paez J G, Janne P A, Lee J C, et al. EGFR mutations in lung cancer: correlation with clinical response to gefitinib therapy. Science 2004; 304: 1497-500.
19. Pao W, Miller V, Zakowski M, et al. EGF receptor gene mutations are common in lung cancers from "never smokers" and are associated with sensitivity of tumors to gefitinib and erlotinib. Proc Natl Acad Sci USA 2004; 101: 13306-11.
20. Fernbach N V, Planyaysky M, Muller A, et al. Acid elution and one-dimensional shotgun analysis on an Orbitrap mass spectrometer: an application to drug affinity chromatography. J Proteome Res 2009; 8: 4753-65.
21. Haura E B, Muller A, Brietwieser F P, et al. Using iTRAQ® Combined with Tandem Affinity Purification to Enhance Low-abundance Proteins Associated with Somatically-mutated EGFR Core Complexes in Lung Cancer. J Proteome Res.
22. Massinen S, Tammimies K, Tapia-Paez I, et al. Functional interaction of DYX1C1 with estrogen receptors suggests involvement of hormonal pathways in dyslexia. Hum Mol Genet 2009; 18: 2802-12.
23. Soderberg O, Leuchowius K J, Gullberg M, et al. Characterizing proteins and their interactions in cells and tissues using the in situ proximity ligation assay. Methods 2008; 45: 227-32.
24. Melin J, Jarvius J, Larsson C, Soderberg O, Landegren U, Nilsson M. Ligation-based molecular tools for lab-on-a-chip devices. N Biotechnol 2008; 25: 42-8.
25. Soderberg O, Leuchowius K J, Kamali-Moghaddam M, et al. Proximity ligation: a specific and versatile tool for the proteomic era. Genet Eng (N Y) 2007; 28: 85-93.
26. Jarvius M, Paulsson J, Weibrecht I, et al. In situ detection of phosphorylated platelet-derived growth factor receptor beta using a generalized proximity ligation method. Mol Cell Proteomics 2007; 6: 1500-9.
27. Soderberg O, Gullberg M, Jarvius M, et al. Direct observation of individual endogenous protein complexes in situ by proximity ligation. Nature methods 2006; 3: 995-1000.
28. Jemal A, Siegel R, Ward E, et al. Cancer statistics, 2008. CA Cancer J Clin 2008; 58: 71-96.
29. Yoshida T, Zhang G, Haura E B. Targeting epidermal growth factor receptor: central signaling kinase in lung cancer. Biochem Pharmacol; 80: 613-23.
30. Gong Y, Yao E, Shen R, et al. High expression levels of total IGF-1R and sensitivity of NSCLC cells in vitro to an anti-IGF-1R antibody (R1507). PLoS One 2009; 4: e7273.
31. Engelman J A, Janne P A, Mermel C, et al. ErbB-3 mediates phosphoinositide 3-kinase activity in gefitinib-sensitive non-small cell lung cancer cell lines. Proc Natl Acad Sci USA 2005; 102: 3788-93.
32. Engelman J A, Zejnullahu K, Mitsudomi T, et al. MET amplification leads to gefitinib resistance in lung cancer by activating ERBB3 signaling. Science 2007; 316: 1039-43.
33. Gale N W, Kaplan S, Lowenstein E J, Schlessinger J, Bar-Sagi D. Grb2 mediates the EGF-dependent activation of guanine nucleotide exchange on Ras. Nature 1993; 363: 88-92.
34. Rozakis-Adcock M, McGlade J, Mbamalu G, et al. Association of the Shc and Grb2/Sem5 SH2-containing proteins is implicated in activation of the Ras pathway by tyrosine kinases. Nature 1992; 360: 689-92.
35. Kowanetz K, Crosetto N, Haglund K, Schmidt M H, Heldin C H, Dikic I. Suppressors of T-cell receptor signaling Sts-1 and Sts-2 bind to Cbl and inhibit endocytosis of receptor tyrosine kinases. J Biol Chem 2004; 279: 32786-95.
36. Raguz J, Wagner S, Dikic I, Hoeller D. Suppressor of T-cell receptor signalling 1 and 2 differentially regulate endocytosis and signalling of receptor tyrosine kinases. FEBS Lett 2007; 581: 4767-72.
37. Descot A, Hoffmann R, Shaposhnikov D, Reschke M, Ullrich A, Posern G. Negative regulation of the EGFR-MAPK cascade by actin-MAL-mediated Mig6/Errfi-1 induction. Mol Cell 2009; 35: 291-304.
38. Frosi Y, Anastasi S, Ballaro C, et al. A two-tiered mechanism of EGFR inhibition by RALT/MIG6 via kinase suppression and receptor degradation. J Cell Biol; 189: 557-71.
39. Haura E B, Tanvetyanon T, Chiappori A, et al. Phase I/II study of the Src inhibitor dasatinib in combination with erlotinib in advanced non-small-cell lung cancer. J Clin Oncol; 28: 1387-94.
40. Kim L C, Song L, Haura E B. Src kinases as therapeutic targets for cancer. Nat Rev Clin Oncol 2009; 6: 587-95.
41. Song L, Morris M, Bagui T, Lee F Y, Jove R, Haura E B. Dasatinib (BMS-354825) selectively induces apoptosis in lung cancer cells dependent on epidermal growth factor receptor signaling for survival. Cancer Res 2006; 66: 5542-8.
42. Bordeaux J, Welsh A, Agarwal S, et al. Antibody validation. Biotechniques; 48: 197-209.
43. Haura E B, Sommers E, Song L, Chiappori A, Becker A. A Pilot Study of Preoperative Gefitinib for Early-Stage Lung Cancer to Assess Intratumor Drug Concentration and Pathways Mediating Primary Resistance. J Thorac Oncol.
44. Haura E B, Zheng Z, Song L, Cantor A, Bepler G. Activated epidermal growth factor receptor-Stat-3 signaling promotes tumor survival in vivo in non-small cell lung cancer. Clin Cancer Res 2005; 11: 8288-94.
45. Zheng Z, Bepler G, Cantor A, Haura E B. Small tumor size and limited smoking history predicts activated epidermal growth factor receptor in early-stage non-small cell lung cancer. Chest 2005; 128: 308-16.
46. Zheng Z, Chen T, Li X, Haura E, Sharma A, Bepler G. DNA synthesis and repair genes RRM1 and ERCC1 in lung cancer. N Engl J Med 2007; 356: 800-8.
47. Zheng Z, Li X, Schell M J, et al. Thymidylate synthase in situ protein expression and survival in stage I nonsmall-cell lung cancer. Cancer 2008; 112: 2765-73.
48. Clark G M, Zborowski D M, Culbertson J L, et al. Clinical utility of epidermal growth factor receptor expression for selecting patients with advanced non-small cell lung cancer for treatment with erlotinib. J Thorac Oncol 2006; 1: 837-46.
49. Clark G M, Zborowski D M, Santabarbara P, et al. Smoking history and epidermal growth factor receptor expression as predictors of survival benefit from erlotinib for patients with non-small-cell lung cancer in the National Cancer Institute of Canada Clinical Trials Group study BR.21. Clin Lung Cancer 2006; 7: 389-94.
50. Miller R, Siegmund, D. Maximally selected chi-square statistics. Biometrics 1982; 38: 1011-6.
51. Hilsenbeck S G, Clark G M. Practical p-value adjustment for optimally selected cutpoints. Stat Med 1996; 15: 103-12.
52. Wang L, Zhu J, Zou H. Hybrid huberized support vector machines for microarray classification and gene selection. Bioinformatics 2008; 24: 412-9.

53. Sha N, Vannucci M, Tadesse M G, et al. Bayesian variable selection in multinomial probit models to identify molecular signatures of disease stage. Biometrics 2004; 60: 812-9.
54. Koos B, Paulsson J, Jarvius M, et al. Platelet-derived growth factor receptor expression and activation in choroid plexus tumors. Am J Pathol 2009; 175: 1631-7.
55. Gorgoulis V G, Vassiliou L V, Karakaidos P, et al. Activation of the DNA damage checkpoint and genomic instability in human precancerous lesions. Nature 2005; 434: 907-13.
56. Metro G, Zheng Z, Fabi A, et al. In situ protein expression of RRM1, ERCC1, and BRCA1 in metastatic breast cancer patients treated with gemcitabine-based chemotherapy. Cancer Invest; 28: 172-80.
57. Reynolds C, Obasaju C, Schell M J, et al. Randomized phase III trial of gemcitabine-based chemotherapy with in situ RRM1 and ERCC1 protein levels for response prediction in non-small-cell lung cancer. J Clin Oncol 2009; 27: 5808-15.
58. Gao J, Zheng Z, Rawal B, Schell M J, Bepler G, Haura E B. Mirk/Dyrk1B, a novel therapeutic target, mediates cell survival in non-small cell lung cancer cells. Cancer Biol Ther 2009; 8: 1671-9.
59. Golas J M, Arndt K, Etienne C, et al. SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice. Cancer Res 2003; 63: 375-81.
60. Golas J M, Lucas J, Etienne C, et al. SKI-606, a Src/Abl inhibitor with in vivo activity in colon tumor xenograft models. Cancer Res 2005; 65: 5358-64.

I claim:
1. A method for treating a malignancy in a subject, comprising administering a protein-protein interaction (PPI) inhibitor or inducer to the subject, wherein the subject is predetermined to have two or more target binding partners of a cancer cell signaling network that are detected by proximity ligation assay (PLA), wherein the target binding partners are selected from among the following pairs of binding pairs tyrosine-protein kinase Met (MET) and growth factor receptor-bound protein 2 (Grb2); epidermal growth factor receptor (EGFR) and GRB2 associated binding protein 2 (GAB2); and tyrosine-protein kinase Met (MET) and another binding partner of MET; and wherein the PPI inhibitor or inducer inhibits or induces protein-protein interaction between the two or more target binding partners.

2. A method for treating a malignancy in a subject, comprising:
(a) measuring a protein-protein interaction (PPI) of a cancer signaling network using a proximity ligation assay (PLA) in a cancer cell sample obtained from the subject, wherein said measuring comprises measuring two or more target binding partners of the cancer signaling network, wherein the target binding partners are selected from among the following pairs of binding pairs: tyrosine-protein kinase Met (MET) and growth factor receptor-bound protein 2 (Grb2); epidermal growth factor receptor (EGFR) and GRB2 associated binding protein 2 (GAB2); and tyrosine-protein kinase Met (MET) and another binding partner of MET; and
(b) administering a PPI inhibitor or inducer to the subject, wherein the PPI inhibitor or inducer inhibits or induces protein-protein interaction between the two or more target binding partners.

3. The method of claim 1, wherein the PPI inhibitor or inducer is a kinase inhibitor.
4. The method of claim 2, wherein the PPI inhibitor or inducer is a kinase inhibitor.
5. The method of claim 1, wherein the PPI inhibitor or inducer is a tyrosine kinase inhibitor.
6. The method of claim 2, wherein the PPI inhibitor or inducer is a tyrosine kinase inhibitor.
7. The method of claim 1, wherein the two or more target binding partners comprise MET and Grb2.
8. The method of claim 2, wherein the two or more target binding partners comprise MET and Grb2.
9. The method of claim 1, wherein the two or more target binding partners comprise EGFR and GAB2.
10. The method of claim 2, wherein the two or more target binding partners comprise EGFR and GAB2.
11. The method of claim 1, wherein the two or more target binding partners comprise MET and another binding partner of MET.
12. The method of claim 1, wherein the two or more target binding partners comprise MET and another binding partner of MET.
13. The method of claim 1, wherein the malignancy is lung cancer, gastric cancer, or breast cancer.
14. The method of claim 2, wherein the malignancy is lung cancer, gastric cancer, or breast cancer.
15. The method of claim 1, wherein the PLA comprises:
contacting the cancer cell sample with a first primary antibody and a second primary antibody, wherein the first primary antibody is specific for one of the two or more target binding partners and the second primary antibody is specific for another of the two or more target binding partners;
contacting the sample with a first proximity probe and a second proximity probe, wherein the first proximity probe comprises a first secondary antibody specific for the first primary antibody, wherein the second proximity probe comprises a second secondary antibody specific for the second primary antibody, wherein the first proximity probe further comprises an oligonucleotide and the second proximity probe further comprises an oligonucleotide, wherein the oligonucleotides of the first proximity probe and the second proximity probe become ligated when in sufficient proximity to each other, thereby forming a template for rolling circle amplification, resulting in an amplification product; and detecting the amplification product.
16. The method of claim 15, wherein the amplification product is detected by contacting the amplification product with labeled oligonucleotides that hybridize with the amplification product.
17. The method of claim 16, wherein the label of the labeled oligonucleotides is detected or visualized by an antibody-based detection method or histochemical technique.
18. The method of claim 2, wherein the PLA comprises:
contacting the cancer cell sample with a first primary antibody and a second primary antibody, wherein the first primary antibody is specific for one of the two or more target binding partners and the second primary antibody is specific for another of the two or more target binding partners;
contacting the sample with a first proximity probe and a second proximity probe, wherein the first proximity probe comprises a first secondary antibody specific for the first primary antibody, wherein the second proximity probe comprises a second secondary antibody specific for the second primary antibody, wherein the first proximity probe further comprises an oligonucleotide and the second proximity probe further comprises an oligonucleotide, wherein the oligonucleotides of the first proximity probe and the second proximity probe become ligated when in sufficient proximity to each other, thereby forming a template for rolling circle amplification, resulting in an amplification product; and detecting the amplification product.

19. The method of claim 18, wherein the amplification product is detected by contacting the amplification product with labeled oligonucleotides that hybridize with the amplification product.

20. The method of claim 19, wherein the label of the labeled oligonucleotides is detected or visualized by an antibody-based detection method or histochemical technique.

* * * * *

UNITED STATES PATENT AND TRADEMARK OFFICE
CERTIFICATE OF CORRECTION

PATENT NO.        : 10,139,410 B2                                                      Page 1 of 3
APPLICATION NO.   : 15/796755
DATED             : November 27, 2018
INVENTOR(S)       : Eric B. Haura It is certified that error appears in the above--identified patent and that said Letters Patent is hereby corrected as shown below:

In the Specification

Column 25,
Line 62, "(MM)" should read --(MRI)--.

Column 33,
Line 3, "doxorubi cin" should read --doxorubicin--.

Column 47,
Line 6, "KruskalWallis test" should read --Kruskal-Wallis test--.

Column 48,
Line 1, "Egfr and Grb2" should read --EGFR and GRB2--.
Line 55, "Egfr and Grb2" should read --EGFR and GRB2--.

Column 135,
Lines 6-7, "ARHGAPS (233849" should read --ARHGAP5 (233849--.
Line 22, "ATP5H" should read --ATP5H--.
Line 23, "ATP50" should read --ATP5O--.
Line 45, "BENDS" should read --BEND5--.
Line 66, "CCRS" should read --CCR5--.

Column 136,
Line 29, "CDHS" should read --CDH5--.
Line 53, "COLO" should read --COLQ--.

Column 137,
Line 65, "3798_at" should read --37986_at--.

Signed and Sealed this
Twenty-fifth Day of June, 2019

Andrei Iancu
*Director of the United States Patent and Trademark Office*

CERTIFICATE OF CORRECTION (continued)
U.S. Pat. No. 10,139,410 B2

Column 139,
Line 8, "20927_s_at" should read --209276_s_at--.
Line 36, "HESS" should read --HES5--.
Line 54, "HSP9OAA1" should read --HSP90AA1--.

Column 140,
Line 35, "(2092979_at" should read --(209297_at--.
Line 44, "KCNQS" should read --KCNQ5--.

Column 141,
Line 50, "2248239_at" should read --224823_at--.

Column 142,
Line 23, "(2107459_at)," should read --(210745_at),--.

Column 143,
Line 31, "PRMTS" should read --PRMT5--.
Line 49, "PTPNS" should read --PTPN5--.

Column 144,
Line 35, "SCAMPI" should read --SCAMP1--.

Column 145,
Line 50, "STATSA" should read --STAT5A--.
Line 51, "STATE" should read --STAT6--.

Column 146,
Line 66, "WNTSA" should read --WNT5A--.

Column 147,
Lines 7-8, "Egfr and Grb2" should read --EGFR AND GRB2--.

Column 148,
Line 49, "Egfr and Grb2" should read --EGFR AND GRB2--.

Column 149,
Line 13, "Ethanol Gradient" should read --ethanol gradient--.
Line 35, "PB ST (0.05%)" should read --PBST (.05%)--.

Column 150,
Line 36, "at 76μm provides" should read --at .76μm provides--.

Column 152,
Line 26, "Egfr and Grb2" should read --EGFR AND GRB2--.
Line 54, "Ethanol Gradient" should read --ethanol gradient--.

Column 153,
Line 9, " PB ST (0/05%)" should read --PBST (.05%)--.
Line 22, "(0/05% PB ST)" should read --(0.05% PBST)--.

Column 155,
Line 9, "Planyaysky m," should read --Planyavsky m,--.